(12) United States Patent
Aicher et al.

(10) Patent No.: US 8,088,776 B2
(45) Date of Patent: Jan. 3, 2012

(54) BIPHENYL AMIDE LACTAM DERIVATIVES AS INHIBITORS OF 11-BETA-HYDROXYSTEROID DEHYDROGENASE 1

(75) Inventors: Thomas Daniel Aicher, Superior, CO (US); Zhaogen Chen, Shanghai (CN); Ronald Jay Hinklin, Longmont, CO (US); Gary Alan Hite, Indianapolis, IN (US); Alexei Pavlovych Krasutsky, Zionsville, IN (US); Renhua Li, Fishers, IN (US); Jefferson Ray McCowan, Indianapolis, IN (US); Ashraf Saeed, Westfield, IN (US); Nancy June Snyder, Lizton, IN (US); James Lee Toth, Knightstown, IN (US); Owen Brendan Wallace, Westfield, IN (US); Leonard Larry Winneroski, Jr., Greenwood, IN (US); Yanping Xu, Noblesville, IN (US); Jeremy Schulenburg York, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 432 days.

(21) Appl. No.: 12/297,349

(22) PCT Filed: Apr. 19, 2007

(86) PCT No.: PCT/US2007/066921
§ 371 (c)(1),
(2), (4) Date: Jan. 15, 2009

(87) PCT Pub. No.: WO2007/124337
PCT Pub. Date: Nov. 1, 2007

(65) Prior Publication Data
US 2009/0156571 A1 Jun. 18, 2009

Related U.S. Application Data

(60) Provisional application No. 60/745,311, filed on Apr. 21, 2006.

(51) Int. Cl.
*A61K 31/496* (2006.01)
*A61K 31/453* (2006.01)
*C07D 403/02* (2006.01)
*C07D 405/14* (2006.01)

(52) U.S. Cl. .................. 514/254.01; 514/326; 544/372; 546/208

(58) Field of Classification Search ............... 514/210.2, 514/326, 254.01, 235.5, 227.8, 211.15; 546/194; 544/372, 141, 60; 540/544
See application file for complete search history.

(56) References Cited

U.S. PATENT DOCUMENTS

| | | |
|---|---|---|
| 2008/0207691 A1 | 8/2008 | Aicher et al. |
| 2008/0214621 A1 | 9/2008 | Aicher et al. |
| 2008/0275043 A1 | 11/2008 | Aicher et al. |
| 2009/0069326 A1 | 3/2009 | Allen et al. |
| 2009/0088428 A1 | 4/2009 | Saeed et al. |
| 2009/0088430 A1 | 4/2009 | Wallace et al. |
| 2009/0099180 A1 | 4/2009 | Mabry et al. |
| 2009/0099182 A1 | 4/2009 | Li et al. |
| 2009/0111800 A1 | 4/2009 | Aicher et al. |
| 2009/0111809 A1 | 4/2009 | Bush et al. |
| 2009/0239911 A1 | 9/2009 | Wallace et al. |
| 2009/0264650 A1 | 10/2009 | Yamashita et al. |
| 2009/0275613 A1 | 11/2009 | Li et al. |

FOREIGN PATENT DOCUMENTS

| | | |
|---|---|---|
| EP | 1864971 | 12/2007 |
| WO | WO 2004/056744 | 7/2004 |
| WO | WO 2005/108360 | 11/2005 |
| WO | WO 2005/108361 | 11/2005 |
| WO | WO 2006/040329 | 4/2006 |
| WO | WO 2006/049952 | 5/2006 |
| WO | WO 2006/053024 | 5/2006 |
| WO | WO 2006/068991 | 6/2006 |
| WO | WO 2006/068992 | 6/2006 |
| WO | WO 2006/104280 | 10/2006 |
| WO | WO 2007/084314 | 7/2007 |

(Continued)

OTHER PUBLICATIONS

Patani et al., Bioisosterism: A Rational Approach in Drug Design, 1996, Chem. Rev., 96, 3147-3176.*
Yeh et al.: Discovery of orally active butyrolactam 11 β-HSD1 inhibitors, Bioorganic & Medicinal Chemistry Letters, Nov. 1, 2006, 16(21), pp. 5555-5560.

(Continued)

Primary Examiner — Kamal Saeed
Assistant Examiner — Kristin Bianchi
(74) Attorney, Agent, or Firm — Dan L. Wood

(57) ABSTRACT

The present invention discloses novel compounds of Formula I: possessing 11 β-HSD type 1 antagonist activity, as well as methods for preparing such compounds. In another embodiment, the invention discloses pharmaceutical compositions comprising compounds of Formula I, as well as methods of using the compounds and compositions to treat diabetes, hyperglycemia, obesity, hypertension, hyperlipidemia, metabolic syndrome, cognitive disorders, and other conditions associated with 11 β-HSD type 1 activity.

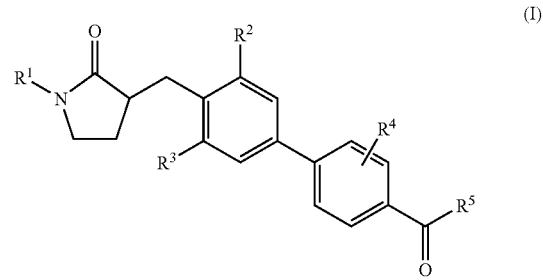

(I)

20 Claims, No Drawings

FOREIGN PATENT DOCUMENTS

| WO | WO 2007/124254 | 11/2007 |
|---|---|---|
| WO | WO 2007/124329 | 11/2007 |
| WO | WO 2007/127688 | 11/2007 |
| WO | WO 2007/127693 | 11/2007 |
| WO | WO 2007/127704 | 11/2007 |
| WO | WO 2007/127726 | 11/2007 |
| WO | WO 2007/127763 | 11/2007 |
| WO | WO 2007/127765 | 11/2007 |
| WO | WO 2007/127901 | 11/2007 |
| WO | WO 2008/157752 | 12/2008 |

OTHER PUBLICATIONS

Schuster, Daniela et al.: The Discovery of New 11β-Hydroxysteroid Dehydrogenase Type 1 Inhibitors by Common Feature Pharmacophore Modeling and Virtual Screening, J. Medicinal Chemistry, 2006, 49, pp. 3454-3466.

Konno et al.: Electrolytic Partial Fluorination of Organic Compounds. 6. Highly Regioselective Eletrochemical Monofluorination of Aliphatic Nitrogen-Containing Heterocycles, Tetrahedron Letters, 1992, vol. 33, No. 46, pp. 7017-7020.

* cited by examiner

BIPHENYL AMIDE LACTAM DERIVATIVES AS INHIBITORS OF 11-BETA-HYDROXYSTEROID DEHYDROGENASE 1

This is the national phase application, under 35 USC 371, for PCT/US2007/066921, filed Apr. 19, 2007, which claims the benefit, under 35 USC 119(e), of U.S. provisional application 60/745,311 filed Apr. 21, 2006.

This invention relates to compounds that are inhibitors of 11-β-hydroxysteroid dehydrogenase type 1 ("11-β-HSD1"), and to pharmaceutical compositions thereof, and the uses of these compounds and compositions in the treatment of the human or animal body, and to novel intermediates useful in preparation of the inhibitors. The present compounds show potent and selective inhibition of 11-β-HSD1, and as such are useful in the treatment of disorders responsive to the modulation of 11-β-HSD1, such as diabetes, metabolic syndrome, cognitive disorders, and the like.

Glucocorticoids acting in the liver, adipose tissue, and muscle, are important regulators of glucose, lipid, and protein metabolism. Chronic glucocorticoid excess is associated with insulin resistance, visceral obesity, hypertension, and dyslipidemia, which also represent the classical hallmarks of metabolic syndrome. 11-β-HSD1 catalyses the conversion of inactive cortisone to active cortisol, and has been implicated in the development of metabolic syndrome. Evidence in rodents and humans links 11-β-HSD1 to metabolic syndrome. Evidence suggests that a drug which specifically inhibits 11-β-HSD1 in type 2 diabetic patients will lower blood glucose by reducing hepatic gluconeogenesis, reduce central obesity, improve atherogenic lipoprotein phenotypes, lower blood pressure, and reduce insulin resistance. Insulin effects in muscle will be enhanced, and insulin secretion from the beta cells of the islet may also be increased. Evidence from animal and human studies also indicates that an excess of glucocorticoids impair cognitive function. Recent results indicate that inactivation of 11-β-HSD1 enhances memory function in both men and mice. The 11-β-HSD inhibitor carbenoxolone was shown to improve cognitive function in healthy elderly men and type 2 diabetics, and inactivation of the 11-β-HSD1 gene prevented aging-induced impairment in mice. Selective inhibition of 11-β-HSD1 with a pharmaceutical agent has recently been shown to improve memory retention in mice.

A number of publications have appeared in recent years reporting agents that inhibit 11-β-HSD1. See International Application WO2004/056744 which discloses adamantyl acetamides as inhibitors of 11-β-HSD, International Application WO2005/108360 which discloses pyrrolidin-2-one and piperidin-2-one derivatives as inhibitors of 11-β-HSD, and International Application WO2005/108361 which discloses adamantyl pyrrolidin-2-one derivatives as inhibitors of 11-β-HSD. In spite of the number of treatments for diseases that involve 11-β-HSD1, the current therapies suffer from one or more inadequacies, including poor or incomplete efficacy, unacceptable side effects, and contraindications for certain patient populations. Thus, there remains a need for an improved treatment using alternative or improved pharmaceutical agents that inhibit 11-β-HSD1 and treat the diseases that could benefit from 11-β-HSD1 inhibition. The present invention provides such a contribution to the art based on the finding that a novel class of compounds has a potent and selective inhibitory activity on 11-β-HSD1. The present invention is distinct in the particular structures and their activities. There is a continuing need for new methods of treating diabetes, metabolic syndrome, and cognitive disorders, and it is an object of this invention to meet these and other needs.

The present invention provides a compound structurally represented by formula I:

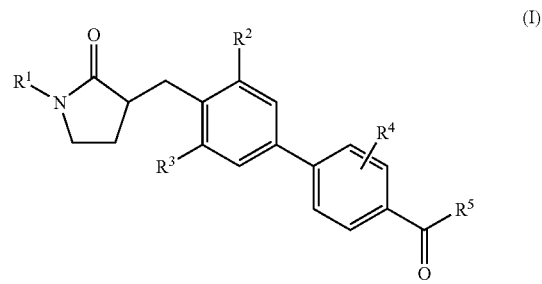

or a pharmaceutically acceptable salt thereof, wherein $R^1$ is

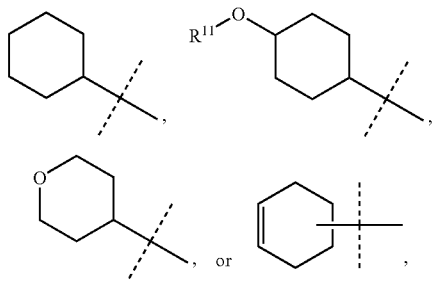

wherein the dashed line represents the point of attachment to the $R^1$ position in formula I;

$R^2$ is

—H, -halogen, —$CH_3$ (optionally substituted with 1 to 3 halogens), or —O—$CH_3$ (optionally substituted with 1 to 3 halogens);

$R^3$ is

-halogen, —$CH_3$ (optionally substituted with 1 to 3 halogens), or —O—$CH_3$ (optionally substituted with 1 to 3 halogens);

$R^4$ is —H or -halogen;

$R^5$ is

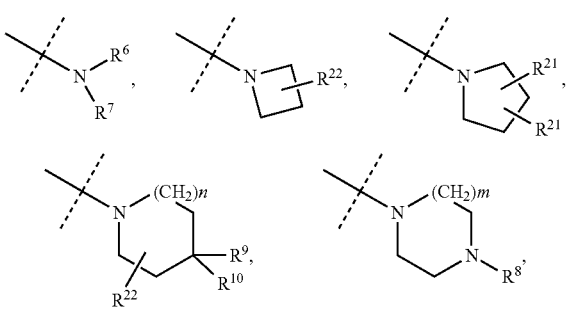

-continued

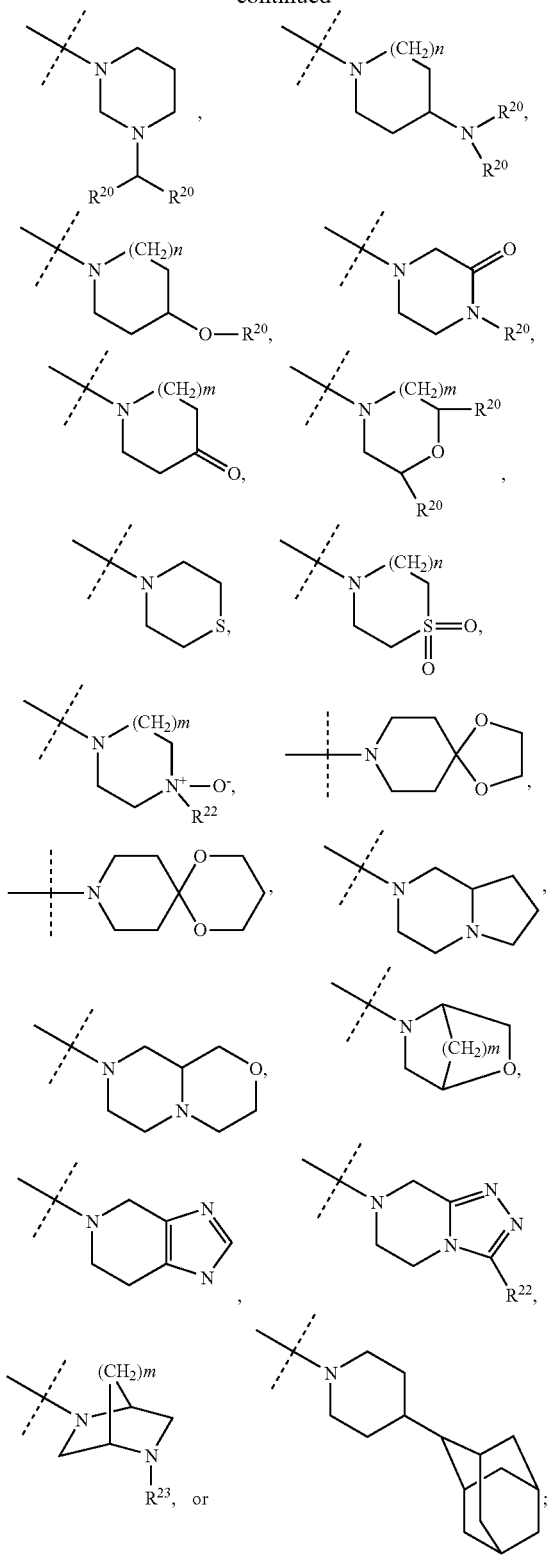

wherein the dashed line represents the point of attachment to the R⁵ position in formula I;

wherein n is 0, 1, or 2, and wherein when n is 0, then "(CH₂)n" is a bond;

wherein m is 1 or 2;

$R^6$ is

—H, —($C_1$-$C_3$)alkyl (optionally substituted with 1 to 3 halogens), —($C_1$-$C_3$)alkyl-O—$R^{20}$, —($C_1$-$C_3$)alkyl-pyrrolidinyl, phenyl, -HET$^1$, -HET$^2$, —CH$_2$-phenyl, —CH$_2$-HET$^1$, —CH$_2$-HET$^2$, —($C_1$-$C_3$)alkyl-N($R^{20}$)($R^{20}$), —($C_1$-$C_3$)alkyl-N$^+$(O$^-$)(CH$_3$)$_2$, —($C_1$-$C_3$)alkyl-C(O)N($R^{41}$)($R^{41}$), —CH(C(O)OH)(CH$_2$O$R^{20}$), —CH(C(O)OH)(CH$_2$N($R^{20}$)($R^{20}$)), —($C_1$-$C_3$)alkyl-C(O)O—$R^{20}$,

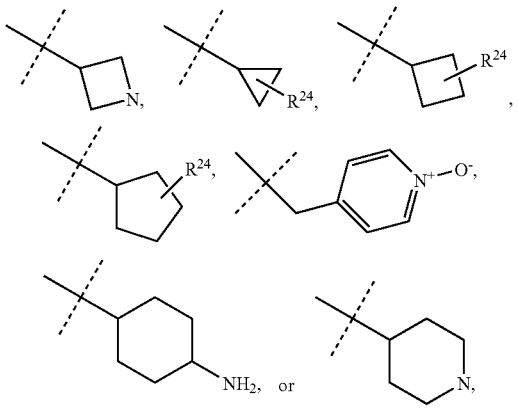

wherein the dashed line indicates the point of attachment to the position indicated by $R^6$;

HET$^1$ is

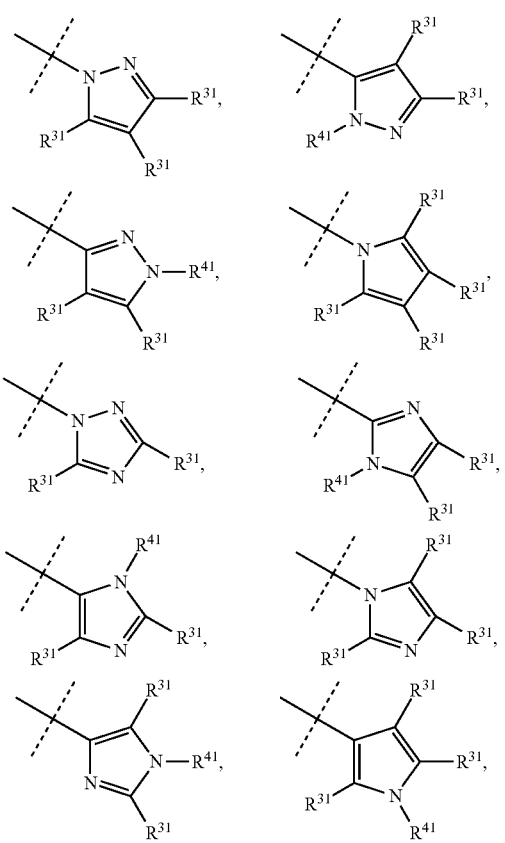

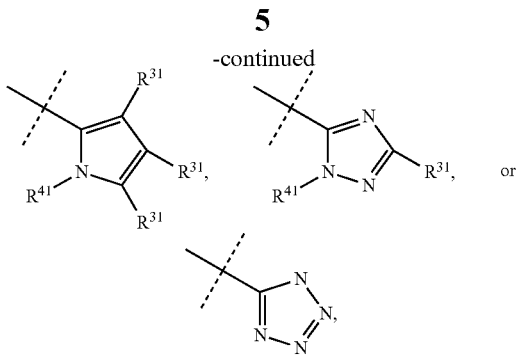

wherein the dashed line indicates the point of attachment to the position indicated by HET¹;
HET² is

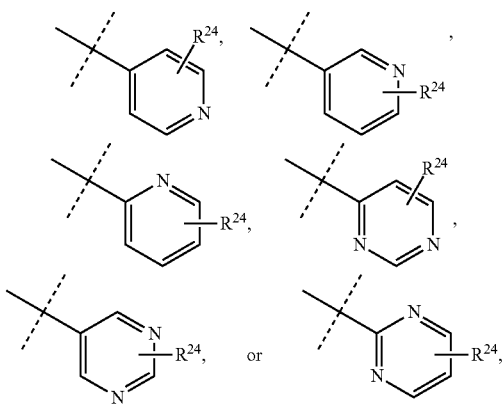

or wherein the dashed line indicates the point of attachment to the position indicated by HET²;

R⁷ is
—H, —(C₁-C₃)alkyl (optionally substituted with 1 to 3 halogens), or —(C₁-C₃)alkyl-O—R²⁰;

R⁸ is
—H, —OH, —(C₁-C₆)alkyl (optionally substituted with 1 to 3 halogens), —(C₁-C₃)alkyl-O—R²⁰, —C(O)—(C₁-C₄)alkyl (optionally substituted with 1 to 3 halogens), —C(O)O—(C₁-C₄)alkyl (optionally substituted with 1 to 3 halogens), or —C(O)—N(R²⁰)(R²⁰);

R⁹ is
—H, -halogen, —CH₃ (optionally substituted with 1 to 3 halogens), or —O—CH₃ (optionally substituted with 1 to 3 halogens);

R¹⁰ is independently at each occurrence —H, or -halogen;
R¹¹ is independently at each occurrence —H, —CH₃ or —CH₂—CH₃;
R²⁰ is independently at each occurrence —H, or —(C₁-C₄) alkyl (optionally substituted with 1 to 3 halogens);
R²¹ is independently at each occurrence —H, -halogen, or —(C₁-C₄)alkyl (optionally substituted with 1 to 3 halogens);
R²² is independently at each occurrence —H, or —(C₁-C₆) alkyl (optionally substituted with 1 to 3 halogens);
R²³ is independently at each occurrence —H, —(C₁-C₄) alkyl, or —C(O)O—(C₁-C₄)alkyl;
R²⁴ is independently at each occurrence —H, -halogen, or —(C₁-C₆)alkyl (optionally substituted with 1 to 3 halogens);
R³¹ is independently at each occurrence —H, -halogen, or —(C₁-C₆)alkyl (optionally substituted with 1 to 3 halogens); and
R⁴¹ is independently at each occurrence —H, or —(C₁-C₆) alkyl (optionally substituted with 1 to 3 halogens);

provided the compound is not {[3'-Chloro-4'-(1-cyclohexyl-2-oxo-pyrrolidin-3-ylmethyl)-biphenyl-4-carbonyl]-amino}-acetic acid, 4-{[3'-Chloro-4'-(1-cyclohexyl-2-oxo-pyrrolidin-3-ylmethyl)-biphenyl-4-carbonyl]-amino}-butyric acid, 3'-Chloro-4'-(1-cyclohexyl-2-oxo-pyrrolidin-3-ylmethyl)-biphenyl-4-carboxylic acid piperidin-4-ylamide, or 3-[3-Chloro-4'-(4-methyl-piperazine-1-carbonyl)-biphenyl-4-ylmethyl]-1-cyclohexyl-pyrrolidin-2-one.

The present invention provides compounds of formula I that are useful as potent and selective inhibition of 11-β-HSD1. The present invention further provides a pharmaceutical composition which comprises a compound of Formula I, or a pharmaceutical salt thereof, and a pharmaceutically acceptable carrier, diluent, or excipient. In addition, the present invention provides a method for the treatment of metabolic syndrome, and related disorders, which comprise administering to a patient in need thereof an effective amount of a compound of formula I or a pharmaceutically acceptable salt thereof.

In one embodiment, the present invention provides compounds of Formula I or a pharmaceutically acceptable salt thereof as described in detail above. While all of the compounds of the present invention are useful, certain of the compounds are particularly interesting and are preferred. The following listings set out several groups of preferred compounds.

In another embodiment the invention provides a compound structurally represented by formula I, or a pharmaceutically acceptable salt thereof, wherein
R¹ is

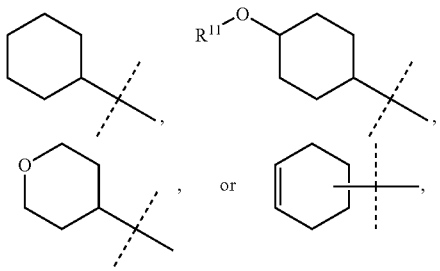

wherein the dashed line represents the point of attachment to the R¹ position in formula I;
R² is -halogen;
R³ is -halogen;
R⁴ is —H or -halogen;
R⁵ is

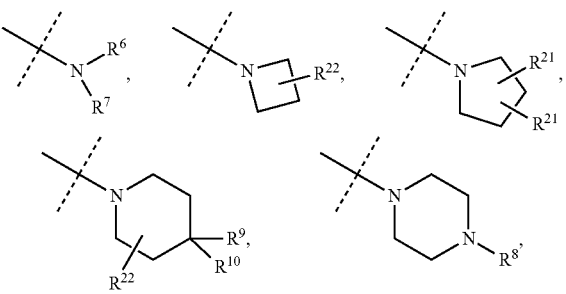

-continued

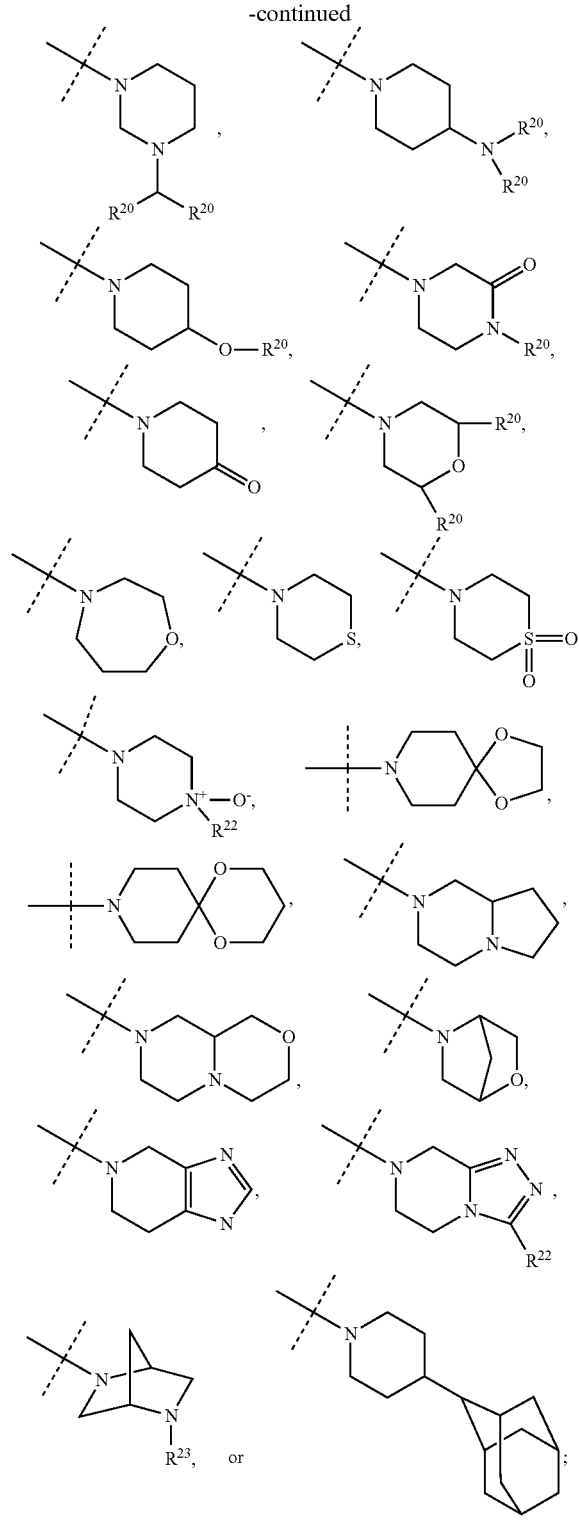

wherein the dashed line represents the point of attachment to the R⁵ position in formula I;

R⁶ is
—H, —($C_1$-$C_3$)alkyl (optionally substituted with 1 to 3 halogens), —($C_1$-$C_3$)alkyl-O—$R^{10}$, —($C_1$-$C_3$)alkyl-pyrrolidinyl, phenyl, -HET¹, -HET², —CH₂-phenyl, —CH₂-HET¹, —CH₂-HET², —($C_1$-$C_3$)alkyl-N($R^{20}$)($R^{20}$), —($C_1$-$C_3$)alkyl-N⁺(O⁻)(CH₃)₂, —($C_1$-$C_3$)alkyl-C(O)N($R^{41}$)($R^{41}$), —CH(C(O)OH)(CH₂O$R^{20}$), —CH(C(O)OH)(CH₂N($R^{20}$)($R^{20}$)), —($C_1$-$C_3$)alkyl-C(O)O—$R^{20}$,

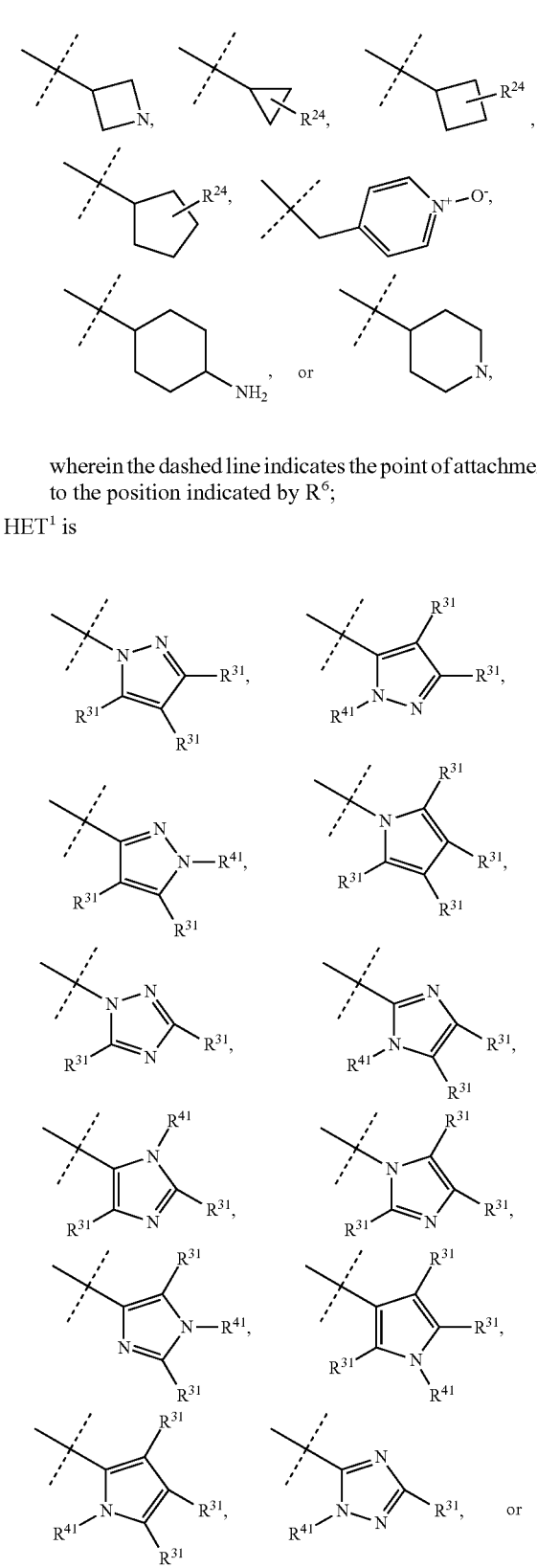

wherein the dashed line indicates the point of attachment to the position indicated by R⁶;

HET¹ is

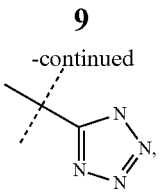

wherein the dashed line indicates the point of attachment to the position indicated by HET¹;

HET² is

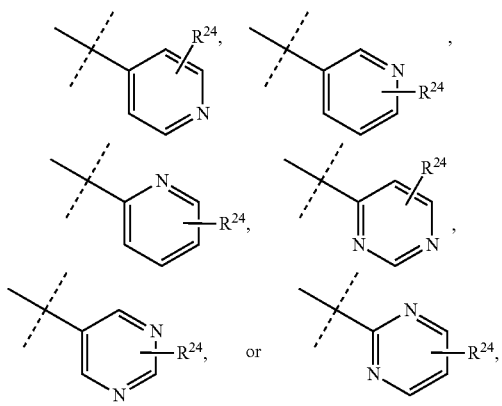

wherein the dashed line indicates the point of attachment to the position indicated by HET²;

$R^7$ is
—H, —($C_1$-$C_3$) alkyl (optionally substituted with 1 to 3 halogens), or —($C_1$-$C_3$)alkyl-O—$R^{10}$;

$R^8$ is
—H, —OH, —($C_1$-$C_6$)alkyl (optionally substituted with 1 to 3 halogens), —($C_1$-$C_3$)alkyl-O—$R^{20}$, —C(O)—($C_1$-$C_4$)alkyl (optionally substituted with 1 to 3 halogens), —C(O)O—($C_1$-$C_4$)alkyl (optionally substituted with 1 to 3 halogens), or —C(O)—N($R^{20}$)($R^{20}$);

$R^9$ is
—H, -halogen, —$CH_3$ (optionally substituted with 1 to 3 halogens), or —O—$CH_3$ (optionally substituted with 1 to 3 halogens);

$R^{10}$ is independently at each occurrence —H or -halogen;

$R^{11}$ is independently at each occurrence —H, —$CH_3$, or —$CH_2$—$CH_3$;

$R^{20}$ is independently at each occurrence —H or —($C_1$-$C_4$) alkyl (optionally substituted with 1 to 3 halogens);

$R^{21}$ is independently at each occurrence —H, -halogen, or —($C_1$-$C_4$)alkyl (optionally substituted with 1 to 3 halogens);

$R^{22}$ is independently at each occurrence —H, or —($C_1$-$C_6$) alkyl (optionally substituted with 1 to 3 halogens);

$R^{23}$ is independently at each occurrence —H, —($C_1$-$C_4$) alkyl, or —C(O)O—($C_1$-$C_4$)alkyl;

$R^{24}$ is independently at each occurrence —H, -halogen, or —($C_1$-$C_6$)alkyl (optionally substituted with 1 to 3 halogens);

$R^{31}$ is independently at each occurrence —H, -halogen, or —($C_1$-$C_6$)alkyl (optionally substituted with 1 to 3 halogens); and $R^{41}$ is independently at each occurrence —H or —($C_1$-$C_6$) alkyl (optionally substituted with 1 to 3 halogens).

In another embodiment the invention provides a compound structurally represented by formula I, or a pharmaceutically acceptable salt thereof, wherein $R^1$ is

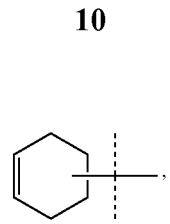

wherein the dashed line represents the point of attachment to the $R^1$ position in formula I;

$R^2$ is -halogen;

$R^3$ is -halogen;

$R^4$ is —H or -halogen;

$R^5$ is

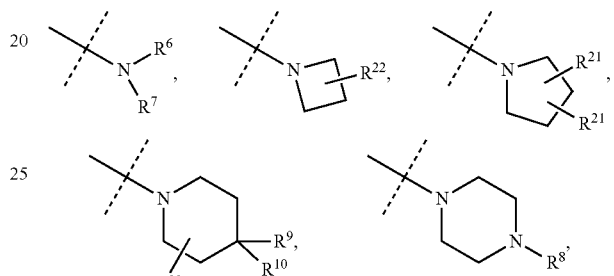

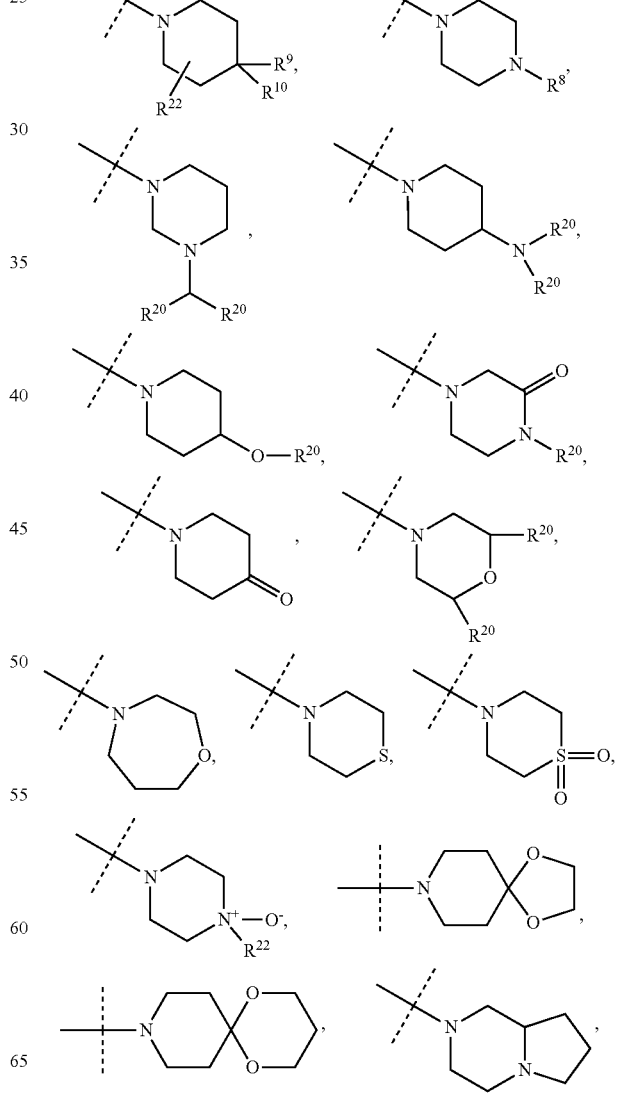

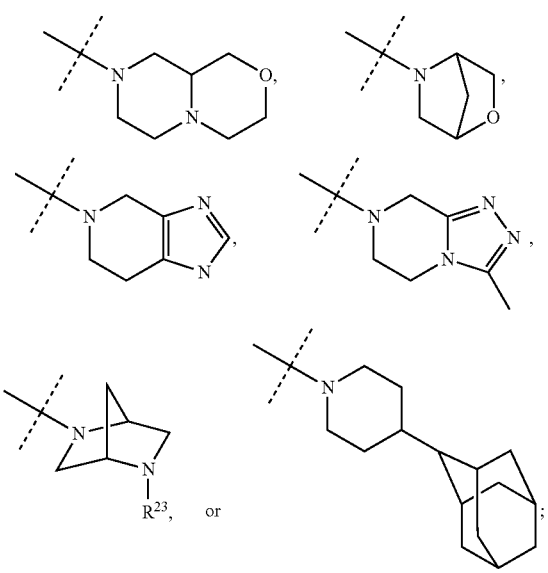

wherein the dashed line represents the point of attachment to the $R^5$ position in formula I;

$R^6$ is

—H, —$(C_1$-$C_3)$alkyl (optionally substituted with 1 to 3 halogens), —$(C_1$-$C_3)$alkyl-O—$R^{20}$, —$(C_1$-$C_3)$alkyl-pyrrolidinyl, phenyl, -HET$^1$, -HET$^2$, —$CH_2$-phenyl, —$CH_2$-HET$^1$, —$CH_2$-HET$^2$, —$(C_1$-$C_3)$alkyl-N$(R^{20})(R^{20})$, —$(C_1$-$C_3)$alkyl-N$^+(O^-)(CH_3)_2$, —$(C_1$-$C_3)$alkyl-C(O)N$(R^{41})(R^{41})$, —CH(C(O)OH)(CH$_2$OR$^{20}$), —CH(C(O)OH)(CH$_2$N$(R^{20})(R^{20})$), —$(C_1$-$C_3)$alkyl-C(O)O—$R^{20}$,

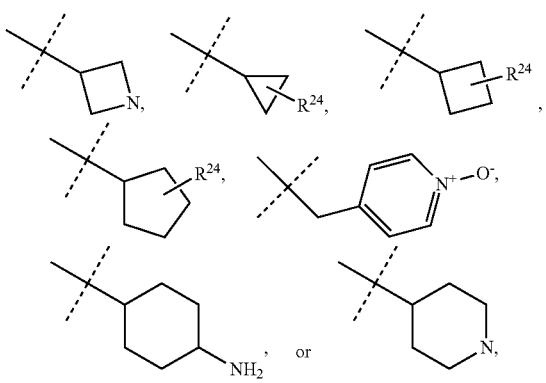

wherein the dashed line indicates the point of attachment to the position indicated by $R^6$;

HET$^1$ is

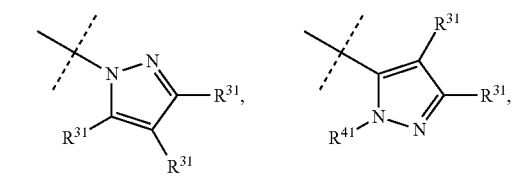

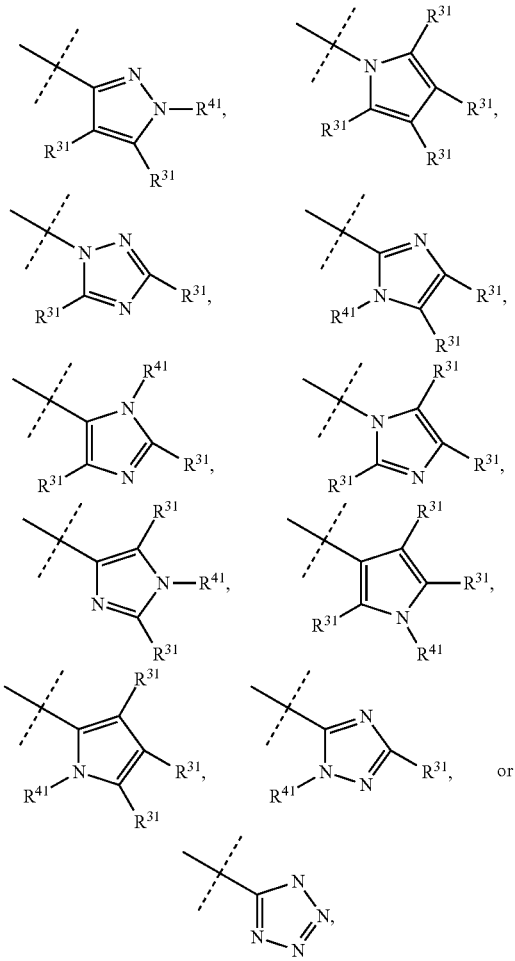

wherein the dashed line indicates the point of attachment to the position indicated by HET$^1$;

HET$^2$ is

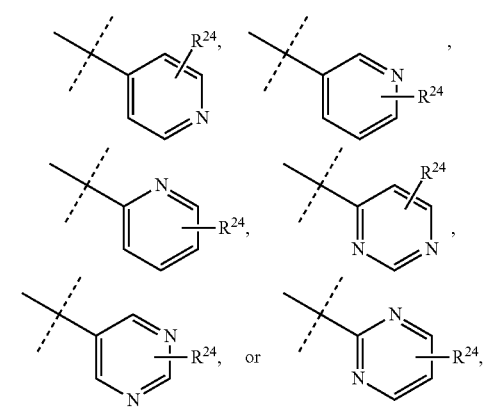

wherein the dashed line indicates the point of attachment to the position indicated by HET$^2$;

$R^7$ is

—H, —$(C_1$-$C_3)$alkyl (optionally substituted with 1 to 3 halogens), or —$(C_2$-$C_3)$alkyl-O—$R^{20}$;

$R^8$ is
—H, —OH, —$(C_1-C_4)$alkyl (optionally substituted with 1 to 3 halogens), —$(C_2-C_3)$alkyl-O—$R^{20}$, —C(O)—$(C_1-C_4)$alkyl, —C(O)O—$(C_1-C_4)$alkyl, or —C(O)—N($R^{20}$)($R^{20}$);

$R^9$ is
—H, -halogen, —$CH_3$ (optionally substituted with 1 to 3 halogens), or —O—$CH_3$ (optionally substituted with 1 to 3 halogens);

$R^{10}$ is independently at each occurrence —H or -halogen;

$R^{11}$ is independently at each occurrence —H, —$CH_3$, or —$CH_2$—$CH_3$;

$R^{20}$ is independently at each occurrence —H or —$(C_1-C_3)$alkyl (optionally substituted with 1 to 3 halogens);

$R^{21}$ is independently at each occurrence —H, -halogen, or —$(C_1-C_3)$alkyl;

$R^{22}$ is independently at each occurrence —H or —$(C_1-C_3)$alkyl (optionally substituted with 1 to 3 halogens);

$R^{23}$ is independently at each occurrence —H, —$(C_1-C_3)$alkyl, or —C(O)O—$(C_1-C_4)$alkyl;

$R^{24}$ is independently at each occurrence —H, -halogen, or —$(C_1-C_3)$alkyl (optionally substituted with 1 to 3 halogens);

$R^{31}$ is independently at each occurrence —H, -halogen, or —$(C_1-C_3)$alkyl; and $R^{41}$ is independently at each occurrence —H or —$CH_3$.

In another embodiment the invention provides a compound structurally represented by formula I, or a pharmaceutically acceptable salt thereof, wherein
$R^1$ is

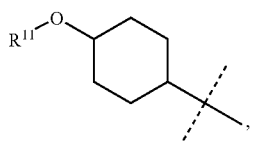

wherein the dashed line represents the point of attachment to the $R^1$ position in formula I;

$R^2$ is -halogen;
$R^3$ is -halogen;
$R^4$ is —H or -halogen;
$R^5$ is

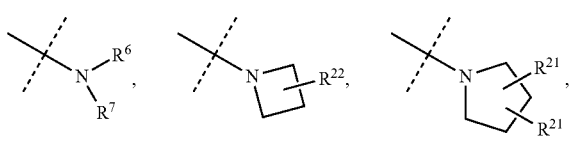

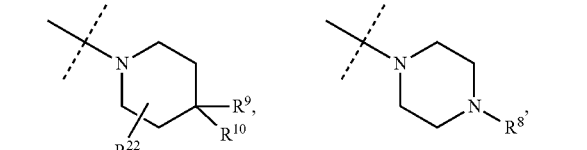

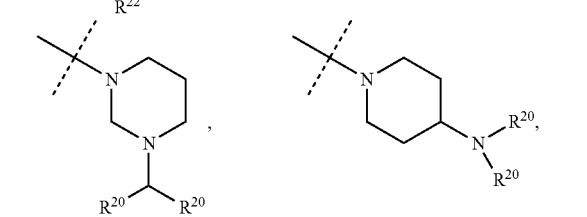

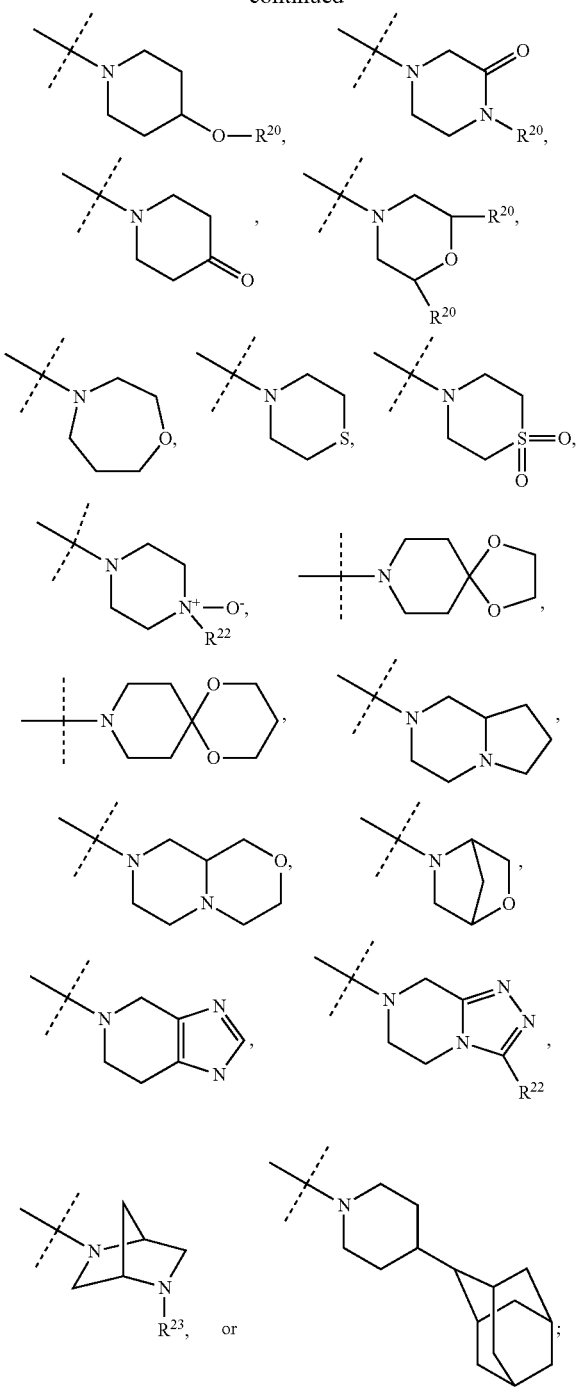

wherein the dashed line represents the point of attachment to the $R^5$ position in formula I;

$R^6$ is
—H, —$(C_1-C_3)$alkyl (optionally substituted with 1 to 3 halogens), —$(C_1-C_3)$alkyl-O—$R^{20}$, —$(C_1-C_3)$alkyl-pyrrolidinyl, phenyl, -HET$^1$, -HET$^2$, —$CH_2$-phenyl, —$CH_2$-HET$^1$, —$CH_2$-HET$^2$, —$(C_1-C_3)$alkyl-N($R^{20}$)($R^{20}$), —$(C_1-C_3)$alkyl-N$^+$(O$^-$)($CH_3$)$_2$, —$(C_1-C_3)$alkyl-C(O)N($R^{41}$)($R^{41}$), —CH(C(O)OH)($CH_2$O$R^{20}$), —CH(C(O)OH)($CH_2$N($R^{20}$)($R^{20}$)), —$(C_1-C_3)$alkyl-C(O)O—$R^{20}$,

15

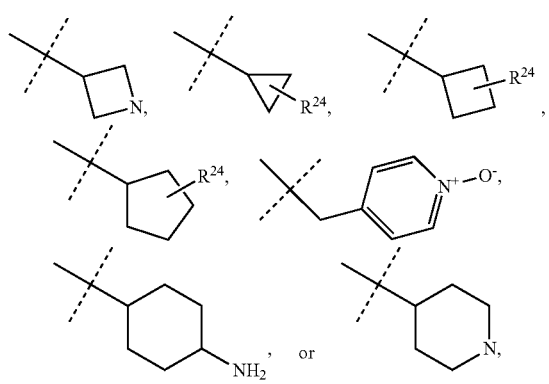

wherein the dashed line indicates the point of attachment to the position indicated by $R^6$;

HET$^1$ is

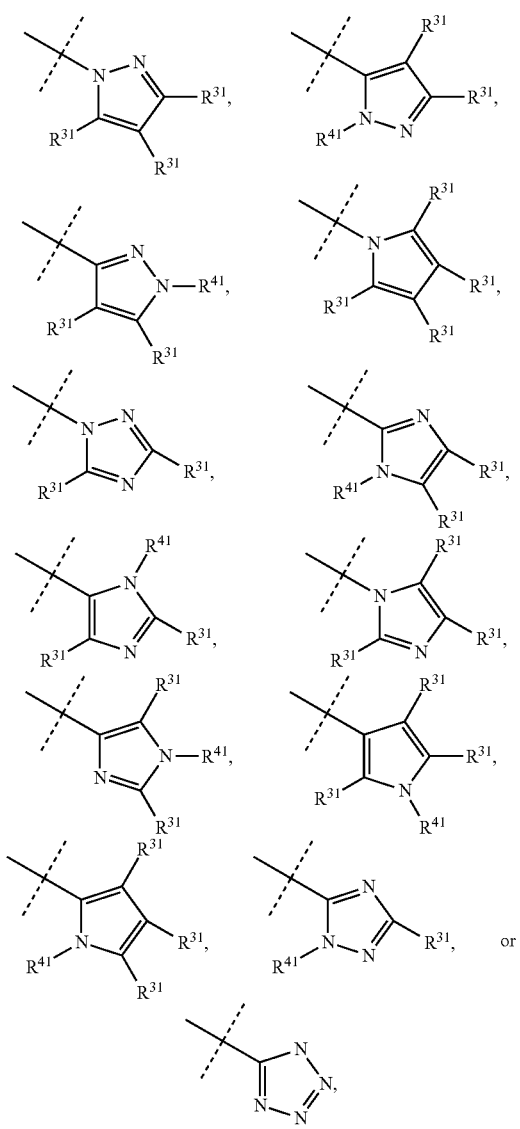

wherein the dashed line indicates the point of attachment to the position indicated by HET$^1$;

HET$^2$ is

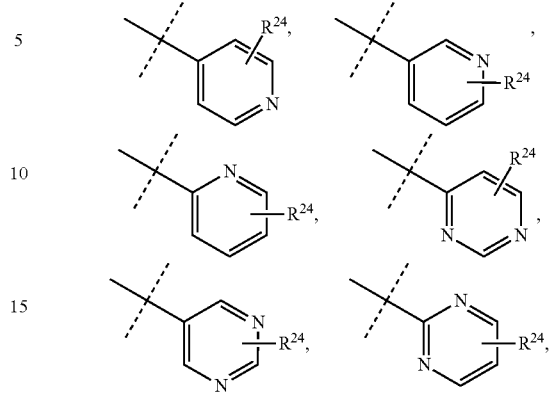

wherein the dashed line indicates the point of attachment to the position indicated by HET$^2$;

$R^7$ is
—H, —($C_1$-$C_3$)alkyl (optionally substituted with 1 to 3 halogens), or —($C_2$-$C_3$)alkyl-O—$R^{20}$;

$R^8$ is
—H, —OH, —($C_1$-$C_4$)alkyl (optionally substituted with 1 to 3 halogens), —($C_2$-$C_3$)alkyl-O—$R^{20}$, —C(O)—($C_1$-$C_4$)alkyl, —C(O)O—($C_1$-$C_4$)alkyl, or —C(O)—N($R^{20}$)($R^{20}$);

$R^9$ is
—H, -halogen, —$CH_3$ (optionally substituted with 1 to 3 halogens), or —O—$CH_3$ (optionally substituted with 1 to 3 halogens);

$R^{10}$ is independently at each occurrence —H or -halogen;

$R^{11}$ is independently at each occurrence —H, —$CH_3$, or —$CH_2$—$CH_3$;

$R^{20}$ is independently at each occurrence —H or —($C_1$-$C_3$)alkyl (optionally substituted with 1 to 3 halogens);

$R^{21}$ is independently at each occurrence —H, -halogen, or —($C_1$-$C_3$)alkyl;

$R^{22}$ is independently at each occurrence —H, or —($C_1$-$C_3$)alkyl (optionally substituted with 1 to 3 halogens);

$R^{23}$ is independently at each occurrence —H, —($C_1$-$C_3$)alkyl, or —C(O)O—($C_1$-$C_4$)alkyl;

$R^{24}$ is independently at each occurrence —H, -halogen, or —($C_1$-$C_3$)alkyl (optionally substituted with 1 to 3 halogens);

$R^{31}$ is independently at each occurrence —H, -halogen, or —($C_1$-$C_3$)alkyl; and $R^{41}$ is independently at each occurrence —H or —$CH_3$.

In another embodiment the invention provides a compound structurally represented by formula I, or a pharmaceutically acceptable salt thereof, wherein $R^1$ is

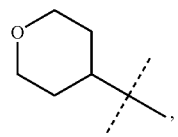

wherein the dashed line represents the point of attachment to the $R^1$ position in formula I;

$R^2$ is -halogen;

$R^3$ is -halogen;

$R^4$ is —H or -halogen;

$R^5$ is

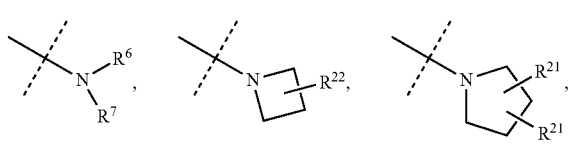

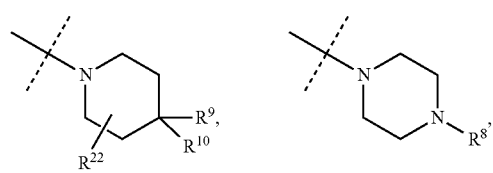

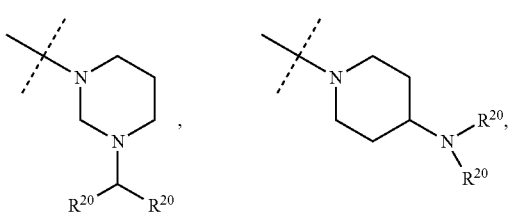

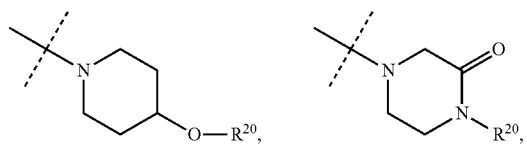

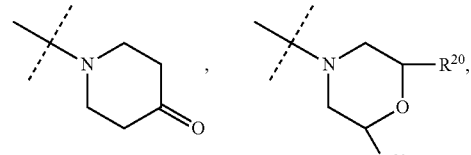

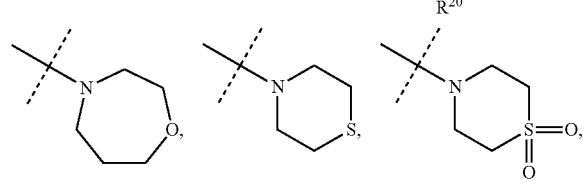

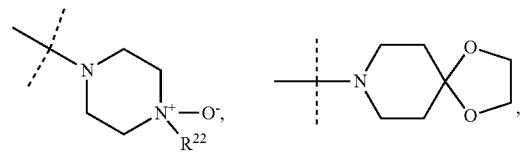

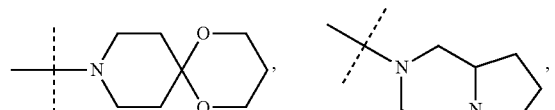

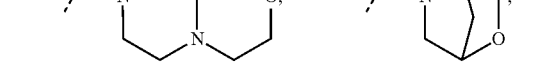

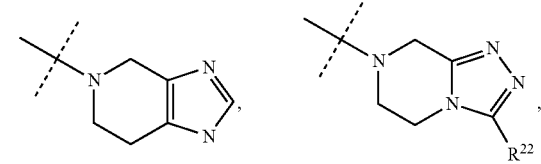

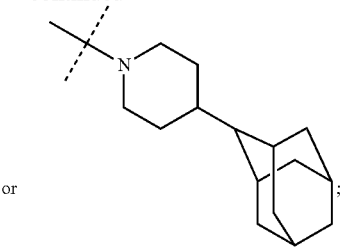

wherein the dashed line represents the point of attachment to the $R^5$ position in formula I;

$R^6$ is
—H, —($C_1$-$C_3$)alkyl (optionally substituted with 1 to 3 halogens), —($C_1$-$C_3$)alkyl-O—$R^{20}$, —($C_1$-$C_3$)alkyl-pyrrolidinyl, phenyl, -HET$^1$, -HET$^2$, —$CH_2$-phenyl, —$CH_2$-HET$^1$, —$CH_2$-HET$^2$, —($C_1$-$C_3$)alkyl-N($R^{20}$)($R^{20}$), —($C_1$-$C_3$)alkyl-$N^+$($O^-$)($CH_3$)$_2$, —($C_1$-$C_3$)alkyl-C(O)N($R^{41}$)($R^{41}$), —CH(C(O)OH)($CH_2$O$R^{20}$), —CH(C(O)OH)($CH_2$N($R^{20}$)($R^{20}$)), —($C_1$-$C_3$)alkyl-C(O)O—$R^{20}$,

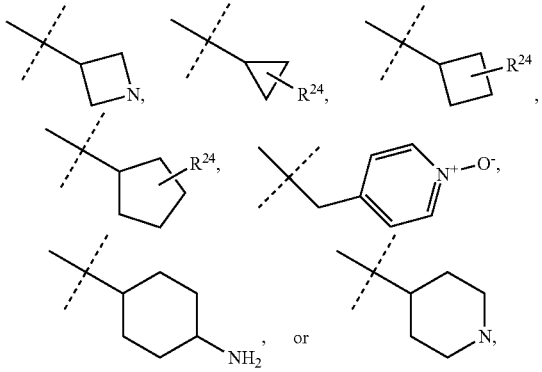

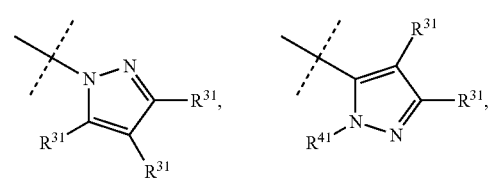

wherein the dashed line indicates the point of attachment to the position indicated by $R^6$;

HET$^1$ is

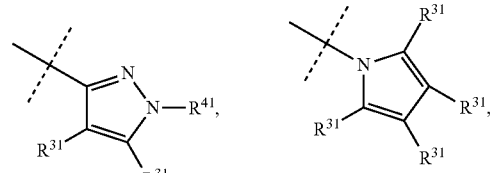

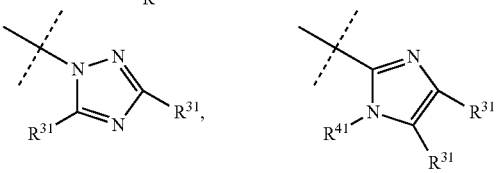

-continued

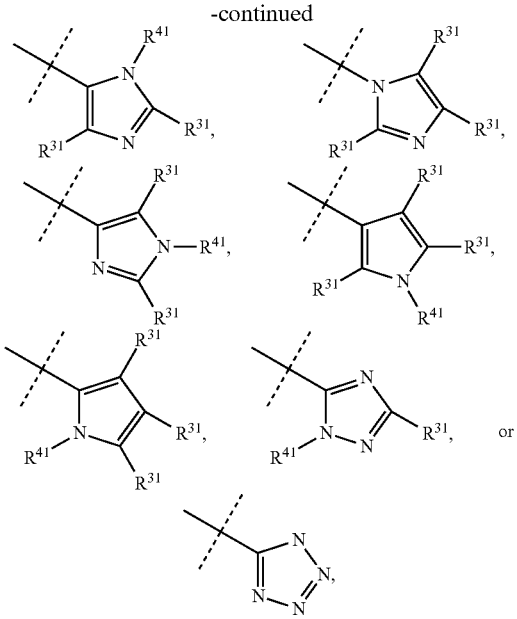

wherein the dashed line indicates the point of attachment to the position indicated by HET¹;
HET² is

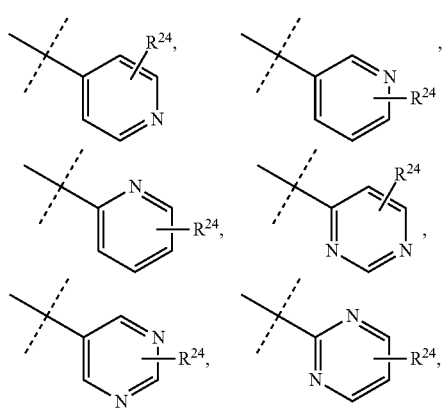

wherein the dashed line indicates the point of attachment to the position indicated by HET²;

$R^7$ is
—H, —($C_1$-$C_3$)alkyl (optionally substituted with 1 to 3 halogens), or —($C_2$-$C_3$)alkyl-O—$R^{20}$;

$R^8$ is
—H, —OH, —($C_1$-$C_4$)alkyl (optionally substituted with 1 to 3 halogens), —($C_2$-$C_3$)alkyl-O—$R^{20}$, —C(O)—($C_1$-$C_4$)alkyl, —C(O)O—($C_1$-$C_4$)alkyl, or —C(O)—N($R^{20}$)($R^{20}$);

$R^9$ is
—H, -halogen, —$CH_3$ (optionally substituted with 1 to 3 halogens), or —O—$CH_3$ (optionally substituted with 1 to 3 halogens);

$R^{10}$ is independently at each occurrence —H or -halogen;
$R^{20}$ is independently at each occurrence —H or —($C_1$-$C_3$) alkyl (optionally substituted with 1 to 3 halogens);
$R^{21}$ is independently at each occurrence —H, -halogen, or —($C_1$-$C_3$)alkyl;
$R^{22}$ is independently at each occurrence —H or —($C_1$-$C_3$) alkyl (optionally substituted with 1 to 3 halogens);

$R^{23}$ is independently at each occurrence —H, —($C_1$-$C_3$) alkyl, or —C(O)O—($C_1$-$C_4$)alkyl;
$R^{24}$ is independently at each occurrence —H, -halogen, or —($C_1$-$C_3$)alkyl (optionally substituted with 1 to 3 halogens);
$R^{31}$ is independently at each occurrence —H, -halogen, or —($C_1$-$C_3$)alkyl; and
$R^{41}$ is independently at each occurrence —H or —$CH_3$.

In another embodiment the invention provides a compound structurally represented by formula I, or a pharmaceutically acceptable salt thereof, wherein
$R^1$ is

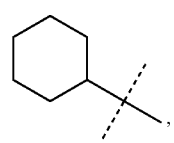

wherein the dashed line represents the point of attachment to the $R^1$ position in formula I;
$R^2$ is -halogen;
$R^3$ is -halogen;
$R^4$ is —H or -halogen;
$R^5$ is

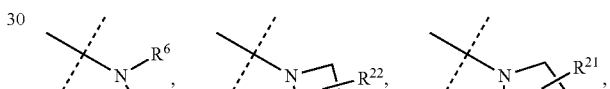

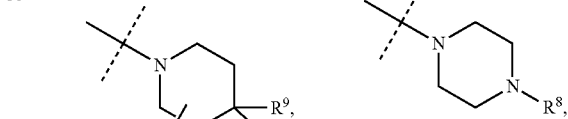

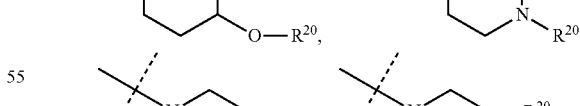

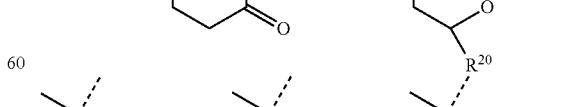

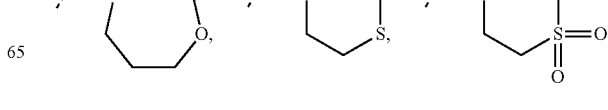

-continued

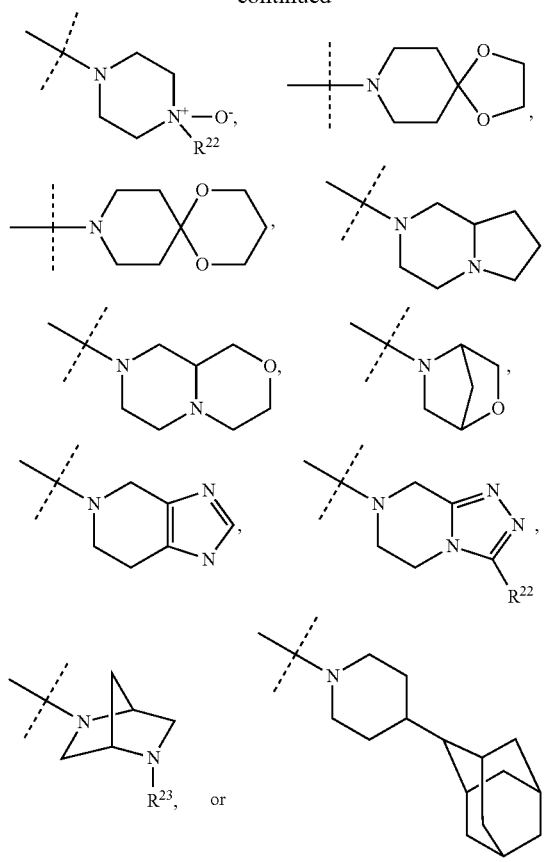

or ; wherein the dashed line represents the point of attachment to the R⁵ position in formula I;

R⁶ is

—H, —(C₁-C₃)alkyl (optionally substituted with 1 to 3 halogens), —(C₁-C₃)alkyl-O—R²⁰, —(C₁-C₃)alkyl-pyrrolidinyl, phenyl, -HET¹, -HET², —CH₂-phenyl, —CH₂-HET¹, —CH₂-HET², —(C₁-C₃)alkyl-N(R²⁰)(R²⁰), —(C₁-C₃)alkyl-N⁺(O⁻)(CH₃)₂, —(C₁-C₃)alkyl-C(O)N(R⁴¹)(R⁴¹), —CH(C(O)OH)(CH₂OR²⁰), —CH(C(O)OH)(CH₂N(R²⁰)(R²⁰)), —(C₁-C₃)alkyl-C(O)O—R²⁰,

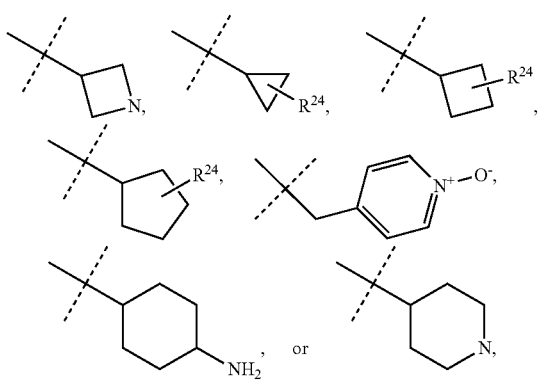

wherein the dashed line indicates the point of attachment to the position indicated by R⁶;

HET¹ is

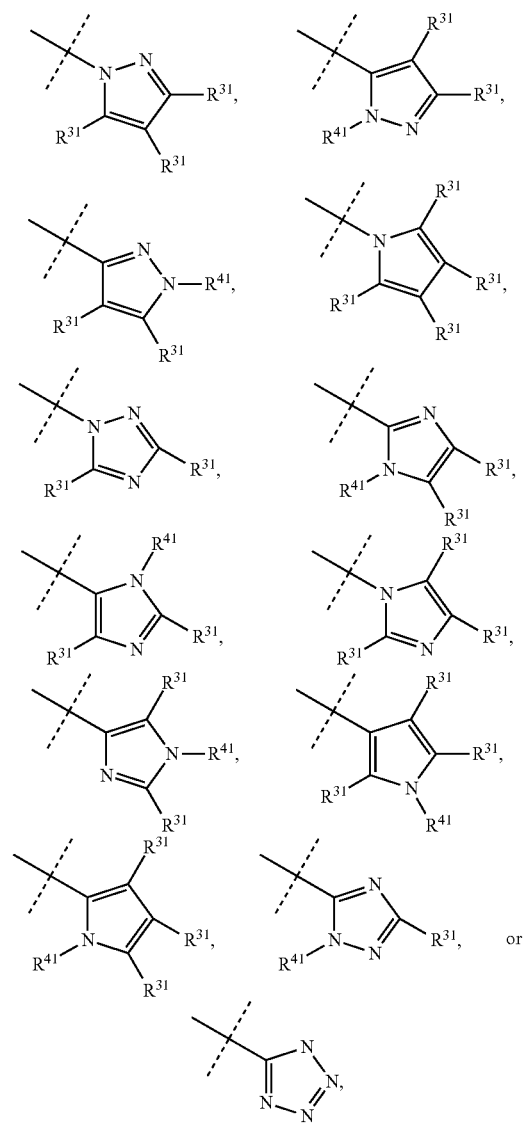

wherein the dashed line indicates the point of attachment to the position indicated by HET¹;

HET² is

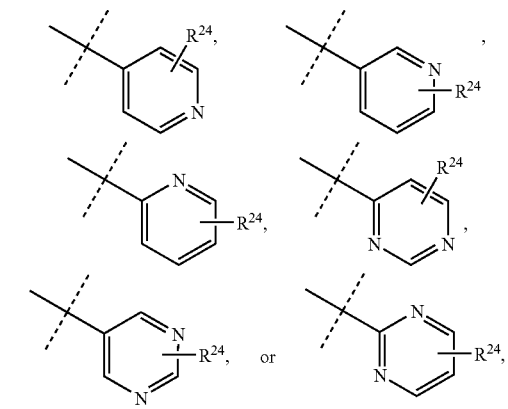

wherein the dashed line indicates the point of attachment to the position indicated by HET²;

R⁷ is
—H, —(C₁-C₃)alkyl (optionally substituted with 1 to 3 halogens), or —(C₂-C₃)alkyl-O—R²⁰;

R⁸ is
—H, —OH, —(C₁-C₄)alkyl (optionally substituted with 1 to 3 halogens), —(C₂-C₃)alkyl-O—R²⁰, —C(O)—(C₁-C₄)alkyl, —C(O)O—(C₁-C₄)alkyl, or —C(O)—N(R²⁰)(R²⁰);

R⁹ is
—H, -halogen, —CH₃ (optionally substituted with 1 to 3 halogens), or —O—CH₃ (optionally substituted with 1 to 3 halogens);

R¹⁰ is independently at each occurrence —H or -halogen;

R²⁰ is independently at each occurrence —H or —(C₁-C₃)alkyl (optionally substituted with 1 to 3 halogens);

R²¹ is independently at each occurrence —H, -halogen, or —(C₁-C₃)alkyl;

R²² is independently at each occurrence —H or —(C₁-C₃)alkyl (optionally substituted with 1 to 3 halogens);

R²³ is independently at each occurrence —H, —(C₁-C₃)alkyl, or —C(O)O—(C₁-C₄)alkyl;

R²⁴ is independently at each occurrence —H, -halogen, or —(C₁-C₃)alkyl (optionally substituted with 1 to 3 halogens);

R³¹ is independently at each occurrence —H, -halogen, or —(C₁-C₃)alkyl; and

R⁴¹ is independently at each occurrence —H or —CH₃.

In another embodiment the invention provides a compound structurally represented by formula I, or a pharmaceutically acceptable salt thereof, wherein R¹ is

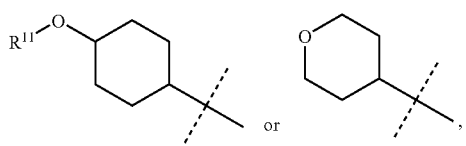

or wherein the dashed line represents the point of attachment to the R¹ position in formula I;

R² is -fluorine, -chlorine, or -bromine;

R³ is -fluorine, -chlorine, or -bromine;

R⁴ is —H or -halogen;

R⁵ is

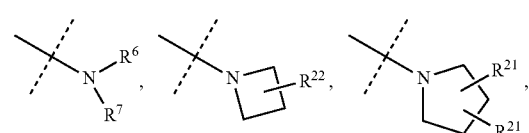

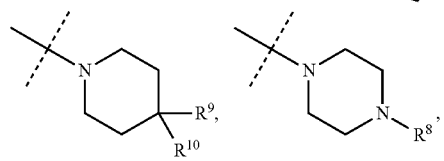

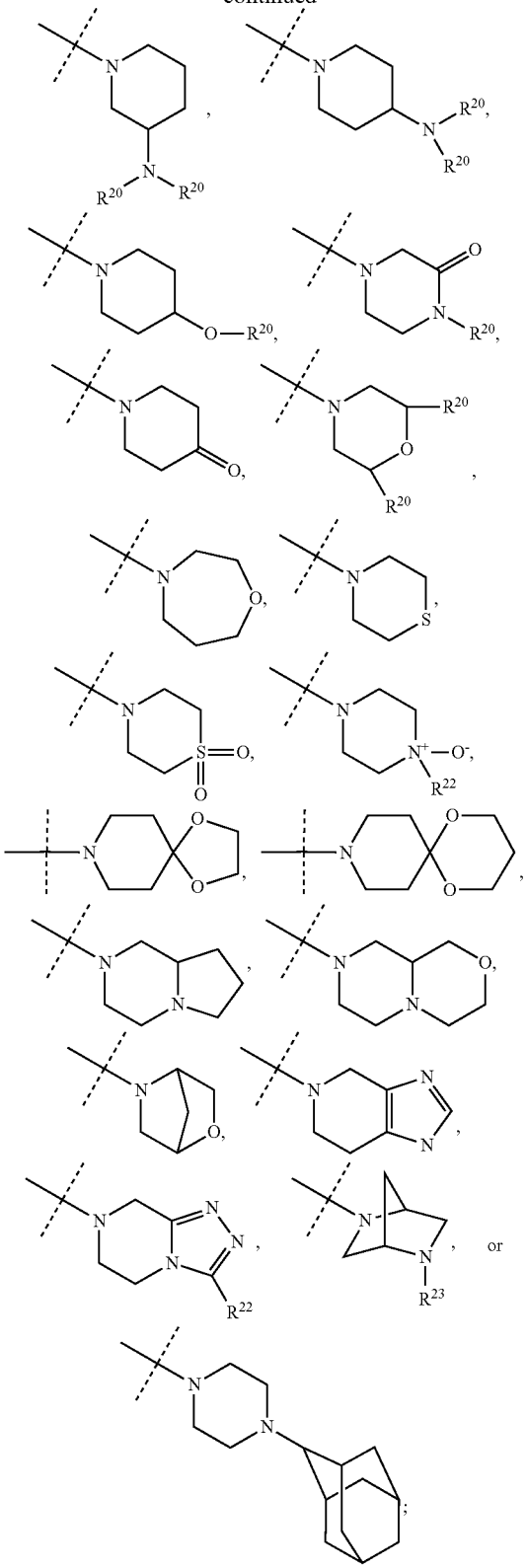

wherein the dashed line represents the point of attachment to the R⁵ position in formula I;

R⁶ is
—H, —(C₁-C₃)alkyl (optionally substituted with 1 to 3 halogens), —(C₁-C₃)alkyl-O—R²⁰, —(C₁-C₃)alkyl-pyrrolidinyl, phenyl, -HET$^1$, -HET$^2$, —CH$_2$-phenyl, —CH$_2$-HET$^1$, —CH$_2$-HET$^2$, —(C$_1$-C$_3$)alkyl-N(R$^{20}$)(R$^{20}$), —(C$_1$-C$_3$)alkyl-N$^+$(O$^-$)(CH$_3$)$_2$, —(C$_1$-C$_3$)alkyl-C(O)N(R$^{41}$)(R$^{41}$), —CH(C(O)OH)(CH$_2$OR$^{20}$), —CH(C(O)OH)(CH$_2$N(R$^{20}$)(R$^{20}$)), —(C$_1$-C$_3$)alkyl-C(O)O—R$^{20}$,

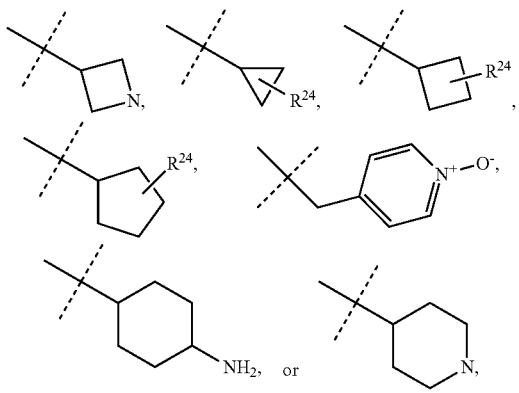

wherein the dashed line indicates the point of attachment to the position indicated by R$^6$;

HET$^1$ is

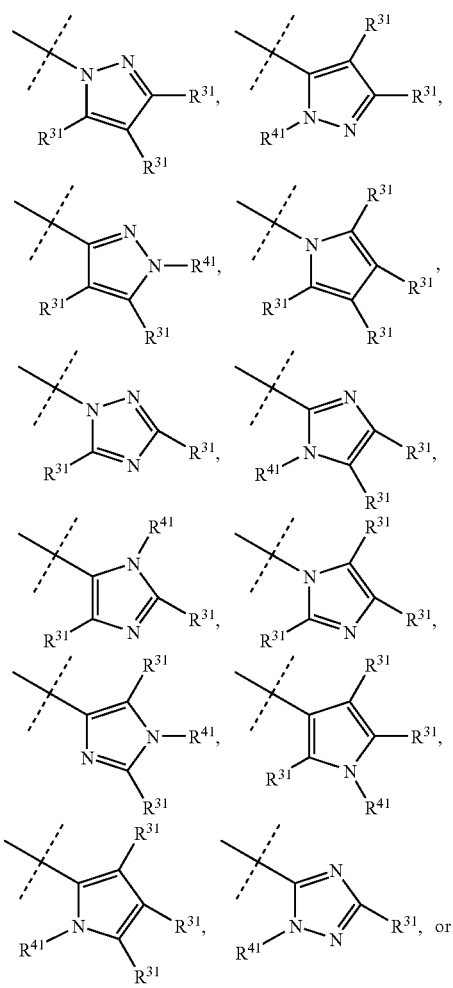

-continued

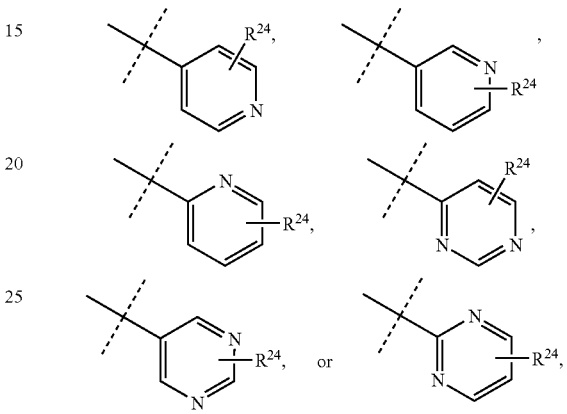

wherein the dashed line indicates the point of attachment to the position indicated by HET$^1$;

HET$^2$ is

[pyridinyl and pyrimidinyl structures with R$^{24}$ substituents]

wherein the dashed line indicates the point of attachment to the position indicated by HET$^2$;

R$^7$ is
—H, —(C$_1$-C$_3$)alkyl (optionally substituted with 1 to 3 halogens), or —(C$_2$-C$_3$)alkyl-O—R$^{20}$;

R$^8$ is
—H, —(C$_1$-C$_4$)alkyl (optionally substituted with 1 to 3 halogens), —(C$_2$-C$_3$)alkyl-O—R$^{20}$, —C(O)—(C$_1$-C$_4$)alkyl, —C(O)O—(C$_1$-C$_4$)alkyl, or —C(O)—N(R$^{20}$)(R$^{20}$);

R$^9$ is
—H, -halogen, —CH$_3$ (optionally substituted with 1 to 3 halogens), or —O—CH$_3$ (optionally substituted with 1 to 3 halogens);

R$^{10}$ is independently at each occurrence —H or -halogen;

R$^{11}$ is independently at each occurrence —H or —CH$_3$;

R$^{20}$ is independently at each occurrence —H or —(C$_1$-C$_3$)alkyl (optionally substituted with 1 to 3 halogens);

R$^{21}$ is independently at each occurrence —H, -halogen, or —(C$_1$-C$_3$)alkyl;

R$^{22}$ is independently at each occurrence —H or —(C$_1$-C$_3$)alkyl (optionally substituted with 1 to 3 halogens);

R$^{23}$ is independently at each occurrence —H, —(C$_1$-C$_3$)alkyl, or —C(O)O—(C$_1$-C$_4$)alkyl;

R$^{24}$ is independently at each occurrence —H;

R$^{31}$ is independently at each occurrence —H; and

R$^{41}$ is independently at each occurrence —H.

In another embodiment the invention provides a compound structurally represented by formula I, or a pharmaceutically acceptable salt thereof, wherein $R^1$ is

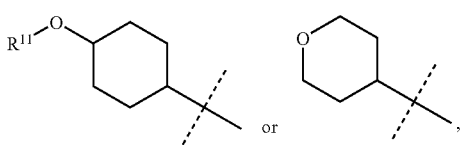

wherein the dashed line represents the point of attachment to the $R^1$ position in formula I;
$R^2$ is -fluorine, -chlorine, or -bromine;
$R^3$ is -fluorine, -chlorine, or -bromine;
$R^4$ is —H;
$R^5$ is

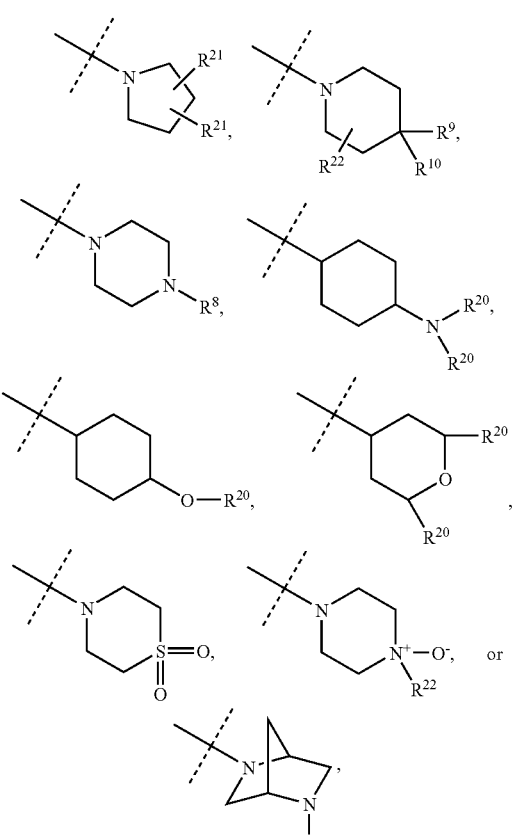

wherein the dashed line represents the point of attachment to the $R^5$ position in formula I;
$R^8$ is
—H, —$(C_1-C_4)$alkyl (optionally substituted with 1 to 3 halogens), —$(C_2-C_3)$alkyl-O—$R^{20}$, —C(O)—$(C_1-C_4)$alkyl, —C(O)O—$(C_1-C_4)$alkyl, or —C(O)—N($R^{20}$)($R^{20}$);
$R^9$ is
—H, -halogen, —$CH_3$ (optionally substituted with 1 to 3 halogens), or —O—$CH_3$ (optionally substituted with 1 to 3 halogens);
$R^{10}$ is independently at each occurrence —H or -halogen;
$R^{11}$ is independently at each occurrence —H;
$R^{20}$ is independently at each occurrence —H, or —$(C_1-C_3)$ alkyl (optionally substituted with 1 to 3 halogens);
$R^{21}$ is independently at each occurrence —H, -halogen, or —$(C_1-C_3)$alkyl;

$R^{22}$ is independently at each occurrence —H or —$(C_1-C_3)$ alkyl (optionally substituted with 1 to 3 halogens); and
$R^{23}$ is independently at each occurrence —H, —$(C_1-C_3)$ alkyl, or —C(O)O—$(C_1-C_4)$alkyl.

In another embodiment the invention provides a compound structurally represented by formula I, or a pharmaceutically acceptable salt thereof, wherein
$R^1$ is

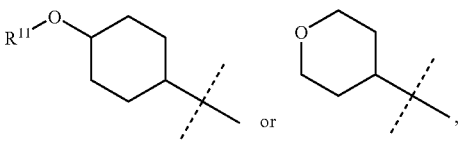

wherein the dashed line represents the point of attachment to the $R^1$ position in formula I;
$R^2$ is -fluorine, -chlorine, or -bromine;
$R^3$ is -fluorine, -chlorine, or -bromine;
$R^4$ is —H;
$R^5$ is

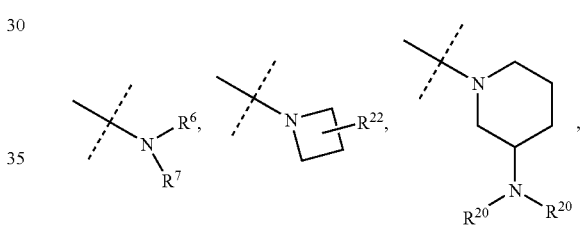

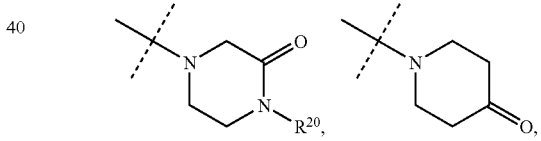

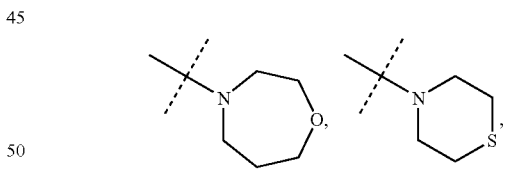

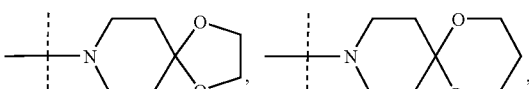

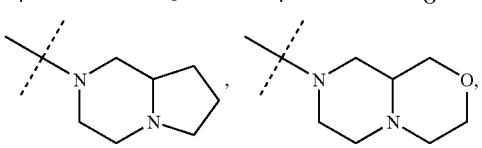

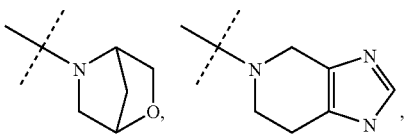

-continued

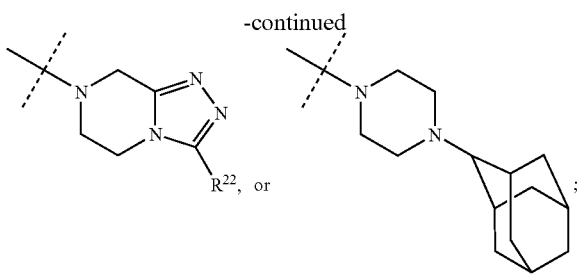
R²², or wherein the dashed line represents the point of attachment to the R⁵ position in formula I;

R⁶ is
—H, —($C_1$-$C_3$)alkyl (optionally substituted with 1 to 3 halogens), —($C_1$-$C_3$)alkyl-O—$R^{10}$, —($C_1$-$C_3$)alkyl-pyrrolidinyl, phenyl, -HET¹, -HET², —$CH_2$-phenyl, —$CH_2$-HET¹, —$CH_2$-HET², —($C_1$-$C_3$)alkyl-N($R^{20}$)($R^{20}$), —($C_1$-$C_3$)alkyl-$N^+$($O^-$)($CH_3$)$_2$, —($C_1$-$C_3$)alkyl-C(O)N($R^{41}$)($R^{41}$), —CH(C(O)OH)($CH_2$O$R^{20}$), —CH(C(O)OH)($CH_2$N($R^{20}$)($R^{20}$)), —($C_1$-$C_3$)alkyl-C(O)O—$R^{20}$,

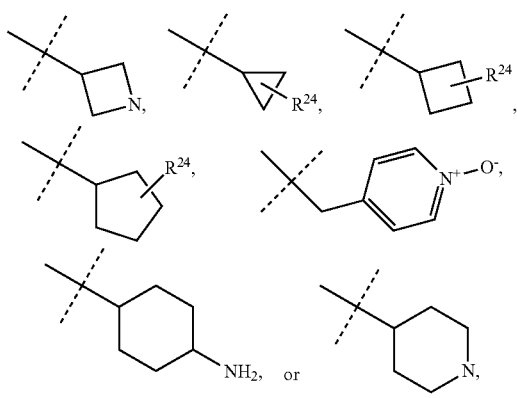

wherein the dashed line indicates the point of attachment to the position indicated by R⁶;

HET¹ is

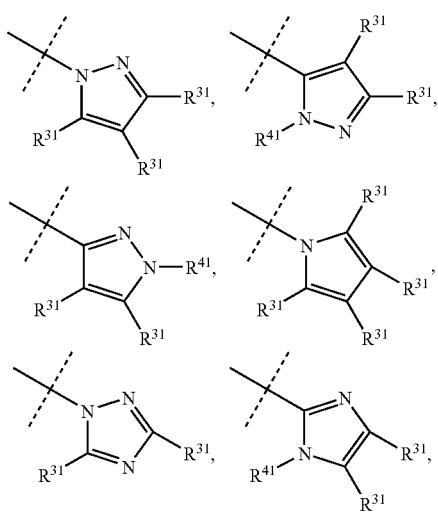

-continued

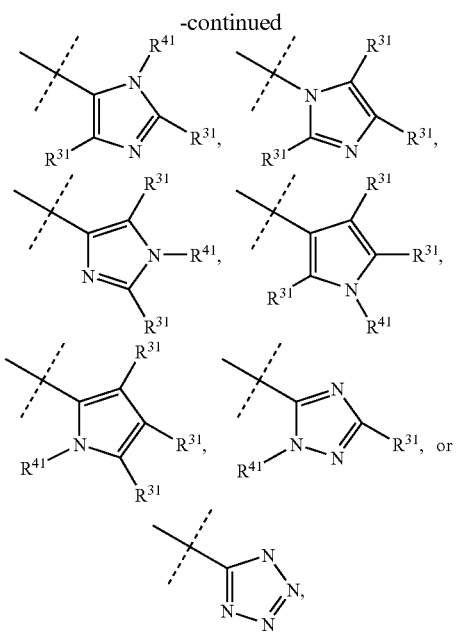

wherein the dashed line indicates the point of attachment to the position indicated by HET¹;

HET² is

[pyridine and pyrimidine variants with $R^{24}$]

wherein the dashed line indicates the point of attachment to the position indicated by HET²;

R⁷ is
—H, —($C_1$-$C_3$)alkyl (optionally substituted with 1 to 3 halogens), or —($C_2$-$C_3$)alkyl-O—$R^{20}$;

$R^{11}$ is independently at each occurrence —H or —$CH_3$;

$R^{20}$ is independently at each occurrence —H or —($C_1$-$C_3$) alkyl (optionally substituted with 1 to 3 halogens);

$R^{21}$ is independently at each occurrence —H, -halogen, or —($C_1$-$C_3$)alkyl;

$R^{22}$ is independently at each occurrence —H or —($C_1$-$C_3$) alkyl (optionally substituted with 1 to 3 halogens);

$R^{23}$ is independently at each occurrence —H, —($C_1$-$C_3$) alkyl, or —C(O)O—($C_1$-$C_4$)alkyl;

$R^{24}$ is independently at each occurrence —H;

$R^{31}$ is independently at each occurrence —H; and $R^{41}$ is independently at each occurrence —H.

Other embodiments of the invention are provided wherein each of the embodiments described herein above is further narrowed as described in the following preferences. Specifically, each of the preferences below is independently combined with each of the embodiments above, and the particular combination provides another embodiment in which the variable indicated in the preference is narrowed according to the preference.

Preferably embodiments of the invention are structurally represented by the formula:

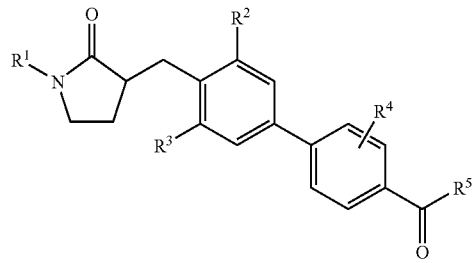

wherein R¹ is

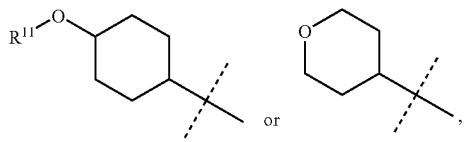

Preferably R¹ is

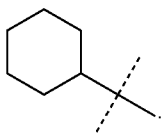

Preferably R¹ is

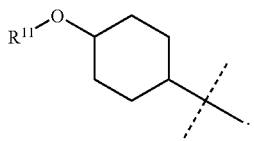

Preferably R¹ is

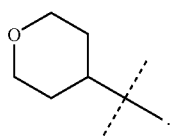

Preferably R¹ is

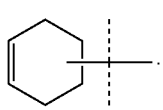

Preferably R¹ is

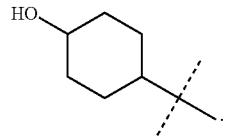

Preferably R¹ is

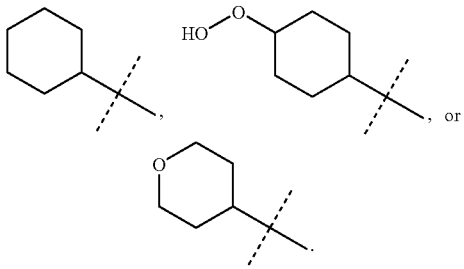

Preferably R² is -halogen, —CH₃ (optionally substituted with 1 to 3 halogens), or —O—CH₃ (optionally substituted with 1 to 3 halogens). Preferably R² is -halogen. Preferably R² is —CH₃ (optionally substituted with 1 to 3 halogens). Preferably R² is —O—CH₃ (optionally substituted with 1 to 3 halogens). Preferably R² is -chlorine, -fluorine, or -bromine. Preferably R² is -chlorine. Preferably R³ is -halogen, —CH₃ (optionally substituted with 1 to 3 halogens), or —O—CH₃ (optionally substituted with 1 to 3 halogens). Preferably R³ is -halogen. Preferably R³ is —CH₃ (optionally substituted with 1 to 3 halogens). Preferably R³ is —O—CH₃ (optionally substituted with 1 to 3 halogens). Preferably R³ is chlorine, -fluorine, or -bromine. Preferably R³ is chlorine. Preferably R³ is -fluorine. Preferably R² is -chlorine, -fluorine, or -bromine, and R³ is -chlorine, -fluorine, or -bromine. Preferably R² and R³ are chlorine. Preferably R⁴ is —H. Preferably R⁴ is -halogen. Preferably R⁴ is -fluorine or -chlorine. Preferably R⁵ is

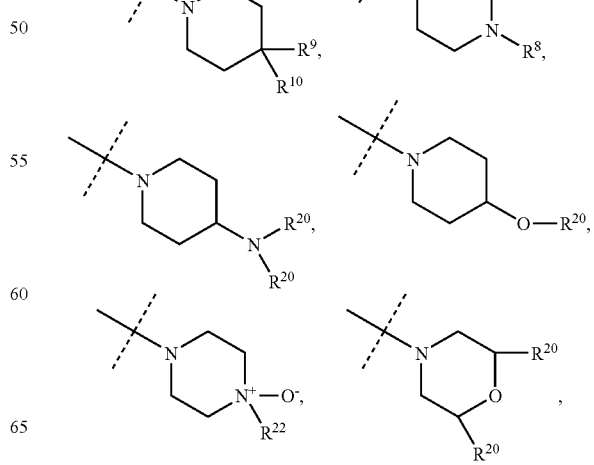

-continued
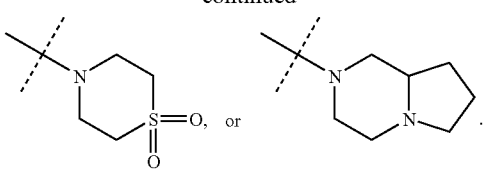
Preferably R⁵ is
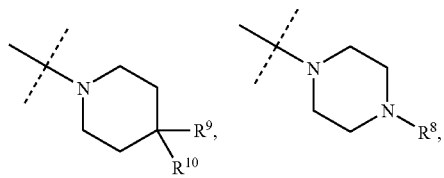
Preferably R⁵ is
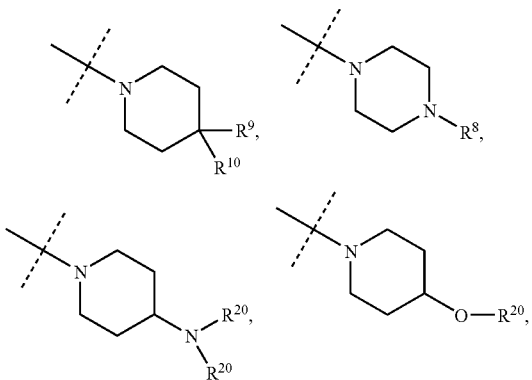
Preferably R⁵ is
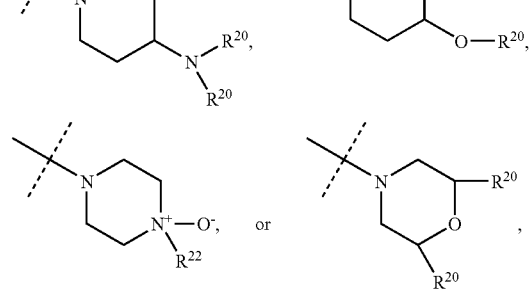
Preferably R⁵ is
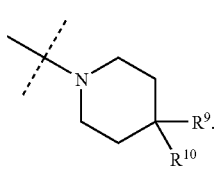
Preferably R⁵ is
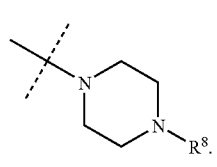
Preferably R⁵ is
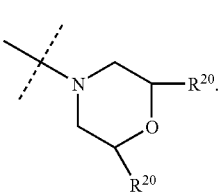
Preferably R⁵ is
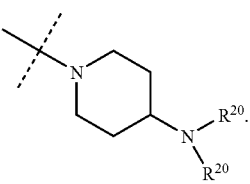
Preferably R⁵ is
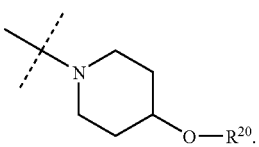
Preferably R⁵ is
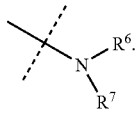
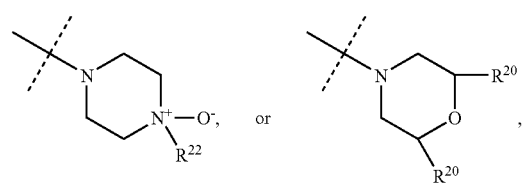
Preferably R⁵ is
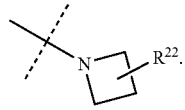
Preferably R⁵ is
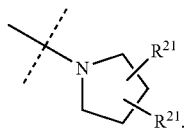
Preferably R⁵ is
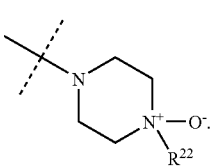
Preferably R⁵ is
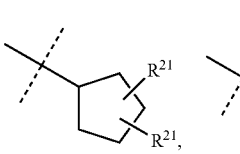 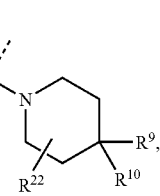

-continued

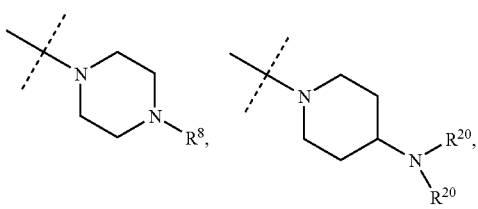

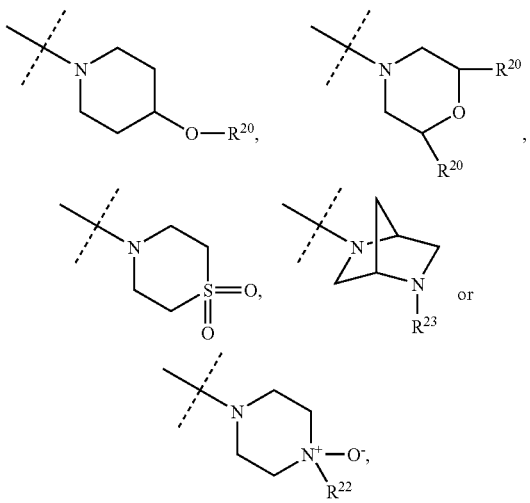

wherein
R[8] is —H, —(C$_1$-C$_4$)alkyl (optionally substituted with 1 to 3 halogens), —(C$_2$-C$_3$)alkyl-O—R[20], —C(O)—(C$_1$-C$_4$)alkyl, —C(O)O—(C$_1$-C$_4$)alkyl, or —C(O)—N(R[20])(R[20]); R[9] is —H, -halogen, —CH$_3$ (optionally substituted with 1 to 3 halogens), or —O—CH$_3$ (optionally substituted with 1 to 3 halogens); R[10] is independently at each occurrence —H or -halogen; R[20] is independently at each occurrence —H, or —(C$_1$-C$_3$)alkyl (optionally substituted with 1 to 3 halogens); R[21] is independently at each occurrence —H, -halogen, or —(C$_1$-C$_3$)alkyl; R[22] is independently at each occurrence —H or —(C$_1$-C$_3$)alkyl (optionally substituted with 1 to 3 halogens); and R[23] is independently at each occurrence —H, —(C$_1$-C$_3$)alkyl, or —C(O)O—(C$_1$-C$_4$)alkyl. Preferably R[5] is

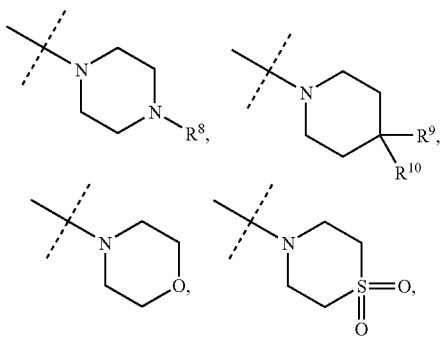

wherein R[8] is —(C$_1$-C$_4$)alkyl (optionally substituted with 1 to 3 halogens); R[9] is —H, -halogen, —CH$_3$ (optionally substituted with 1 to 3 halogens; and R[10] is independently at each occurrence —H or -halogen. Preferably R[5] is

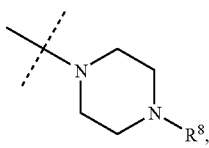

wherein R[8] is —(C$_1$-C$_3$)alkyl (optionally substituted with 1 to 3 halogens). Preferably R[5] is

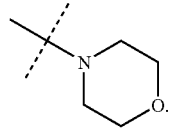

Preferably R[5] is

Preferably R[5] is

Preferably R[6] is —(C$_1$-C$_3$)alkyl (optionally substituted with 1 to 3 halogens), —(C$_1$-C$_3$)alkyl-O—R[20], —(C$_1$-C$_3$)alkyl-pyrrolidinyl, phenyl, -HET[1], -HET[2], —CH$_2$-phenyl, —CH$_2$-HET[1], —CH$_2$-HET[2], —(C$_1$-C$_3$)alkyl-N(R[20])(R[20]), —(C$_1$-C$_3$)alkyl-N$^+$(O$^-$)(CH$_3$)$_2$, —(C$_1$-C$_3$)alkyl-C(O)N(R[41])(R[41]), —CH(C(O)OH)(CH$_2$OR[20]), —CH(C(O)OH)(CH$_2$N(R[20])(R[20])), —(C$_1$-C$_3$)alkyl-C(O)O—R[20],

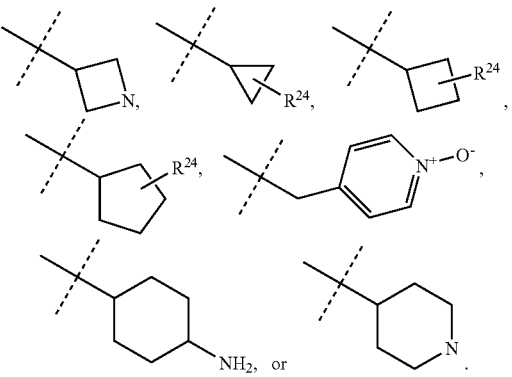

Preferably R[6] is —(C$_1$-C$_3$)alkyl (optionally substituted with 1 to 3 halogens), —(C$_1$-C$_3$)alkyl-O—R[20], —(C$_1$-C$_3$)alkyl-pyrrolidinyl, —(C$_1$-C$_3$)alkyl-N(R[20])(R[20]), —(C$_1$-C$_3$)alkyl-N$^+$ (O⁻)(CH₃)₂, -(C₁-C₃)alkyl-C(O)N(R⁴¹)(R⁴¹), —CH(C(O)OH)(CH₂OR²⁰), —CH(C(O)OH)(CH₂N(R²⁰)(R²⁰)), —(C₁-C₃)alkyl-C(O)O—R²⁰, R⁵ is

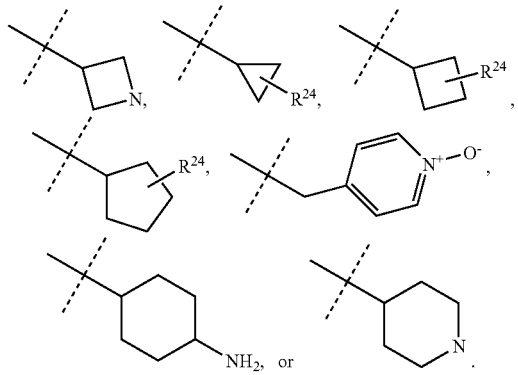

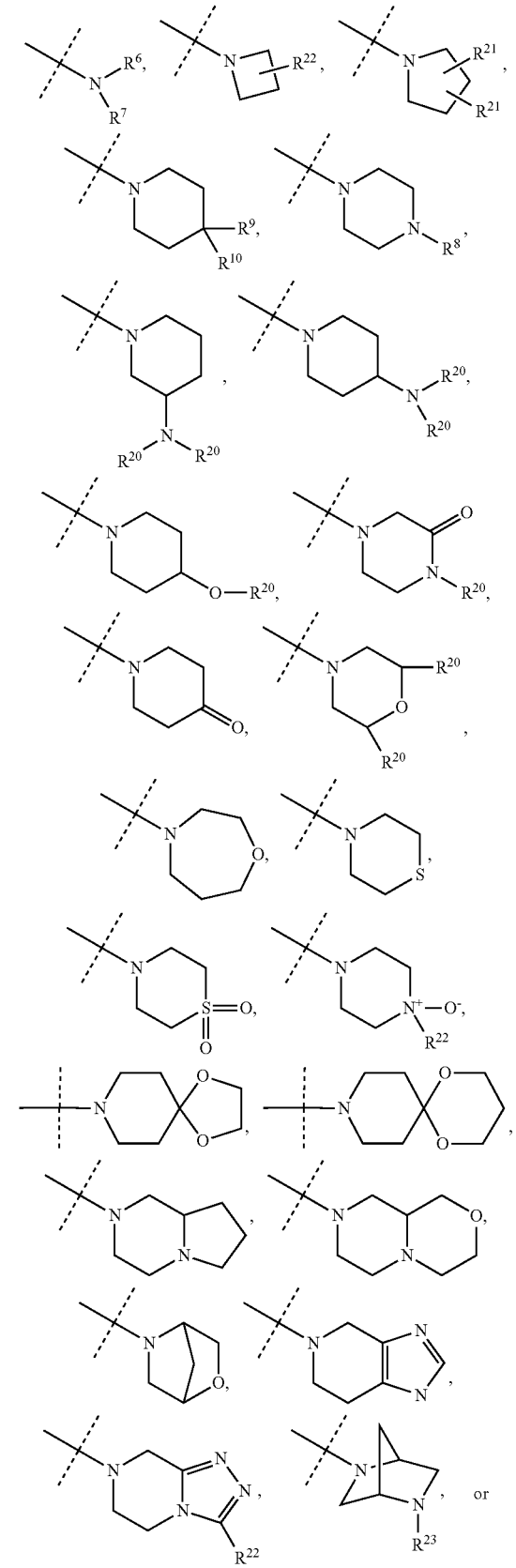

Preferably R⁷ is —H. Preferably R⁷ is —(C₁-C₃)alkyl (optionally substituted with 1 to 3 halogens). Preferably R⁷ is —(C₂-C₃)alkyl-O—R²⁰.

Preferably R⁸ is —H. Preferably R⁸ is —(C₁-C₄)alkyl (optionally substituted with 1 to 3 halogens), —(C₂-C₃)alkyl-O—R²⁰, —C(O)—(C₁-C₄)alkyl, —C(O)O—(C₁-C₄)alkyl, or —C(O)—N(R²⁰)(R²⁰). Preferably R⁸ is —(C₁-C₄)alkyl (optionally substituted with 1 to 3 halogens). Preferably R⁸ is —(C₂-C₃)alkyl-O—R²⁰, —C(O)—(C₁-C₄)alkyl, —C(O)O—(C₁-C₄)alkyl, or —C(O)—N(R¹⁰)(R²⁰). Preferably R⁸ is —(C₂-C₃)alkyl-O—R²⁰. Preferably R⁸ is —C(O)—(C₁-C₄)alkyl. Preferably R⁸ is —C(O)O—(C₁-C₄)alkyl. Preferably R⁵ is —C(O)—N(R²⁰)(R²⁰).

Preferably R⁹ is —H. Preferably R⁹ is -halogen. Preferably R⁹ is —CH₃ (optionally substituted with 1 to 3 halogens), or —O—CH₃ (optionally substituted with 1 to 3 halogens). Preferably R¹⁰ is —H. Preferably R¹⁰ is -halogen. Preferably R⁹ is —H and R¹⁰ is —H. Preferably R⁹ is -halogen and R¹⁰ is -halogen.

Preferably R¹¹ is —H. Preferably R¹¹ is —CH₃ or —CH₂—CH₃. Preferably R¹¹ is —CH₃. Preferably R¹¹ is —CH₂—CH₃.

In another embodiment the invention provides a compound structurally represented by formula I, or a pharmaceutically acceptable salt thereof, wherein
R¹ is

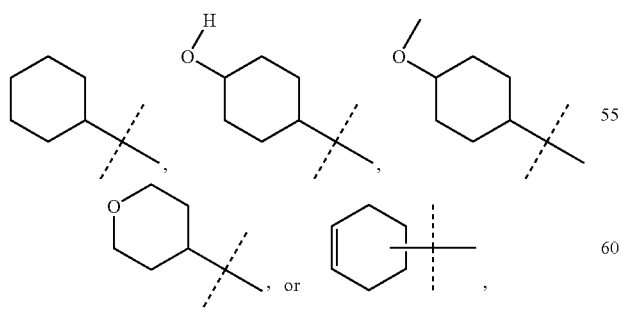

wherein the dashed line represents the point of attachment to the R¹ position in formula I;
R² is -chlorine; R³ is -chlorine; R⁴ is —H or -fluorine;

-continued

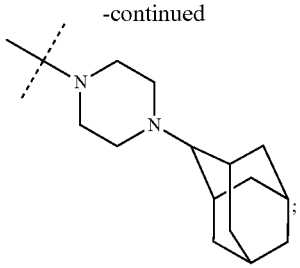

or wherein the dashed line represents the point of attachment to the $R^5$ position in formula I;

$R^6$ is
—H, —$CH_3$, —$CH_2$—$CH_3$, —$CH_2$—$CF_3$, —$C(CH_3)_2$, —$CH_2$—$CH_2$—OH, —$CH_2$—$CH_2$—O—$CH_3$, —$CH_2$—$CH_2$-pyrrolidinyl, —$CH_2$—$CH_2$—$N(CH_3)_2$, —$CH_2$—$CH_2$—$NH_2$, —$CH_2$—C(O)OH,

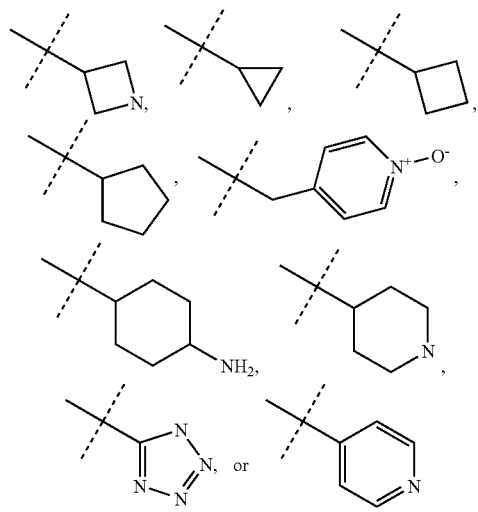

or wherein the dashed line indicates the point of attachment to the position indicated by $R^6$;

$R^7$ is —H, —$CH_3$, or —$CH_2$—$CH_2$—O—$CH_3$;

$R^8$ is —H, —$CH_3$, —$CH(CH_3)_2$, —$CH_2$—$CH_2$—O—H, —$CH_2$—$CH_3$, —$CH_2$—$CH_2$F, —$CH_2$—$CF_3$, —C(O)$CH_3$, —C(O)$N(CH_3)_2$, —C(O)$NH_2$, or —C(O)O—$CH_3$;

$R^9$ is —H, -fluorine, or —$CF_3$; $R^{10}$ is —H or -fluorine; $R^{11}$ is —H or —$CH_3$;

$R^{20}$ is independently at each occurrence —H or —$CH_3$;

$R^{21}$ is independently at each occurrence —H or -fluorine;

$R^{22}$ is independently at each occurrence —H, —$CH_3$, or —$CF_3$; and $R^{23}$ is —H Embodiments of the invention include all stereoisomeric forms and conformational forms of compounds of formula I and the narrower embodiments described above.

A preferred embodiment of the invention are compounds of the formula I-cyclohexyl-3-{3,5-dichloro-4'-[4-(2-fluoroethyl)-piperazine-1-carbonyl]-biphenyl-4-ylmethyl}-pyrrolidin-2-one and (R)-3-[3,5-dichloro-4'-(4-trifluoromethyl-piperidine-1-carbonyl)-biphenyl-4-ylmethyl]-1-(tetrahydropyran-4-yl)-pyrrolidin-2-one. A further embodiment of the invention are the novel intermediate preparations described herein which are useful for preparing the 11-β-HSD1 inhibitors according to formula I and the embodiments described herein. A further embodiment of the invention are the novel intermediate preparations described herein which are useful for preparing 1-cyclohexyl-3-{3,5-dichloro-4'-[4-(2-fluoroethyl)-piperazine-1-carbonyl]-biphenyl-4-ylmethyl}-pyrrolidin-2-one and (R)-3-[3,5-dichloro-4'-(4-trifluoromethyl-piperidine-1-carbonyl)-biphenyl-4-ylmethyl]-1-(tetrahydropyran-4-yl)-pyrrolidin-2-one or a pharmaceutically acceptable salt thereof.

Patients with type 2 diabetes often develop "insulin resistance" which results in abnormal glucose homeostasis and hyperglycemia leading to increased morbidity and premature mortality. Abnormal glucose homeostasis is associated with obesity, hypertension, and alterations in lipid, lipoprotein, and apolipoprotein metabolism. Type 2 diabetics are at increased risk of developing cardiovascular complications, e.g., atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are important in the management and treatment of diabetes mellitus. Many patients who have insulin resistance but have not developed type 2 diabetes are also at risk of developing "Syndrome X" or "Metabolic syndrome". Metabolic syndrome is characterized by insulin resistance along with abdominal obesity, hyperinsulinemia, high blood pressure, low HDL, high VLDL, hypertension, atherosclerosis, coronary heart disease, and chronic renal failure. These patients are at increased risk of developing the cardiovascular complications listed above whether or not they develop overt diabetes mellitus.

Due to their inhibition of 11-β-HSD1, the present compounds are useful in the treatment of a wide range of conditions and disorders in which inhibition of 11-β-HSD1 is beneficial. These disorders and conditions are defined herein as "diabetic disorders" and "metabolic syndrome disorders". One of skill in the art is able to identify "diabetic disorders" and "metabolic syndrome disorders" by the involvement of 11-β-HSD1 activity either in the pathophysiology of the disorder, or in the homeostatic response to the disorder. Thus, the compounds may find use for example to prevent, treat, or alleviate, diseases or conditions or associated symptoms or sequelae, of "Diabetic disorders" and "metabolic syndrome disorders".

"Diabetic disorders" and "metabolic syndrome disorders" include, but are not limited to, diabetes, type 1 diabetes, type 2 diabetes, hyperglycemia, hyper insulinemia, beta-cell rest, improved beta-cell function by restoring first phase response, prandial hyperglycemia, preventing apoptosis, impaired fasting glucose (IFG), metabolic syndrome, hypoglycemia, hyper-/hypokalemia, normalizing glucagon levels, improved LDL/HDL ratio, reducing snacking, eating disorders, weight loss, polycystic ovarian syndrome (PCOS), obesity as a consequence of diabetes, latent autoimmune diabetes in adults (LADA), insulitis, islet transplantation, pediatric diabetes, gestational diabetes, diabetic late complications, micro-/macroalbuminuria, nephropathy, retinopathy, neuropathy, diabetic foot ulcers, reduced intestinal motility due to glucagon administration, short bowel syndrome, antidiarrheic, increasing gastric secretion, decreased blood flow, erectile dysfunction, glaucoma, post surgical stress, ameliorating organ tissue injury caused by reperfusion of blood flow after ischemia, ischemic heart damage, heart insufficiency, congestive heart failure, stroke, myocardial infarction, arrhythmia, premature death, anti-apoptosis, wound healing, impaired glucose tolerance (IGT), insulin resistance syndromes, metabolic syndrome, syndrome X, hyperlipidemia, dyslipidemia, hypertriglyceridemia, hyperlipoproteinemia, hypercholesterolemia, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc. Thus the present invention also provides a method of treatment of "Diabetic disorders" and "metabolic syndrome disorders" while reducing and or eliminating one or more of the unwanted side effects associated with the current treatments.

In addition, the present invention provides a compound of Formula I, or a pharmaceutical salt thereof, or a pharmaceutical composition which comprises a compound of Formula I, or a pharmaceutical salt thereof, and a pharmaceutically acceptable carrier, diluent, or excipient: for use in inhibiting 11-β-HSD1 activity; for use in inhibiting a 11-β-HSD1 activity mediated cellular response in a mammal; for use in reducing the glycemic level in a mammal; for use in treating a disease arising from excessive 11-β-HSD1 activity; for use in treating diabetic and other metabolic syndrome disorders in a mammal; and for use in treating diabetes, metabolic syndrome, obesity, hyperglycemia, atherosclerosis, ischemic heart disease, stroke, neuropathy, and wound healing. Thus, the methods of this invention encompass a prophylactic and therapeutic administration of a compound of Formula I.

The present invention further provides the use of a compound of Formula I, or a pharmaceutical salt thereof for the manufacture of a medicament for inhibiting 11-β-HSD1 activity; for the manufacture of a medicament for inhibiting 11-β-HSD1 activity mediated cellular response in a mammal; for the manufacture of a medicament for reducing the glycemic level in a mammal; for the manufacture of a medicament for treating a disease arising from excessive 11-β-HSD1 activity; for the manufacture of a medicament for treating diabetic and other metabolic syndrome disorders in a mammal; and for the manufacture of a medicament for preventing or treating diabetes, metabolic syndrome, obesity, hyperglycemia, atherosclerosis, ischemic heart disease, stroke, neuropathy, and improper wound healing.

The present invention further provides a method of treating conditions resulting from excessive 11-β-HSD1 activity in a mammal; a method of inhibiting 11-β-HSD1 activity in a mammal; a method of inhibiting a 11-β-HSD1 activity mediated cellular response in a mammal; a method of reducing the glycemic level in a mammal; a method of treating diabetic and other metabolic syndrome disorders in a mammal; a method of preventing or treating diabetes, metabolic syndrome, obesity, hyperglycemia, atherosclerosis, ischemic heart disease, stroke, neuropathy, and improper wound healing; said methods comprising administering to a mammal in need of such treatment a 11-β-HSD1 activity inhibiting amount of a compound of Formula I, or a pharmaceutically acceptable salt thereof, or a pharmaceutical composition which comprises a compound of Formula I, or a pharmaceutical salt thereof, and a pharmaceutically acceptable carrier, diluent, or excipient.

In addition, the present invention provides a pharmaceutical composition which comprises a compound of Formula I, or a pharmaceutical salt thereof, and a pharmaceutically acceptable carrier, diluent, or excipient: adapted for use in inhibiting 11-β-HSD1 activity; adapted for use in inhibiting 11-β-HSD1 activity mediated cellular responses; adapted for use in reducing the glycemic level in a mammal; adapted for use in treating diabetic and other metabolic syndrome disorders in a mammal; and adapted for use in preventing or treating diabetes, metabolic syndrome, obesity, hyperglycemia, atherosclerosis, ischemic heart disease, stroke, neuropathy, and wound healing.

In a further aspect of the invention the present compounds are administered in combination with one or more further active substances in any suitable ratios. Such further active substances may for example be selected from antidiabetics, antiobesity agents, antihypertensive agents, agents for the treatment of complications resulting from or associated with diabetes and agents for the treatment of complications and disorders resulting from or associated with obesity. The following listing sets out several groups of combinations. It will be understood that each of the agents named may be combined with other agents named to create additional combinations.

Thus, in a further embodiment of the invention the present compounds may be administered in combination with one or more antidiabetics.

Suitable antidiabetic agents include insulin, insulin analogues and derivatives such as those disclosed in EP 792 290 (Novo Nordisk A/S), for example $N^{\epsilon B29}$-tetradecanoyl des (B30) human insulin, EP 214 826 and EP 705 275 (Novo Nordisk A/S), for example $ASP^{B28}$ human insulin, U.S. Pat. No. 5,504,188 (Eli Lilly), for example $Lys^{B28}$ $Pro^{B29}$ human insulin, EP 368 187 (Aventis), for example Lantus®, GLP-1 and GLP-1 derivatives such as those disclosed in WO 98/08871 (Novo Nordisk A/S), as well as orally active hypoglycemic agents.

The orally active hypoglycemic agents preferably comprise imidazolines, sulphonylureas, biguanides, meglitinides, oxadiazolidinediones, thiazolidinediones, insulin sensitizers, insulin secretagogues, such as glimepiride, α-glucosidase inhibitors, agents acting on the ATP-dependent potassium channel of the β-cells for example potassium channel openers such as those disclosed in WO 97/26265, WO 99/03861 and WO 00/37474 (Novo Nordisk A/S), or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), GLP-1 antagonists, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, activators of glucokinase (GK) such as those disclosed in WO 00/58293, WO 01/44216, WO 01/83465, WO 01/83478, WO 01/85706, WO 01/85707, and WO 02/08209 (Hoffman-La Roche) or those disclosed in WO 03/00262, WO 03/00267 and WO 03/15774 (AstraZeneca), GSK-3 (glycogen synthase kinase-3) inhibitors, compounds modifying the lipid metabolism such as antilipidemic agents such as HMG CoA inhibitors (statins), compounds lowering food intake, PPAR (Peroxisome proliferator-activated receptor) ligands including the PPAR-alpha, PPAR-gamma and PPAR-delta subtypes, and RXR (retinoid X receptor) agonists, such as ALRT-268, LG-1268 or LG-1069.

In another embodiment, the present compounds are administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, Lantus®, or a mix-preparation comprising one or more of these.

In a further embodiment of the invention the present compounds are administered in combination with a sulphonylurea such as glibenclamide, glipizide, tolbautamide, chloropamidem, tolazamide, glimepride, glicazide and glyburide.

In another embodiment of the invention the present compounds are administered in combination with a biguanide, for example, metformin.

In yet another embodiment of the invention the present compounds are administered in combination with a meglitinide, for example, repaglinide or nateglinide.

In still another embodiment of the invention the present compounds are administered in combination with a thiazolidinedione insulin sensitizer, for example, troglitazone, ciglitazone, pioglitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation).

In still another embodiment of the invention the present compounds may be administered in combination with an insulin sensitizer, for example, such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 such as ragaglitazar (NN 622 or (−)DRF 2725) (Dr. Reddy's Research Foundation) and WO 00/23425, WO 00/23415, WO 00/23451, WO 00/23445, WO 00/23417, WO 00/23416, WO 00/63153, WO 63196, WO 00/63209, WO 00/63190 and WO 00/63189 (Novo Nordisk A/S).

In a further embodiment of the invention the present compounds are administered in combination with an α-glucosidase inhibitor, for example, voglibose, emiglitate, miglitol or acarbose.

In another embodiment of the invention the present compounds are administered in combination with an agent acting on the ATP-dependent potassium channel of the β-cells, for example, tolbutamide, glibenclamide, glipizide, glicazide, BTS-67582 or repaglinide.

In yet another embodiment of the invention the present compounds may be administered in combination with nateglinide.

In still another embodiment of the invention the present compounds are administered in combination with an antilipidemic agent or antihyperlipidemic agent for example cholestyramine, colestipol, clofibrate, gemfibrozil, lovastatin, pravastatin, simvastatin, pitavastatin, rosuvastatin, probucol, dextrothyroxine, fenofibrate or atorvastin.

In still another embodiment of the invention the present compounds are administered in combination with compounds lowering food intake.

In another embodiment of the invention, the present compounds are administered in combination with more than one of the above-mentioned compounds for example in combination with metformin and a sulphonylurea such as glyburide; a sulphonylurea and acarbose; nateglinide and metformin; repaglinide and metformin, acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

General terms used in the description of compounds herein described bear their usual meanings.

As used herein, the terms "$(C_1\text{-}C_3)$alkyl", "$(C_1\text{-}C_4)$alkyl" or "$(C_1\text{-}C_6)$alkyl" refer to straight-chain or branched-chain saturated aliphatic groups of the indicated number of carbon atoms, such as methyl, ethyl, n-propyl, isopropyl, n-butyl, isobutyl, sec-butyl, t-butyl, and the like. The term "$(C_1\text{-}C_6)$ alkoxy" represents a $C_1\text{-}C_6$ alkyl group attached through an oxygen and include moieties such as, for example, methoxy, ethoxy, n-propoxy, isopropoxy, and the like. The term "halogen" refers to fluoro, chloro, bromo, and iodo. The term "$(C_3\text{-}C_8)$cycloalkyl" refers to a saturated or partially saturated carbocycle ring of from 3 to 8 carbon atoms, typically 3 to 7 carbon atoms. Examples of $(C_3\text{-}C_8)$cycloalkyl include but are not limited to cyclopropyl, cyclobutyl, cyclopentyl, cyclohexyl, cycloheptyl, and the like.

The term "optionally substituted," or "optional substituents," as used herein, means that the groups in question are either unsubstituted or substituted with one or more of the substituents specified. When the groups in question are substituted with more than one substituent, the substituents may be the same or different. Furthermore, when using the terms "independently," "independently are," and "independently selected from" mean that the groups in question may be the same or different. Certain of the herein defined terms may occur more than once in the structural formulae, and upon such occurrence each term shall be defined independently of the other.

It is understood that guinea pigs, dogs, cats, rats, mice, hamsters, and primates, including humans, are examples of patients within the scope of the meaning of the term "patient". Preferred patients include humans. The term "patient" includes livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. The patient to be treated is preferably a mammal, in particular a human being.

The terms "treatment", "treating" and "treat", as used herein, include their generally accepted meanings, i.e., the management and care of a patient for the purpose of preventing, reducing the risk in incurring or developing a given condition or disease, prohibiting, restraining, alleviating, ameliorating, slowing, stopping, delaying, or reversing the progression or severity, and holding in check and/or treating existing characteristics, of a disease, disorder, or pathological condition, described herein, including the alleviation or relief of symptoms or complications, or the cure or elimination of the disease, disorder, or condition. The present method includes both medical therapeutic and/or prophylactic treatment, as appropriate.

As used herein, the term "therapeutically effective amount" means an amount of compound of the present invention that is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated.

"Composition" means a pharmaceutical composition and is intended to encompass a pharmaceutical product comprising the active ingredient(s) including compound(s) of Formula I, and the inert ingredient(s) that make up the carrier. Accordingly, the pharmaceutical compositions of the present invention encompass any composition made by admixing a compound of the present invention and a pharmaceutically acceptable carrier.

The term "substantially pure" refers to pure crystalline form of a compound comprising greater than about 90% of the desired crystalline form, and preferably, greater than about 95% of the desired crystal form.

The term "suitable solvent" refers to any solvent, or mixture of solvents, inert to the ongoing reaction that sufficiently solubilizes the reactants to afford a medium within which to effect the desired reaction.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

The compounds of the present invention may have one or more chiral centers and may exist in a variety of stereoisomeric configurations. As a consequence of these chiral centers the compounds of the present invention can occur as racemates, as individual enantiomers or mixtures of enantiomers, as well as diastereomers and mixtures of diastereomers. All such racemates, enantiomers, diastereomers and mixtures are within the scope of the present invention, whether pure, partially purified, or unpurified mixtures. For the examples provided herein, when a molecule which contains a chiral center or centers of known configuration is presented, its stereochemistry is designated in the name and in the structural representation of the molecule. If the stereochemistry is unknown or undefined its stereochemistry is not designated in the name or in the structural representation of the molecule. Embodiments of the invention include the Examples provided herein, and although the Example provided may be of one chiral or conformational form, or a salt thereof, further embodiments of the invention include all other stereoisomeric and or conformational forms of the examples described, as well as pharmaceutically acceptable salts thereof. These embodiments include any isolated enantiomers, diastereomers, and or conformers of these structures, as well as any mixtures containing more than one form.

Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention. Furthermore, some of the compounds of the present invention may exist in different tautomeric forms and it is intended that any tautomeric forms which the compounds are able to form are included within the scope of the present invention.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of formula I can be prepared by one of ordinary skill in the art utilizing well known techniques and processes, such as those disclosed by J. Jacques, et al., "*Enantiomers, Racemates, and Resolutions*", John Wiley and Sons, Inc., 1981, and E. L. Eliel and S. H. Wilen, "*Stereochemistry of Organic Compounds*", (Wiley-Interscience 1994), and European Patent Application No. EP-A-838448, published Apr. 29, 1998. Examples of resolutions include recrystallization techniques or chiral chromatography.

The compounds of Formula I, can be prepared by one of ordinary skill in the art following a variety of procedures, some of which are illustrated in the procedures and schemes set forth below. The particular order of steps required to produce the compounds of Formula I is dependent upon the particular compound to being synthesized, the starting compound, and the relative lability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Preparations, Examples and Procedures are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The optimal time for performing the reactions of the Schemes, Preparations, Examples and Procedures can be determined by monitoring the progress of the reaction via conventional chromatographic techniques. Furthermore, it is preferred to conduct the reactions of the invention under an inert atmosphere, such as, for example, argon, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The terms and abbreviations used in the instant Schemes, Preparations, Examples and Procedures have their normal meanings unless otherwise designated. For example, as used herein, the following terms have the meanings indicated: "eq" refers to equivalents; "psi" refers to pounds per square inch; "min" refers to minutes; "h" or "hr" refers to hours. "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "MS" refers to mass spectrometry, Observed Mass indicates [M+H] unless indicated otherwise. "MS(FD)" refers to field desorption mass spectrometry, "MS(IS)" refers to ion spray mass spectrometry, "Mass spectrum (ion spray)" refers to ion-spray ionization mode. "MS(FIA)" refers to flow injection analysis mass spectrometry, "MS(FAB)" refers to fast atom bombardment mass spectrometry, "MS(EI)" refers to electron impact mass spectrometry, "MS(ES)" refers to electron spray mass spectrometry, "MS(EI)" refers to electron impact mass spectrometry-electrospray ionization, "MS (ES+)" refers to mass spectrometry-electrospray ionization, "MS(APCi) refers to atmospheric pressure chemical ionization mass spectrometry, "UV" refers to ultraviolet spectrometry, "$^1$H NMR" refers to proton nuclear magnetic resonance spectrometry. "LC-MS" refers to liquid chromatography-mass spectrometry, "GC/MS" refers to gas chromatography/mass spectrometry. "IR" refers to infra red spectrometry, and the absorption maxima listed for the IR spectra are only those of interest and not all of the maxima observed. "RT" refers to room temperature.

"THF" refers to tetrahydrofuran, "LAH" refers to lithium aluminum hydride, "LDA" refers to lithium diisopropylamide, "DMSO" refers to dimethylsulfoxide, "DMF" refers to dimethylforamide, "EtOAc" refers to ethyl acetate, "Pd—C" refers to palladium on carbon, "DCM" refers to dichloromethane, "DMAP" refers to dimethylaminopyridine, "LiHMDS" refers to Lithium Hexamethyldisilisane, "TFA" refers to trifluoroacetic acid, "EDAC" refers to N-Ethyl-N'-(3-dimethylaminopropyl)carbodiimide hydrochloride, "HOBT" refers to 1-Hydroxy benzotriazole, "Bn-9-BBN" refers to Benzyl-9-borabicyclo[3.3.1]nonane, "Pd(dppf)Cl$_2$," refers to [1,1'-Bis(diphenylphosphino)-ferrocene)dichloropalladium(II), "EDCI" refers to N-Ethyl-N'-(3-dimethylaminopropyl)carbodiimide hydrochloride, "DBU" refers to 1,8-Diazabicyclo[5.4.0]undecene-7, "TBSCl" refers to tert-butyl-dimethyl-silanyloxymethyl chloride, "NBS" refers to N-Bromosuccinimide, "TsOH" refers to p-toluenesulfonic acid, "DCE" refers to dichloroethane, "DAST" refers to (Diethylamino)sulfur trifluoride, "EA/H" refers to ethyl acetate/hexanes mixture, "Pd$_2$(dba)$_3$" refers to Bis(dibenzylideneacetone)palladium, "BINAP" refers to 2,2'-Bis(diphenylpospino-1,1'-binaphthalene, "NMP" refers to N-Methylpyrrollidine, "TMSCN" refers to Trimethylsilyl cyanide, "TBAF" refers to Tetrabutylammonium fluoride, "Tf$_2$O" refers to trifluoromethanesulfonic anhydride, "TBSO" refers to tert-butyl-dimethyl-silanyloxy, "OTf" refers to trifluoromethanesulfonate, MeTi(Oi-Pr)$_3$ refers to methyltitanium triisopropoxide, "BBr$_3$" refers to boron tribromide, "PBr$_3$" refers to phosphorous tribromide, "Pd (PPh$_3$)$_4$" refers to tetrakis(triphenylphoshine)palladium (0), "OAc" refers to acetate, "DME" refers to dimethylethane, "Et$_2$O" refers to diethyl ether, "(Ph$_3$P)$_4$Pd" refers to tetrakis(triphenylphoshine)palladium (0), "DMFDMA" refers to N,N-dimethylformamide dimethyl acetal, "Et$_3$N" refers to triethylamine, "tBu" refers to t-butyl, "DIPEA" refers to diisopropylethyl amine, "EDC" refers to -(3-Dimethylaminopropyl)-3-ethylcarbodiimide hydrochloride, "HOAc" refers to acetic acid, "boc" refers to t-butoxycarbonyl. In a structure, "Ph" refers to phenyl, "Me" refers to methyl, "Et" refers to ethyl, "Bn" refers to benzyl, "MeOH" refers to methanol, "OTf" refers to trifluoromethanesulfonate, "TIPSO" refers to triisopropylsilanyloxy, "TBSO" refers to tert-butyl-dimethyl-silanyloxy.

The Examples provided herein are illustrative of the invention claimed herein and are not intended to limit the scope of the claimed invention in any way. The preparations and examples are named using AutoNom 2.2 in ChemDraw Ultra, or AutoNom 2000 in MDL ISIS/Draw version 2.5 SPI from MDL Information Systems, Inc., or are provided by Chemical Abstracts Services.

A Varian INOVA 400 MHz spectrometer is used to obtain $^1$H NMR Specta the in the solvent indicated. An Agilent HP1100 instrument equipped with a Mass Spectrometer (Agilent MSD SL) is used to obtain LCMS. A Waters Xterra C18 (2.1×50 mm, 3.5 micron) is used as stationary phase and a standard method is a gradient of 5-100% acetonitrile/methanol (50:50) with 0.2% ammonium formate over 3.5 minutes then held at 100% B for 0.5 minutes at a column temperature of 50° C. and a flow rate of 1.0 mL/min. Another standard method is a gradient of 5-100% acetonitrile/methanol (50:50) with 0.2% ammonium formate over 7.0 minutes then held at 100% B for 1.0 minutes at a column temperature of 50° C. and a flow rate of 1.0 mL/min. Additional MS analysis via Agilent MSD (loop machine) is standard Flow injection Analysis (FIA), no column is present and flow is 0.5 ml/min of 80% MeOH with 6.5 mM Ammonium Acetate for 30 secs run time.

Scheme A

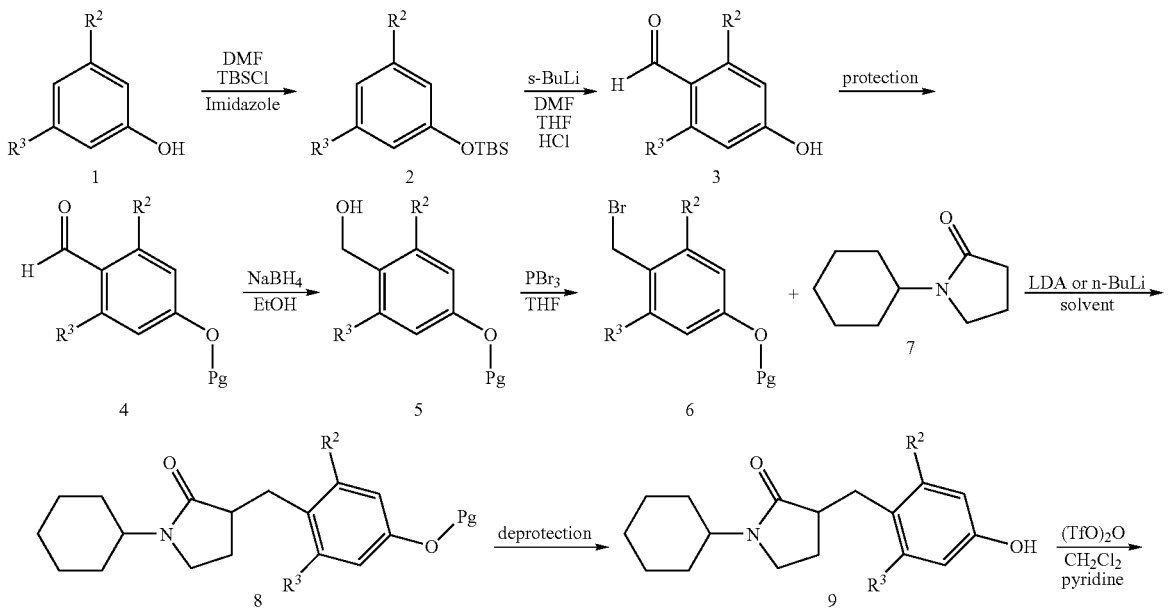

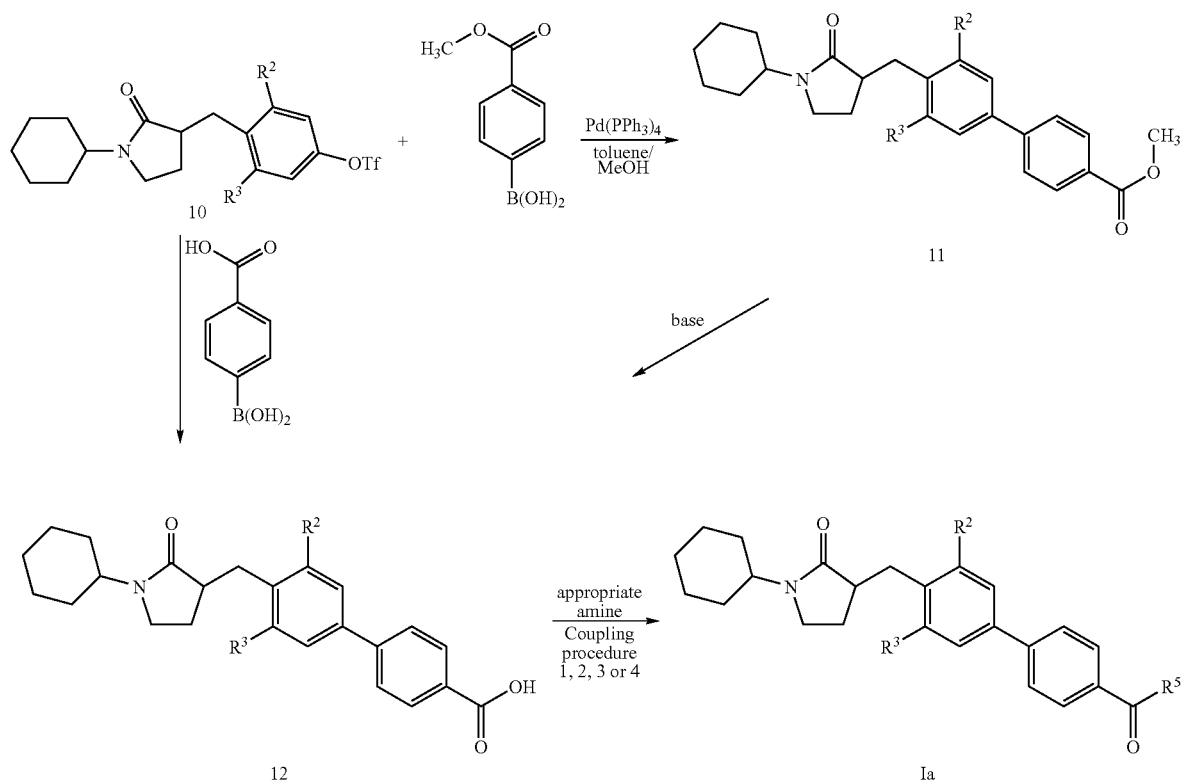

In Scheme A, an optionally substituted phenol (1) is protected (e.g, with TBSCl) to form compound 2, and then compound 2 is converted to the aldehyde (3). Compound 3 is reacted with a compound containing a protecting group (Pg) and leaving group (Lg) to give the ether compound 4. Pg can be —CH₃ or —CH₂-phenyl and Lg can be mesylate or halo. Preferably, the Lg-Pg compound is ICH₃ or Br—CH₂-phenyl. The aldehyde is reduced to form the alcohol (5) and then converted to compound 6, a suitable form which can be used for to react with compound 7. Preferably, compound 5 is halogenated with PBr₃ to give the 2-bromo-methyl compound. The lactam (7) is reacted with a base such as LDA, n-BuLi, or potassium tert-butoxide (preferably LDA) and then alkylated in a non-protic solvent (preferably THF) with compound 6 to form compound 8. Compound 8 is deprotected by a suitable method, such as using BBr₃ or hydrogen with a catalyst, to form the phenol (9). Compound 9 is converted to (10) by reacting with triflic anhydride (trifluoromethanesulfonic anhydride) and a base, for example pyridine. A coupling reaction is performed on (10) using a phenylboronic acid reagent and a catalyst, such as palladium tetrakistriphenylphosphine. The phenylboronic acid can be p-carboxyphenyboronic acid or p-carboxymethylphenylboronic acid. If p-carboxyphenylboronic acid is used, compound 12 is formed. However, if p-carboxymethylphenylboronic acid is used, compound 11 is obtained. Therefore, hydrolysis of the methyl ester is necessary using a suitable base such as potassium hydroxide. The amide (Ia) can be formed using a coupling procedure as described in coupling procedure 1, 2, 3, or 4 as described in Preparations and Examples.

Protection and deprotection of the compounds to form compounds of formula Ia and others are well known to the skilled artisan and are described in the literature. (For example, see: Greene and Wuts, *Protective Groups in Organic Synthesis*, Third Edition, John Wiley and Sons Inc., 1999).

Scheme B

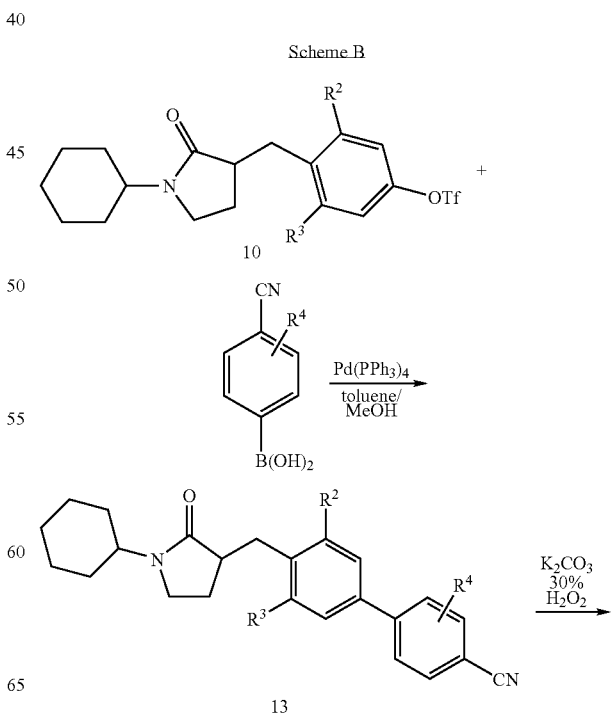

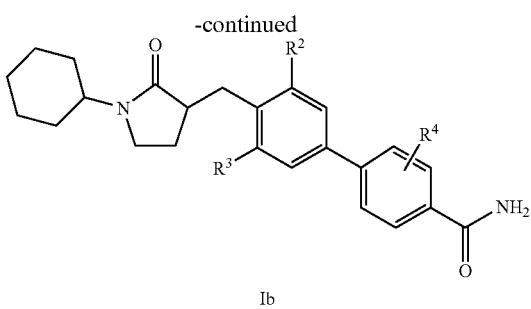

In Scheme B, the amide (Ib) can be formed from compound 10 by reacting with an optionally substituted 4-cyanophenyl-boronic acid to form the compound 13. Compound 13 is then oxidized to form the amide Ib.

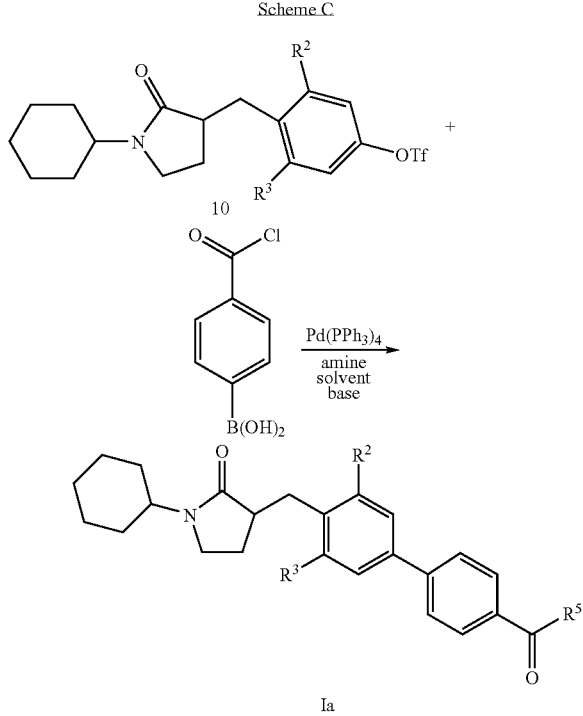

In Scheme C, compound 10 can be converted to Ic in one pot using a catalyst such as palladium, p-chlorocarbonylphenylboronic acid, a base and an amine in a suitable solvent such as dimethoxyethane.

PREPARATION 1

2,6-dichloro-4-hydroxy-benzaldehyde

Dissolve 3,5 dichlorophenol (1 kg, 6.13 mol) in 3 L dimethylformamide (DMF) and cool to 0° C. Add imidazole (918.74 g, 6.75 mol), followed by tertbutyldimethylsilyl chloride (1017.13 g, 6.75 mol). Warm the mixture to room temperature and stir for 15 minutes. Pour into water (6 L) and extract with ether (4 L). Wash the organic layer with water 2 times, 10% aqueous lithium chloride solution then brine before drying over sodium sulfate. Filter and concentrate under vacuum to obtain tert-butyl-(3,5-dichloro-phenoxy)-dimethyl-silane (1700 g) as an oil.

Dissolve tert-butyl-(3,5-dichloro-phenoxy)-dimethyl-silane (425 g, 1.5 mol) in 4 L dry tetrahydrofuran and cool to −68° C. Slowly add 1.1 equivalents of sec-butyl lithium (103.1 g, 1.61 mol) at −68° C. (~1.75 hr). After addition is complete stir the reaction at −70° C. for 30 min. Add dimethylformamide (168.5 g, 2.3 mol) and stir the reaction at −70° C. for 1 hr. Add 1 M hydrochloric acid in water (3.5 L) and allow the reaction to warm to room temperature.

Pour the reaction mixture into ether (5 L), wash with water then brine. Dry over sodium sulfate and concentrate under vacuum to an orange solid. Triturate with cold dichloromethane and filter to recover 250 g (80%) pale yellow solid.

PREPARATION 2

2,6-dichloro-4-methoxy-benzaldehyde

Combine 2,6-dichloro-4-hydroxy-benzaldehyde (120 g, 628.24 mmol) and potassium carbonate (173.65 g, 1256.5 mmol) in 900 mL dimethylformamide and treat with iodomethane (107 g, 753.9 mmol). Stir the reaction at room temperature for 3 hours. Filter off solids and pour into 6 L of water. Filter solids, wash several times with water, air dry and dissolve in ethyl acetate. Wash with water, followed by brine and then dry over sodium sulfate. Filter and concentrate under vacuum to ~100 mL volume, at which point, solids start to crash out. Filter then concentrate down the filtrate to yield a second crop. Wash with hexane, combine all solids and vacuum dry to yield 112.3 g of off-white, solid: $^1$H NMR (400 MHz, CDCl$_3$) δ 10.41 (s, 1H), 6.90 (s, 2H), 3.87 (s, 3H).

PREPARATION 3

2,6-dichloro-4-benzyloxy-benzaldehyde

Treat a mixture of 2,6-dichloro-4-hydroxy-benzaldehyde (250 g, 1.3 mol) and potassium carbonate (361.8 g, 2.62 mol) in 2 L dimethylformamide with benzyl bromide (268.64 g, 1.57 mol). Stir the reaction at room temperature for 1 hour. Filter off solids and pour into 12 L of water. Filter off solid, wash several times with water, air dry and dissolve in ethyl acetate. Dry over magnesium sulfate, filter and concentrate under vacuum to ~1.5 L. Allow to sit overnight then filter. Wash solid with minimal amount of hexane and vacuum dry. Concentrate the filtrate under vacuum and triturate with hexane to yield a second crop of product which when combined with the first crop equals 245 g white crystals. Repeat to obtain a 3rd crop of 80 g as a light-tan powder (88% overall yield): 1H NMR (400 MHz, DMSO-d6) δ 10.26 (s, 1H), 7.43 (m, 5H), 7.28 (s, 2H), 5.25 (s, 2H).

PREPARATION 4

(2,6-dichloro-4-methoxy-phenyl)-methanol

Suspend 2,6-dichloro-4-methoxy-benzaldehyde (112 g, 546 mmol) in 1500 mL ethanol and cool in an ice bath to 7° C. Add sodium borohydride (20.67, 546 mmol) portionwise to obtain a solution. Remove the ice bath and stir for 2 hours. Carefully add reaction mixture to saturated ammonium chloride solution (~4 L) and stir until fully quenched. Extract with dichloromethane (3×1 L) and dry the combined organic extracts over sodium sulfate. Filter and concentrate under vacuum to yield 113 g of a light-tan solid: 1H NMR (400 MHz, CDCl$_3$) δ 6.86 (s, 2H), 4.86 (s, 2H), 3.78 (s, 3H), 2.07 (s, 1H).

PREPARATION 5

(2,6-dichloro-4-benzyloxy-phenyl)-methanol

Prepare the title compound essentially as prepared by the method of Preparation 4. NMR (DMSO-$d_6$) δ 7.38 (m, 4H), 7.33 (m, 1H), 7.12 (s, 2H), 5.14 (s, 2H), 5.05 (t, 1H), 4.59 (d, 2H).

PREPARATION 6

2-bromomethyl-1,3-dichloro-5-methoxy-benzene

Dissolve (2,6-dichloro-4-methoxy-phenyl)-methanol (113 g, 545.76 mmol) in 1200 mL dry THF and cool to 0 deg under nitrogen. Add $PBr_3$ (59.1 g, 218.3 mmol) under nitrogen and stir at 0° C. for 30 minutes. Pour into saturated aqueous $NaHCO_3$ and extract with EtOAc. Dry and concentrate under vacuum to obtain 129.4 g product as an off-white solid. NMR ($CDCl_3$) δ 6.88 (s, 2H), 4.73 (s, 2H), 3.79 (s, 3H).

PREPARATION 7

2-bromomethyl-1,3-dichloro-5-benzyloxy-benzene

Prepare the title compound essentially as prepared by the method of Preparation 6 in an 89% yield. ES MS (m/z): 347 (M+1).

PREPARATION 8

1-cyclohexyl-3-(2,6-dichloro-4-methoxy-benzyl)-pyrrolidin-2-one

Dissolve commercially available 1-cyclohexyl-pyrrolidin-2-one (88.2 g, 527.9 mmol) in 2500 mL tetrahydrofuran and cool to −78° C. Add 176 mL 2 M LDA and stir for ~5 min. Add 2-bromomethyl-1,3-dichloro-5-methoxy-benzene (95 g, 351.9 mmol) and allow the reaction to warm to room temperature. Pour the mixture into saturated ammonium chloride and extract twice with dichloromethane. Dry over sodium sulfate, filter and concentrate under vacuum to obtain a tan solid. Add hexanes and stir rapidly before filtering. Wash the filter cake several times with cold hexane to obtain 86 g (69%) of a light-tan solid: MS (m/z): 356 (M+).

PREPARATION 9

1-cyclohexyl-3-(2,6-dichloro-4-hydroxy-benzyl)-pyrrolidin-2-one

Dissolve 1-cyclohexyl-3-(2,6-dichloro-4-methoxy-benzyl)-pyrrolidin-2-one (86 g, 241.4 mmol) in 1300 mL dichloromethane then cool to 0° C. under nitrogen. Slowly add $BBr_3$ (120.9 g, 482.75 mmol) to the stirring cold solution keeping the internal temperature below 3.5° C. Stir the solution cold for ~2 hours, then pour into 4 L of saturated sodium bicarbonate and stir rapidly for ~20 minutes. Filter and wash the solid with water, then air dry on the funnel. Separate the organic portion of the filtrate and wash with water then brine. Dry over sodium sulfate, filter and concentrate under vacuum. Suspend the resultant tan solid in dichloromethane, filter, wash the solid with dichloromethane and dry to yield 10.5 g of off-white solid. Combine all solids and dry over night in a vacuum oven at 45° C. to yield 78.6 g (95%) of a light-tan solid: MS: (m/z) 342 (M+).

PREPARATION 10

Trifluoro-methanesulfonic acid 3,5-dichloro-4-(1-cyclohexyl-2-oxo-pyrrolidin-3-ylmethyl)-phenyl ester Suspend 1-cyclohexyl-3-(2,6-dichloro-4-hydroxy-benzyl)-pyrrolidin-2-one 73.5 g, 214.75 mmol) in 1200 mL dichloromethane and cool to 0° C. Add pyridine (169.9 g, 2147.5 mmol) followed by triflic anhydride (90.9 g, 322.12 mmol).

Pour mixture into 2 L of water, and separate layers. Wash with saturated $CuSO_4$ to obtain an emulsion. Add solid NaCl to get a solid blue precipitate with the emulsion. Add water to make the mixture fluid and filter off the solid. Rinse the solid with water then with dichloromethane and separate the blue aqueous layer from the red organic layer. Dry over sodium sulfate, filter and concentrate under vacuum to yield a viscous red oil. Purify by silica gel chromatography using 2 kg of silica gel and 25% ethyl acetate/hexane to obtain 78.4 g (77%) of an off-white solid: $^1$H NMR (400 MHz, DMSO-$d_6$) δ 7.8 (s, 2H), 3.7 (m, 1H), 3.3 (m, 2H), 3.15 (m, 1H), 2.85 (m, 1H), 2.67 (m, 1H), 1.95 (m, 1H), 1.7 (m, 3H), 1.58 (m, 3H), 1.4-1.2 (m, 4H), 1.15 (m, 1H).

PREPARATION 11

3',5'-dichloro-4'-(1-cyclohexyl-2-oxo-pyrrolidin-3-ylmethyl)-biphenyl-4-carboxylic acid methyl ester Dissolve trifluoro-methanesulfonic acid 3,5-dichloro-4-(1-cyclohexyl-2-oxo-pyrrolidin-3-ylmethyl)-phenyl ester (5 g, 10.54 mmol) in 50 mL toluene, add aqueous 2 M sodium carbonate and evacuate/purge with nitrogen 3 times. Add p-carboxymethylphenylboronic acid (2.85 g, 15.81 mmol), degas again, then add Pd(PPh$_3$)$_4$ (1.22 g, 1.05 mmol). Degass/purge one more time then reflux overnight. Separate layers, wash the organic layer with water twice, then wash with brine. Dry over sodium sulfate, filter and concentrate under vacuum to yield a brown foam. Add ethyl acetate to get a tan solid and filter to get 3.8 g product. Concentrate the filtrate to recover 0.4 g more product after purification via silica gel chromatography using 25% ethyl acetate: MS (m/z): 460 (M+).

PREPARATION 12

3',5'-dichloro-4'-(1-cyclohexyl-2-oxo-pyrrolidin-3-ylmethyl)-biphenyl-4-carboxylic acid Place 3',5'-dichloro-4'-(1-cyclohexyl-2-oxo-pyrrolidin-3-ylmethyl)-biphenyl-4-carboxylic acid methyl ester (45 g, 97.74 mmol) in 2 L of ethanol and add KOH (27.42 g, 488.7 mmol). Heat the mixture to 50° C. for ~4 hours. Filter the dark mixture through Celite® while still hot. Dilute with ~3 L of water and allow to cool to room temperature. Acidify with 1N hydrochloric acid to pH of 2, while rapidly stirring. Filter, rinse with water and vacuum dry to yield 42 g (96%) of a light-tan solid: MS (m/z): 446 (M+). Synthesis of 3',5'-dichloro-4'-(1-cyclohexyl-2-oxo-pyrrolidin-3-ylmethyl)-3-fluoro-biphenyl-4-carbonitrile.

PREPARATION 13

Combine Preparation 10 (trifluoro-methanesulfonic acid 3,5-dichloro-4-(1-cyclohexyl-2-oxo-pyrrolidin-3-ylmethyl)-phenyl ester) (1.85 g, 3.90 mmol), THF (40 mL), 4-cyano-3-fluorophenylboronic acid (0.77 g, 4.68 mmol), sodium carbonate (1.24 g, 11.70 mmol) and water (10 mL) in a round bottom flask. Stir the mixture at 60° C. for 5 minutes and then add palladium tetrakistriphenylphosphine (0.225 g, 0.20 mmol). Warm the mixture at 80° C. and stir for 3 hours. Cool and partition between ethyl acetate and aqueous hydrochloric acid (1 N). Separate the organic phase, wash with water then brine. Dry the liquid over sodium sulfate, filter, and concentrate under vacuum. Purify by silica gel (25% ethyl acetate/hexane) to afford 1.07 g (62%) of product: MS (m/z): 445.0 (M+).

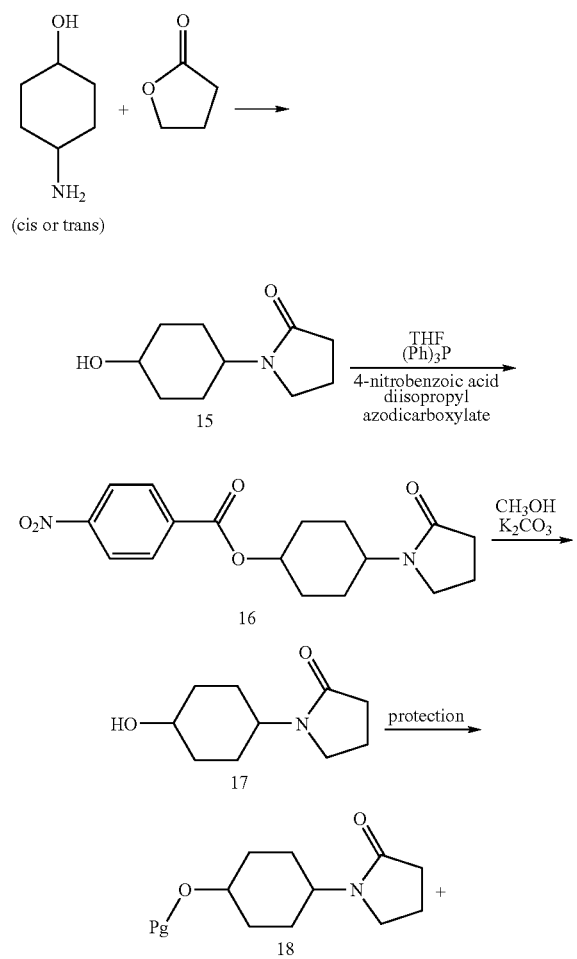

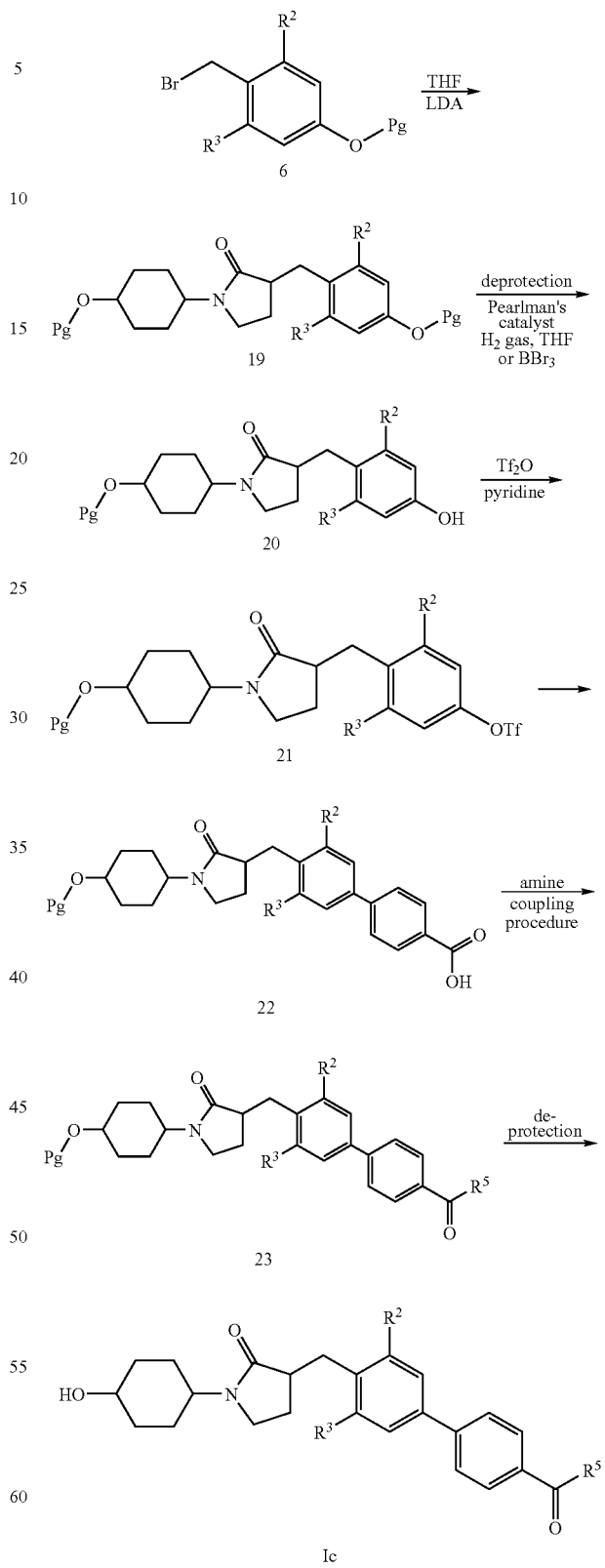

In Scheme D, the lactam (15) is formed by reacting the lactone with cis or trans 4-aminocyclohexanol. Then, the nitro-benzoic acid 4-(2-oxo-pyrrolidin-1-yl)-cyclohexyl ester (16) is formed by reacting (15) with 4-nitrobenzoic acid. In this reaction, if 15 is the cis hydroxy compound, then 16 is the trans nitro-benzoic acid 4-(2-oxo-pyrrolidin-1-yl)-cyclohexyl ester and the 4-hydroxy in compound Id is trans. If 15 is the trans hydroxy compound, then 16 is the cis nitro-benzoic acid 4-(2-oxo-pyrrolidin-1-yl)-cyclohexyl ester and the 4-hydroxy in compound 1d is cis. The 4-hydroxy compound (17) is suitably protected (See Greene), preferably with TBSCl, and the protected lactam (18) is alkylated with 6 (see Scheme A) to form the compound 19. The ether (19) is deprotected to form 20 and reacted with triflic anhydride to form 21. The carboxylic acid (22) is formed by a boronic acid coupling reaction. The amide (23) is formed and then deprotected to form the compound of formula Ic.

PREPARATION 14

1-(trans-4-hydroxy-cyclohexyl)-pyrrolidin-2-one

Add trans-4-aminocyclohexanol (230 g, 2.0 mol) to γ-butyrolactone (140 mL, 1.82 mol) in a 1 L round-bottom flask equipped with large magnetic stirrer, thermometer and condenser/nitrogen bubbler. Heat the mixture at 190° C. for 68 hours. Cool to ambient temperature and mix with water (1 L). Extract into dichloromethane (10×1.5 L). Dry the extracts over magnesium sulfate, filter and evaporate to a brown solid. Triturate with diethyl ether to afford 144.7 g (43%) of the title compound: MS (m/z): 184 (M+1).

PREPARATION 15 cis-4-nitro-benzoic acid 4-(2-oxo-pyrrolidin-1-yl)-cyclohexyl ester

Dissolve 1-(trans-4-hydroxy-cyclohexyl)-pyrrolidin-2-one (144 g, 0.79 mol) in dry tetrahydrofuran (5 L) and cool to −5° C. under nitrogen. Add triphenylphosphine (310 g, 1.185 mol) and 4-nitrobenzoic acid (198 g, 1.185 mol). Add diisopropyl azodicarboxylate (230 mL, 1.185 mol) drop-wise and stir at room temperature overnight. Add saturated aqueous sodium bicarbonate (IL) and extract into dichloromethane (2×2.5 L) in a 20 L separating funnel. Dry the combined organic layers over magnesium sulfate, filter and concentrate. Purify over silica gel (iso-hexane/ethyl acetate 50-100% then 10% methanol in ethyl acetate) to afford 163 g (62%) of the title compound.

PREPARATION 16 cis-1-(4-hydroxy-cyclohexyl)-pyrrolidin-2-one

Dissolve cis-4-nitro-benzoic acid 4-(2-oxo-pyrrolidin-1-yl)-cyclohexyl ester (87.9 g, 264 mmol) in methanol (1.35 L) and water (150 mL) and treat with potassium carbonate (109.5 g, 800 mmol). Stir at room temperature overnight to give a white precipitate. Evaporate to dryness. Remove excess water by mixing with ethanol and concentrating to dryness under vacuum. Repeat this procedure. Stir in tetrahydrofuran (1 L) for 1 hour then filter. Evaporate the filtrate to an oil and crystallize from diethyl ether (100 mL) to afford 40 g (83%) of the title compound.

PREPARATION 17 cis-1-[4-(tert-butyl-dimethyl-silanyloxy)-cyclohexyl]-pyrrolidin-2-one

Dissolve cis-1-(4-hydroxy-cyclohexyl)-pyrrolidin-2-one (40 g, 220 mmol) in dry dichloromethane (1 L). Add imidazole (22.5 g, 330 mmol) followed by tert-butyldimethylsilyl chloride (50 g, 330 mmol). Stir under nitrogen at room temperature overnight. Wash with water (250 mL) and saturated aqueous sodium bicarbonate (250 mL). Dry over magnesium sulfate, filter and evaporate to an oil. Pass through a silica gel pad with iso-hexane/ethyl acetate (0-50%) to afford 51 g (79%) the title compound as a clear, pale-yellow oil: MS (m/z): 298 (M+1).

PREPARATION 18

3-(4-benzyloxy-2,6-dichloro-benzyl)-cis-1-[4-(tert-butyl-dimethyl-silanyloxy)-cyclohexyl]-pyrrolidin-2-one Prepare the title compound essentially by the method of Preparation 8 (1-cyclohexyl-3-(2,6-dichloro-4-methoxy-benzyl)-pyrrolidin-2-one) in a 53% yield starting from 2-bromomethyl-1,3-dichloro-5-benzyloxy-benzene and cis-1[4-(tert-butyl-dimethyl-silanyloxy)-cyclohexyl]-pyrrolidin-2-one.

PREPARATION 19 cis-1-[4-(tert-butyl-dimethyl-silanyloxy)-cyclohexyl]-3-(2,6-dichloro-4-hydroxy-benzyl)-pyrrolidin-2-one Add a solution of 3-(4-benzyloxy-2,6-dichloro-benzyl)-cis-1-[4-(tert-butyl-dimethyl-silanyloxy)-cyclohexyl]-pyrrolidin-2-one (8.5 g 15.1 mmol) in 25 mL tetrahydrofuran to 0.5 g Pearlman's catalyst and hydrogenate the resulting mixture under a balloon of hydrogen gas 2 hr. Filter through Celite® and concentrate to get a solid. Purify by silica gel chromatography using hexanes/ethyl acetate to recover 4.4 g (61%) of product.

PREPARATION 20

Trifluoro-methanesulfonic acid 4-{cis-1-[4-(tert-butyl-dimethyl-silanyloxy)-cyclohexyl]-2-oxo-pyrrolidin-3-ylmethyl}-3,5-dichloro-phenyl ester Prepare the title compound essentially by the method of Preparation 10 in an 88% yield starting from cis-1-[4-(tert-butyl-dimethyl-silanyloxy)-cyclohexyl]-3-(2,6-dichloro-4-hydroxy-benzyl)-pyrrolidin-2-one.

PREPARATION 21

4'-{cis-1-[4-(tert-butyl-dimethyl-silanyloxy)-cyclohexyl]-2-oxo-pyrrolidin-3-ylmethyl}-3',5'-dichloro-biphenyl-4-carboxylic acid Prepare the title compound essentially by the method of making Preparation 11 in an 88% yield starting from trifluoro-methanesulfonic acid 4-{cis-1-[4-(tert-butyl-dimethyl-silanyloxy)-cyclohexyl]-2-oxo-pyrrolidin-3-ylmethyl}-3,5-dichloro-phenyl ester and 4-carboxyphenyl boronic acid.

TABLE 1

The Preparations in Table 1 may be prepared essentially as described in Example 3 except for the amine is replaced with the amine as indicated.

| Preparation | Structure and name | Amine | Mass Spec |
|---|---|---|---|
| 22 | 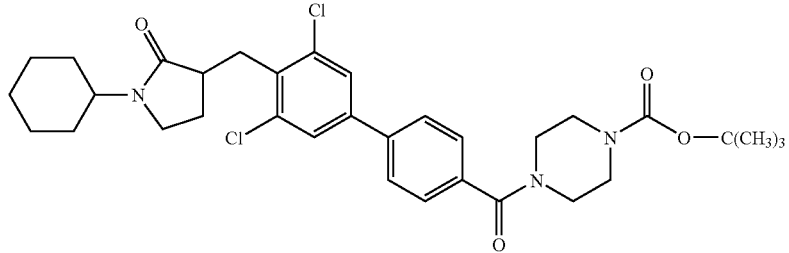<br>4-[3',5'-Dichloro-4'-(1-cyclohexyl-2-oxo-pyrrolidin-3-ylmethyl)-biphenyl-4-carbonyl]-piperazine-1-carboxylic acid tert-butyl ester | 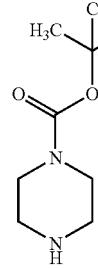 | MS (m/z) 614 (M+) |
| 23 | 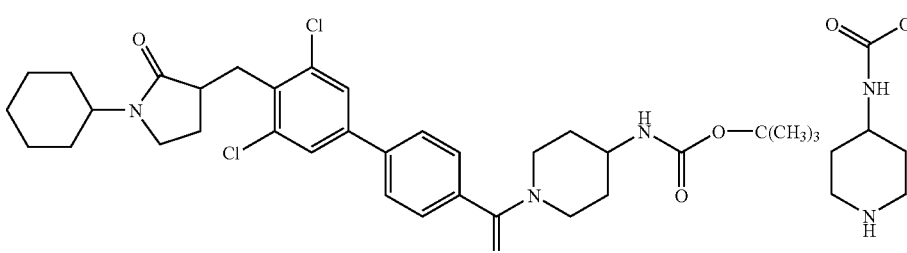<br>1-[3',5'-Dichloro-4'-(1-cyclohexyl-2-oxo-pyrrolidin-3-ylmethyl)-biphenyl-4-carbonyl]-piperidin-4-yl}-carbamic acid tert-butyl ester | 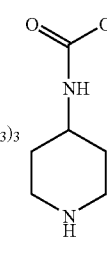 | MS (m/z) 628 (M+) |

TABLE 2

The preparation in Table 2 may be prepared essentially as described in Preparation 8a except for the amine is replaced with the amine as indicated.

| Preparation | Structure and name | Amine | Data |
|---|---|---|---|
| 24 | 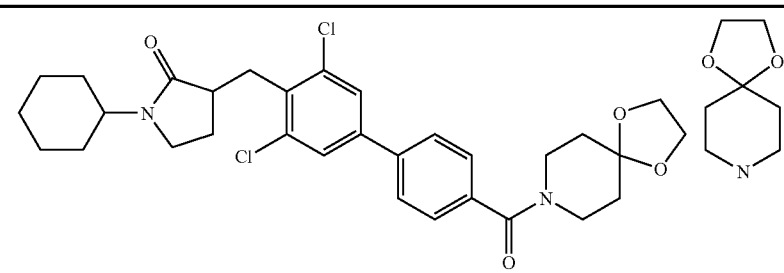<br>1-Cyclohexyl-3-[3,5-dichloro-4'-(1,4-dioxa-8-aza-spiro[4.5]decane-8-carbonyl)-biphenyl-4-ylmethyl]-pyrrolidin-2-one | 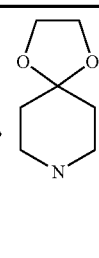 | *NMR below |

*$^1$H NMR (400 MHz, DMSO-d$_6$) δ 7.8-7.75 (m, 4H), 7.45 (d, 2H), 3.85 (s, 4H), 3.6-3.55 (m, 2H), 3.4-3.2 (m, 5H), 3.15 (q, 1H), 2.9-2.8 (m, 1H), 2.75-2.65 (m, 1H), 1.95-1.85 (m, 1H), 1.75-1.5 (m, 10H), 1.45-1.15 (m, 4H), 1.1-1.0 (m, 1H).

Scheme E

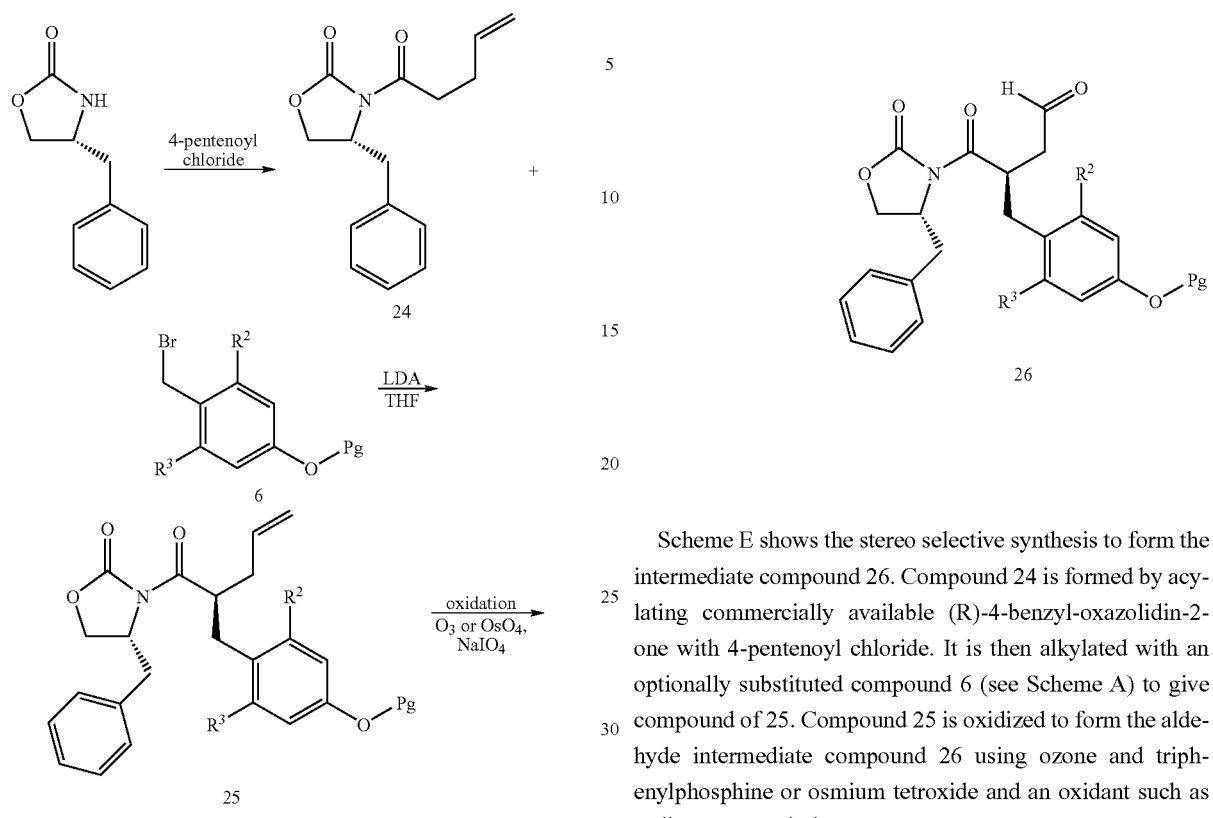

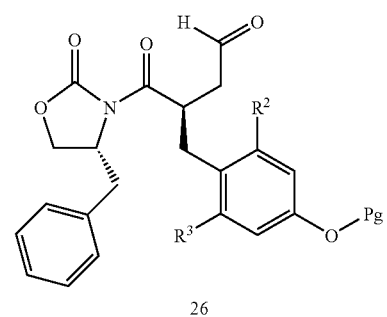

Scheme E shows the stereo selective synthesis to form the intermediate compound 26. Compound 24 is formed by acylating commercially available (R)-4-benzyl-oxazolidin-2-one with 4-pentenoyl chloride. It is then alkylated with an optionally substituted compound 6 (see Scheme A) to give compound of 25. Compound 25 is oxidized to form the aldehyde intermediate compound 26 using ozone and triphenylphosphine or osmium tetroxide and an oxidant such as sodium metaperiodate.

Scheme F

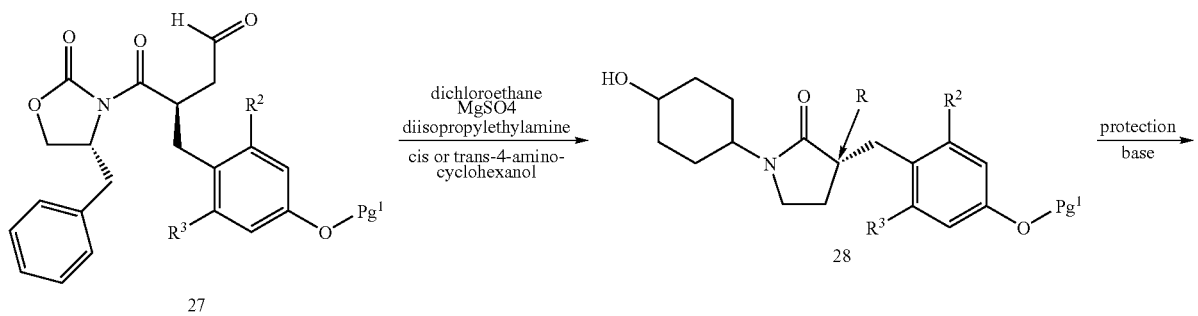

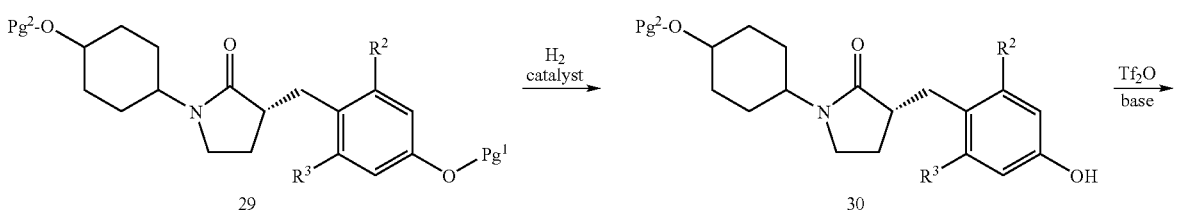

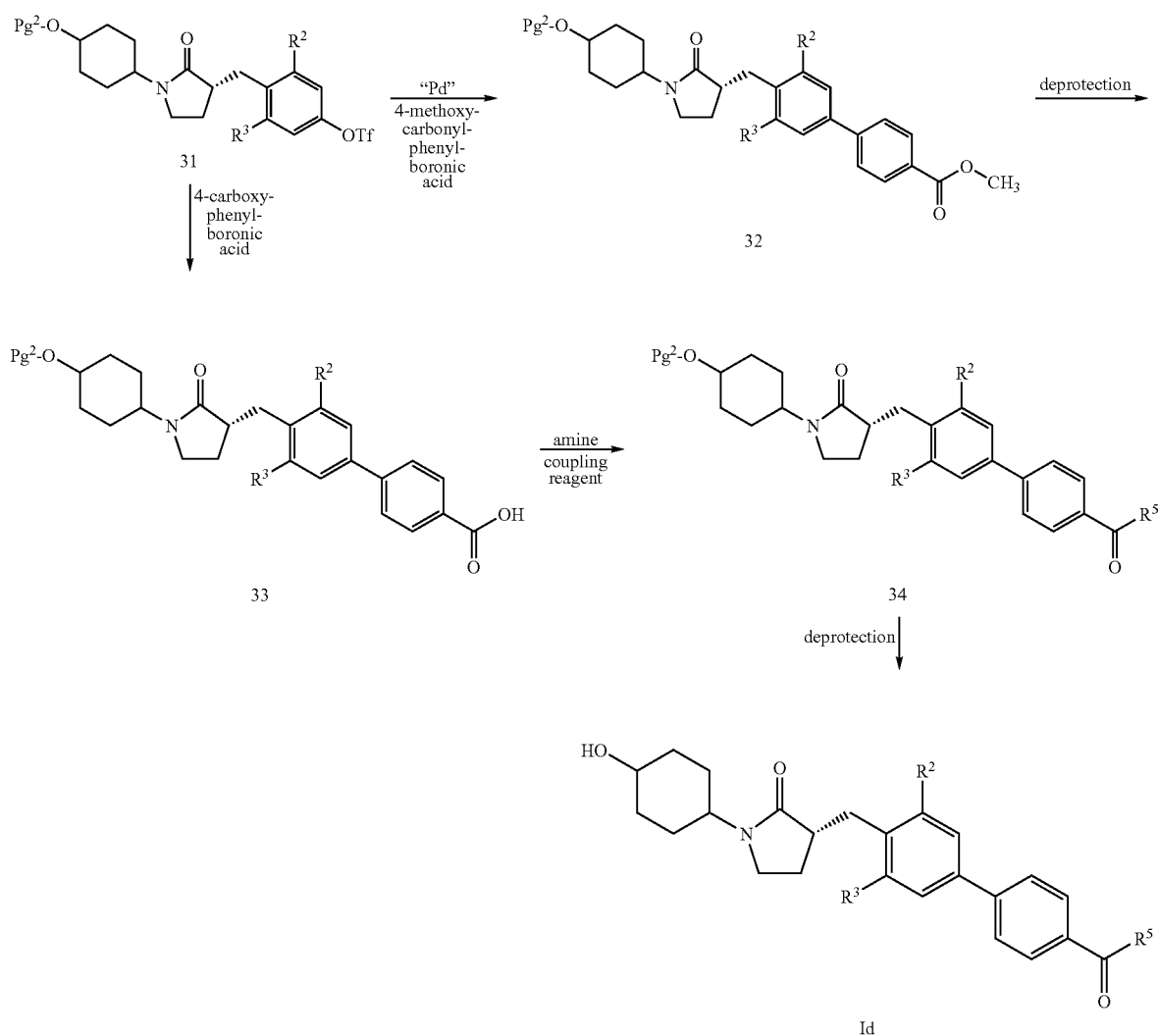

In Scheme F, the intermediate (27) is converted to the lactam compound 28 which is in the "R" configuration. The alcohol on the cyclohexyl is protected (see Greene) with a suitable protecting group, for example by reacting with TBSCl or triisopropylsilyltrifluoromethane sulfonate to form compound 29. A deprotection is performed to give compound 30 which is then trfliated to form compound 31. The carboxylic ester compound (32) is formed and converted to the acid (33) via a hydrolysis. Optionally, compound 31 can be converted to the carboxylic acid 33 directly by using 4-carboxyphenylboronic acid. The amide (34) is formed by reacting the acid with an appropriated amino containing compound and then deprotected to form the compound of formula Id.

Scheme G

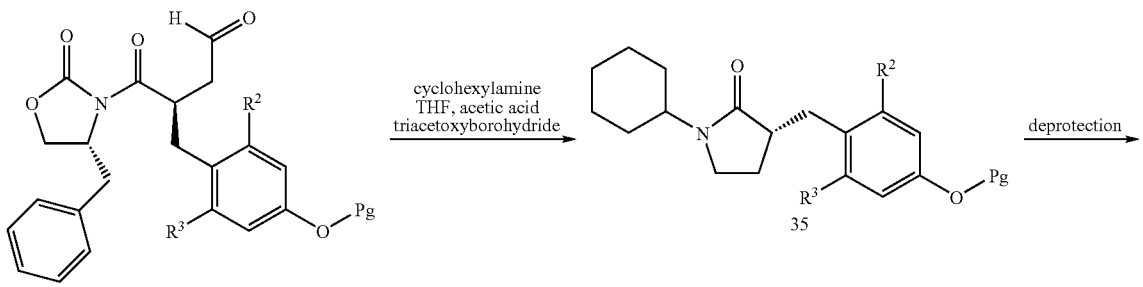

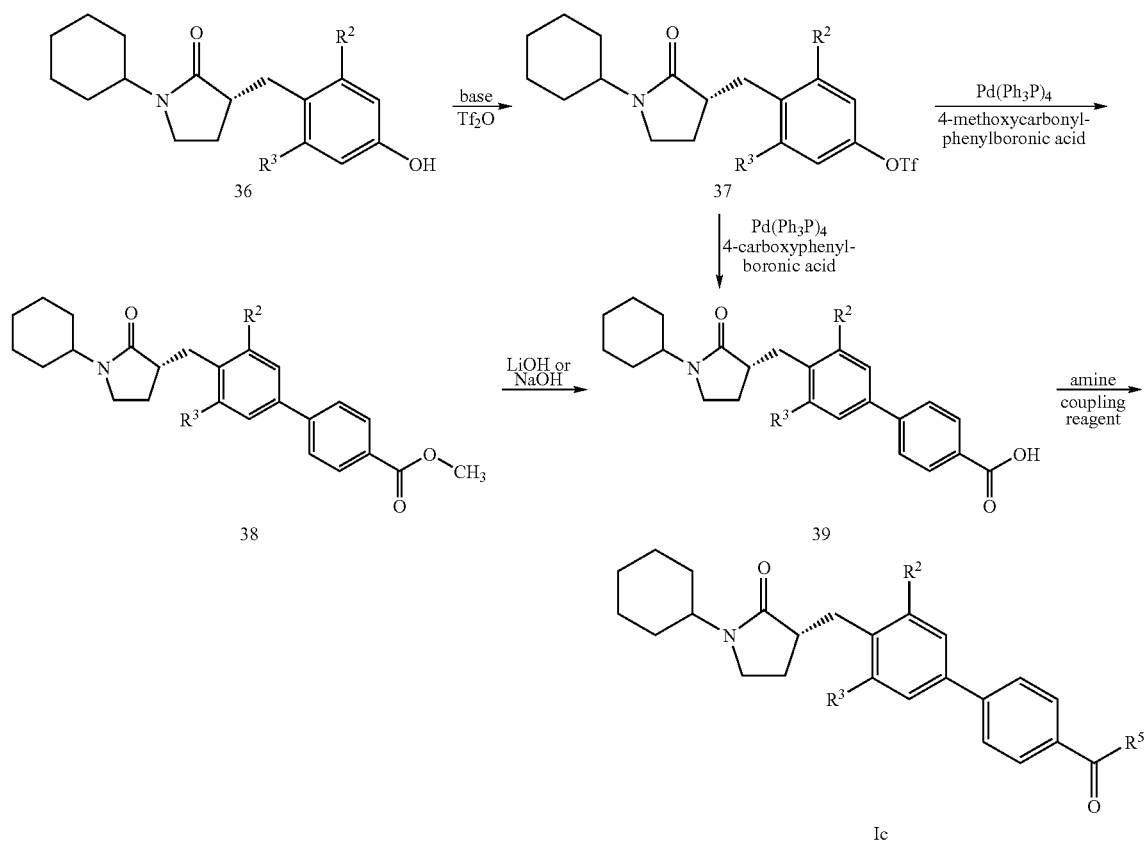
In Scheme G, the aldehyde (27) is converted into the lactam (35) with the stereo designation of "R." The benzyl is removed to form 36 and then 36 is triflated to form 37. The carboxylic acid ester (38) is formed and then the acid is formed. The amide (Ie) is formed by reacting the appropriate amine containing compound with the acid (39).
Scheme H
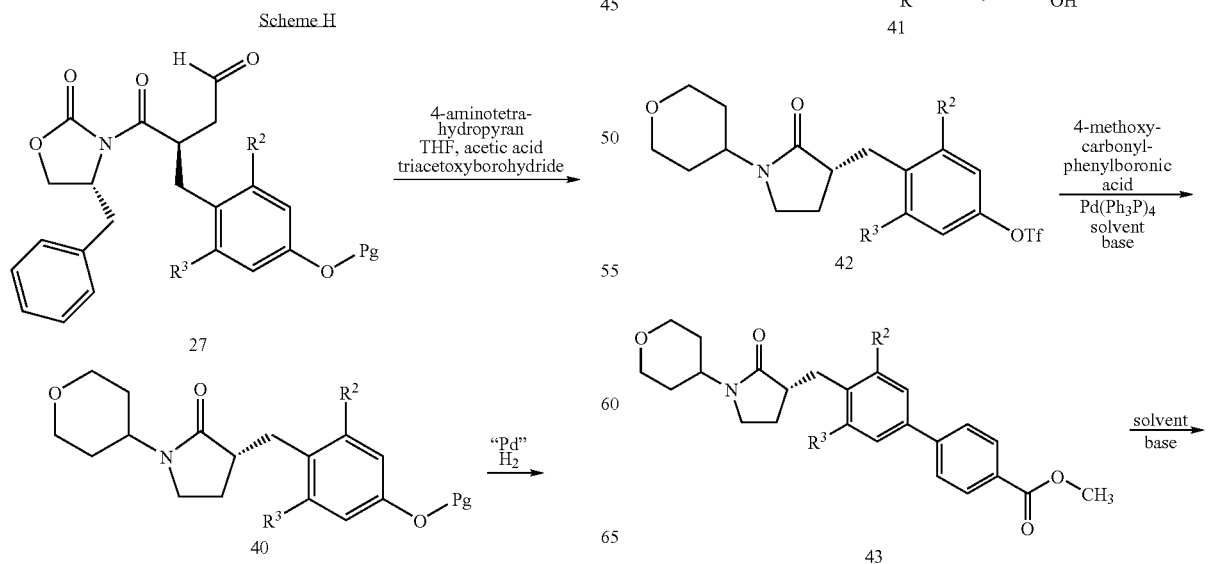

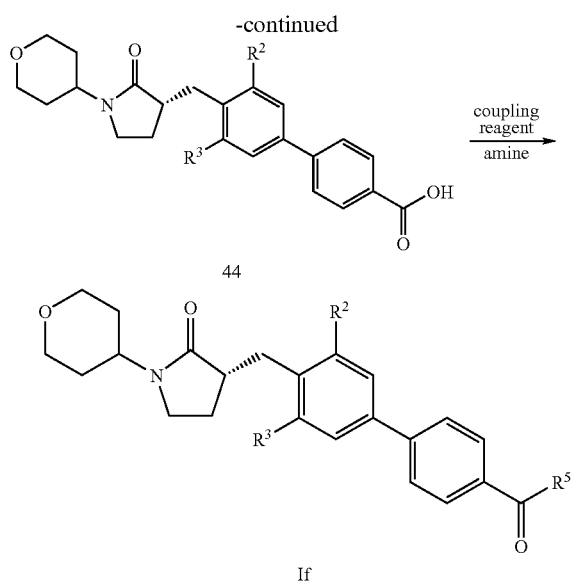

In Scheme H, the tetrahydropyran lactam (40) is formed by reacting the aldehyde of 27 with 4-aminotetrahydropyran. The reaction results in compound 40 to be in the "R" stereo configuration. The benzyl group on 40 is removed to form the alcohol of 41. Compound 41 is triflated to form 42, and then the carboxylic acid ester (43) is formed by reacting with 4-methoxycarbonylphenylboronic acid. The acid (44) is formed and then the appropriated amine containing compound is reacted with the acid (44) to form the amide of compound If.

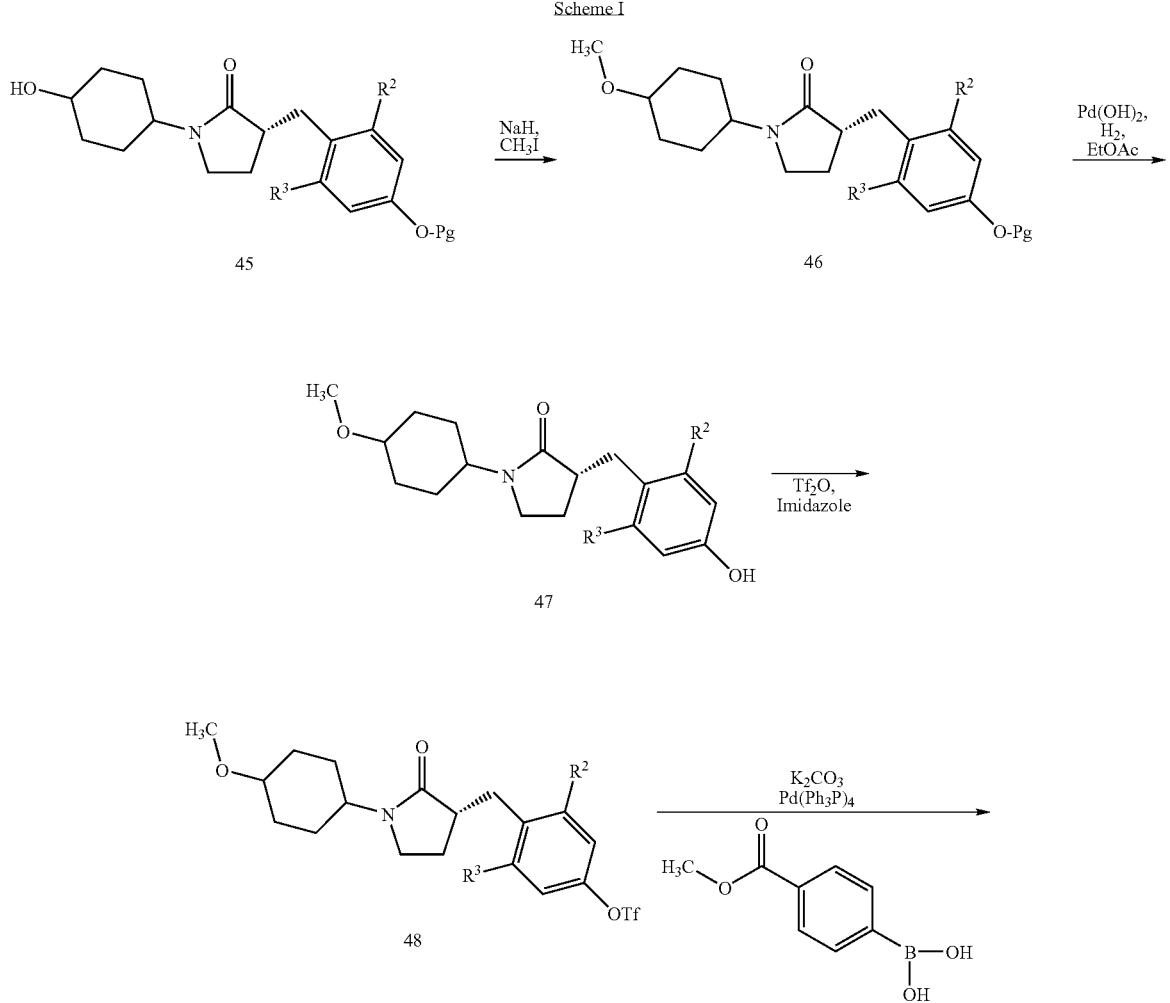

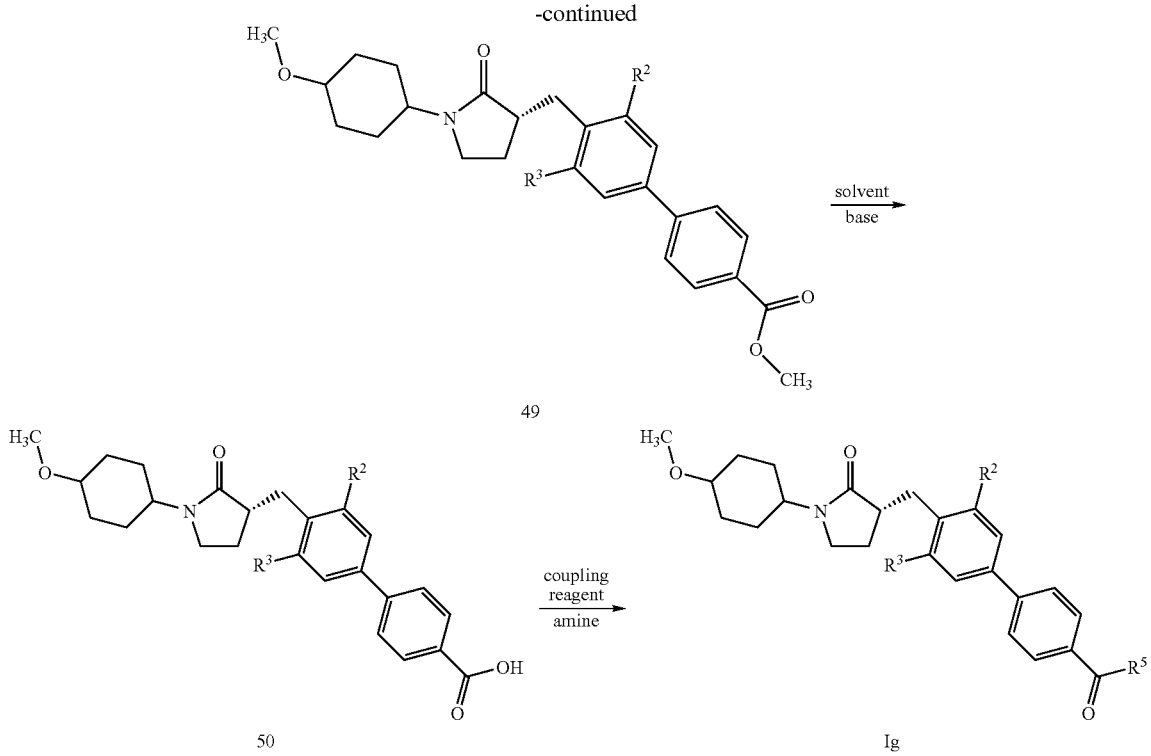

In Scheme I, the methoxy compound (46) is formed by reacting the hydroxy compound (45) with iodomethane. Then, compound 46 is deprotected to form compound 47 which is triflated to form compound 48. The carboxylic acid ester (49) is formed by reacting with 4-methoxycarbonylphenylboronic acid. The acid (50) is formed and then the appropriate amine containing compound is reacted with the acid (50) to form the compound 1 g.

PREPARATION 25

(R)-4-benzyl-3-pent-4-enoyl-oxazolidin-2-one

Flush with nitrogen a 12 L 3-neck round bottom flask equipped with a mechanical stirrer, internal temperature probe/$N_2$ inlet, and 1 L addition funnel for 20 min and then add (R)-4-benzyl-2-oxazolidinone (250 g, 1.41 mol). Dilute with tetrahydrofuran (THF) (1.8 L) and cool in a dry ice/acetone bath until the internal temperature is −74° C. Transfer a 1.6M hexanes solution of n-butyllithium (970 mL, 1.552 mol) to the addition funnel via cannula, and add to the oxazolidinone solution at a rate such that the internal temperature does not reach above −65° C. After the addition is complete, allow the reaction to stir in the cooling bath 30 min. Transfer 4-pentenoyl chloride (175 mL, 1.585 mol) to the addition funnel and add dropwise to the anion solution over a 25 min period. Stir the reaction for 45 min in the cooling bath. Remove the cooling bath and stir the reaction 18 hr as it slowly reaches room temperature. Dilute the mixture with 1N aqueous hydrochloric acid (1.5 L) and diethyl ether (1 L). Separate the layers and wash the organic phase with water (2×1 L) then brine (1 L). Extract the combined aqueous washes with ether (1 L). Dry the combined organic phases over anhydrous magnesium sulfate, filter, and concentrate to 390 g of a light tan oil. Purify this material by silica gel chromatography using hexanes:ethyl acetate to obtain 345 g (94.5%) of a clear, yellow oil.

PREPARATION 26

(R)-4-benzyl-3-[2-(4-benzyloxy-2,6-dichloro-benzyl)-pent-4-enoyl]-oxazolidin-2-one Stir a mixture of (R)-4-benzyl-3-pent-4-enoyl-oxazolidin-2-one (345 g, 1.33 mol) and THF (1.8 L) in a 12 L 3-neck round bottom flask, with internal temperature probe/nitrogen inlet and addition funnel, under a nitrogen atmosphere and cool to −75° C. Transfer 1 M LiHMDS (1.6 L) to the addition funnel and add at a rate such that the internal temperature does not reach above −60° C. After the addition is complete, allow the reaction to stir at −25° C. for 30 min then cool to about −60° C. At this point add solid 2-bromomethyl-1,3-dichloro-5-benzyloxy-benzene portionwise over 5 min. After the addition is complete, transfer the reaction vessel to a −10° C. acetone bath and maintain the internal reaction temperature below 10° C. for 1 hr. Cool the mixture to 0° C. then quench with 2 L aqueous 1N hydrochloric acid. Transfer the mixture to a 22 L separatory funnel and dilute with 2.5 L water and 2 L ether. Separate the layers and extract the aqueous layer with ether. Dry the combined organic phase over anhydrous magnesium sulfate, filter and concentrate to 800 g of a thick oil. Purify by silica gel chromatography using hexanes:ethyl acetate to obtain 597 g, (86%) of a colorless oil.

PREPARATION 27

4-(4-(R)-benzyl-2-oxo-oxazolidin-3-yl)-3-(4-benzyloxy-2,6-dichloro-benzyl)-4-oxo-butyraldehyde Cool a mixture of (R)-4-benzyl-3-[2-(4-benzyloxy-2,6-dichloro-benzyl)-pent-4-enoyl]-oxazolidin-2-one (100 g, 190.68 mmol) and dichloromethane (800 mL) to −74° C. Bubble ozone, produced via the A-113 ozone generator at a rate of 75%, through the reaction via carrier air at a rate of 5 CFM until the solution takes on a blue color (approx 3 hr). Add triphenylphosphine (60 g, 228.8 mmol) as a solution in 200 mL dichloromethane and allow the reaction to stir while reaching room temperature over night. Concentrate the solution under vacuum and purify by silica gel chromatography using a gradient of 20-50% ethyl acetate in hexanes to obtain 82.1 g (82%) of the product as a white foam: MS (m/z): 526 (M+).

Alternate procedure for making 4-(4-(R)-benzyl-2-oxo-oxazolidin-3-yl)-3-(4-benzyloxy-2,6-dichloro-benzyl)-4-oxo-butyraldehyde:

Treat a mixture of (R)-4-benzyl-3-[2-(4-benzyloxy-2,6-dichloro-benzyl)-pent-4-enoyl]-oxazolidin-2-one (0.96 g, 1.8 mmol), THF (21 mL) and water (7 mL) with 2.5% osmium tetroxide in t-butanol (46 mg, 0.18 mmol). Add sodium periodate (1.17 g, 5.5 mmol) and stir the reaction 4 hr at room temperature. Quench the reaction with water and extract with ethyl acetate. Wash the organic phase with aqueous 1N sodium thiosulfate then brine. Dry the organic layer over magnesium sulfate, filter, and concentrate under vacuum. Purify the crude material by silica gel chromatography using hexanes:ethyl acetate to elute the pure product. Concentrate the fractions containing product under vacuum to afford 0.46 g (48%) of desired product. MS (m/z): 526 (M+).

PREPARATION 28

3-(R)-3-(4-benzyloxy-2,6-dichloro-benzyl)-cis-1-(4-hydroxy-cyclohexyl)-pyrrolidin-2-one Stir a mixture of dichloroethane (600 mL), magnesium sulfate (100 g), diisopropylethylamine (20.26 g, 156.7 mmol), cis-4-amino-cyclohexanol (1 g, 95.5 mmol), and 4-(4-(R)-benzyl-2-oxo-oxazolidin-3-yl)-3-(4-benzyloxy-2, 6-dichloro-benzyl)-4-oxo-butyraldehyde (32 g, 62.69 mmol) at room temperature in a nitrogen purged flask for 24 hr, under a nitrogen bubbler. Add sodium triacetoxyborohydride (80 g) and stir 1 hr. Add 50 mL diisopropylethylamine and 20 g sodium triacetoxyborohydride before heating the mixture to 50° C. on rotavap while rotating at ambient pressure. After 1 hr heat the mixture to an internal temperature of 70° C. Cool the reaction to 35° C., add water and filter. Dilute the filtrate with ether and separate the layers. Wash the organic layer with 1:1 water:brine, then extract the combined aqueous layers with ether. Dry the combined organic phases over sodium sulfate, and concentrate to about 48 g of a an oil. Purify via silica column using a stepwise gradient of 9:1, then 9:5 ethyl acetate:methanol to obtain 22 g (78%) of the product as a white foam: MS (m/z): 448 (M+).

PREPARATION 29

3-(R)-3-(4-benzyloxy-2,6-dichloro-benzyl)-trans-1-(4-hydroxy-cyclohexyl)-pyrrolidin-2-one Prepare the title compound essentially by the method of Preparation 28 in an 54% yield starting from trans-aminocyclohexanol and 4-(4-(R)-benzyl-2-oxo-oxazolidin-3-yl)-3-(4-benzyloxy-2,6-dichloro-benzyl)-4-oxo-butyraldehyde: MS (m/z): 448 (M+).

PREPARATION 30

3-(R)-3-(4-benzyloxy-2,6-dichloro-benzyl)-1-cis-(4-triisopropylsilanyloxy-cyclohexyl)-pyrrolidin-2-one Stir a mixture of 3-(R)-3-(4-benzyloxy-2,6-dichloro-benzyl)-cis-1-(4-hydroxy-cyclohexyl)-pyrrolidin-2-one (20.3 g, 45.27 mmol) and 30 mL dichloromethane in an ice/acetone bath. Add pyridine (4.3 g, 54.33 mmol) followed by triisopropylsilyltrifluoromethane sulfonate (15.3, 49.8 mmol). Remove the cold bath and stir the reaction 30 min. Pour into 500 mL water, separate the layers and extract the aqueous phase with 50 mL dichloromethane. Dry the combined organic phase over sodium sulfate, filter, and concentrate. Purify the residue by silica gel chromatography by eluting with 9:1 to 7:3 hexanes:ethyl acetate to give 24.3 g (88.8%) of the product as a pale ivory foam: MS (m/z): 604 (M+).

PREPARATION 31

3-(R)-3-(4-Benzyloxy-2,6-dichloro-benzyl)-trans-1-(4-triisopropylsilanyloxy-cyclohexyl)-pyrrolidin-2-one Prepare the title compound essentially by the method of Preparation 31 in an 99% yield starting from 3-(R)-3-(4-benzyloxy-2,6-dichloro-benzyl)-trans-1-(4-hydroxy-cyclohexyl)-pyrrolidin-2-one: MS (m/z): 604 (M+).

PREPARATION 32

(R)-3-(4-benzyloxy-2,6-dichloro-benzyl)-cis-1-[4-(tert-butyl-dimethyl-silanyloxy)-cyclohexyl]-pyrrolidin-2-one Combine 10.8 g (R)-3-(4-benzyloxy-2,6-dichloro-benzyl)-cis-1-(4-hydroxy-cyclohexyl)-pyrrolidin-2-one, 5.4 g tert-butyldimethylsilylchloride, and 2.7 g imidazole in 50 mL dry dimethylformamide and stir at ambient temperature over night. Pour into 300 mL brine and extract twice with 200 mL diethyl ether. Wash the combined extracts with brine, dry over magnesium sulfate and concentrate to dryness under vacuum. Purify by silica gel chromatography using 10-15% ethyl acetate in hexanes to recover 11.5 g of the product as an oil.

PREPARATION 33

(R)-3-(2,6-dichloro-4-hydroxy-benzyl)-cis-1-(4 triisopropylsilanyloxy-cyclohexyl)-pyrrolidin-2-one Add a solution of 3-(R)-3-(4-benzyloxy-2,6-dichloro-benzyl)-1-cis-(4-triisopropylsilanyloxy-cyclohexyl)-pyrrolidin-2-one (24.3 g, 40.18 mmol) in 250 mL ethyl acetate to 5 g Pearlman's catalyst and hydrogenate the resulting mixture under a balloon of hydrogen gas 2 hr. Filter through Celite® and concentrate to 20.7 g (100%) of a foam: MS (m/z): 515 (M+1).

PREPARATION 34

(R)-3-(4-benzyloxy-2,6-dichloro-benzyl)-trans-1-[4-(tert-butyl-dimethyl-silanyloxy)-cyclohexyl]-pyrrolidin-2-one Prepare the title compound essentially by the method of Preparation 32 in an starting from 3-(R)-3-(4-benzyloxy-2,6- dichloro-benzyl)-trans-1-(4-hydroxy-cyclohexyl)-pyrrolidin-2-one (Preparation 29) and tert-butyldimethylsilyl chloride.

PREPARATION 35

(R)-trans-1-[4-(tert-Butyl-dimethyl-silanyloxy)-cyclohexyl]-3-(2,6-dichloro-4-hydroxy-benzyl)-pyrrolidin-2-one Prepare the title compound essentially by the method of Preparation 34 starting from (R)-3-(4-benzyloxy-2,6-dichloro-benzyl)-trans-1-[4-(tert-butyl-dimethyl-silanyloxy)-cyclohexyl]-pyrrolidin-2-one.

PREPARATION 36

(R)-Cis-1-[4-(tert-Butyl-dimethyl-silanyloxy)-cyclohexyl]-3-(2,6-dichloro-4-hydroxy-benzyl)-pyrrolidin-2-one Prepare the title compound essentially by the method of Preparation 34 starting from (R)-3-(4-benzyloxy-2,6-dichloro-benzyl)-cis-1-[4-(tert-butyl-dimethyl-silanyloxy)-cyclohexyl]-pyrrolidin-2-one.

PREPARATION 37

(R)-Trans-1-[4-(triisopropyl-silanyloxy)-cyclohexyl]-3-(2,6-dichloro-4-hydroxy-benzyl)-pyrrolidin-2-one Prepare the title compound essentially by the method of Preparation 35 in a 91% yield starting from (R)-3-(4-benzyloxy-2,6-dichloro-benzyl)-trans-1-[4-(triisopropyl-silanyloxy)-cyclohexyl]-pyrrolidin-2-one: MS (m/z): 514 (M+).

PREPARATION 38

Trifluoro-methanesulfonic acid 3,5-dichloro-4-[(R)-2-oxo-cis-1-(4-triisopropylsilanyloxy-cyclohexyl)-pyrrolidin-3-ylmethyl]-phenyl ester Stir a solution of (R)-3-(2,6-dichloro-4-hydroxy-benzyl)-cis-1-(4 triisopropylsilanyloxy-cyclohexyl)-pyrrolidin-2-one (20.7 g, 40.22 mmol) in 150 mL pyridine in an ice/water bath 10 min, then add triflic anhydride (12.48 g, 44.25 mmol) over 5 min via syringe. Remove the cooling bath and stir the reaction 18 hr at room temp. Cool to 0° C. in an ice/brine bath and add 500 mL water slowly so that internal temp does not rise above 5° C. Transfer to separatory funnel, dilute with 300 mL ether, separate the layers and then extract the aqueous layer with 150 mL ether. Wash the combined organic layer with water, dry over sodium sulfate, filter and concentrate under vacuum. Purify via silica gel chromatography by eluting with 40-50% ethyl acetate/hexanes to recover 25 g (96%) of the product: MS (m/z): 646 (M+).

PREPARATION 39

Trifluoro-methanesulfonic acid 3,5-dichloro-4-[(R)-2-oxo-trans-1-(4-triisopropylsilanyloxy-cyclohexyl)-pyrrolidin-3-ylmethyl]-phenyl ester Prepare the title compound essentially by the method of Preparation 38 starting from (R)-trans-1-[4-(triisopropyl-silanyloxy)-cyclohexyl]-3-(2,6-dichloro-4-hydroxy-benzyl)-pyrrolidin-2-one.

PREPARATION 40

Trifluoro-methanesulfonic acid 4-{(R)-cis-1-[4-(tert-butyl-dimethyl-silanyloxy)-cyclohexyl]-2-oxo-pyrrolidin-3-ylmethyl}-3,5-dichloro-phenyl ester Prepare the title compound essentially by the method of Preparation 38 starting from (R)-cis-1-[4-(tert-butyl-dimethyl-silanyloxy)-cyclohexyl]-3-(2,6-dichloro-4-hydroxy-benzyl)-pyrrolidin-2-one.

PREPARATION 41

Trifluoro-methanesulfonic acid 4-{(R)-trans-1-[4-(tert-butyl-dimethyl-silanyloxy)-cyclohexyl]-2-oxo-pyrrolidin-3-ylmethyl}-3,5-dichloro-phenyl ester Stir a solution of (R)-3-(2,6-dichloro-4-hydroxy-benzyl)-trans-1-(4 tert-butyldimethylsilanyloxy-cyclohexyl)-pyrrolidin-2-one (4.2 g, 8.9 mmol) and N-phenyl-bis-trifluoromethanesulfonimide (3.2 g, 8.9 mmol) in 50 mL dichloromethane. Add triethylamine (1.8 g, 17.8 mmol) and stir the reaction 18 hr at room temp. Wash the mixture with a solution of 5% citric acid in water, dry over magnesium sulfate, filter and concentrate under vacuum. Purify via silica gel chromatography by eluting with hex-30% ethyl acetate to recover 4.3 g (79%) of the product.

PREPARATION 42

4'-{(R)-trans-1-[4-(tert-Butyl-dimethyl-silanyloxy)-cyclohexyl]-2-oxo-pyrrolidin-3-ylmethyl}-3',5'-dichloro-biphenyl-4-carboxylic acid Prepare the title compound essentially by the method of Preparation 44 in a starting from trifluoro-methanesulfonic acid 4-{(R)-trans-1-[4-(tert-butyl-dimethyl-silanyloxy)-cyclohexyl]-2-oxo-pyrrolidin-3-ylmethyl}-3,5-dichloro-phenyl ester and 4-carboxyphenylboronic acid.

PREPARATION 43

3',5'-dichloro-4'-[(R)-2-oxo-cis-1-(4-triisopropylsilanyloxy-cyclohexyl)-pyrrolidin-3-ylmethyl]-biphenyl-4-carboxylic acid methyl ester Bubble nitrogen through a mixture of trifluoro-methanesulfonic acid 3,5-dichloro-4-[(R)-2-oxo-cis-1-(4-triisopropylsilanyloxy-cyclohexyl)-pyrrolidin-3-ylmethyl]-phenyl ester (12.2 g, 18.87 mmol), 4-methoxycarbonylphenylboronic acid (4.1 g, 22.64 mmol), sodium carbonate (6 g, 56.6 mmol), 50 mL water, and 150 mL tetrahydrofuran for 30 min at room temperature. Add tetrakis(triphenylphosphine)palladium (1.7 g, 1.47 mmol) by weighing into a nitrogen filled vial and transferring the material as a dry solid to the reaction flask. Sparge an additional 5 min, then heat at 80° C. 1 hr. Dilute with 50 mL each of water and ethyl acetate, separate layers and extract the aqueous layer with 25 mL ethyl acetate. After combining the organic layers, wash with 50 mL brine, dry over magnesium sulfate and concentrate under vacuum. Purify on silica by eluting with 10-30% ethyl acetate in hexanes to give 11.1 g (93%) of product as an ivory foam: MS (m/z): 632 (M+).

PREPARATION 44

3',5'-dichloro-4'-[(R)-2-oxo-trans-1-(4-triisopropylsilanyloxy-cyclohexyl)-pyrrolidin-3-ylmethyl]-biphenyl-4-carboxylic acid methyl ester Prepare the title compound essentially by the method of Preparation 43 in an 80% yield starting from trifluoro-methanesulfonic acid 3,5-dichloro-4-[(R)-2-oxo-trans-1-(4-triisopropylsilanyloxy-cyclohexyl)-pyrrolidin-3-ylmethyl]-phenyl ester: MS (m/z): 632 (M+).

PREPARATION 45

3,5'-dichloro-4'-[(R)-2-oxo-cis-1-(4-triisopropylsilanyloxy cyclohexyl)-pyrrolidin-3-ylmethyl]-biphenyl-4-carboxylic acid Stir a mixture of 3',5'-dichloro-4'-[(R)-2-oxo-cis-1-(4-triisopropylsilanyloxy-cyclohexyl)-pyrrolidin-3-ylmethyl]-biphenyl-4-carboxylic acid methyl ester (35.6 g, 56.26 mmol), 150 mL THF and 100 mL methanol under nitrogen in an ice/water bath. Add a solution of lithium hydroxide (4.04 g, 168.79 mmol) in 100 mL water. Stir the mixture 4 hr at RT. Cool the solution to about 1° C. in an ice/acetone bath, dilute with 500 mL water, then adjust the pH to about 2-3 with 0.5 M aqueous hydrochloric acid. Extract with ethyl acetate (3×150 mL), wash with 100 mL each, water and brine then dry over magnesium sulfate. Filter, and concentrate to 34.6 g (99%) of a foam.

PREPARATION 46

3',5'-dichloro-4'-[(R)-2-oxo-trans-1-(4-triisopropylsilanyloxy cyclohexyl)-pyrrolidin-3-ylmethyl]-biphenyl-4-carboxylic acid Prepare the title compound essentially by the method of Preparation 42 in a 74% yield starting from 3',5'-dichloro-4'-[(R)-2-oxo-trans-1-(4-triisopropylsilanyloxy-cyclohexyl)-pyrrolidin-3-ylmethyl]-biphenyl-4-carboxylic acid methyl ester and sodium hydroxide: MS (m/z): 617 (M−H).

PREPARATION 47

4'-{(R)-cis-1-[4-(tert-Butyl-dimethyl-silanyloxy)-cyclohexyl]-2-oxo-pyrrolidin-3-ylmethyl}-3',5'-dichloro-biphenyl-4-carboxylic acid Treat a solution of trifluoro-methanesulfonic acid 4-{(R)-cis-1-[4-(tert-butyl-dimethyl-silanyloxy)-cyclohexyl]-2-oxo-pyrrolidin-3-ylmethyl}-3,5-dichloro-phenyl ester (3 g, 4.96 mmol) in 90 mL dimethoxyethane with triphenylphosphine (525 mg, 2 mmol). Degas by placing under vacuum and replacing atmosphere with nitrogen several times. Add Pd(OAc)$_2$ (150 mg, 0.67 mmol), 4-phenylboronic acid (0.82 g, 4.96 mmol), 15 mL methanol and then 12 mL 2 N sodium carbonate. Reflux for 2 hrs. Concentrate under vacuum and dilute the residue with 100 mL 5% aqueous citric acid and 100 mL ethyl acetate. Separate the layers, dry the organic layer over magnesium sulfate and concentrate under vacuum. Purify by silica gel chromatography using 70% (hexanes/ethyl acetate 90/10) in chloroform to recover 2.62 g solid.

PREPARATION 48

(R)-3-{3,5-dichloro-4'-[4-(2-fluoro-ethyl)-piperazine-1-carbonyl]-biphenyl-4-ylmethyl}-cis-1-(4-triisopropylsilanyloxy-cyclohexyl)-pyrrolidin-2-one Treat a mixture of 3',5'-dichloro-4'-[(R)-2-oxo-cis-1-(4-triisopropylsilanyloxy-cyclohexyl)-pyrrolidin-3-ylmethyl]-biphenyl-4-carboxylic acid (4 g, 5.46 mmol), 1-(2-fluoro-ethyl)-piperazine (2.97 g, 12.12 mmol) and diisopropylethylamine (3.13 g, 24.24 mmol) in 125 mL dichloromethane with 1-(3-dimethylaminopropyl)-3-ethyl-carbodiimide hydrochloride (3.1 g, 16.16 mmol) and stir at room temperature overnight. Dilute with 150 mL saturated sodium bicarbonate and separate layers. Wash the organic layer with 150 mL water then 100 mL brine. Extract the combined aqueous layers with 100 mL dichloromethane and combine with original organic layer. Dry over sodium sulfate, filter, concentrate, and purify via silica chromatography to give 4 g (67%) product as a foam: MS (m/z): 732 (M+).

PREPARATION 49

(Racemic)-cis-1-[4-(tert-Butyl-dimethyl-silanyloxy) cyclohexyl]-3-[3,5-dichloro-4'-(thiomorpholine-4-carbonyl)-biphenyl-4-ylmethyl]-pyrrolidin-2-one The title compound may be prepared essentially as described in Preparation 8a except for using 4'-{cis-1-[4-(tert-Butyl-dimethyl-silanyloxy)-cyclohexyl]-2-oxo-pyrrolidin-3-ylmethyl}-3',5'-dichloro-biphenyl-4-carboxylic acid and thiomorpholine.

TABLE 1

The preparations in Table 1 may be prepared essentially as described in Preparation 6a except for using 4'-{(R)-cis-1-[4-(tert-Butyl-dimethyl-silanyloxy)-cyclohexyl]-2-oxo-pyrrolidin-3-ylmethyl}-3',5'-dichloro-biphenyl-4-carboxylic acid (Preparation 44) and the amine is replaced with the amine as indicated.

| Preparation | Chemical Name | Amine |
|---|---|---|
| 50 | (R)-cis 1-[4-(tert-butyl-dimethyl-silanyloxy)-cyclohexyl]-3-[3,5-dichloro-4'-(morpholine-4-carbonyl)-biphenyl-4-ylmethyl]-pyrrolidin-2-one | HN⌒O (morpholine) |
| 51 | (R)-cis-1-[4-(tert-Butyl-dimethyl-silanyloxy)-cyclohexyl]-3-[3,5-dichloro-4'-(4-trifluoromethyl-piperidine-1-carbonyl)-biphenyl-4-ylmethyl]-pyrrolidin-2-one | 4-(trifluoromethyl)piperidine, CF$_3$ |
| 52 | (R)-cis-1-[4-(tert-Butyl-dimethyl-silanyloxy)-cyclohexyl]-3-[4'-(4-tert-butyl-piperazine-1-carbonyl)-3,5-dichloro-biphenyl-4-ylmethyl]-pyrrolidin-2-one | 4-tert-butylpiperazine, C(CH$_3$)$_3$ |

TABLE 1-continued

The preparations in Table 1 may be prepared essentially as described in Preparation 6a except for using 4'-{(R)-cis-1-[4-(tert-Butyl-dimethyl-silanyloxy)-cyclohexyl]-2-oxo-pyrrolidin-3-ylmethyl}-3',5'-dichloro-biphenyl-4-carboxylic acid (Preparation 44) and the amine is replaced with the amine as indicated.

| Preparation | Chemical Name | Amine |
|---|---|---|
| 53 | (R)-cis-1-[4-(tert-Butyl-dimethyl-silanyloxy)-cyclohexyl]-3-[3,5-dichloro-4'-([1,4]oxazepane-4-carbonyl)-biphenyl-4-ylmethyl]-pyrrolidin-2-one | (oxazepane structure) |
| 54 | (R)-cis-1-[4-(tert-Butyl-dimethyl-silanyloxy)-cyclohexyl]-3-[3,5-dichloro-4'-(4,4-difluoro-piperidine-1-carbonyl)-biphenyl-4-ylmethyl]-pyrrolidin-2-one | (4,4-difluoropiperidine) |
| 55 | (R)-cis-1-[4-(tert-Butyl-dimethyl-silanyloxy)-cyclohexyl]-3-[3,5-dichloro-4'-(3,3-difluoro-pyrrolidine-1-carbonyl)-biphenyl-4-ylmethyl]-pyrrolidin-2-one | (3,3-difluoropyrrolidine) |
| 56 | (R)-cis-1-[4-(tert-Butyl-dimethyl-silanyloxy)-cyclohexyl]-3-[3,5-dichloro-4'-(4-methoxy-piperidine-1-carbonyl)-biphenyl-4-ylmethyl]-pyrrolidin-2-one | (4-methoxypiperidine) |
| 57 | (R)-cis-1-[4-(tert-Butyl-dimethyl-silanyloxy)-cyclohexyl]-3-[3,5-dichloro-4'-((2R,6S)-2,6-dimethyl-morpholine-4-carbonyl)-biphenyl-4-ylmethyl]-pyrrolidin-2-one | (2,6-dimethylmorpholine) |
| 58 | 4-(4'-{(R)-cis-1-[4-(tert-Butyl-dimethyl-silanyloxy)-cyclohexyl]-2-oxo-pyrrolidin-3-ylmethyl}-3',5'-dichloro-biphenyl-4-carbonyl)-piperazine-1-carboxylic acid tert-butyl ester | (Boc-piperazine) |
| 59 | (R)-cis-1-[4-(tert-Butyl-dimethyl-silanyloxy)-cyclohexyl]-3-{3,5-dichloro-4'-[4-(2,2,2-trifluoro-ethyl)-piperazine-1-carbonyl]-biphenyl-4-ylmethyl}-pyrrolidin-2-one | (trifluoroethyl-piperazine) Lit ref for piperazine JOC 31, 11, 3867 (1966) |
| 60 | (R)-cis-1-[4-(tert-Butyl-dimethyl-silanyloxy)-cyclohexyl]-3-[3,5-dichloro-4'-((S)-2-oxa-5-aza-bicyclo[2.2.1]heptane-5-carbonyl)-biphenyl-4-ylmethyl]-pyrrolidin-2-one | (2-oxa-5-aza-bicyclo[2.2.1]heptane) |

PREPARATION 61

Cis-1-[4-(tert-butyl-dimethyl-silanyloxy)-cyclohexyl]-3-[3,5-dichloro-4'-(1,1-dioxo-1lambda*6*-thiomorpholine-4-carbonyl)-biphenyl-4-ylmethyl]-pyrrolidin-2-one Mix racemic cis-1-[4-(tert-butyl-dimethyl-silanyloxy)-cyclohexyl]-3-[3,5-dichloro-4'-(thiomorpholine-4-carbonyl)-biphenyl-4-ylmethyl]-pyrrolidin-2-one (320 mg, 0.5 mmol) with 25 mL dichloromethane and treat with meta-chloroperbenzoic acid (2 equivalents). Stir the mixture 3 hours then purify by ion exchange chromatography using and SAX cartridge and dichloromethane to recover 310 mg (92%) of a solid.

TABLE 2

The Preparation in Table 2 may be prepared essentially as described in Example 3 except for using the 3',5'-dichloro-4'-[(R)-2-oxo-trans-1-(4-triisopropylsilanyloxy cyclohexyl)-pyrrolidin-3-ylmethyl]-biphenyl-4-carboxylic acid and the amine is replaced with the amine as indicated.

| Preparation | Chemical Name | Amine | Comment |
|---|---|---|---|
| 62 | (R)-3-[3,5-Dichloro-4'-(4-trifluoromethyl-piperidine-1-carbonyl)-biphenyl-4-ylmethyl]-trans-1-(4-triisopropylsilanyloxy-cyclohexyl)pyrrolidin-2-one | (4-trifluoromethylpiperidine) | Coupling Procedure 1 |

TABLE 3

The Preparations in Table 3 may be prepared essentially as described in Preparation 8a except using 4'-{(R)-trans-1-[4-(tert-Butyl-dimethyl-silanyloxy)-cyclohexyl]-2-oxo-pyrrolidin-3-ylmethyl}-3',5'-dichloro-biphenyl-4-carboxylic acid (Preparation 39b) and the amine is replaced with the amine as indicated.

| Preparation | Chemical Name | R | Comment |
| --- | --- | --- | --- |
| 63 | (R)-trans-1-[4-(tert-Butyl-dimethyl-silanyloxy)-cyclohexyl]-3-{3,5-dichloro-4'-[4-(2,2,2-trifluoro-ethyl)-piperazine-1-carbonyl]-biphenyl-4-ylmethyl}-pyrrolidin-2-one | CF₃-CH₂-piperazine | Coupling Procedure 2 |
| 64 | (R)-trans-1-[4-(tert-Butyl-dimethyl-silanyloxy)-cyclohexyl]-3-[3,5-dichloro-4'-(morpholine-4-carbonyl)-biphenyl-4-ylmethyl]-pyrrolidin-2-one | morpholine | Coupling Procedure 2 |
| 65 | (R)-trans-1-[4-(tert-Butyl-dimethyl-silanyloxy)-cyclohexyl]-3-[3,5-dichloro-4'-(thiomorpholine-4-carbonyl)-biphenyl-4-ylmethyl]-pyrrolidin-2-one | thiomorpholine | Coupling Procedure 2 |
| 66 | (R)-trans-1-[4-(tert-Butyl-dimethyl-silanyloxy)-cyclohexyl]-3-{3,5-dichloro-4'-[4-(2-fluoro-ethyl)-piperazine-1-carbonyl]-biphenyl-4-ylmethyl}-pyrrolidin-2-one | F-CH₂CH₂-piperazine | Coupling Procedure 2 |
| 67 | (R)-trans-1-[4-(tert-Butyl-dimethyl-silanyloxy)-cyclohexyl]-3-[4'-(4-tert-butyl-piperazine-1-carbonyl)-3,5-dichloro-biphenyl-4-ylmethyl]-pyrrolidin-2-one | C(CH₃)₃-piperazine | Coupling Procedure 2 |

PREPARATION 68

Trans-methanesulfonic acid 4-{(R)-3-[3,5-dichloro-4'-(4-trifluoromethyl-piperidine-1-carbonyl)-biphenyl-4-ylmethyl]-2-oxo-pyrrolidin-1-yl}-cyclohexyl ester Dissolve (R)-3-[3,5-dichloro-4'-(4-trifluoromethyl-piperidine-1-carbonyl)-biphenyl-4-ylmethyl]-trans-1-(4-hydroxy-cyclohexyl)-pyrrolidin-2-one (0.419 g, 0.70 mmol) in 10 ml of dry dichloromethane at 0° C. Add triethylamine (0.18 ml, 1.41 mmol) followed by methanesulfonic anhydride (0.06 ml, 0.77 mmol). Stir at room temperature for 5 hours. Quench with aqueous 1N hydrochloric acid and extract with ethyl acetate. Wash the extract with aqueous 1N hydrochloric acid, saturated aqueous sodium bicarbonate then brine. Dry over magnesium sulfate, filter, and concentrate under vacuum. Filter through a short silica plug to recover 0.45 g (95%) of the title compound: MS (m/z): 675 (M+).

PREPARATION 69

(R)-3-(2,6-dichloro-4-hydroxy-benzyl)-1-(tetrahydro-pyran-4-yl)-pyrrolidin-2-one Treat a solution of 4-(4-(R)-benzyl-2-oxo-oxazolidin-3-yl)-3-(4-benzyloxy-2,6-dichloro-benzyl)-4-oxo-butyraldehyde (Preparation 27) (10.4 g, 20 mmol) and 4-aminotetrahydropyran (2 g, 20 mmol) in dichloromethane (100 mL) with acetic acid (1 mL, 20 mmol). Stir the reaction 1 hr at room temperature then add sodium triacetoxyborohydride (12.6 g, 60 mmol) and stir for an additional 4 hr at room temperature. Quench with water and separate the organic layer. Wash with brine, dry over magnesium sulfate, filter, and remove the solvent under vacuum. Purify by silica gel column chromatography using hexanes:ethyl acetate to afford 4.93 g (57%) of desired product: MS (m/z): 434 (M+).

PREPARATION 70

(R)-3-(2,6-dichloro-4-hydroxy-benzyl)-1-(tetrahydro-pyran-4-yl)-pyrrolidin-2-one Hydrogenate a solution of (R)-3-(2,6-dichloro-4-hydroxy-benzyl)-1-(tetrahydro-pyran-4-yl)-pyrrolidin-2-one (4.9 g, 11 mmol) in ethyl acetate (50 mL) with 20% by weight palladium hydroxide on carbon (0.5 g) and 1 atm of hydrogen. Filter through Celite® to remove the catalyst and concentrate under vacuum to afford 3.8 g (97%) of desired product. MS (m/z): 344 (M+).

PREPARATION 71

Trifluoro-methanesulfonic acid 3,5-dichloro-4-[(R)-2-oxo-1-(tetrahydro-pyran-4-yl)-pyrrolidin-3-ylmethyl]-phenyl ester Cool a solution of (R)-3-(2,6-dichloro-4-hydroxy-benzyl)-1-(tetrahydro-pyran-4-yl)-pyrrolidin-2-one (3.8 g, 11 mmol) in pyridine (50 mL) to 0° C. and treat with trifluoromethanesulfonic anhydride (2.8 mL, 16.6 mmol). Allow the reaction to stir for 2 hr at room temperature then quench with 1N hydrochloric acid and extract with ethyl acetate. Wash the organic layer with brine, dry over magnesium sulfate, and filter. Concentrate under vacuum to afford 4.58 g (87%) of desired product: MS (m/z): 475 (M+).

PREPARATION 72

3',5'-dichloro-4'-[(R)-2-oxo-1-(tetrahydro-pyran-4-yl)-pyrrolidin-3-ylmethyl]-biphenyl-4-carboxylic acid methyl ester Treat a solution of trifluoro-methanesulfonic acid 3,5-dichloro-4-[(R)-2-oxo-1-(tetrahydro-pyran-4-yl)-pyrrolidin-3-ylmethyl]-phenyl ester (3.0 g, 6.3 mmol), 4-methoxycarbonylphenylboronic acid (2.3 g, 13 mmol), and tetrakis(triphenylphosphine)palladium(0) (0.73 g, 0.63 mmol) in dimethoxyethane (40 mL) with 2M aqueous potassium carbonate (9.5 mL). Heat the mixture to 80° C. overnight. Cool to room temperature, quench with 1N hydrochloric acid and extract with ethyl acetate. Wash the organic layer with brine, dry over magnesium sulfate, and filter. Purify the crude material by silica gel chromatography using hexanes:ethyl acetate to afford 2.56 g (88%) of desired product: MS (m/z): 462 (M+).

PREPARATION 73

3',5'-dichloro-4'-[(R)-2-oxo-1-(tetrahydro-pyran-4-yl)-pyrrolidin-3-ylmethyl]-biphenyl-4-carboxylic acid Treat a solution of 3',5'-dichloro-4'-[(R)-2-oxo-1-(tetrahydro-pyran-4-yl)-pyrrolidin-3-ylmethyl]-biphenyl-4-carboxylic acid methyl ester (2.56 g, 5.5 mmol) in methanol (25 mL) with 5N aqueous sodium hydroxide (5.5 mL). Heat the reaction to 60° C. and stir for 1 hr. Cool to room temperature, quench with 1N hydrochloric acid and extract the aqueous with ethyl acetate. Wash the organic layer with brine, dry over magnesium sulfate, and filter. Remove the solvent under vacuum to afford 2.48 g (100%) of desired product: MS (m/z): 448 (M+).

PREPARATION 74

(R)-3-[3,5-dichloro-4'-(4,4-difluoro-piperidine-1-carbonyl)-biphenyl-4-ylmethyl]-trans-1-(4-triisopropylsilanyloxy-cyclohexyl)-pyrrolidin-2-one Prepare the title compound in a quantitative yield by coupling procedure 1 starting from 3',5'-dichloro-4'-[(R)-2-oxo-trans-1-(4-triisopropylsilanyloxy-cyclohexyl)-pyrrolidin-3-ylmethyl]-biphenyl-4-carboxylic acid and 4-difluoropiperidine hydrochloride.

Mix 3',5'-dichloro-4'-[(R)-2-oxo-trans-1-(4-triisopropylsilanyloxy-cyclohexyl)-pyrrolidin-3-ylmethyl]-biphenyl-4-carboxylic acid (0.15 g, 0.24 mmol), N-ethyl-N'-(3-dimethylaminopropyl)carbodiimide hydrochloride (0.058 g, 0.3 mmol), N-methylmorpholine (0.1 mL, 0.9 mmol), hydroxy benzotriazole (0.041 g, 0.3 mmol) and 4-difluoropiperidine hydrochloride (0.08 g, 0.49 mmol) in $CH_2Cl_2$ (15 mL). Stir the reaction for 12 hours at room temperature then quench with 1N aqueous hydrochloric acid and extract with ethyl acetate. Wash the extract with saturated aqueous sodium bicarbonate then brine. Dry over magnesium sulfate, filter, and concentrate. Purify by silica gel chromatography to recover 0.175 g (100%) of the title compound.

PREPARATION 75

(R)-3-[3,5-dichloro-4'-(4-trifluoromethyl-piperidine-1-carbonyl)-biphenyl-4-ylmethyl]-trans-1-(4-triisopropylsilanyloxy-cyclohexyl)-pyrrolidin-2-one Prepare the title compound in a 51% yield by coupling procedure 1 starting from 3',5'-dichloro-4'-[(R)-2-oxo-trans-1-(4-triisopropylsilanyloxy-cyclohexyl)-pyrrolidin-3-ylmethyl]-biphenyl-4-carboxylic acid and 4-trifluoromethyl-piperidine hydrochloride.

Mix 3',5'-dichloro-4'-[(R)-2-oxo-trans-1-(4-triisopropylsilanyloxy-cyclohexyl)-pyrrolidin-3-ylmethyl]-biphenyl-4-carboxylic acid (0.94 g, 1.52 mmol), N-ethyl-N'-(3-dimethylaminopropyl)carbodiimide hydrochloride (0.358 g, 1.83 mmol), N-methylmorpholine (0.50 mL, 4.57 mmol), hydroxy benzotriazole (0.511 g, 1.52 mmol) and 4-trifluoromethyl-piperidine hydrochloride (0.466 g, 3.05 mmol) in $CH_2Cl_2$ (15 mL). Stir the reaction for 12 hours at room temperature then quench with 1N aqueous hydrochloric acid and extract with ethyl acetate. Wash the extract with saturated aqueous sodium bicarbonate then brine. Dry over magnesium sulfate, filter, and concentrate. Purify by silica gel chromatography to recover 0.586 g (51%) of the title compound: MS (m/z): 753 (M+).

PREPARATION 76

3-[3-Chloro-2'-(4-methyl-piperazine-1-carbonyl)-biphenyl-4-ylmethyl]-1-cyclohexyl-pyrrolidin-2-one hydrochloride salt Charge a vial with 3'-chloro-4'-(1-cyclohexyl-2-oxo-pyrrolidin-3-ylmethyl)-biphenyl-2-carboxylic acid (70 mg, 0.17 mmol), EDCI (65 mg, 0.34 mmol) and HOBt (23 mg, 0.17 mmol). Dissolve in DMF (0.1 M) and add triethylamine (95 µL, 0.68 mmol) and N-methyl piperazine (34 mg, 0.34 mmol). Stir at room temperature overnight. Pour into water and extract with ether. Dry over sodium sulfate, filter and concentrate. Purify over silica gel. Dissolve the residue in methylene chloride and acidify with 4N HCl in dioxane.

Concentrate in vacuo which affords 57 mg (63%) of the title compound: Mass spectrum m/z=494.3 (M+H–HCl).

PREPARATION 77

4-Bromo-2-trifluoromethoxy-benzaldehyde

Add 4-bromo-1-iodo-2-(trifluoromethoxy)benzene (22.04 g, 60 mmol) to a 1000 mL 3-neck flask equipped with a magnetic stir bar, thermocouple, addition funnel, and $N_2$ inlet and replace the atmosphere in the flask with nitrogen. After adding anhydrous THF (300 mL), cool the mixture to –74° C. and treat dropwise with a solution of t-butyllithium (70 mL of 1.7 M solution, 120 mmol). Stir the resulting solution for 90 minutes and then treated dropwise with a solution of N-formyl morpholine (14.52 g, 126 mmol) in THF (15 mL). Stir the mixture an additional 15 minutes at –74° C. and then allow to warm to 0° C. over 1 hour. Quench the reaction by the adding 0.25 M citric acid (200 mL) and extract with ethyl acetate (1×300 mL). Wash the organic layer with saturated sodium chloride solution (1×200 mL), dry over anhydrous magnesium sulfate, filter through Celite®, and concentrate to an oil. Purify the crude product via silica gel chromatography eluting with hexanes to afford 8.24 g (51%) of the product as white crystals: $^1$H NMR (300 MHz, $CDCl_3$) δ 10.32 (s, 1H), 7.85 (d, J=8.3 Hz, 1H), 7.63-7.53 (m, 2H).

PREPARATION 78

(4-Bromo-2-trifluoromethoxy-phenyl)-methanol

Prepare the title compound essentially by the method of Preparation 4 in a 98% yield starting from 4-bromo-2-trifluoromethoxy-benzaldehyde: $^1$H NMR (300 MHz, $CDCl_3$) δ 7.50-7.44 (m, 2H), 7.43-7.39 (m, 1H), 7.74 (d, J=5.8 Hz, 2H), 1.79 (t, J=6.1 Hz, 1H).

PREPARATION 79

4-Bromo-1-bromomethyl-2-trifluoromethoxy-benzene

Add (4-bromo-2-(trifluoromethoxy)phenyl)methanol (9.757 g, 36 mmol) and dichloromethane (180 mL) to a 500 mL flask equipped with a magnetic stir bar and $N_2$ inlet. Cool the solution to 0° C. and then treat with triphenylphosphine (11.33 g, 43 mmol) and carbon tetrabromide (14.26 g, 43 mmol). Stir the reaction at 0° C. for 45 minutes, warm to room temperature and stir an additional 1 hour. Wash the reaction with water (2×180 mL) and saturated sodium chloride solution (1×180 mL), then dry over anhydrous magnesium sulfate. Filter through Celite® and concentrate under vacuum to dryness. Dissolve the residue in hexanes, filter to remove the triphenyl phosphine oxide, and concentrate to a colorless oil. Purify the crude product via silica gel chromatography eluting with hexanes to afford 10.5 g (88%) of the product as a colorless oil: $^1$H NMR (300 MHz, $CDCl_3$) δ 7.46-7.40 (m, 2H), 7.38-7.33 (m, 1H), 4.46 (s, 3H).

PREPARATION 80

4-Bromo-1-dibromomethyl-2-trifluoromethyl-benzene

Add 4-methyl-3(trifluoromethyl) bromo benzene (5.0 g, 20.9 mmol), N-bromosuccinimide (9.308 g, 52.3 mmol), benzoyl peroxide (200 mg, 0.84 mmol), and carbon tetrachloride (100 mL) to a 500 mL flask equipped with a magnetic stir bar, reflux condenser, and $N_2$ inlet. Reflux the reaction with stirring for 16 hours then cool to room temperature. Concentrate the mixture under vacuum to an orange residue and add hexanes. Filter through a small plug of silica gel and concentrate the filtrate under vacuum to give 7.6 g (92%) of the product as a white solid: $^1$H NMR (300 MHz, $CDCl_3$) δ 8.08 (d, 1H, J=8.3 Hz), 7.80 (dd, 1H, J=1.8 Hz, J=8.6 Hz), 7.70 (d, 1H, J=1.9 Hz), 7.91 (s, 1H).

PREPARATION 81

4-Bromo-2-trifluoromethyl-benzaldehyde

Combine 4-bromo-1-(dibromomethyl)-2-(trifluoromethyl)benzene (6.66 g, 16.8 mmol), silver nitrate (14.8 g, 87.3 mmol), THF (250 mL), and water (35 mL) in a 500 mL flask equipped with a magnetic stir bar, reflux condenser, and $N_2$ inlet. Reflux the mixture while stirring for 2.5 hours then cool to room temperature. Filter the reaction through Celite®, add ethyl acetate (250 mL) and wash with water (2×200 mL) then saturated aqueous sodium chloride solution (1×200 mL). Dry over anhydrous magnesium sulfate, concentrate to an orange oil, and purify the crude product via silica gel chromatography eluting with hexanes to afford 3.46 g (81%) of the product as a clear oil: $^1$H NMR (300 MHz, $CDCl_3$) δ 10.35-10.33 (m, 1H), 8.0 (d, 1H, J=8.3 Hz), 7.93 (d, 1H, J=1.4 Hz), 7.86 (dd, 1H, J=1.2 Hz, J=8.3 Hz).

PREPARATION 82

4-Bromo-1-bromomethyl-2-trifluoromethyl-benzene

Treat a mixture of 4-bromo-2-(trifluoromethyl)benzaldehyde (6.52 g, 25.8 mmol) and methanol (250 mL) in a 500 mL flask with sodium borohydride (778 mg, 20.6 mmol). Stir the reaction at room temperature for 1 hour then dilute with ethyl acetate (300 mL). Wash with water (2×200 mL) and saturated sodium chloride solution (1×200 mL), then dry over anhydrous magnesium sulfate. After filtering, concentrate the solution under vacuum to dryness. Add dimethylformamide (250 mL) to the residue and cool in an ice bath before treating with carbon tetrabromide (12.78 g, 38.5 mmol) and triphenylphosphine (10.11 g, 38.5 mmol) for 3 hours. Add ethyl acetate (300 mL) and wash with water (2×200 mL) then saturated sodium chloride solution (1×200 mL). Dry over anhydrous magnesium sulfate and concentrate under vacuum. Purify the crude product via silica gel chromatography eluting with hexanes to afford 6.02 g (74%) of the product as a clear oil: $^1$H NMR (300 MHz, $CDCl_3$) δ 7.78 (d, 1H, J=1.9 Hz), 7.68 (dd, 1H, J=1.9 Hz, J=8.3 Hz), 7.47 (d, 1H, J=8.3 Hz), 4.57 (s, 2H).

TABLE 4

The Preparations in Table 4 are prepared essentially by the method of Preparation 8 except for the substitution of the 2-bromomethyl-1,3-dichloro-5-methoxy-benzene with the reagent as shown in column 3.

| Preparation | Chemical name | Reagent used | Physical data |
|---|---|---|---|
| 83 | 3-(4-Bromo-2-trifluoromethoxy-benzyl)-1-cyclohexyl-pyrrolidin-2-one | Preparation 79 | MS (m/z): 421 (M + 1) |
| 84 | 3-(4-Bromo-2-trifluoromethyl-benzyl)-1-cyclohexyl-pyrrolidin-2-one | Preparation 82 | MS (m/z): 404 (M + 1). |

PREPARATION 85

4'-(1-Cyclohexyl-2-oxo-pyrrolidin-3-ylmethyl)-3'-trifluoromethoxy-biphenyl-4-carboxylic acid methyl ester Combine 3-(4-bromo-2-(trifluoromethoxy)benzyl)-1-cyclohexylpyrrolidin-2-one (9.68 g, 23.0 mmol), 4-(methoxycarbonyl)phenylboronic acid (8.29 g, 46.1 mmol), dichloro[1,1'-bis(diphenylphosphino)ferrocene]palladium (II) (2.87 g, 3.9 mmol), dioxane (400 mL) and DMSO (8 mL) in a 1 L flask equipped with a magnetic stir bar, reflux condenser, and $N_2$ inlet. Add potassium acetate (9.04 g, 92.1 mmol) and heat to 80° C. while stirring for 2 hours. Cool to room temperature, filter through silica gel and rinse with ethyl acetate (400 mL). Wash with water (2×400 mL) and saturated sodium chloride solution (1×400 mL), then dry over anhydrous magnesium sulfate and concentrate to an oil. Purify the crude product via silica gel chromatography eluting with 10% to 20% ethyl acetate in hexanes to afford 9.86 g (90%) of the product as a white solid. MS (m/z): 476 (M+1).

PREPARATION 86

4'-(1-Cyclohexyl-2-oxo-pyrrolidin-3-ylmethyl)-3'-trifluoromethyl-biphenyl-4-carboxylic acid methyl ester Prepare the title compound essentially by the method described for Preparation 85 except use 3-(4-Bromo-2-trifluoromethyl-benzyl)-1-cyclohexyl-pyrrolidin-2-one (Preparation 84). MS (m/z): 460 (M+1).

PREPARATION 87

4'-(1-Cyclohexyl-2-oxo-pyrrolidin-3-ylmethyl)-3'-trifluoromethoxy-biphenyl-4-carboxylic acid Combine methyl 4'-((1-cyclohexyl-2-oxopyrrolidin-3-yl)methyl)-3'-(trifluoromethoxy)biphenyl-4-carboxylate (9.15 g, 19.2 mmol), THF (175 mL) and water (175 mL) in a 500 mL flask equipped with a magnetic stir bar. While stirring in an ice bath treat the mixture with lithium hydroxide monohydrate (2.42 g, 57.7 mmol). Stir the reaction for 30 minutes, warm to room temperature and stir an additional 16 hours. Dilute with ethyl acetate (250 mL) and wash with water (250 mL). Add hydrochloric acid (2N) to the aqueous layer until it is acidic then extract with ethyl acetate (2×300 mL). Wash the extracts with aqueous saturated sodium chloride solution (1×250 mL), dry over anhydrous magnesium sulfate and concentrate to afford 6.98 g (79%) of the product as a white solid: MS (m/z): 462 (M+1).

PREPARATION 88

4'-(1-Cyclohexyl-2-oxo-pyrrolidin-3-ylmethyl)-3'-trifluoromethyl-biphenyl-4-carboxylic acid Prepare the title compound essentially by the method described for Preparation 87 except use 4'-(1-Cyclohexyl-2-oxo-pyrrolidin-3-ylmethyl)-3'-trifluoromethyl-biphenyl-4-carboxylic acid methyl ester. MS (m/z): 446 (M+1).

TABLE 5

The Preparations in Table 5 are prepared essentially by the method of Preparation 74 except for the substitution of 4-difluoropiperidine hydrochloride with the reagent as shown in column 3.

| Preparation | Structure and Chemical name | Reagent used | Physical data |
|---|---|---|---|
| 89 | 3',5'-Dichloro-4'-[(R)-2-oxo-trans-1-(4-triisopropylsilanyloxy-cyclohexyl)-pyrrolidin-3-ylmethyl]-biphenyl-4-carboxylic acid methylcarbamoylmethyl-amide | $H_2N$—CH$_2$—C(O)—NH—CH$_3$ | MS (m/z): 688 (M+) |
| 90 | (R)-3-[3,5-Dichloro-4'-(4-methyl-piperidine-1-carbonyl)-biphenyl-4-ylmethyl]-trans-1-(4-triisopropylsilanyloxy-cyclohexyl)-pyrrolidin-2-one | 4-methylpiperidine | MS (m/z): 699 (M+) |
| 91 | 3',5'-Dichloro-4'-[(R)-2-oxo-trans-1-(4-triisopropylsilanyloxy-cyclohexyl)-pyrrolidin-3-ylmethyl]-biphenyl-4-carboxylic acid dimethylcarbamoylmethyl-amide | $H_2N$—CH$_2$—C(O)—N(CH$_3$)$_2$ | MS (m/z): 702 (M+) |
| 92 | 3',5'-Dichloro-4'-[(R)-2-oxo-trans-1-(4-triisopropylsilanyloxy-cyclohexyl)-pyrrolidin-3-ylmethyl]-biphenyl-4-carboxylic acid carbamoylmethyl-amide | $H_2N$—CH$_2$—C(O)—NH$_2$ | MS (m/z): 674 (M+) |

PREPARATION 93

(R)-cis-1-[4-(tert-Butyl-dimethyl-silanyloxy)-cyclohexyl]-3-{3,5-dichloro-4'-[4-(2-fluoro-ethyl)-piperazine-1-carbonyl]-biphenyl-4-ylmethyl}-pyrrolidin-2-one Prepare the titled compound by the procedure in Preparation 6a using 4'-{(R)-cis-1-[4-(tert-Butyl-dimethyl-silanyloxy)-cyclohexyl]-2-oxo-pyrrolidin-3-ylmethyl}-3',5'-dichloro-biphenyl-4-carboxylic acid and 1-(2-fluoro-ethyl)-piperazine.

PREPARATION 94

(R)-3-(4-Benzyloxy-2,6-dichloro-benzyl)-trans-1-(4-methoxy-cyclohexyl)-pyrrolidin-2-one Suspend sodium hydride (0.45 g, 11.15 mmol) in 10 ml of dry dimethylformamide at 0° C. After stirring for 10 minutes, add the solution of (R)-3-(4-benzyloxy-2,6-dichloro-benzyl)-trans-1-(4-hydroxy-cyclohexyl)-pyrrolidin-2-one (2.50 g, 5.58 mmol) in 5 ml of dry dimethylformamide. Stir the resulting mixture for 15 minutes at 0° C. Add iodomethane (1.40 ml, 22.32 mmol) and allow the mixture to warm to room temperature. Stir the reaction at room temperature for an additional 12 hours then quench with water and filter the white precipitate. Dry under vacuum to recover 2.59 g of the title compound: MS (m/z): 462 (M+).

PREPARATION 95

(R)-3-(2,6-Dichloro-4-hydroxy-benzyl)-trans-1-(4-methoxy-cyclohexyl)-pyrrolidin-2-one Stir (R)-3-(4-benzyloxy-2,6-dichloro-benzyl)-trans-1-(4-methoxy-cyclohexyl)-pyrrolidin-2-one (2.59 g, 5.61 mmol) and palladium hydroxide (20% on carbon) (0.300 g, 10% by weight) in 100 ml of ethyl acetate. Bubble hydrogen gas through the solution while stirring at room temperature for 5 minutes. Stir the mixture under the hydrogen gas atmosphere for 5 hours. Filter through Celite® and concentrate under vacuum to recover 2.08 g of the title compound (99%). MS (m/z): 372 (M+).

PREPARATION 96

Trifluoro-methanesulfonic acid 3,5-dichloro-4-[(R)-trans-1-(4-methoxy-cyclohexyl)-2-oxo-pyrrolidin-3-ylmethyl]-phenyl ester Dissolve (R)-3-(2,6-dichloro-4-hydroxy-benzyl)-trans-1-(4-methoxy-cyclohexyl)-pyrrolidin-2-one (2.08 g, 5.63 mmol) in 15 ml of dry pyridine at 0° C. Add trifluoromethanesulfonic anhydride (1.42 ml, 8.45 mmol) dropwise. Stir at room temperature for 2 hours. Quench with 1N HCl and extract with ethyl acetate. Wash the extract with 1N HCl, saturated aqueous sodium bicarbonate then brine. Dry over magnesium sulfate, filter, and concentrate under vacuum. Purify by flash column chromatography recover 2.134 g (76%) of the title compound: MS (m/z): 504 (M+).

PREPARATION 97

3',5'-Dichloro-4'-[(R)-trans-1-(4-methoxy-cyclohexyl)-2-oxo-pyrrolidin-3-ylmethyl]-biphenyl-4-carboxylic acid methyl ester Mix trifluoro-methanesulfonic acid 3,5-dichloro-4-[(R)-trans-1-(4-methoxy-cyclohexyl)-2-oxo-pyrrolidin-3-ylmethyl]-phenyl ester (2.134 g, 4.24 mmol), (4-methoxycarbonylphenyl)boronic acid (0.926 g, 5.09 mmol), tetrakis(triphenylphosphine)palladium(0) (0.490 g, 0.42 mmol) and 6.36 ml of 2M solution of $K_2CO_3$ in DME (10 mL). Stir for 12 hours at 80° C. Quench the reaction with water and extract with ethyl acetate. Wash the extract with brine and dry over magnesium sulfate. Purify by flash chromatography to recover 1.68 g (81%) of the title compound: MS (m/z): 490 (M+).

PREPARATION 98

3',5'-Dichloro-4'-[(R)-trans-1-(4-methoxy-cyclohexyl)-2-oxo-pyrrolidin-3-ylmethyl]-biphenyl-4-carboxylic acid Combine 3',5'-dichloro-4'-[(R)-trans-1-(4-methoxy-cyclohexyl)-2-oxo-pyrrolidin-3-ylmethyl]-biphenyl-4-carboxylic acid methyl ester (1.60 g, 3.3 mmol), MeOH (15 mL) and 1N NaOH solution (15 mL). Stir for 3 hours at 70° C. Concentrate under vacuum and quench with 1N HCl. Filter the white precipitate and rinse the solid with water. Dry under vacuum to recover 1.32 g (86%) of the title compound: MS (m/z): 476 (M+).

EXAMPLE 1

3',5'-dichloro-4'-(1-cyclohexyl-2-oxo-pyrrolidin-3-ylmethyl)-3-fluoro-biphenyl-4-carboxylic acid amide

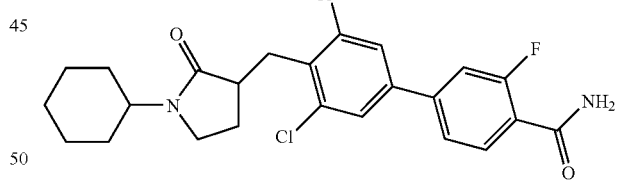

Add potassium carbonate (83 mg, 0.6 mmol) and hydrogen peroxide (30% in water, 0.5 mL) to a solution of Preparation 13 (3',5'-dichloro-4'-(1-cyclohexyl-2-oxo-pyrrolidin-3-ylmethyl)-3-fluoro-biphenyl-4-carbonitrile) (88 mg, 0.2 mmol) in DMSO (3 mL). Stir the reaction at room temperature for 12 h. Partition the mixture between ethyl acetate (20 mL) and water (20 mL). Separate the organic layer, wash three times with water (15 mL each) then brine (15 mL). After drying the organic layer over sodium sulfate, filter and concentrate under vacuum. Purify the residue by silica gel chromatography with 1:1 ethyl acetate/hexane to afford the title compound: MS (m/z): 463 (M+).

EXAMPLE 2

1-Cyclohexyl-3-{3,5-dichloro-4'-[4-(2-hydroxy-ethyl)-piperazine-1-carbonyl]-biphenyl-4-ylmethyl}-pyrrolidin-2-one hydrochloride salt

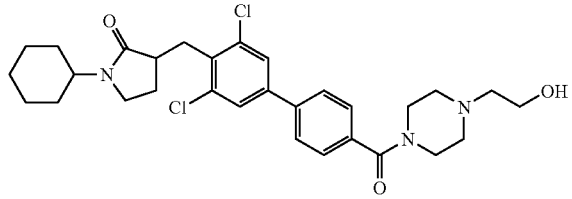

Combine Preparation 10 (trifluoro-methanesulfonic acid 3,5-dichloro-4-(1-cyclohexyl-2-oxo-pyrrolidin-3-ylmethyl)-phenyl ester) (250 mg, 0.53 mmol), 4-chlorocarbonylphenyl-boronic anhydride (263 mg, 0.53 mmol) and Pd(PPh$_3$)$_4$ (61 mg, 0.053 mmol) and purge with nitrogen. Add 2-(piperazin-1-yl)ethanol (0.32 mL, 2.6 mmol) followed quickly by dimethoxyethane (5 mL) and 2M sodium carbonate (1 mL) and heat to 80° C. for 1 hour. Cool to room temperature and pour into 1N sodium hydroxide. Extract with ethyl acetate and wash the organic layer twice with water, followed by brine. Dry over sodium sulfate and concentrate in vacuo. Purify on SCX column (load and wash with methanol, elute with 2M ammonia in methanol). Dissolve resultant oil in methylene chloride. Add 2M hydrochloric acid in ether (1 mL) and concentrate under vacuum. Re-dissolve in small amount of methylene chloride and add dropwise to vigorously stirred ether. Filter precipitate and dry in vacuum oven to afford 231 mg (74%) of the title compound: MS (m/z): 558 (M+).

EXAMPLE 3

1-cyclohexyl-3-[3,5-dichloro-4'-(piperidine-1-carbonyl)-biphenyl-4-ylmethyl]-pyrrolidin-2-one

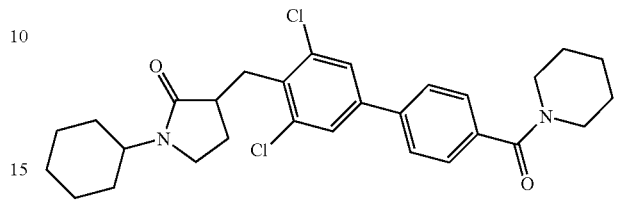

Coupling Procedure 1

Dissolve 3',5'-dichloro-4'-(1-cyclohexyl-2-oxo-pyrrolidin-3-ylmethyl)-biphenyl-4-carboxylic acid (0.200 g, 0.448 mmol) in dichloromethane (5 mL) and add piperidine (50 mg., 0.582 mmol) as well as diisopropylethylamine (0.26 mL, 1.48 mmol) under inert atmosphere. Chill reaction on ice bath (0° C.) and add (N-ethyl-N'-(3-dimethylaminopropyl)carbo-diimide hydrochloride (0.112 g, 0.582 mmol). Allow reaction to rise to room temperature over 2 hours, dilute with dichloromethane (50 mL) and wash with 1.0 N sodium hydroxide (30 mL) and brine (30 mL). Collect organic phase, dry over anhydrous magnesium sulfate and concentrate under reduced pressure. Purify by silica gel chromatography to obtain 109 mg (47%) of the product as an off white solid: MS (m/z): 513 (M+).

TABLE 6

The Examples in Table 6 may be prepared essentially as described by the coupling procedure 1 in Example 3 except for the amine is replaced with the amine as indicated.

| Example | Structure and name | Amine | Mass Spec |
|---|---|---|---|
| 4 | 1-Cyclohexyl-3-[3,5-dichloro-4'-(morpholine-4-carbonyl)-biphenyl-4-ylmethyl]-pyrrolidin-2-one | Morpholine | MS (m/z) 515 (M+) |
| 5 | 3',5'-Dichloro-4'-(1-cyclohexyl-2-oxo-pyrrolidin-3-ylmethyl)-biphenyl-4-carboxylic acid bis-(2-hydroxy-ethyl)-amide | | MS (m/z) 561 (M+) |

PREPARATION 6a 1-cyclohexyl-3-[3,5-dichloro-4'-(4-methyl-piperazine-1-carbonyl)-biphenyl-4-ylmethyl]-pyrrolidin-2-one

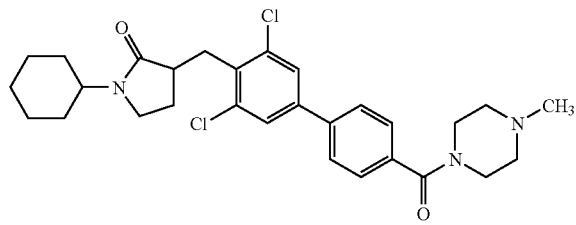

Coupling Procedure 2

Dissolve 3',5'-dichloro-4'-(1-cyclohexyl-2-oxo-pyrrolidin-3-ylmethyl)-biphenyl-4-carboxylic acid (10 g, 22.40 mmol) in dichloromethane (100 mL) and add 1,1'-carbonyldiimidazole (3.81 g, 23.5 mmol). Stir under argon atmosphere at room temperature 1 hour then add N-methylpiperazine (2.36 g, 23.5 mmol). Stir 1 hour, dilute reaction with water, separate layers then wash sequentially with 1.0 N sodium hydroxide, water and brine. Collect organic phase, dry over anhydrous magnesium sulfate and concentrate under reduced pressure. Purify via flash chromatography using 5% methanol in dichloromethane to recover 10.8 g (78%) of the product as a white solid: MS (m/z): 528 (M+).

TABLE 7

The Examples or preparations in Table 7 may be prepared essentially as described by coupling procedure 2 in Preparation 6a except for the amine is replaced with the amine as indicated.

| Example or Preparation | Structure and name | Amine | Mass Spec |
|---|---|---|---|
| 7 | 1-Cyclohexyl-3-[3,5-dichloro-4'-(4-isopropyl-piperazine-1-carbonyl)-biphenyl-4-ylmethyl]-pyrrolidin-2-one | | MS (m/z) 556 (M+) |
| Preparation 8a | 3',5'-Dichloro-4'-(1-cyclohexyl-2-oxo-pyrrolidin-3-ylmethyl)-biphenyl-4-carboxylic acid (2-pyrrolidin-1-yl-ethyl)-amide | | MS (m/z) 542 (M+) |
| 9 | | | MS (m/z) 516 (M+) |

TABLE 7-continued

The Examples or preparations in Table 7 may be prepared essentially as described by coupling procedure 2 in Preparation 6a except for the amine is replaced with the amine as indicated.

| Example or Preparation | Structure and name | Amine | Mass Spec |
|---|---|---|---|
| | 3',5'-Dichloro-4'-(1-cyclohexyl-2-oxo-pyrrolidin-3-ylmethyl)-biphenyl-4-carboxylic acid (2-dimethylamino-ethyl)-amide | | |
| 10 | 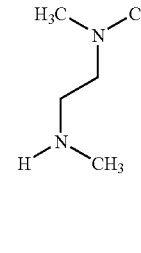 3',5'-Dichloro-4'-(1-cyclohexyl-2-oxo-pyrrolidin-3-ylmethyl)-biphenyl-4-carboxylic acid (2-dimethylamino-ethyl)-methyl-amide | | MS (m/z) 530 (M+) |
| Preparation 11a | 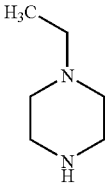 1-Cyclohexyl-3-[3,5-dichloro-4'-(4-ethyl-piperazine-1-carbonyl)-biphenyl-4-ylmethyl]-pyrrolidin-2-one | | MS (m/z) 542 (M+) |
| 12 | 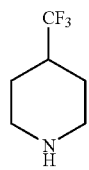 1-Cyclohexyl-3-[3,5-dichloro-4'-(4-trifluoromethyl-piperidine-1-carbonyl)-biphenyl-4-ylmethyl]-pyrrolidin-2-one | | MS (m/z) 581 (M+) |

TABLE 7-continued

The Examples or preparations in Table 7
may be prepared essentially as
described by coupling procedure 2 in Preparation 6a
except for the amine is replaced with
the amine as indicated.

| Example or Preparation | Structure and name | Amine | Mass Spec |
|---|---|---|---|
| 13 | 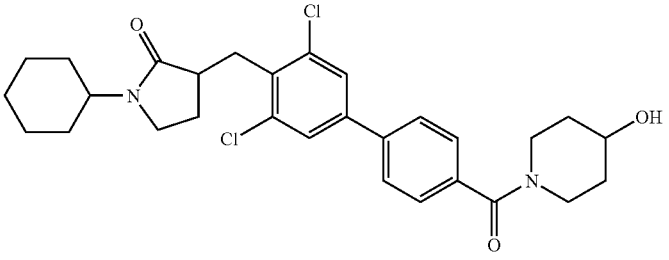<br>1-Cyclohexyl-3-[3,5-dichloro-4'-(4-hydroxy-piperidine-1-carbonyl)-biphenyl-4-ylmethyl]-pyrrolidin-2-one | 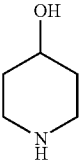 | MS (m/z) 529 (M+) |
| 14 | 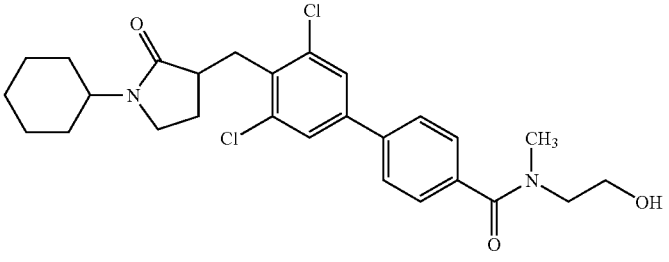<br>3',5'-Dichloro-4'-(1-cyclohexyl-2-oxo-pyrrolidin-3-ylmethyl)-biphenyl-4-carboxylic acid (2-hydroxy-ethyl)-methyl-amide | 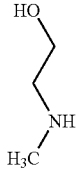 | MS (m/z) 503 (M+) |
| Preparation 15a | 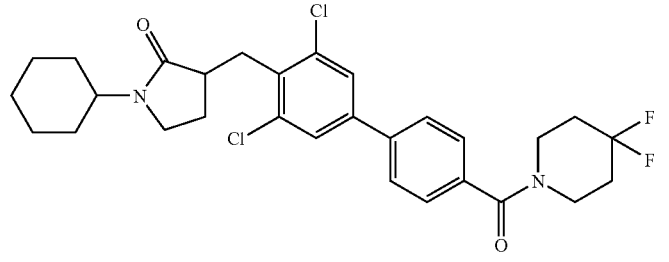<br>1-Cyclohexyl-3-[3,5-dichloro-4'-(4,4-difluoro-piperidine-1-carbonyl)-biphenyl-4-ylmethyl]-pyrrolidin-2-one |  | MS (m/z) 549 (M+) |
| 16 | 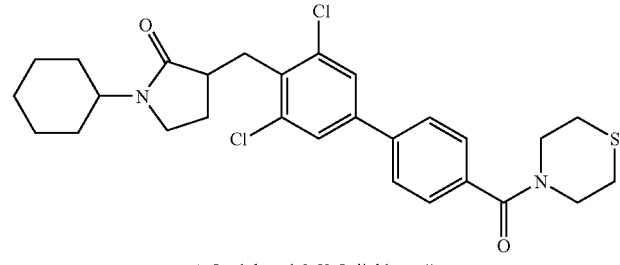<br>1-Cyclohexyl-3-[3,5-dichloro-4'-(thiomorpholine-4-carbonyl)-biphenyl-4-ylmethyl]-pyrrolidin-2-one |  | MS (m/z) 531 (M+) |

TABLE 7-continued

The Examples or preparations in Table 7
may be prepared essentially as
described by coupling procedure 2 in Preparation 6a
except for the amine is replaced with
the amine as indicated.

| Example or Preparation | Structure and name | Amine | Mass Spec |
|---|---|---|---|
| 17 | 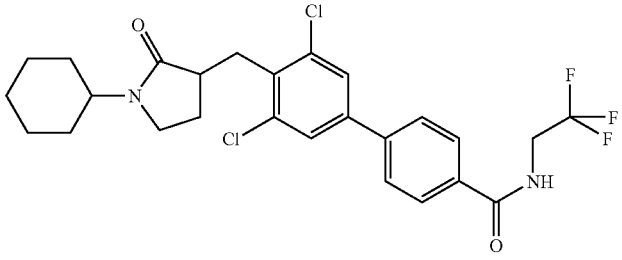<br>3',5'-Dichloro-4'-(1-cyclohexyl-2-oxo-pyrrolidin-3-ylmethyl)-biphenyl-4-carboxylic acid (2,2,2-trifluoro-ethyl)-amide | 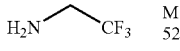 | MS (m/z) 527 (M+) |
| 18 | 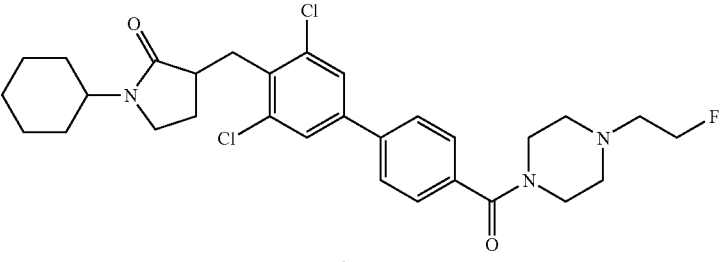<br>1-Cyclohexyl-3-{3,5-dichloro-4'-[4-(2-fluoro-ethyl)-piperazine-1-carbonyl]-biphenyl-4-ylmethyl}-pyrrolidin-2-one | 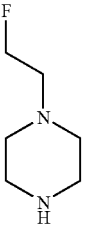 | MS (m/z) 560 (M+) |
| 19 | 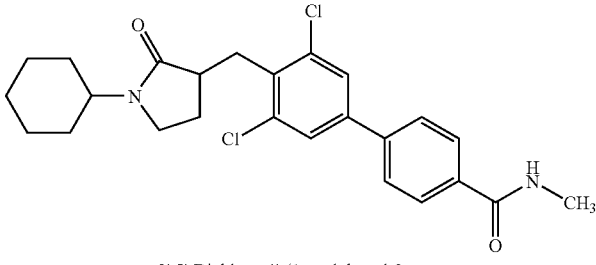<br>3',5'-Dichloro-4'-(1-cyclohexyl-2-oxo-pyrrolidin-3-ylmethyl)-biphenyl-4-carboxylic acid methylamide | $NH_2CH_3$ | MS (m/z) 459 (M+) |
| 20 | 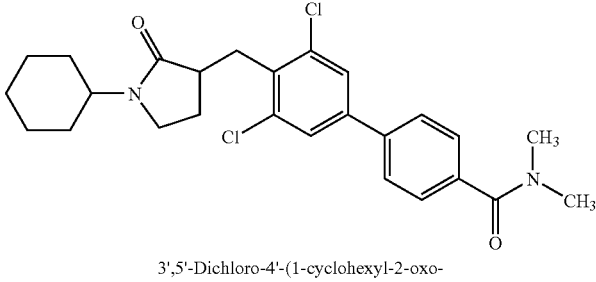<br>3',5'-Dichloro-4'-(1-cyclohexyl-2-oxo-pyrrolidin-3-ylmethyl)-biphenyl-4-carboxylic acid dimethylamide | $NH(CH_3)_2$ | MS (m/z) 475 (M+) |

TABLE 7-continued

The Examples or preparations in Table 7
may be prepared essentially as
described by coupling procedure 2 in Preparation 6a
except for the amine is replaced with
the amine as indicated.

| Example or Preparation | Structure and name | Amine | Mass Spec |
|---|---|---|---|
| 21 | 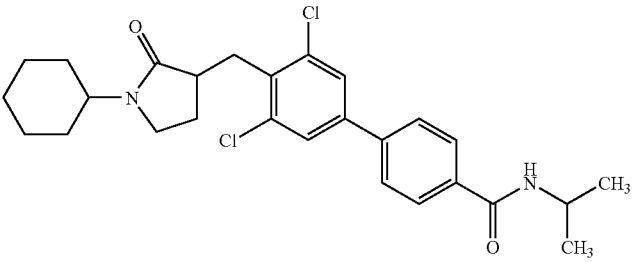\n3',5'-Dichloro-4'-(1-cyclohexyl-2-oxo-pyrrolidin-3-ylmethyl)-biphenyl-4-carboxylic acid isopropylamide | $NH_2CH(CH_3)_2$ | MS (m/z) 487 (M+) |
| 22 | 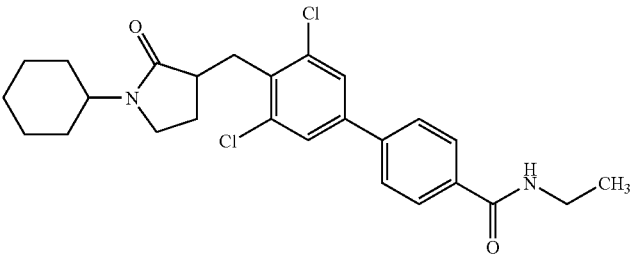\n3',5'-Dichloro-4'-(1-cyclohexyl-2-oxo-pyrrolidin-3-ylmethyl)-biphenyl-4-carboxylic acid ethylamide | $NH_2CH_2CH_3$ | MS (m/z) 473 (M+) |
| 23 | 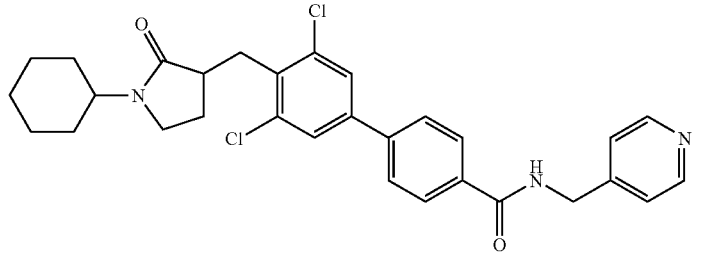\n3',5'-Dichloro-4'-(1-cyclohexyl-2-oxo-pyrrolidin-3-ylmethyl)-biphenyl-4-carboxylic acid (pyridin-4-ylmethyl)-amide | 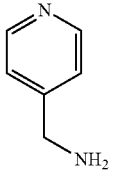 | MS (m/z) 536 (M+) |
| 24 | 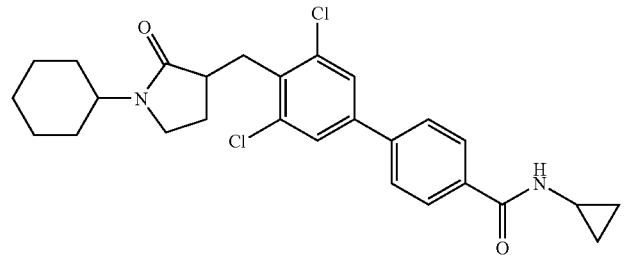\n3',5'-Dichloro-4'-(1-cyclohexyl-2-oxo-pyrrolidin-3-ylmethyl)-biphenyl-4-carboxylic acid cyclopropylamide | 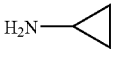 | MS (m/z) 485 (M+) |

TABLE 7-continued

The Examples or preparations in Table 7 may be prepared essentially as described by coupling procedure 2 in Preparation 6a except for the amine is replaced with the amine as indicated.

| Example or Preparation | Structure and name | Amine | Mass Spec |
|---|---|---|---|
| 25 | 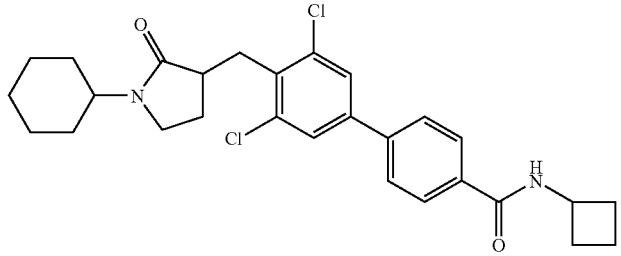<br>3',5'-Dichloro-4'-(1-cyclohexyl-2-oxo-pyrrolidin-3-ylmethyl)-biphenyl-4-carboxylic acid cyclobutylamide | 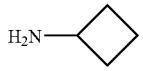 | MS (m/z) 501 (M+) |
| 26 | 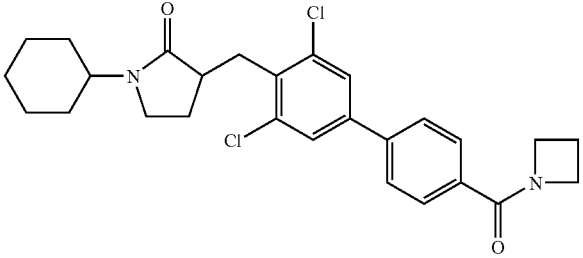<br>3-[4'-(Azetidine-1-carbonyl)-3,5-dichloro-biphenyl-4-ylmethyl]-1-cyclohexyl-pyrrolidin-2-one |  | MS (m/z) 485 (M+) |
| 27 | 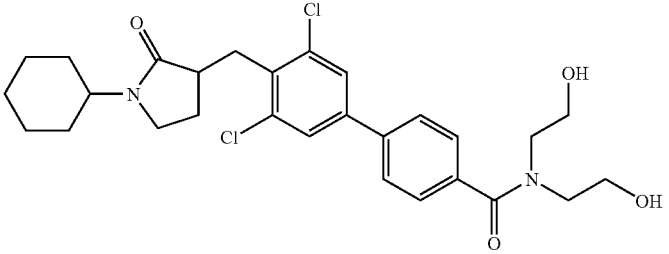<br>3',5'-Dichloro-4'-(1-cyclohexyl-2-oxo-pyrrolidin-3-ylmethyl)-biphenyl-4-carboxylic acid bis-(2-hydroxy-ethyl)-amide | 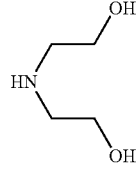 | MS (m/z) 533 (M+) |
| 28 | 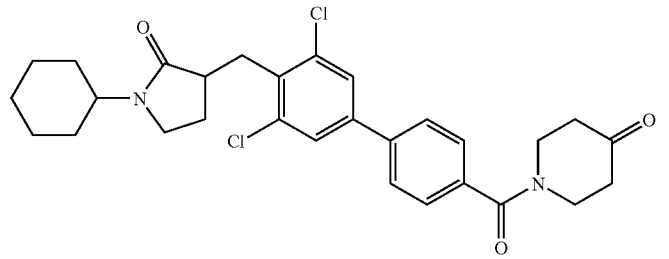<br>1-[3',5'-Dichloro-4'-(1-cyclohexyl-2-oxo-pyrrolidin-3-ylmethyl)-biphenyl-4-carbonyl]-piperidin-4-one | 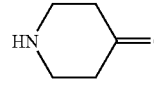 | MS (m/z) 527 (M+) |

TABLE 7-continued

The Examples or preparations in Table 7 may be prepared essentially as described by coupling procedure 2 in Preparation 6a except for the amine is replaced with the amine as indicated.

| Example or Preparation | Structure and name | Amine | Mass Spec |
|---|---|---|---|
| Preparation 29a | 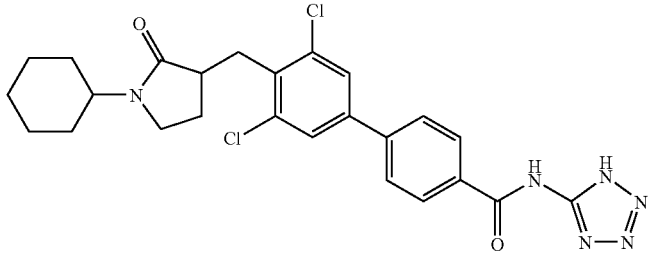<br>3',5'-Dichloro-4'-(1-cyclohexyl-2-oxo-pyrrolidin-3-ylmethyl)-biphenyl-4-carboxylic acid (2H-tetrazol-5-yl)-amide | 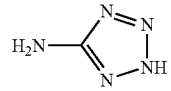 | MS (m/z) 513 (M+) |
| 30 | 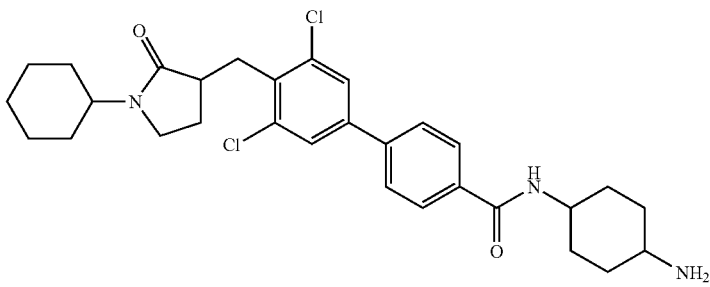<br>3',5'Dichloro-4'-(1-cyclohexyl-2-oxo-pyrrolidin-3-ylmethyl)-biphenyl-4-carboxylic acid (4-amino-cyclohexyl)-amide | 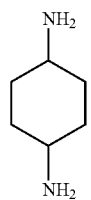 | MS (m/z) 542 (M+) |
| 31 | 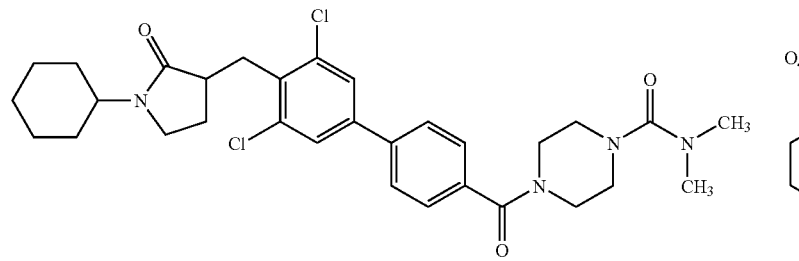<br>4-[3',5'-Dichloro-4'-(1-cyclohexyl-2-oxo-pyrrolidin-3-ylmethyl)-biphenyl-4-carbonyl]-piperazine-1-carboxylic acid dimethylamide | 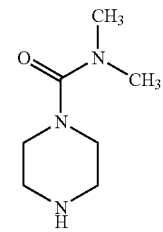 | MS (m/z) 585 (M+) |

TABLE 7-continued

*The Examples or preparations in Table 7 may be prepared essentially as described by coupling procedure 2 in Preparation 6a except for the amine is replaced with the amine as indicated.*

| Example or Preparation | Structure and name | Amine | Mass Spec |
|---|---|---|---|
| 32 | 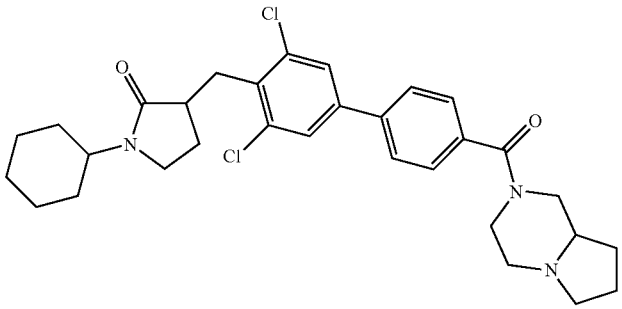<br>1-Cyclohexyl-3-[3,5-dichloro-4'-(hexahydro-pyrrolo[1,2 a]pyrazine-2-carbonyl)-biphenyl-4-ylmethyl]-pyrrolidin-2-one | 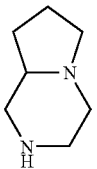 | MS (m/z) 554 (M+) |
| 33 | 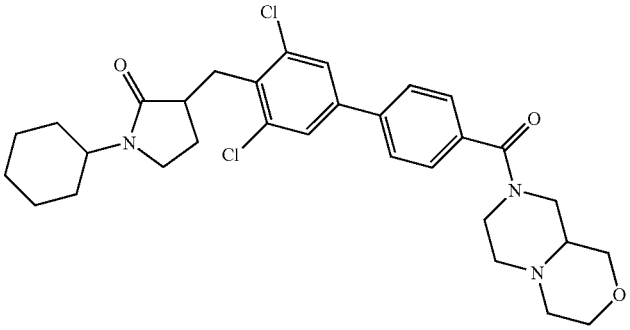<br>1-Cyclohexyl-3-[3,5-dichloro-4'-(hexahydro-pyrazino[2,1-c][1,4]oxazine-8-carbonyl)-biphenyl-4-ylmethyl]-pyrrolidin-2-one | 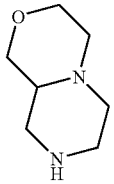 | MS (m/z) 570 (M+) |
| 34 | 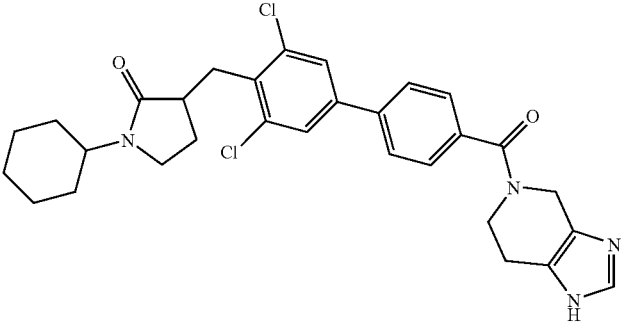<br>1-Cyclohexyl-3-[3,5-dichloro-4'-(1,4,6,7-tetrahydro-imidazo[4,5-c]pyridine-5-carbonyl)-biphenyl-4-ylmethyl]-pyrrolidin-2-one | 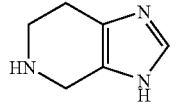 | MS (m/z) 551 (M+) |

TABLE 7-continued

The Examples or preparations in Table 7
may be prepared essentially as
described by coupling procedure 2 in Preparation 6a
except for the amine is replaced with
the amine as indicated.

| Example or Preparation | Structure and name | Amine | Mass Spec |
|---|---|---|---|
| 35 | 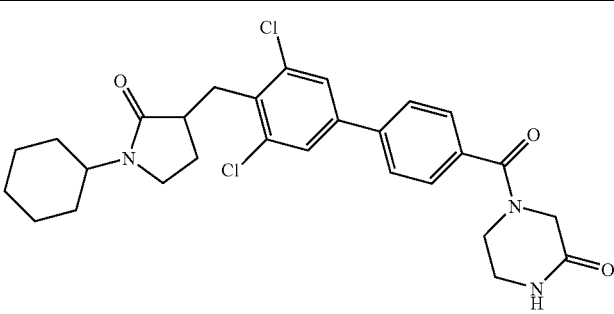<br>1-Cyclohexyl-3-[3,5-dichloro-4'-(hexahydro-pyrrolo[1,2-a]pyrazine-2-carbonyl)-biphenyl-4-ylmethyl]-pyrrolidin-2-one | 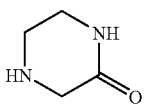 | MS (m/z) 528 (M+) |
| 36 | 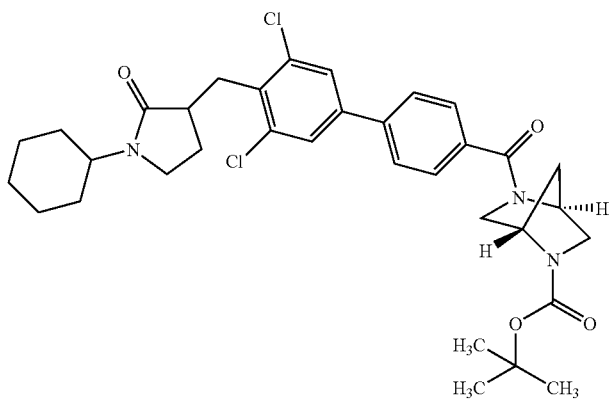<br>5-[3'5'-Dichloro-4'-(1-cyclohexyl-2-oxo-pyrrolidin-3-ylmethyl)-biphenyl-4-carbonyl]-2,5-diaza-bicyclo[2.2.1]heptane-2-carboxylic acid tert-butyl ester | 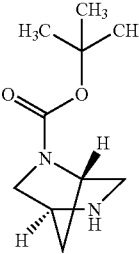 | MS (m/z) 626 (M+) |
| Preparation 37a | 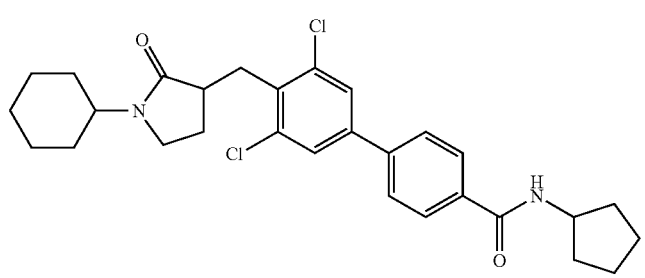<br>3'5'-Dichloro-4'-(1-cyclohexyl-2-oxo-pyrrolidin-3-ylmethyl)-biphenyl-4-carboxylic acid cyclopentyl | 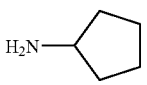 | MS (m/z) 513 (M+) |

TABLE 7-continued

The Examples or preparations in Table 7 may be prepared essentially as described by coupling procedure 2 in Preparation 6a except for the amine is replaced with the amine as indicated.

| Example or Preparation | Structure and name | Amine | Mass Spec |
|---|---|---|---|
| 38 | ![structure] 1-Cyclohexyl-3-[3,5-dichloro-4'-(pyrrolidine-1-carbonyl)-biphenyl-4-ylmethyl]-pyrrolidin-2-one | HN⟨pyrrolidine⟩ | MS (m/z) 499 (M+) |

Alternate procedure to make Example 7 and the HCl salt thereof: Place 3',5'-dichloro-4'-(1-cyclohexyl-2-oxo-pyrrolidin-3-ylmethyl)-biphenyl-4-carboxylic acid (2.277 g, 5.1 mmol) in dry dichloromethane (50 mL) and add oxalyl chloride (647 mg, 5.1 mmol), and stir for one hour. Concentrate to give 3',5'-dichloro-4'-(1-cyclohexyl-2-oxo-pyrrolidin-3-ylmethyl)-biphenyl-4-acid chloride. Dissolve in THF (20 mL) and add 1-methylpiperazine (1.2 g, 12.4 mmol) and stir for 16 hours. Add dichloromethane and wash with 1M NaOH and water. Dry over sodium sulfate, filter, and concentrate. Dissolve in dichloromethane (10 mL) and add HCl in ether (2M, 1 mL) and concentrate to give 67 mg (36%) of the title compound as a tan solid. Mass spectrum (apci) m/z=556.2 (M+H).

EXAMPLE 39

{[3',5'-dichloro-4'-(1-cyclohexyl-2-oxo-pyrrolidin-3-ylmethyl)-biphenyl-4-carbonyl]-amino}-acetic acid

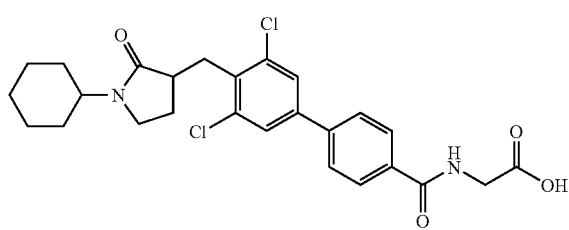

Coupling Procedure 3

Suspend 3',5'-dichloro-4'-(1-cyclohexyl-2-oxo-pyrrolidin-3-ylmethyl)-biphenyl-4-carboxylic acid (0.25 g, 0.56 mmol) and N-hydroxysuccinimide (0.078 g, 0.67 mmol) in anhydrous dioxane (5 mL). Stir at room temperature and add N,N'-dicyclohexylcarbodiimide (0.138 g, 0.67 mmol) dissolved in anhydrous dioxane (5 mL), drop-wise, over 20 minutes. Stir reaction overnight. Filter off white precipitant (urea) and wash with cold dioxane (10 mL).

Add glycine (0.057 g, 0.75 mmol) and sodium bicarbonate (0.063 g, 0.75 mmol) to the solution (10 mL, 0.56 mmol). Stir the reaction sealed, at room temperature overnight. Concentrate the volume of the reaction mixture by ⅔ under reduced vacuum, acidify with concentrated hydrochloric acid at 0° C. and collect the resultant white solid via filtration. Purify via flash chromatography by eluding with gradient of 5% isopropanol/93% dichloromethane/2% acetic acid to 20% isopropanol/78% dichloromethane/2% acetic acid to recover 0.097 g (35%) product as a white solid: MS (m/z): 503 (M+).

TABLE 8

The Examples in Table 8 may be prepared essentially as described by coupling procedure 3 in Example 39 except for the amine is replaced with the amine as indicated.

| Example | Structure and name | Amine | Mass Spec |
|---|---|---|---|
| 40 | (S)-2-{[3',5'-Dichloro-4'-(1-cyclohexyl-2-oxo-pyrrolidin-3-ylmethyl)-biphenyl-4-carbonyl]-amino}-3-hydroxy-propionic acid | L-Serine | MS (m/z) 533 (M+) |
| 41 | (R)-2-{[3',5'-Dichloro-4'-(1-cyclohexyl-2-oxo-pyrrolidin-3-ylmethyl)-biphenyl-4-carbonyl]-amino}-3-hydroxy-propionic acid | D-Serine | MS (m/z) 533 (M+) |
| 42 | 2-{[3',5'-Dichloro-4'-(1-cyclohexyl-2-oxo-pyrrolidin-3-ylmethyl)-biphenyl-4-carbonyl]-amino}-3-dimethylamino-propionic acid | 2-amino-3-(dimethylamino)propanoic acid | MS (m/z) 560 (M+) |

EXAMPLE 43

3',5'-Dichloro-4'-(1-cyclohexyl-2-oxo-pyrrolidin-3-ylmethyl)-biphenyl-4-carboxylic acid methyl-(1H-tetrazol-5-yl)-amide

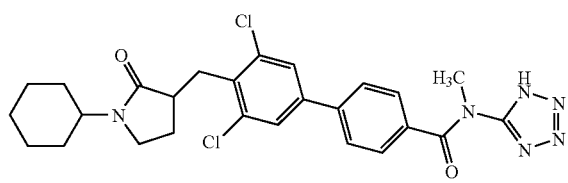

Coupling Procedure 4

Treat a solution of 3',5'-dichloro-4'-(1-cyclohexyl-2-oxo-pyrrolidin-3-ylmethyl)-biphenyl-4-carboxylic acid (0.50 g, 1.12 mmol) in dichloromethane (15 mL) with 3 drops of dimethylformamide then oxalyl chloride (0.14 g, 1.14 mmol) and stir for 1 hour at room temperature. Add this solution dropwise to another solution of methyl-(1H-tetrazol-5-yl)-amine [Finnegan, W. G. et. al., JOC, 1953, 18, 770] (0.166 g, 1.67 mmol), triethylamine (0.34 g, 3.36 mmol) and DMAP (0.014 g, 0.114 mmol) in tetrahydrofuran (10 mL) at 0° C. Warm the reaction to room temperature and stir for 16 hours under $N_2$. Quench the reaction with 1 N hydrochloric acid, dilute with water and extract with dichloromethane. Dry the organic layer with sodium sulfate and purify the crude product by HPLC to afford 188 mg (32%) of the title compound: MS (m/z): 527 (M+).

TABLE 9

The Examples in Table 9 may be prepared essentially as described by coupling procedure 4 in Example 43 except for the amine is replaced with the amine as indicated.

| Example | Structure and name | Amine | Mass Spec |
|---|---|---|---|
| 44 | 3-[4'-(4-tert-Butyl-piperazine-1-carbonyl)-3,5-dichloro-biphenyl-4-ylmethyl]-1-cyclohexyl-pyrrolidin-2-one | | MS (m/z) 570 (M+) |
| 45 | 1-Cyclohexyl-3-[3,5-dichloro-4'-(3-trifluoromethyl-5,6-dihydro-8H-[1,2,4]triazolo[4,3-a]pyrazine-7-carbonyl)-biphenyl-4-ylmethyl]-pyrrolidin-2-one | | MS (m/z) 620 (M+) |

EXAMPLE 46

1-cyclohexyl-3-[3,5-dichloro-4'-(4-methyl-piperazine-1-carbonyl)-biphenyl-4-ylmethyl]-pyrrolidin-2-one hydrochloride

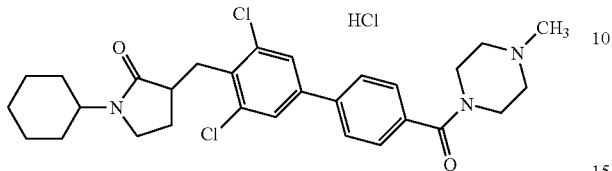

Dissolve 10.6 g (20.07 mmol) racemic 1-cyclohexyl-3-[3,5-dichloro-4'-(4-methyl-piperazine-1-carbonyl)-biphenyl-4-ylmethyl]-pyrrolidin-2-one in dichloromethane (~20 mL) and, while rapidly stirring, slowly add 21 mL of 1N hydrochloric acid in diethyl ether. Stir rapidly for ~15 minutes, filter and rinse the solid with diethyl ether. Vacuum dry to yield 11.2 g (100%) of a white solid: MS (m/z): 528.

Alternative procedure to prepare Example 46: Using the procedure to synthesize Preparation 76 and using reagents 3',5'-dichloro-4'-(1-cyclohexyl-2-oxo-pyrrolidin-3-ylmethyl)-biphenyl-4-carboxylic acid (350 mg, 0.78 mmol) and N-methyl piperazine (157 mg, 1.6 mmol) affords 103 mg (23%) of the title compound: Mass spectrum (apci) m/z=528.2 (M+H−HCl).

EXAMPLE 47

3',5'-dichloro-4'-(1-cyclohexyl-2-oxo-pyrrolidin-3-ylmethyl)-biphenyl-4-carboxylic acid azetidin-3-ylamide

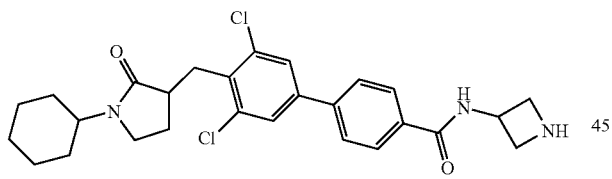

Dissolve racemic 3',5'-dichloro-4'-(1-cyclohexyl-2-oxo-pyrrolidin-3-ylmethyl)-biphenyl-4-carboxylic acid (0.200 g, 0.448 mmol) in dichloromethane (5 mL) and add 1,1'-carbonyl-diimidazole (0.110 g, 0.670 mmol). Stir under argon atmosphere at room temperature and check reaction progress via TLC. Add 3-amino-azetidine-1-carboxylic acid tert-butyl ester (0.093 g, 0.538 mmol) and continue to stir, checking progress via LC/MS. Once starting material has been fully consumed, dilute reaction with dichloromethane (50 mL) and wash with 1.0 N sodium hydroxide (30 mL) then brine (30 mL). Collect the organic phase, dry over anhydrous magnesium sulfate and concentrate under reduced pressure. Dissolve the residue in dioxane (20 mL), add 4N hydrochloric acid -dioxane (10 mL) and stir /2 hour to obtain an oily residue in reaction vessel. Concentrate and then dilute with dichloromethane (100 mL). Quench with saturated sodium bicarbonate solution (50 mL), dry organic phase of magnesium sulfate and concentrate to foam. Purify via flash chromatography, elude with gradient of 100% dichloromethane to 10% ammonia methanol/90% dichloromethane to obtain 0.014 g (7.6%) of a white foam: MS (m/z): 500 (M+).

EXAMPLE 48

3',5'-dichloro-4'-(1-cyclohexyl-2-oxo-pyrrolidin-3-ylmethyl)-biphenyl-4-carboxylic acid (3-amino-cyclohexyl)-amide

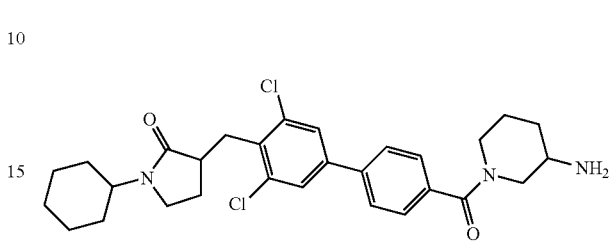

Dissolve racemic 3',5'-dichloro-4'-(1-cyclohexyl-2-oxo-pyrrolidin-3-ylmethyl)-biphenyl-4-carboxylic acid (1.00 eq.) in dichloromethane (5-10 mL) and add 1,1'-carbonyl-diimidazole (1.50 eq.). Stir under argon atmosphere at room temperature and check reaction progress via TLC. Add (3-amino-cyclohexyl)-carbamic acid tert-butyl ester (1.05-2.0 eq.) and continue to stir, checking progress via LC/MS. Once starting material has been fully consumed, dilute reaction with dichloromethane (50 mL) and wash with 1.0 N sodium hydroxide (30 mL) and brine (30 mL). Collect the organic phase, dry over anhydrous magnesium sulfate and concentrate under reduced pressure. Purify via flash chromatography by eluding with gradient of 100% dichloromethane to 10% ammonia methanol/90% dichloromethane to recover {1-[3',5'-dichloro-4'-(1-cyclohexyl-2-oxo-pyrrolidin-3-ylmethyl)-biphenyl-4-carbonyl]-piperidin-3-yl}-carbamic acid tert-butyl ester. Dissolve the {1-[3',5'-dichloro-4'-(1-cyclohexyl-2-oxo-pyrrolidin-3-ylmethyl)-biphenyl-4-carbonyl]-piperidin-3-yl}-carbamic acid tert-butyl ester (0.40, 0.65 mmol) in dioxane (20 mL), add 4N hydrochloric acid -dioxane (10 mL) and stir 30 min. Concentrate under vacuum, dilute in dichloromethane (100 mL) and add saturated aqueous sodium bicarbonate (50 mL). Dry the organic phase with magnesium sulfate and concentrate to a foam: MS (m/z): 528 (M+).

EXAMPLE 49

1-cyclohexyl-3-[3,5-dichloro-4'-(piperazine-1-carbonyl)-biphenyl-4-ylmethyl]-pyrrolidin-2-one

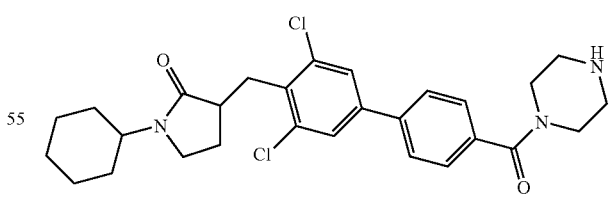

Dissolve racemic 4-[3',5'-dichloro-4'-(1-cyclohexyl-2-oxo-pyrrolidin-3-ylmethyl)-biphenyl-4-carbonyl]-piperazine-1-carboxylic acid tert-butyl ester (0.843 g, 1.37 mmol) in dichloromethane (25 mL) and cool in ice bath to 0° C. while stirring under an inert atmosphere. Add triethylsilane (0.5 mL) and trifluoroacetic acid (5.0 mL) to the mixture and allow the temperature to rise to room temperature. Monitor the reaction via TLC. Once starting material is consumed, dilute the reaction with dichloromethane and quench with saturated sodium bicarbonate. Collect the organic phase and the extract aqueous phase with dichloromethane (2×50 mL). Combine organic phases and dry over magnesium sulfate. Extract desired material with resin bound acidic media (SCX) to obtain 0.656 g (93%) of white solid: MS (m/z): 514.0 (M+1).

EXAMPLE 50

3',5'-dichloro-4'-(1-cyclohexyl-2-oxo-pyrrolidin-3-ylmethyl)-biphenyl-4-carboxylic acid (4-amino-cyclohexyl)-amide

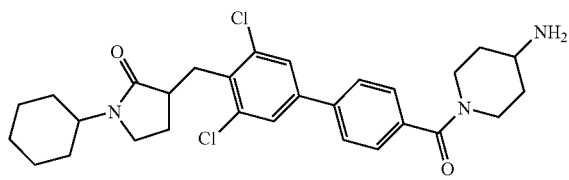

Dissolve racemic 1-[3',5'-dichloro-4'-(1-cyclohexyl-2-oxo-pyrrolidin-3-ylmethyl)-biphenyl-4-carbonyl]-piperidin-4-yl}-carbamic acid tert-butyl ester (1.21 g, 1.92 mmol) in dichloromethane (25 mL) and cool in an ice bath (0° C.) while stirring under inert atmosphere. Add triethylsilane (0.5 mL) and trifluoroacetic acid (5.0 mL) to the mixture and allow the temperature to rise to room temperature. Once starting material is consumed, dilute the reaction with dichloromethane and quench with saturated aqueous sodium bicarbonate. Separate the layers and extract the aqueous phase with dichloromethane (2×50 mL). Combine the organic phases and dry over magnesium sulfate. Extract desired material with resin bound acidic media (SCX) to obtain 0.945 g (93%) of a foam (93%): MS (m/z) 528 (M+).

EXAMPLE 51

3',5'-dichloro-4'-(1-cyclohexyl-2-oxo-pyrrolidin-3-ylmethyl)-biphenyl-4-carboxylic acid (2-dimethylamino-ethyl)-amide N-oxide

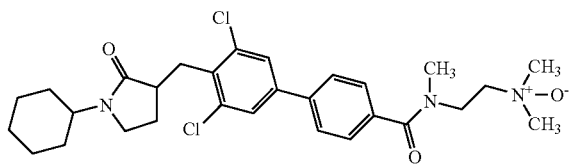

Dissolve racemic 3',5'-dichloro-4'-(1-cyclohexyl-2-oxo-pyrrolidin-3-ylmethyl)-biphenyl-4-carboxylic acid (2-dimethylamino-ethyl)-methyl-amide (0.097 g, 0.183 mmol) in dichloromethane (5 mL) under argon atmosphere. Add 3-chloroperoxybenzoic acid (0.045 g, 0.200 mmol) and stir at room temperature for 1 hour. Concentrate under reduced pressure and purify via flash chromatography by eluding with a gradient (100%) dichloromethane to 25% methanol/75% dichloromethane to obtain 0.086 g (87%) of a white solid: MS (m/z): 546 (M+).

EXAMPLE 52

3',5'-dichloro-4'-(1-cyclohexyl-2-oxo-pyrrolidin-3-ylmethyl)-biphenyl-4-carboxylic acid (1-oxy-pyridin-4-ylmethyl)-amide

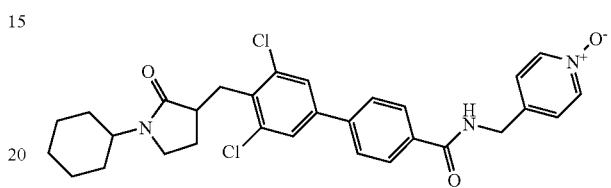

Dissolve racemic 3',5'-dichloro-4'-(1-cyclohexyl-2-oxo-pyrrolidin-3-ylmethyl)-biphenyl-4-carboxylic acid (pyridin-4-ylmethyl)-amide (0.100 g, 0.186 mmol) in dichloromethane (5 mL) under argon atmosphere. Add 3-chloroperoxybenzoic acid (0.055 g, 0.233 mmol) and stir at room temperature for 1 hour. Concentrate under reduced pressure. Purify via flash chromatography by eluding with a gradient of 100% dichloromethane to 25% methanol /dichloromethane to obtain 0.089 g (86%) of product as a white solid: MS (m/z): 552 (M+).

EXAMPLE 53

3-[4'-(4-acetyl-piperazine-1-carbonyl)-3,5-dichloro-biphenyl-4-ylmethyl]-1-cyclohexyl-pyrrolidin-2-one

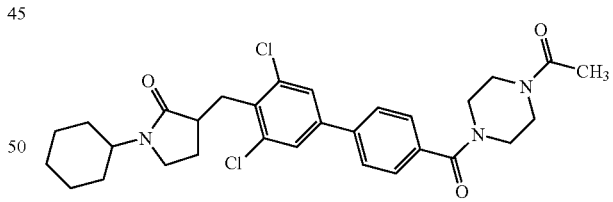

Dissolve racemic 1-cyclohexyl-3-[3,5-dichloro-4'-(piperazine-1-carbonyl)-biphenyl-4-ylmethyl]-pyrrolidin-2-one (0.082 g, 0.158 mmol) in dichloromethane (5 mL), add 1.0 N sodium hydroxide solution (0.5 mL) and acetyl chloride (0.020 mL, 0.281 mmol). Stir the mixture, sealed, overnight at room temperature. Dilute reaction with dichloromethane (20 mL) and wash with 1.0 N sodium hydroxide (10 mL) then brine (5 mL). Collect the organic phase, dry over anhydrous magnesium sulfate and concentrate under reduced pressure. Purify via flash chromatography by eluding with a gradient (100%) dichloromethane to 5% ammonia methanol/95% dichloromethane to obtain 0.065 g (74%) of product as a white foam: MS (m/z): 556 (M+).

EXAMPLE 54

4-[3',5'-dichloro-4'-(1-cyclohexyl-2-oxo-pyrrolidin-3-ylmethyl)-biphenyl-4-carbonyl]-piperazine-1-carboxylic acid amide

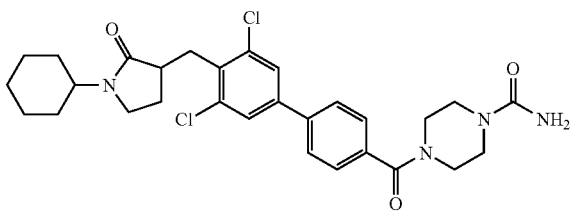

Dissolve racemic 4-[3',5'-dichloro-4'-(1-cyclohexyl-2-oxo-pyrrolidin-3-ylmethyl)-biphenyl-4-carbonyl]-piperazine-1-carboxylic acid tert-butyl ester (0.40, 0.65 mmol) in dioxane (20 mL), add 4N hydrochloric acid in dioxane (10 mL) and stir 30 min to obtain an orange residue in reaction vessel. Concentrate under vacuum, dilute residue with water (10 mL) and add potassium cyanate (0.55 g, 0.68 mmol). Stir the reaction at room temperature to obtain a white precipitate. Filter off solid and wash with water. Dissolve the solid in dichloromethane and concentrate under vacuum to yield a clear foam. Use resin bound solid phase acidic media (SCX) to remove residual starting material and obtain 0.168 g (46%) of product as a white solid: MS (m/z): 557 (M+).

EXAMPLE 55

1-cyclohexyl-3-[3,5-dichloro-4'-(1,1-dioxo-1 lambda*6*-thiomorpholine-4-carbonyl)-biphenyl-4-ylmethyl]-pyrrolidin-2-one

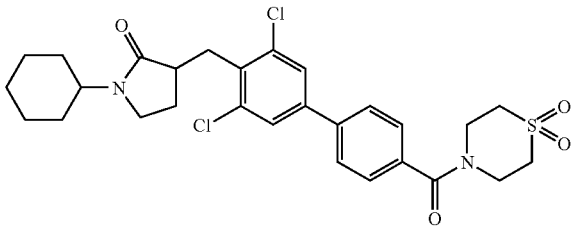

Dissolve racemic 1-cyclohexyl-3-[3,5-dichloro-4'-(thiomorpholine-4-carbonyl)-biphenyl-4-ylmethyl]-pyrrolidin-2-one (0.185 g, 0.349 mmol) in THF (10 mL) and add meta-chloro-perbenzoic acid (0.135 g, 0.785 mmol). Add additional meta-chloro-perbenzoic acid as needed to drive reaction to completion. Dilute the reaction with ethyl acetate, wash twice with 1.0 N sodium hydroxide, dry organic phase over magnesium sulfate and concentrate under reduced pressure to yield a white foam. Purify the crude material via flash chromatography by eluding with a gradient of 100% dichloromethane to 10% isopropanol/dichloromethane to obtain 0.21 g (94%) of product as a white foam: MS (m/z): 563 (M+).

EXAMPLE 56

3',5'-dichloro-4'-(1-cyclohexyl-2-oxo-pyrrolidin-3-ylmethyl)-biphenyl-4-carboxylic acid (2-aminoethyl)-amide

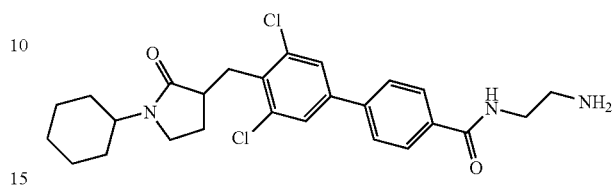

Dissolve racemic 3',5'-dichloro-4'-(1-cyclohexyl-2-oxo-pyrrolidin-3-ylmethyl)-biphenyl-4-carboxylic acid (0.200 g, 0.448 mmol) in dichloromethane (5 mL) and add 1,1'-carbonyl-diimidazole (0.125 g, 0.760 mmol). Stir the mixture under an argon atmosphere at room temperature and check reaction progress via TLC. Add tert-butyl N-(2-aminoethyl) carbamate (0.140 mL, 0.896 mmol) and continue to stir, checking progress via LC/MS. Once the starting material has been fully consumed, dilute the reaction with dichloromethane (50 mL) and wash with 1.0 N sodium hydroxide (30 mL) then brine (30 mL). Collect the organic phase, dry over anhydrous magnesium sulfate and concentrate under reduced pressure. Purify via flash chromatography by eluding with gradient dichloromethane to 10% ammonia methanol/90% dichloromethane. Dissolve recovered material (0.40, 0.65 mmol) in dioxane (20 mL), add 4N hydrochloric acid -dioxane (10 mL) and stir 30 min to obtain an oily residue in the reaction vessel. Concentrate the mixture under vacuum then dilute with dichloromethane (100 mL). Quench with saturated aqueous sodium bicarbonate solution (50 mL), separate the layers, dry organic phase with magnesium sulfate and concentrate to 0.155 g (71%) of product as a white foam: MS (m/z): 490 (M+2).

EXAMPLE 57

3',5'-dichloro-4'-(1-cyclohexyl-2-oxo-pyrrolidin-3-ylmethyl)-biphenyl-4-carboxylic acid piperidin-4-ylamide

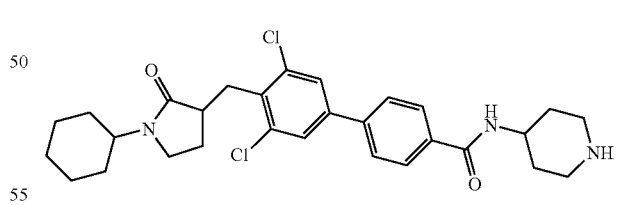

Dissolve racemic 3',5'-dichloro-4'-(1-cyclohexyl-2-oxo-pyrrolidin-3-ylmethyl)-biphenyl-4-carboxylic acid (0.200 g, 0.448 mmol) in dichloromethane (5 mL) and add 1,1'-carbonyl-diimidazole (0.125 g, 0.760 mmol). Stir under argon atmosphere at room temperature and check reaction progress via TLC. Add 4-amino-piperidine-1-carboxylic acid tert-butyl ester (0.180 g, 0.90 mmol) and continue to stir until the starting material has been fully consumed. Dilute the reaction with dichloromethane (50 mL) and wash with 1.0 N sodium hydroxide (30 mL) then brine (30 mL). Collect the organic phase, dry over anhydrous magnesium sulfate and concentrate under reduced pressure. Purify via flash chromatography by eluding with gradient (0-100%) dichloromethane to 15% ammonia methanol/85% dichloromethane. After concentrating, dissolve the 4-{[3',5'-dichloro-4'-(1-cyclohexyl-2-oxo-pyrrolidin-3-ylmethyl)-biphenyl-4-carbonyl]-amino}-piperidine-1-carboxylic acid tert-butyl ester in dioxane (20 mL), add 4N hydrochloric acid -dioxane (10 mL) and stir ½ hour to obtain an oily residue in reaction vessel. Concentrate the mixture under vacuum then dilute in dichloromethane (100 mL). Quench with saturated aqueous sodium bicarbonate solution (50 mL), dry the organic phase over magnesium sulfate and concentrate to obtain 0.195 g (82%) of a yellow foam: MS (m/z): 530 (M+2).

EXAMPLE 58

4-[3',5'-dichloro-4'-(1-cyclohexyl-2-oxo-pyrrolidin-3-ylmethyl)-biphenyl-4-carbonyl]-1-methyl-piperazin-2-one

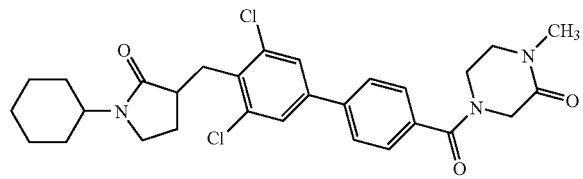

Treat a solution of racemic 1-cyclohexyl-3-[3,5-dichloro-4'-(hexahydro-pyrrolo[1,2-a]pyrazine-2-carbonyl)-biphenyl-4-ylmethyl]-pyrrolidin-2-on (0.245 g, 0.46 mmol) in dimethylformamide (6 mL) with 60% sodium hydride (0.037 g, 0.93 mmol) and stir for 15 minutes at room temperature under a nitrogen atmosphere. Cool the reaction to 0° C., treat with iodomethane (0.25 g, 1.76 mmol) and then stir at room temperature for 16 hours under a nitrogen atmosphere. Quench the reaction with 1N hydrochloric acid, dilute with ethyl acetate and wash with water. Dry the organic layer with sodium sulfate and purify by silica gel chromatography using a gradient of 0 to 10% methanol in dichloromethane to afford product. Re-crystallize from acetone/diethyl ether to afford 81 mg (32%) of the title compound: MS (m/z) 542 (M+).

PREPARATION 59a 1-cyclohexyl-3-[3,5-dichloro-4'-(2,5-diaza-bicyclo[2.2.1]heptane-2-carbonyl)-biphenyl-4-ylmethyl]-pyrrolidin-2-one

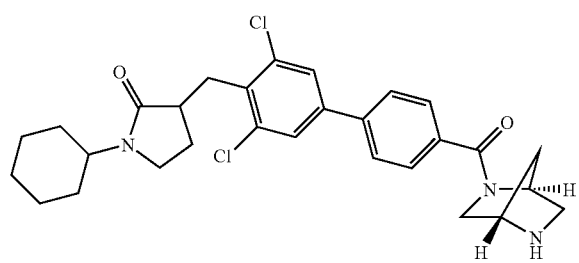

Dissolve chiral 5-[3',5'-dichloro-4'-(1-cyclohexyl-2-oxo-pyrrolidin-3-ylmethyl)-biphenyl-4-carbonyl]-2,5-diaza-bicyclo[2.2.1]heptane-2-carboxylic acid tert-butyl ester (0.119 g, 0.19 mmol) in dichloromethane (3 mL), treat with trifluoroacetic acid (1 mL) and stir for 1 hour at room temperature. Remove the solvent under vacuum, dissolve the residue in ethyl acetate and wash with saturated aqueous sodium bicarbonate then water. Dry the organic layer with sodium sulfate, concentrate under vacuum and purify the crude product by silica gel chromatography using a gradient of 0 to 10% methanol in dichloromethane to afford 100 mg (100%) of the title compound: MS (m/z): 526 (M+).

EXAMPLE 60

1-cyclohexyl-3-[3,5-dichloro-4'-((1S,4S)-5-isopropyl-2,5-diaza-bicyclo[2.2.1]heptane-2-carbonyl)-biphenyl-4-ylmethyl]-pyrrolidin-2-one

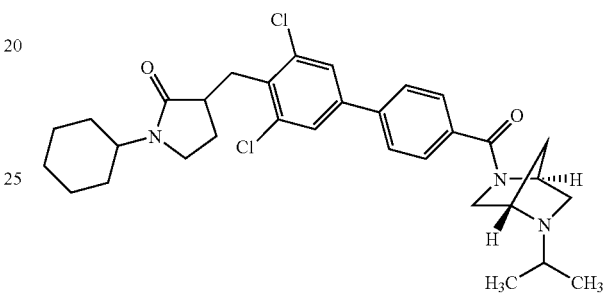

Treat a solution of chiral 1-cyclohexyl-3-[3,5-dichloro-4'-(2,5-diaza-bicyclo[2.2.1]heptane-2-carbonyl)-biphenyl-4-ylmethyl]-pyrrolidin-2-one (0.096 g, 0.18 mmol) in methanol (3 mL) and acetone (0.105 g, 1.81 mmol) with sodium cyanoborohydride (0.055 g, 0.88 mmol) and then acetic acid (0.057 g, 0.94 mmol). Stir the mixture for 3 hours at room temperature under a nitrogen atmosphere, dilute with ethyl acetate and wash with saturated sodium bicarbonate then water. Dry the organic layer with sodium sulfate and purify the crude product by silica gel chromatography using a gradient of 0 to 10% methanol in dichloromethane to afford 71 mg (68%) of the title compound: MS (m/z): 568 (M+).

PREPARATION 61a and EXAMPLE 62

1-cyclohexyl-3-{3,5-dichloro-4'-[4-(2-fluoro-ethyl)-piperazine-1-carbonyl]-biphenyl-4-ylmethyl}-pyrrolidin-2-one

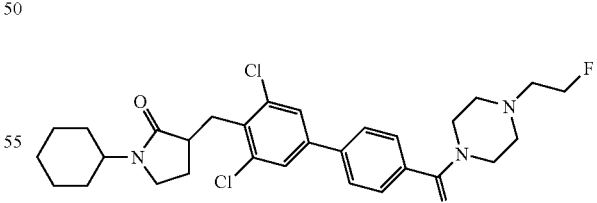

Treat a solution of 1-cyclohexyl-3-[3,5-dichloro-4'-(piperazine-1-carbonyl)-biphenyl-4-ylmethyl]-pyrrolidin-2-one (0.67 g, 1.30 mmol) in dimethylformamide (7 mL) with 1-bromo-2-fluoroethane (0.99 g, 7.80 mmol) and heat to 55° C. for 16 hours under a nitrogen atmosphere. Cool the reaction, dilute with ethyl acetate and wash with saturated aqueous sodium bicarbonate then water. Dry the organic layer with sodium sulfate and purify the crude product by silica gel chromatography using a gradient of 0 to 10% methanol in dichloromethane to afford 0.47 g (64%) of the title compound in its racemic form. Separate into the enantiomers by chiral HPLC (Chiralpak AD 8×33 cm column, isocratic 90:10 3 A ethanol:acetonitrile with 0.2% dimethylethylamine, 400 mL/min, 300 nM UV) to afford 286 mg of Isomer 1 (>99% ee) and 283 mg of Isomer 2 (98.9% ee): MS (m/z): 560. Check the purity of each isomer using chiral HPLC (Chiralpak AD-H 4.6×150 mm column, isocratic 90:10 3A ethanol:acetonitrile with 0.2% dimethylethylamine, 0.6 mL/min, 270 nM).

Preparation 61a: Isomer 1 elutes at 8.2 minutes
Example 62: Isomer 2 elutes at 12.6 minutes.

EXAMPLES 63 and 64

1-cyclohexyl-3-[3,5-dichloro-4'-(morpholine-4-carbonyl)-biphenyl-4-ylmethyl]-pyrrolidin-2-one

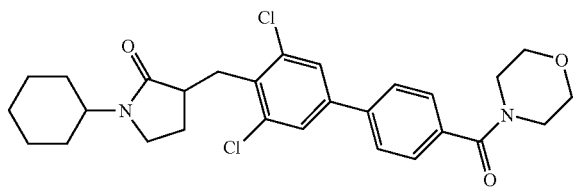

Separate 1.2 g of the racemic title compound (Example 4) into its enantiomers by chiral HPLC (Chiralpak AD 8×33 cm column, isocratic 90:10 3A ethanol:acetonitrile with 0.2% dimethylethylamine, 400 mL/min, 300 nM UV) to afford 528 mg of enantiomer 1 (98.8% ee) and 560 mg of enantiomer 2 (98.7% ee): MS (m/z): 515 (M+). Check the purity of each isomer by chiral HPLC (Chiralpak AD-H 4.6×150 mm column, isocratic 90:10 3A ethanol:acetonitrile with 0.2% dimethylethylamine, 0.6 mL/min, 270 nM).

Example 63 Isomer 1 elutes at 8.5 minutes,
Example 64 Isomer 2 elutes at 11.7 minutes.

EXAMPLES 65 and 66

1-cyclohexyl-3-[3,5-dichloro-4'-(4-methyl-piperazine-1-carbonyl)-biphenyl-4-ylmethyl]-pyrrolidin-2-one hydrochloride

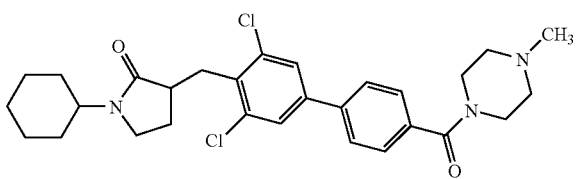

Separate 5.5 g of racemic compound hydrochloride salt (Example 46) into the enantiomers by chiral HPLC (Chiralpak AD 8×33 cm column, isocratic 90:10 3A ethanol:acetonitrile with 0.2% dimethylethylamine, 400 mL/min, 300 nM UV) to afford 2.57 g of enantiomer 1 (>99% ee) and 2.85 g of enantiomer 2 (99% ee): MS (m/z): 528 (M+). Check the purity using chiral HPLC (Chiralpak AD-H 4.6×150 mm column, isocratic 90:10 3A ethanol:acetonitrile with 0.2% dimethylethylamine, 0.6 mL/min, 270 nM).

Example 65 Isomer 1 elutes at 8.8 minutes.
Example 66 Isomer 2 elutes at 13.5 minutes.

EXAMPLES 67 and 68

1-cyclohexyl-3-[3,5-dichloro-4'-(4-isopropyl-piperazine-1-carbonyl)-biphenyl-4-ylmethyl]-pyrrolidin-2-one hydrochloride

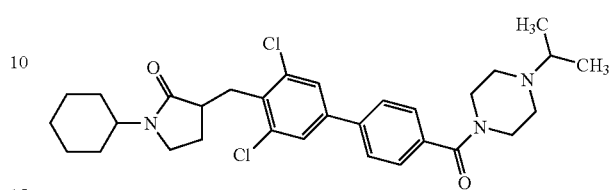

Separate 8.06 g of the racemic compound hydrochloride salt into its enantiomers by chiral HPLC (Chiralpak AD-H 4.6×150 mm column, isocratic 90:10 3A ethanol:acetonitrile with 0.2% dimethylethylamine, 0.6 mL/min, 270 nM UV) to afford 2.56 g of enantiomer 1 (>94% ee) and 3.6 g of enantiomer 2 (99% ee): MS (m/z): 556 (M+). Check the purity using chiral HPLC (Chiralpak AD-H 4.6×150 mm column, isocratic 90:10 3A ethanol:acetonitrile with 0.2% dimethylethylamine, 0.6 mL/min, 270 nM). Isomer 1 elutes at 6.6 minutes. Isomer 2 elutes at 8.9 minutes. Convert each isomer to its hydrochloric acid salt by dissolving in EtOH, treating with one equivalent of acetyl chloride and concentrating to dryness under vacuum.

Example 67 is the HCl salt of Isomer 1.
Example 68 is the HCl salt of Isomer 2.

EXAMPLE 69

1-cyclohexyl-3-[3,5-dichloro-4'-(4-methyl-4-oxy-piperazine-1-carbonyl)-biphenyl-4-ylmethyl]-pyrrolidin-2-one

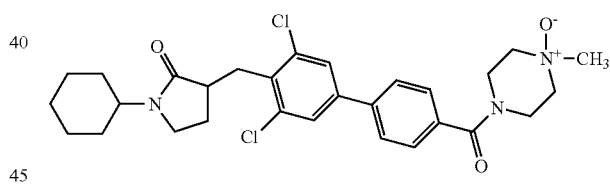

Prepare the title compound essentially by the method of Example 51 in an 56% yield starting from racemic 1-cyclohexyl-3-[3,5-dichloro-4'-(4-methyl-piperazine-1-carbonyl)-biphenyl-4-ylmethyl]-pyrrolidin-2-one: MS (m/z): 544 (M+).

EXAMPLE 70

1-cyclohexyl-3-[3,5-dichloro-4'-(4-methyl-4-oxy-piperazine-1-carbonyl)-biphenyl-4-ylmethyl]-pyrrolidin-2-one

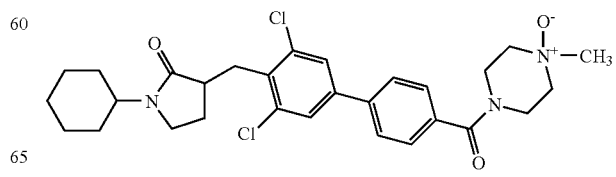

Prepare the title compound essentially by the method of Example 51 in a 95% yield starting from 1-cyclohexyl-3-[3,5-dichloro-4'-(4-methyl-piperazine-1-carbonyl)-biphenyl-4-ylmethyl]-pyrrolidin-2-one (Isomer 2, Example 66): MS (m/z): 544 (M+).

EXAMPLE 71

1-cyclohexyl-3-[3,5-dichloro-4'-(4-isopropyl-4-oxy-piperazine-1-carbonyl)-biphenyl-4-ylmethyl]-pyrrolidin-2-one

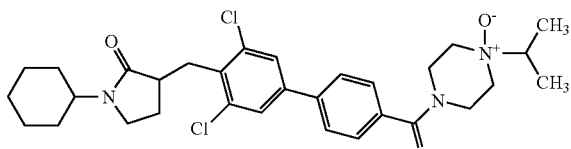

Prepare the title compound essentially by the method of Example 51 starting from racemic 1-cyclohexyl-3-[3,5-dichloro-4'-(4-isopropyl-piperazine-1-carbonyl)-biphenyl-4-ylmethyl]-pyrrolidin-2-one (Example 7): MS (m/z): 572 (M+).

EXAMPLE 72

1-cyclohexyl-3-{3,5-dichloro-4'-[4-(2,2,2-trifluoro-ethyl)-piperazine-1-carbonyl]-biphenyl-4-ylmethyl}-pyrrolidin-2-one

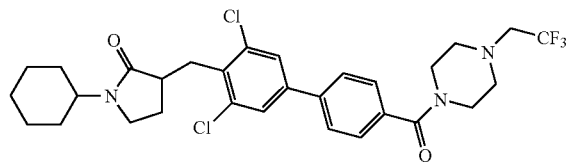

Treat a solution of 1-cyclohexyl-3-[3,5-dichloro-4'-(piperazine-1-carbonyl)-biphenyl-4-ylmethyl]-pyrrolidin-2-one (0.182 g, 0.35 mmol) and N,N-diisopropyl ethyl amine (0.32 g, 2.47 mmol) in THF (10 mL) with trifluoromethane sulfonic acid 2,2,2-trifluoroethyl ester (0.41 g, 1.77 mmol) and heat to reflux for 3 hours under $N_2$. Add more N,N-diisopropyl ethyl amine (0.13 g, 1.03 mmol) and trifluoromethane sulfonic acid 2,2,2-trifluoroethyl ester (0.24 g, 1.03 mmol) and continue to heat at reflux for 2 more hours. Cool the reaction to room temperature, dilute with ethyl acetate and wash with saturated sodium bicarbonate then water. Dry the organic layer with sodium sulfate and purify the crude product by reverse phase HPLC to afford 91 mg (43%) of the title compound: MS (m/z): 596 (M+).

EXAMPLE 73

3-{3,5-Dichloro-4'-[4-(2-fluoro-ethyl)-piperazine-1-carbonyl]-biphenyl-4-ylmethyl}-cis-1-(4-hydroxy-cyclohexyl)-pyrrolidin-2-one Hydrochloride salt

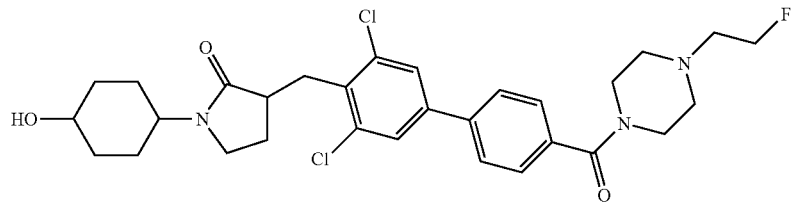

Deprotection Procedure 1:

Stir a mixture of 3-{3,5-dichloro-4'-[4-(2-fluoro-ethyl)-piperazine-1-carbonyl]-biphenyl-4-ylmethyl}-cis-1-(4-triisopropylsilanyloxy-cyclohexyl)-pyrrolidin-2-one (26.2 g, 35.75 mmol), 100 mL tetrahydrofuran and 71.5 mL 1 M tetrabutyl ammonium floride at room temperature overnight. Concentrate under vacuum and dilute with 500 mL saturated sodium bicarbonate, 500 mL water, 250 mL hexanes and 250 mL ethyl acetate. After separating the layers, wash the organic 300 mL 1:1 saturated bicarbonate:water, 250 mL water then 100 mL brine. Dry over magnesium sulfate, filter and concentrate to 20.5 g of a foam. Dissolve in a mixture of 100 mL 3:1 ethanol:ethyl acetate, and treat with 45 mL 1N hydrochloric acid in ether. Concentrate under vacuum and dilute with 150 mL ethyl acetate. Filter the solid and dry under vacuum 1 hr. Mix with 150 mL ethyl acetate, wash, and filter to obtain a white solid. Dry for 72 hrs at 35-37° C. under vacuum to recover 19.2 g (87%) of product: MS (m/z): 576 (M+).

Deprotection Procedure 2:

Alternatively, mix 250 mg of cis-1-[4-(tert-butyl-dimethyl-silanyloxy)-cyclohexyl]-3-[3,5-dichloro-4'-(4-isopropyl-piperazine-1-carbonyl)-biphenyl-4-ylmethyl]-pyrrolidin-2-one with 15 mL methanol and 0.8 mL 1 N hydrochloric acid. Then, warm to 40° C. 4 hrs. Concentrate to dryness under vacuum and purify by silica gel chromatography using 10% methanol in chloroform to recover 105 mg solid. Optionally, to make the HCl salt, dissolve in 20 mL dichloromethane and add 1 equivalent of 1 N hydrochloric acid in diethyl ether. Concentrate to dryness under vacuum: MS (m/z): 576 (M+).

TABLE 10

The Examples in Table 10 may be prepared essentially as described by the Deprotection Procedure 2 in Example 73 except for the Preparation that is deprotected is indicated in column 3.

| Example | Chemical Name | Preparation that is deprotected | Data |
|---|---|---|---|
| 74 | 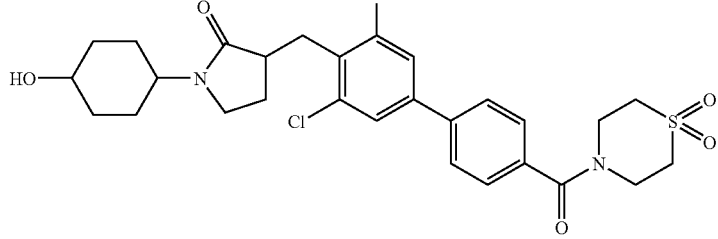<br>3-[3,5-Dichloro-4'-(1,1-dioxo-1-lambda*6*-thiomorpholine-4-carbonyl)-biphenyl-4-ylmethyl]-cis-1-(4-hydroxy-cyclohexyl)-pyrrolidin-2-one | 61 | MS (m/z) 579 (M+) |
| 75 | 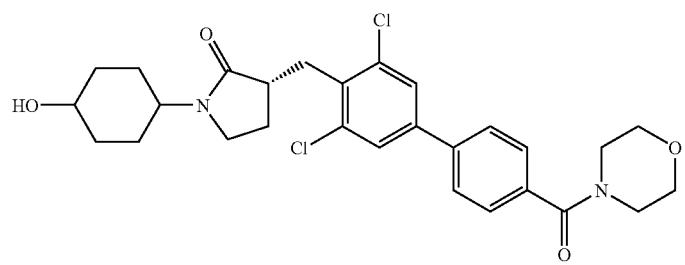<br>(R)-3-[3,5-Dichloro-4'-(morpholine-4-carbonyl)-biphenyl-4-ylmethyl]-cis-1-(4-hydroxy-cyclohexyl)-pyrrolidin-2-one | 50 | MS (m/z) 531 (M+) |
| 76 | 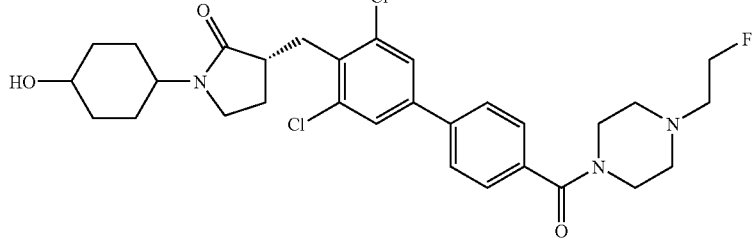<br>(R)-3-{3,5-Dichloro-4'-[4-(2-fluoro-ethyl)-piperazine-1-carbonyl]-biphenyl-4-ylmethyl}-cis-1-(4-hydroxy-cyclohexyl)-pyrrolidin-2-one hydrochloride | 48 | MS (m/z) 576 (M+) |
| 77 | 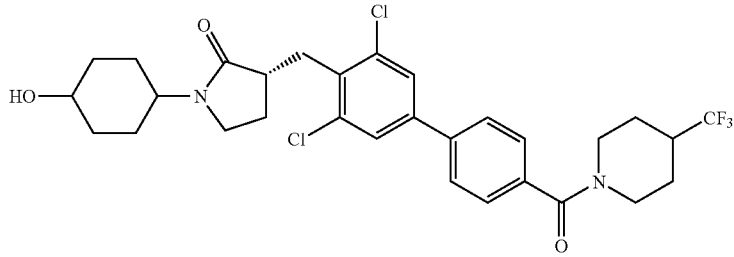<br>(R)-3-[3,5-Dichloro-4'-(4-trifluoromethyl-piperidine-1-carbonyl)-biphenyl-4-ylmethyl]-cis-1-(4-hydroxy-cyclohexyl)-pyrrolidin-2-one | 51 | MS (m/z) 597 (M+) |

TABLE 10-continued

The Examples in Table 10 may be prepared essentially as described by the Deprotection Procedure 2 in Example 73 except for the Preparation that is deprotected is indicated in column 3.

| Example | Chemical Name | Preparation that is deprotected | Data |
|---------|---------------|---------------------------------|------|
| 78 | (R)-3-[4'-(4-tert-Butyl-piperazine-1-carbonyl)-3,5-dichloro-biphenyl-4-ylmethyl]-cis-1-(4-hydroxy-cyclohexyl)-pyrrolidin-2-one hydrochloride | 52 | MS (m/z) 586 (M+) |
| 79 | (R)-3-[3,5-Dichloro-4'-([1,4]oxazepane-4-carbonyl)-biphenyl-4-ylmethyl]-cis-1-(4-hydroxy-cyclohexyl)-pyrrolidin-2-one | 53 | MS (m/z) 545 (M+) |
| 80 | (R)-3-[3,5-Dichloro-4'-(4,4-difluoro-piperidine-1-carbonyl)-biphenyl-4-ylmethyl]-cis-1-(4-hydroxy-cyclohexyl)-pyrrolidin-2-one | 54 | MS (m/z) 565 (M+) |
| 81 | (R)-3-[3,5-Dichloro-4'-(3,3-difluoro-pyrrolidine-1-carbonyl)-biphenyl-4-ylmethyl]-cis-1-(4-hydroxy-cyclohexyl)-pyrrolidin-2-one | 55 | MS (m/z) 551 (M+) |

TABLE 10-continued

The Examples in Table 10 may be prepared essentially as described by the Deprotection Procedure 2 in Example 73 except for the Preparation that is deprotected is indicated in column 3.

| Example | Chemical Name | Preparation that is deprotected | Data |
|---|---|---|---|
| 82 | 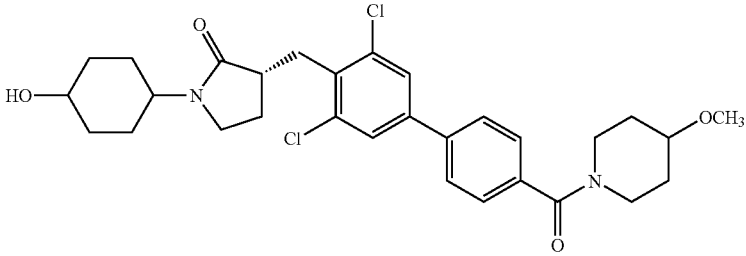<br>(R)-3-[3,5-Dichloro-4'-(4-methoxy-piperidine-1-carbonyl)-biphenyl-4-ylmethyl]-cis-1-(4-hydroxy-cyclohexyl)-pyrrolidin-2-one | 56 | MS (m/z) 559 (M+) |
| 83 | 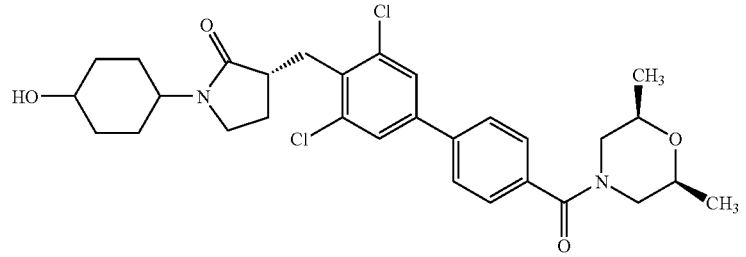<br>(R)-3-[3,5-Dichloro-4'-(2,6-cis-dimethyl-morpholine-4-carbonyl)-biphenyl-4-ylmethyl]-cis-1-(4-hydroxy-cyclohexyl)-pyrrolidin-2-one | 57 | MS (m/z) 559 (M+) |
| 84 | 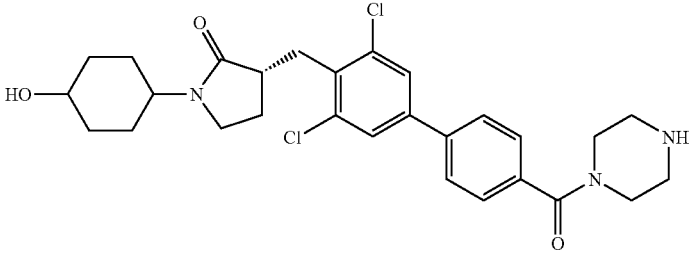<br>(R)-3-[3,5-Dichloro-4'-(piperazine-1-carbonyl)-biphenyl-4-ylmethyl]-cis-1-(4-hydroxy-cyclohexyl)-pyrrolidin-2-one hydrochloride | 58 | MS (m/z) 530 (M+) |
| 85 | 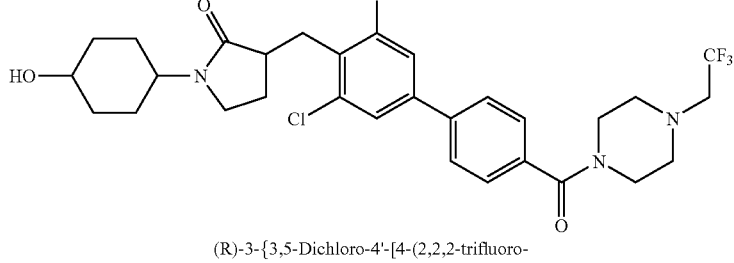<br>(R)-3-{3,5-Dichloro-4'-[4-(2,2,2-trifluoro-ethyl)-piperazine-1-carbonyl]-biphenyl-4-ylmethyl}-cis-1-(4-hydroxy-cyclohexyl)-pyrrolidin-2-one | 59 | MS (m/z) 612 (M+) |

TABLE 10-continued

The Examples in Table 10 may be prepared essentially as described by the Deprotection Procedure 2 in Example 73 except for the Preparation that is deprotected is indicated in column 3.

| Example | Chemical Name | Preparation that is deprotected | Data |
|---|---|---|---|
| 86 | 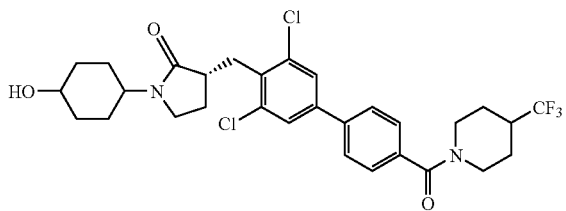<br>(R)-3-[3,5-Dichloro-4'-(2-oxa-5-aza-bicyclo[2.2.1]heptane-5-carbonyl)-biphenyl-4-ylmethyl]-cis-1-(4-hydroxy-cyclohexyl)-pyrrolidin-2-one | 60 | MS (m/z) 543 (M+) |

Examples 76, 78 and 84 are HCl salts.

EXAMPLE 87

(R)-3-[3,5-Dichloro-4'-(4-trifluoromethyl-piperidine-1-carbonyl)-biphenyl-4-ylmethyl]-trans-1-(4-hydroxy-cyclohexyl)-pyrrolidin-2-one Prepare the title compound by using the Deprotection Procedure 1 as described in Example 73 and using Preparation 62 to deprotect. MS (m/z) 596 (M+).

Treat a solution of 3-[3,5-dichloro-4'-(4-trifluoromethyl-piperidine-1-carbonyl)-biphenyl-4-ylmethyl]-trans-1-(4-triisopropylsilanyloxy-cyclohexyl)-pyrrolidin-2-one (0.548 g, 0.78 mmol) in 15 mL dry tetrahydrofuran with a 1M tetrahydrofuran solution of tetrabutylammonium fluoride (1.55 ml, 1.55 mmol) and stir at room temperature for 2 hours. Quench the reaction with saturated aqueous sodium bicarbonate and extract with ethyl acetate. Wash the extract with brine, dry over magnesium sulfate, filter, and concentrate to dryness under vacuum. Purify the residue by silica gel chromatography to recover 0.448 g (97%) of the title compound: MS (m/z): 596 (M+).

TABLE 11

The Examples in Table 11 may be prepared essentially as described by the Deprotection Procedure 2 in Example 73 except for the Preparation that is deprotected is indicated in column 3.

| Example | Chemical Name | Preparation that is deprotected | Physical Data |
|---|---|---|---|
| 88 | (R)-3-{3,5-Dichloro-4'-[4-(2,2,2-trifluoro-ethyl)-piperazine-1-carbonyl]-biphenyl-4-ylmethyl}-trans-1-(4-hydroxy-cyclohexyl)-pyrrolidin-2-one | 63 | MS (m/z) 612 (M+) |

TABLE 11-continued

The Examples in Table 11 may be prepared essentially as described by the Deprotection Procedure 2 in Example 73 except for the Preparation that is deprotected is indicated in column 3.

| Example | Chemical Name | Preparation that is deprotected | Physical Data |
|---|---|---|---|
| 89 | 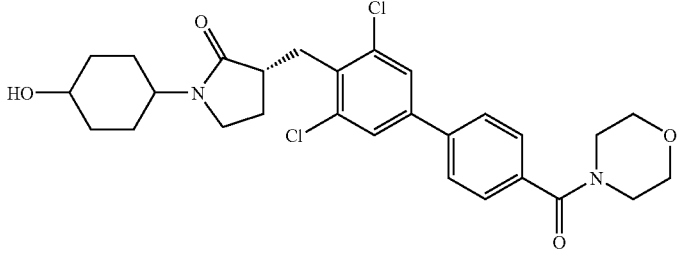<br>(R)-3-[3,5-Dichloro-4'-(morpholine-4-carbonyl)-biphenyl-4-ylmethyl]-trans-1-(4-hydroxy-cyclohexyl)-pyrrolidin-2-one | 64 | MS (m/z) 531 (M+) |
| 90 | 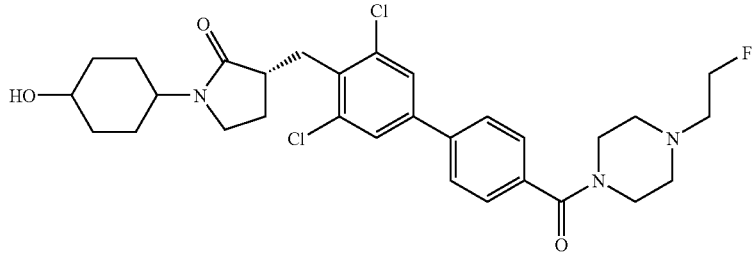<br>(R)-3-{3,5-Dichloro-4'-[4-(2-fluoro-ethyl)-piperazine-1-carbonyl]-biphenyl-4-ylmethyl}-trans-1-(4-hydroxy-cyclohexyl)-pyrrolidin-2-one hydrochloride | 66 | MS (m/z) 576 (M+) |
| 91 | 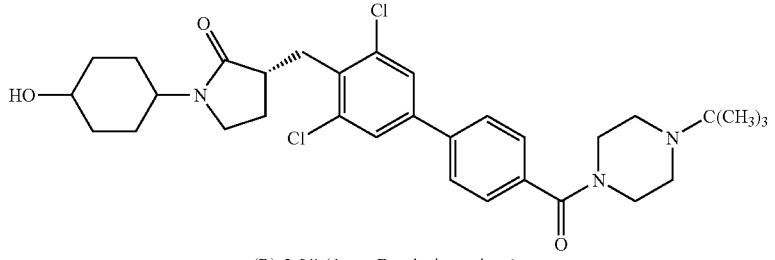<br>(R)-3-[4'-(4-tert-Butyl-piperazine-1-carbonyl)-3,5-dichloro-biphenyl-4-ylmethyl]-trans-1-(4-hydroxy-cyclohexyl)-pyrrolidin-2-one hydrochloride | 67 | MS (m/z) 586 (M+) |

Examples 90 and 91 are HCl salts.

EXAMPLE 92

(R)-1-cyclohex-3-enyl-3-[3,5-dichloro-4'-(4-trifluoromethyl-piperidine-1-carbonyl)-biphenyl-4-ylmethyl]-pyrrolidin-2-one

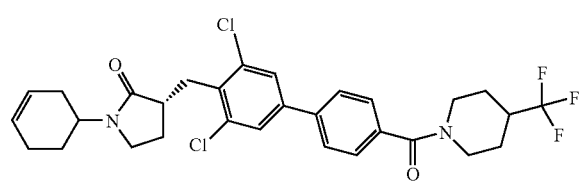

Dissolve tetrabutylammonium fluoride trihydrate (0.436 g, 1.36 mmol) in 5 ml of acetonitrile. Add water (0.05 ml. 2.72 mmol) and stir for 10 minutes. Add trans-methanesulfonic acid 4-{(R)-3-[3,5-dichloro-4'-(4-trifluoromethyl-piperidine-1-carbonyl)-biphenyl-4-ylmethyl]-2-oxo-pyrrolidin-1-yl}-cyclohexyl ester (0.458 g, 0.68 mmol). Stir at 80° C. for 12 hours. Quench with saturated aqueous sodium bicarbonate and extract with ethyl acetate. Wash the extract with brine. Dry the organic layer over magnesium sulfate, filter, and concentrate under vacuum. Purify by silica gel chromatography recover 0.036 g (9%) of the title compound: MS (m/z): 579 (M+).

EXAMPLE 93

(R)-3-{3,5-dichloro-4'-[4-(2-fluoro-ethyl)-4-oxy-piperazine-1-carbonyl]-biphenyl-4-ylmethyl}-cis-1-(4-hydroxy-cyclohexyl)-pyrrolidin-2-one

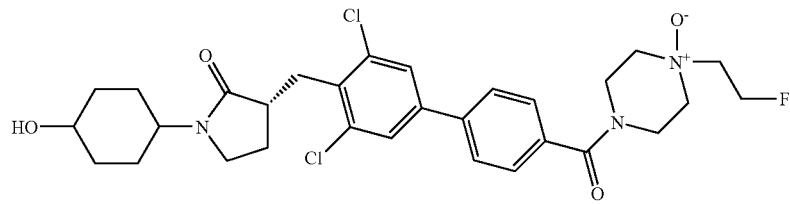

Add (R)-cis-1-[4-(tert-butyl-dimethyl-silanyloxy)-cyclohexyl]-3-{3,5-dichloro-4'-[4-(2-fluoro-ethyl)-piperazine-1-carbonyl]-biphenyl-4-ylmethyl}-pyrrolidin-2-one (Preparation 93) (0.193 g, 0.28 mmol) to 10 ml of dry dichloromethane, cool in an ice bath and treat with m-chloroperoxybenzoic acid (0.075 g of 77% commercial grade, 0.335 mmol). Stir for 30 minutes and concentrate the reaction to dryness. Purify on silica with 10% methanol in chloroform to afford 0.171 g of (R)-1-[4-(tert-butyl-dimethyl-silanyloxy)-cyclohexyl]-3-{3,5-dichloro-4'-[4-(2-fluoro-ethyl)-4-oxy-piperazine-1-carbonyl]-biphenyl-4-ylmethyl}-pyrrolidin-2-one: MS (m/z): 707 (M+1).

Dissolve the (R)-1-[4-(tert-butyl-dimethyl-silanyloxy)-cyclohexyl]-3-{3,5-dichloro-4'-[4-(2-fluoro-ethyl)-4-oxy-piperazine-1-carbonyl]-biphenyl-4-ylmethyl}-pyrrolidin-2-one in 15 ml of ethanol and treat with aqueous 1 N hydrochloric acid solution. Heat the reaction overnight at 40° C. then concentrate under vacuum to afford a quantitative yield of the title compound: MS (m/z): 592 (M+).

EXAMPLE 94

(R)-3-[3,5-dichloro-4'-(1,1-dioxo-1-lambda*6*-thiomorpholine-4-carbonyl)-biphenyl-4-ylmethyl]-trans-1-(4-hydroxy-cyclohexyl)-pyrrolidin-2-one

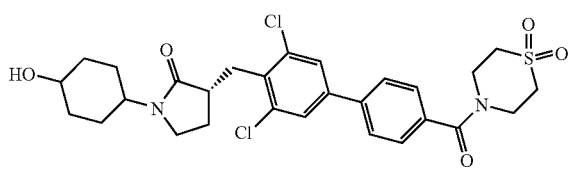

Dissolve (R)-trans-1-[4-(tert-butyl-dimethyl-silanyloxy)-cyclohexyl]-3-[3,5-dichloro-4'-(thiomorpholine-4-carbonyl)-biphenyl-4-ylmethyl]-pyrrolidin-2-one (Preparation 65) (0.366 g, 0.55 mmol) in 25 ml of methanol and cool it in an ice bath. Treat the solution with potassium peroxymonosulfate (0.694 g, 1.13 mmol) dissolved in 5 ml of water. Stir the reaction for 16 hrs at room temperature and then heat to 45° C. for 2 hrs. Remove the solvent under vacuum, dilute with water and extract twice with ethyl acetate. Wash the organic layers with brine, combine and dry over magnesium sulfate. Concentrate under vacuum to afford a quantitative yield of product: MS (m/z): 579 (M+).

EXAMPLE 95

(R)-3-[3,5-dichloro-4'-(4-trifluoromethyl-piperidine-1-carbonyl)-biphenyl-4-ylmethyl]-1-(tetrahydro-pyran-4-yl)-pyrrolidin-2-one

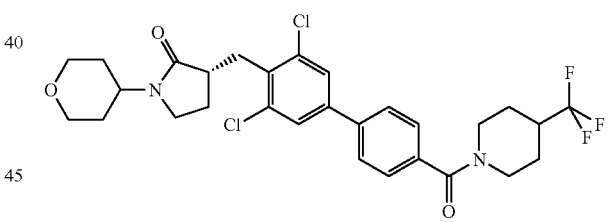

Treat a solution of 3',5'-dichloro-4'-[(R)-2-oxo-1-(tetrahydro-pyran-4-yl)-pyrrolidin-3-ylmethyl]-biphenyl-4-carboxylic acid (0.25 g, 0.56 mmol), 4-(trifluoromethyl)piperidine hydrochloride (0.13 g, 0.67 mmol), 1-hydroxybenzotriazole (0.23 g, 0.67 mmol), and 4-methylmorpholine (0.18 mL, 1.67 mmol) in dichloromethane (10 mL) with N-(3-dimethylaminopropyl)-N-ethylcarbodiimide hydrochloride (0.13 g, 0.67 mmol) and stir at room temperature for 6 hr. Quench the reaction with 1N hydrochloric acid and extract with ethyl acetate. Wash the organic layer with brine, dry over magnesium sulfate, and filter. Purify the crude material by silica gel column chromatography using hexanes:ethyl acetate to afford 0.23 g (72%) of desired product: MS (m/z): 583 (M+).

TABLE 12

The Examples in Table 12 may be prepared essentially as described in Example 95 except for the amine is replaced with the amine as indicated.

| Example | Chemical Name | Amine | Physical Data |
|---|---|---|---|
| 96 | 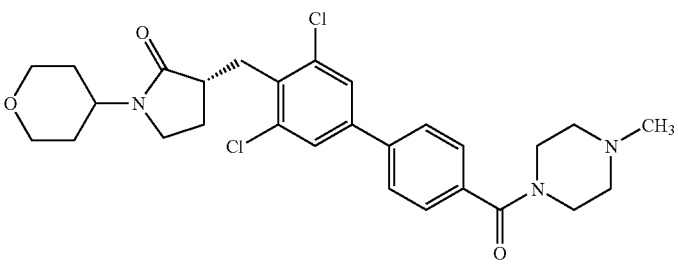<br>(R)-3-[3,5-Dichloro-4'-(4-methyl-piperazine-1-carbonyl)-biphenyl-4-ylmethyl]-1-(tetrahydro-pyran-4-yl)-pyrrolidin-2-one | 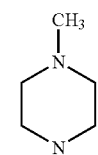 | MS (m/z) 530 (M+) |
| 97 | 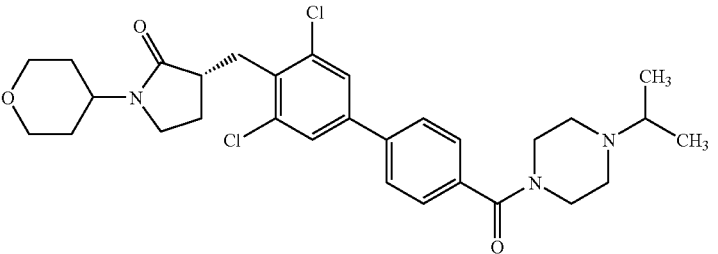<br>(R)-3-[3,5-Dichloro4'-(4-isopropyl-piperazine-1-carbonyl)-biphenyl-4-ylmethyl]-1-(tetrahydro-pyran-4-yl)-pyrrolidin-2-one | 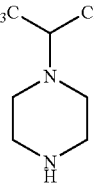 | MS (m/z) 558 (M+) |
| 98 | 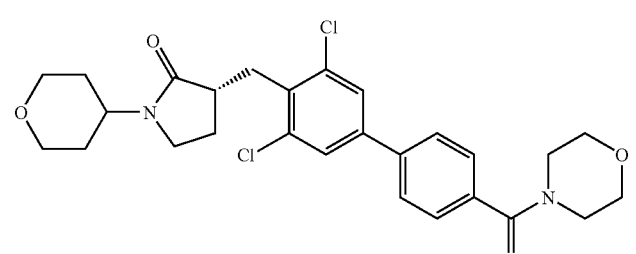<br>(R)-3-[3,5-Dichloro-4'-(morpholine-4-carbonyl)-biphenyl-4-ylmethyl]-1-(tetrahydro-pyran-4-yl)-pyrrolidin-2-one | 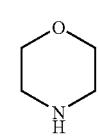 | MS (m/z) 517 (M+) |
| 99 | 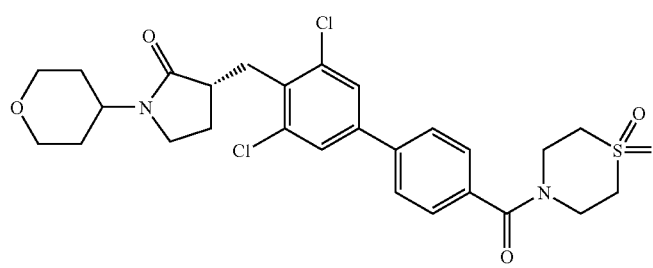<br>(R)-3-[3,5-Dichloro-4'-(1,1-dioxo-1l6-thiomorpholine-4-carbonyl)-biphenyl-4-ylmethyl]-1-(tetrahydro-pyran-4-yl)-pyrrolidin-2-one | 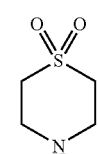 | MS (m/z) 565 (M+) |

TABLE 12-continued

The Examples in Table 12 may be prepared essentially as described in Example 95 except for the amine is replaced with the amine as indicated.

| Example | Chemical Name | Amine | Physical Data |
|---|---|---|---|
| 100 | 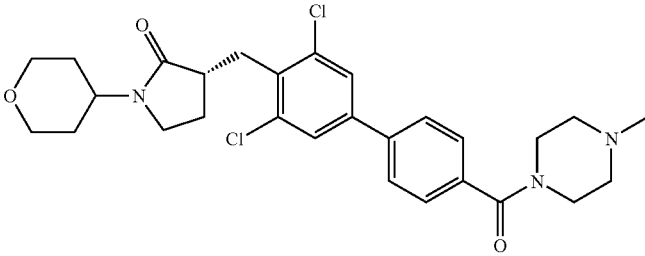<br>(R)-3-{3,5-Dichloro-4'-[4-(2-fluoro-ethyl)-piperazine-1-carbonyl]-biphenyl-4-ylmethyl}-1-(tetrahydro-pyran-4-yl)-pyrrolidin-2-one | 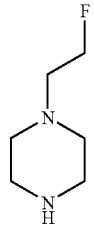 | MS (m/z) 562 (M+) |
| 101 | 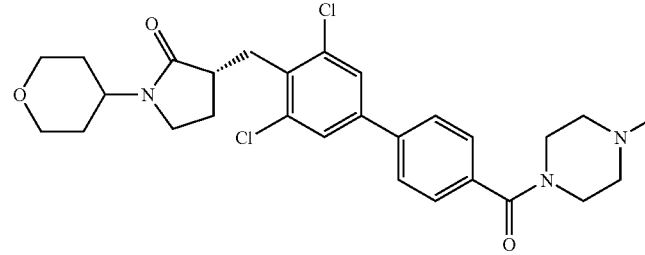<br>(R)-3-{3,5-Dichloro-4'-[4-(2,2,2-trifluoro-ethyl)-piperazine-1-carbonyl]-biphenyl-4-ylmethyl}-1-(tetrahydro-pyran-4-yl)-pyrrolidin-2-one | 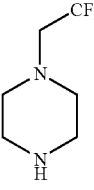 | MS (m/z) 598 (M+) |
| 102 | 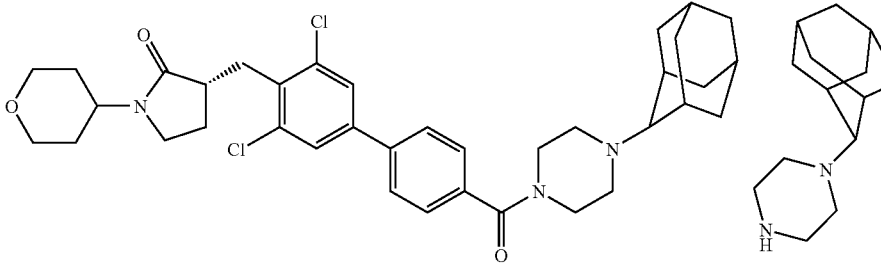<br>(R)-3-[4'-(4-Adamantan-2-yl-piperazine-1-carbonyl)-3,5-dichloro-biphenyl-4-ylmethyl]-1-(tetrahydro-pyran-4-yl)-pyrrolidin-2-one | 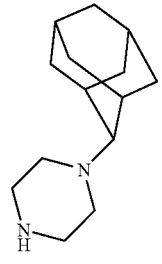 | MS (m/z) 650 (M+) |
| 103 | 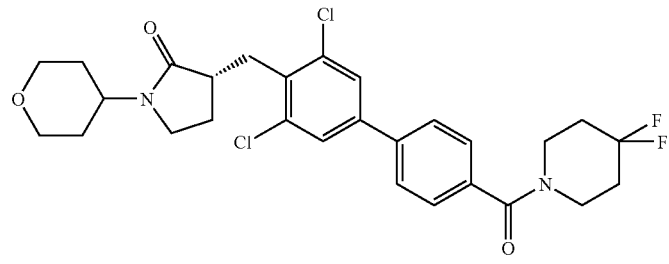<br>(R)-3-[3,5-Dichloro-4'-(4,4-difluoro-piperidine-1-carbonyl)-biphenyl-4-ylmethyl]-1-(tetrahydro-pyran-4-yl)-pyrrolidin-2-one | 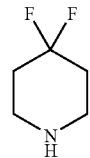 | MS (m/z) 551 (M+) |

EXAMPLE 104

(R)-3-[3,5-dichloro-4'-(4,4-difluoro-piperidine-1-carbonyl)-biphenyl-4-ylmethyl]-trans-1-(4-hydroxy-cyclohexyl)-pyrrolidin-2-one

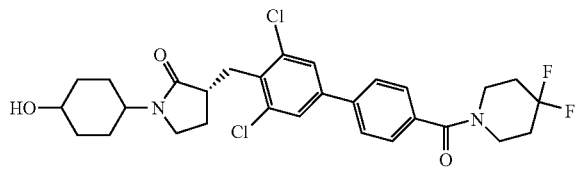

Prepare the title compound in 97% yield by deprotection procedure 1 starting from (R)-3-[3,5-dichloro-4'-(4,4-difluoro-piperidine-1-carbonyl)-biphenyl-4-ylmethyl]-trans-1-(4-triisopropylsilanyloxy-cyclohexyl)-pyrrolidin-2-one.

Treat a solution of (R)-3-[3,5-dichloro-4'-(4,4-difluoro-piperidine-1-carbonyl)-biphenyl-4-ylmethyl]-trans-1-(4-triisopropylsilanyloxy-cyclohexyl)-pyrrolidin-2-one (0.175 g, 0.24 mmol) in 15 mL dry tetrahydrofuran with a 1M tetrahydrofuran solution of tetrabutylammonium fluoride (0.7 ml, 0.7 mmol) and stir at room temperature for 2 hours. Quench the reaction with saturated aqueous sodium bicarbonate and extract with ethyl acetate. Wash the extract with brine, dry over magnesium sulfate, filter, and concentrate to dryness under vacuum. Purify the residue by silica gel chromatography to recover 0.097 g (71%) of the title compound: MS (m/z): 565 (M+).

TABLE 13

The Examples in Table 13 may be prepared essentially as described in Example 3 except use 4'-(1-Cyclohexyl-2-oxo-pyrrolidin-3-ylmethyl)-3'-trifluoromethoxy-biphenyl-4-carboxylic acid (Preparation 87) and replace the amine with the amine as indicated.

| Example | Structure and Chemical Name | Amine | Physical Data |
|---|---|---|---|
| 105 | 1-Cyclohexyl-3-[4'-(4-methyl-piperazine-1-carbonyl)-3-trifluoromethoxy-biphenyl-4-ylmethyl]-pyrrolidin-2-one | 1-methylpiperazine | MS (m/e): 544 (M + 1) |
| 106 | 1-Cyclohexyl-3-[4'-(4-isopropyl-piperazine-1-carbonyl)-3-trifluoromethoxy-biphenyl-4-ylmethyl]-pyrrolidin-2-one | 1-isopropylpiperazine | MS (m/z): 572 (M + 1) |
| 107 | 1-Cyclohexyl-3-[4'-(morpholine-4-carbonyl)-3-trifluoromethoxy-biphenyl-4-ylmethyl]-pyrrolidin-2-one | morpholine | MS (m/z): 531 (M + 1) |

TABLE 13-continued

The Examples in Table 13 may be prepared essentially as described in Example 3 except use 4'-(1-Cyclohexyl-2-oxo-pyrrolidin-3-ylmethyl)-3'-trifluoromethoxy-biphenyl-4-carboxylic acid (Preparation 87) and replace the amine with the amine as indicated.

| Example | Structure and Chemical Name | Amine | Physical Data |
|---|---|---|---|
| 108 | 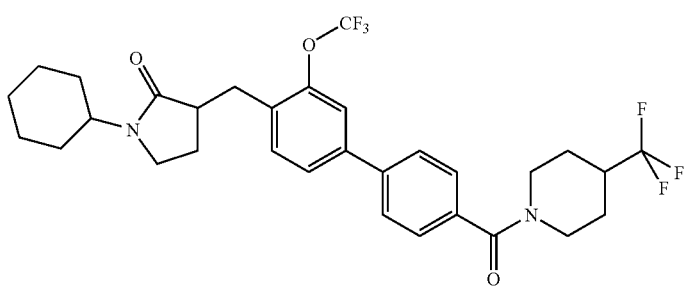<br>1-Cyclohexyl-3-[3-trifluoromethoxy-4'-(4-trifluoromethyl-piperidine-1-carbonyl)-biphenyl-4-ylmethyl]-pyrrolidin-2-one | 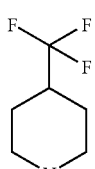 | MS (m/z): 597 (M + 1) |
| 109 | 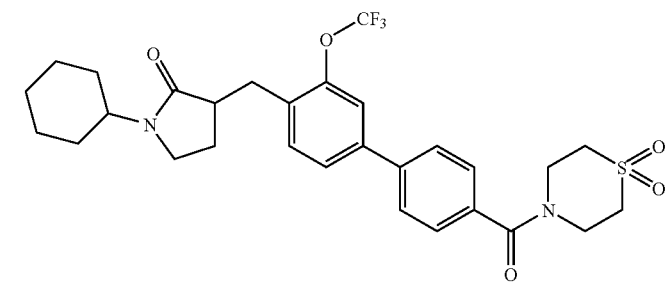<br>1-Cyclohexyl-3-[4'-(1,1-dioxo-1l6-thiomorpholine-4-carbonyl)-3-trifluoromethoxy-biphenyl-4-ylmethyl]-pyrrolidin-2-one | 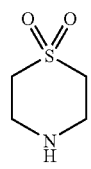 | MS (m/z): 579 (M + 1) |
| 110 | 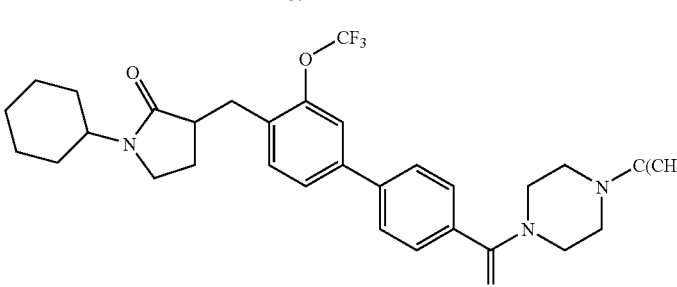<br>3-[4'-(4-tert-Butyl-piperazine-1-carbonyl)-3-trifluoromethoxy-biphenyl-4-ylmethyl]-1-cyclohexyl-pyrrolidin-2-one | 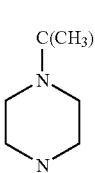 | MS (m/z): 586 (M + 1) |
| 111 | 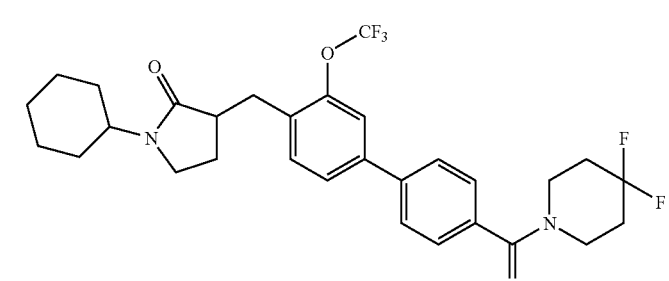<br>1-Cyclohexyl-3-[4'-(4,4-difluoro-piperidine-1-carbonyl)-3-trifluoromethoxy-biphenyl-4-ylmethyl]-pyrrolidin-2-one | 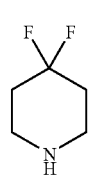 | MS (m/z): 565 (M + 1) |

TABLE 13-continued

The Examples in Table 13 may be prepared essentially as described in Example 3 except use 4'-(1-Cyclohexyl-2-oxo-pyrrolidin-3-ylmethyl)-3'-trifluoromethoxy-biphenyl-4-carboxylic acid (Preparation 87) and replace the amine with the amine as indicated.

| Example | Structure and Chemical Name | Amine | Physical Data |
|---|---|---|---|
| 112 | 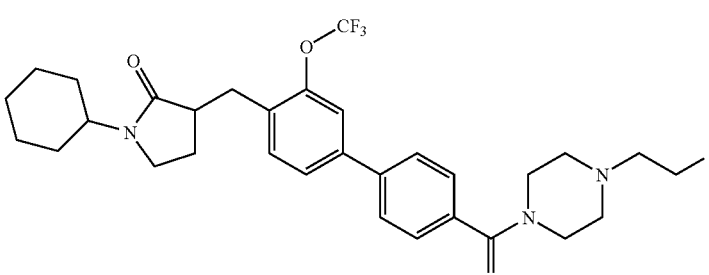<br>1-Cyclohexyl-3-{4'-[4-(2-fluoro-ethyl)-piperazine-1-carbonyl]-3-trifluoromethoxy-biphenyl-4-ylmethyl}-pyrrolidin-2-one | 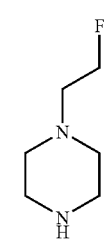 | MS (m/z): 576 (M + 1) |
| 113 | 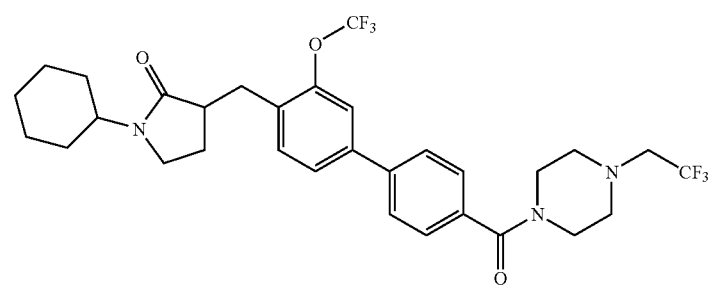<br>1-Cyclohexyl-3-{4'-[4-(2,2,2-trifluoro-ethyl)-piperazine-1-carbonyl]-3-trifluoromethoxy-biphenyl-4-ylmethyl}-pyrrolidin-2-one | 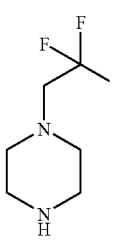 | MS (m/z): 612 (M + 1) |
| 114 | 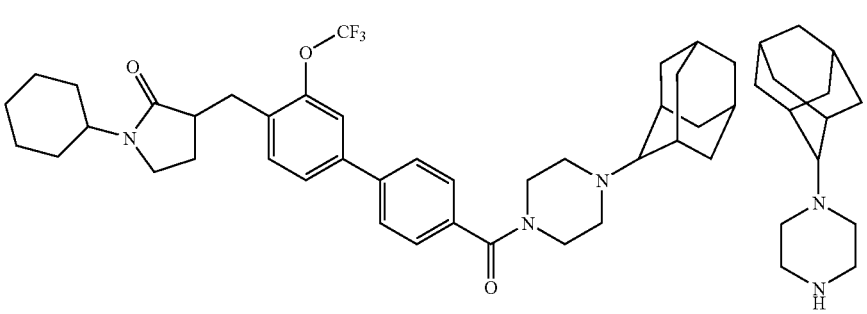<br>3-[4'-(4-Adamantan-2-yl-piperazine-1-carbonyl)-3-trifluoromethoxy-biphenyl-4-ylmethyl]-1-cyclohexyl-pyrrolidin-2-one | 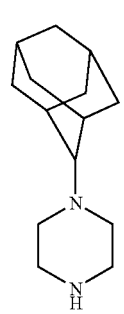 | MS (m/z): 664 (M + 1) |

TABLE 14

The Examples in Table 14 may be prepared essentially as described in Example 3 except use 4'-(1-Cyclohexyl-2-oxo-pyrrolidin-3-ylmethyl)-3'-trifluoromethyl-biphenyl-4-carboxylic acid (Preparation 88) and replace the amine with the amine as indicated.

| Example | Structure and Chemical Name | Amine | Physical Data |
|---|---|---|---|
| 115 | 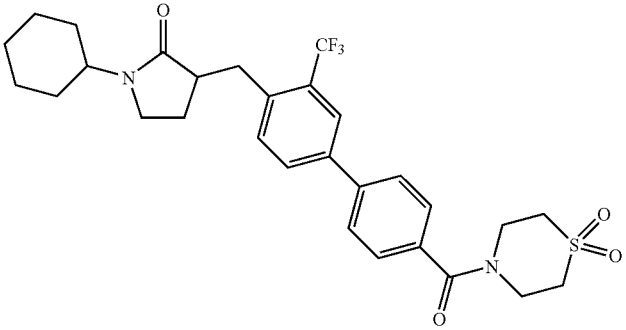<br>1-Cyclohexyl-3-[4'-(1,1-dioxo-1lambda*6*-thiomorpholine-4-carbonyl)-3-trifluoromethyl-biphenyl-4-ylmethyl]-pyrrolidin-2-one | 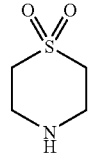 | MS (m/e): 563 (M + 1) |
| 116 | 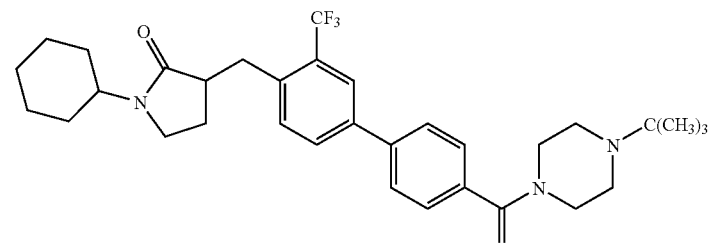<br>3-[4'-(4-tert-Butyl-piperazine-1-carbonyl)-3-trifluoromethyl-biphenyl-4-ylmethyl]-1-cyclohexyl-pyrrolidin-2-one trifluoroacetic acid | 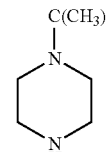 | MS (m/z): 570 (M + 1) |
| 117 | 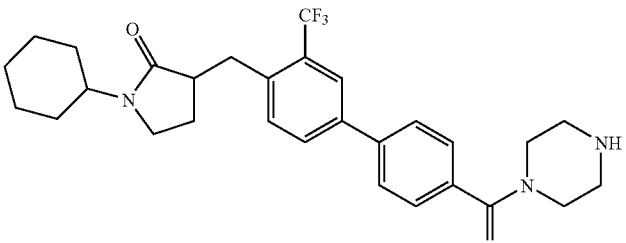<br>1-Cyclohexyl-3-[4'-(piperazine-1-carbonyl)-3-trifluoromethyl-biphenyl-4-ylmethyl]-pyrrolidin-2-one trifluoroacetic acid | 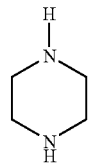 | MS (m/z): 515 (M + 1) |
| 118 | 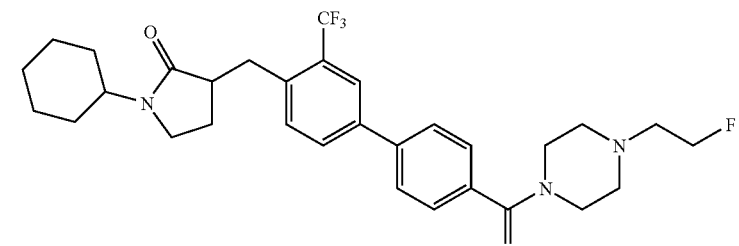<br>1-Cyclohexyl-3-{4'-[4-(2-fluoro-ethyl)-piperazine-1-carbonyl]-3-trifluoromethyl-biphenyl-4-ylmethyl}-pyrrolidin-2-one trifluoroacetic acid | 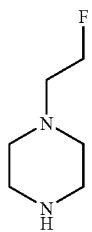 | MS (m/z): 560 (M + 1) |

TABLE 14-continued

The Examples in Table 14 may be prepared essentially as described in Example 3 except use 4'-(1-Cyclohexyl-2-oxo-pyrrolidin-3-ylmethyl)-3'-trifluoromethyl-biphenyl-4-carboxylic acid (Preparation 88) and replace the amine with the amine as indicated.

| Example | Structure and Chemical Name | Amine | Physical Data |
|---|---|---|---|
| 119 | 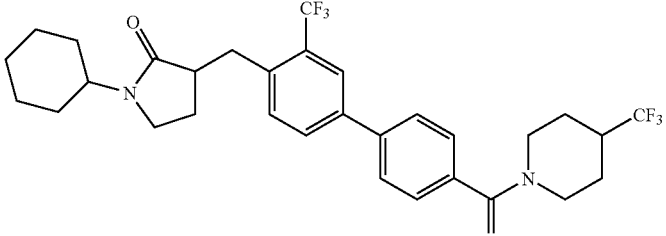<br>1-Cyclohexyl-3-[3-trifluoromethyl-4'-(4-trifluoromethyl-piperidine-1-carbonyl)-biphenyl-4-ylmethyl]-pyrrolidin-2-one trifluoroacetic acid | 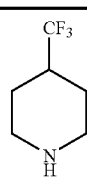 | MS (m/z): 581 (M + 1) |
| 120 | 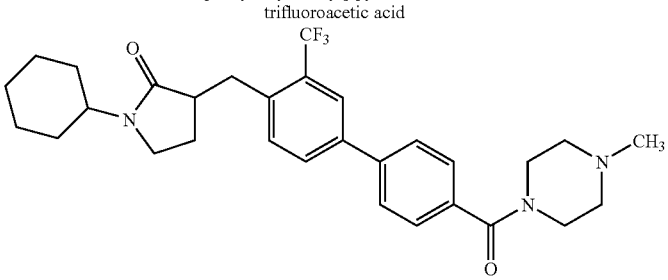<br>1-Cyclohexyl-3-[4-(4-methyl-piperazine-1-carbonyl)-3-trifluoromethyl-biphenyl-4-ylmethyl]-pyrrolidin-2-one trifluoroacetic acid | 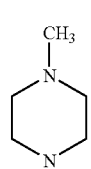 | MS (m/z): 528 (M + 1) |

Examples 116-120 are the TFA salts because TFA is used in purification by reverse phase HPLC.

TABLE 15

The Examples in Table 15 may be prepared essentially as described in Example 3 except use 4'-(1-Cyclohexyl-2-oxo-pyrrolidin-3-ylmethyl)-3'-trifluoromethyl-biphenyl-4-carboxylic acid (Preparation 88) and replace the amine with the amine as indicated.

| Example | Structure and Chemical name | Preparation | Physical data |
|---|---|---|---|
| 121 | 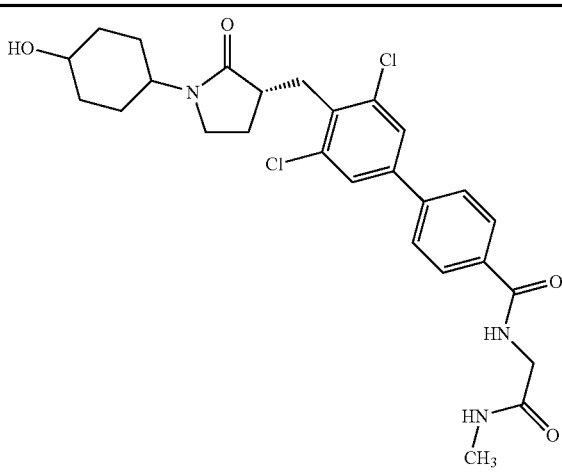<br>3',5'-Dichloro-4'-[(R)-trans-1-(4-hydroxy-cyclohexyl)-2-oxo-pyrrolidin-3-ylmethyl]-biphenyl-4-carboxylic acid methylcarbamoylmethyl-amide | 89 | MS (m/z): 533 (M + 1) |

TABLE 15-continued

The Examples in Table 15 may be prepared essentially as described in Example 3 except use 4'-(1-Cyclohexyl-2-oxo-pyrrolidin-3-ylmethyl)-3'-trifluoromethyl-biphenyl-4-carboxylic acid (Preparation 88) and replace the amine with the amine as indicated.

| Example | Structure and Chemical name | Preparation | Physical data |
|---|---|---|---|
| 122 | 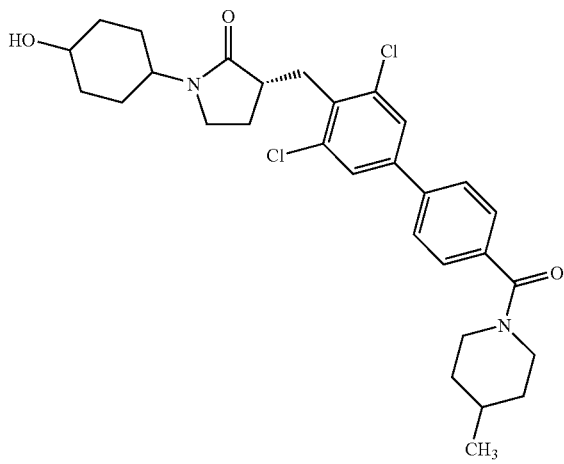<br>(R)-3-[3,5-Dichloro-4'-(4-methyl-piperidine-1-carbonyl)-biphenyl-4-ylmethyl]-trans-1-(4-hydroxy-cyclohexyl)-pyrrolidin-2-one | 90 | MS (m/z): 545 (M + 1) |
| 123 | 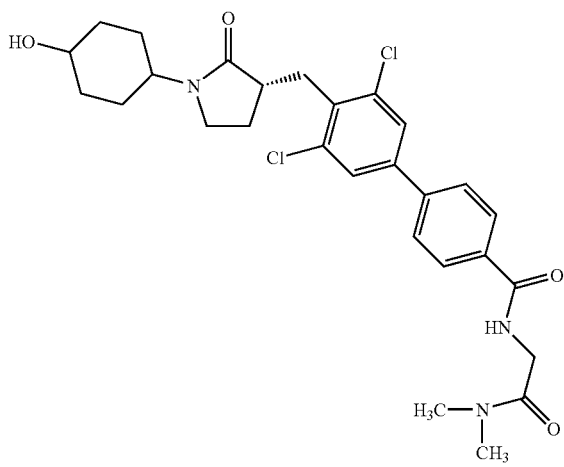<br>3',5'-Dichloro-4'-[(R)-trans-1-(4-hydroxy-cyclohexyl)-2-oxo-pyrrolidin-3-ylmethyl]-biphenyl-4-carboxylic acid dimethylcarbamoylmethyl-amide | 91 | MS (m/z): 548 (M + 1) |

TABLE 15-continued

The Examples in Table 15 may be prepared essentially as described in Example 3 except use 4'-(1-Cyclohexyl-2-oxo-pyrrolidin-3-ylmethyl)-3'-trifluoromethyl-biphenyl-4-carboxylic acid (Preparation 88) and replace the amine with the amine as indicated.

| Example | Structure and Chemical name | Preparation | Physical data |
|---|---|---|---|
| 124 | 3',5'-Dichloro-4'-[(R)-trans-1-(4-hydroxy-cyclohexyl)-2-oxo-pyrrolidin-3-ylmethyl]-biphenyl-4-carboxylic acid carbamoylmethyl-amide | 92 | MS (m/z): 520 (M + 1) |

EXAMPLE 125

(R)-3-[3,5-Dichloro-4'-(4-trifluoromethyl-piperidine-1-carbonyl)-biphenyl-4-ylmethyl]-trans-1-(4-methoxy-cyclohexyl)-pyrrolidin-2-one

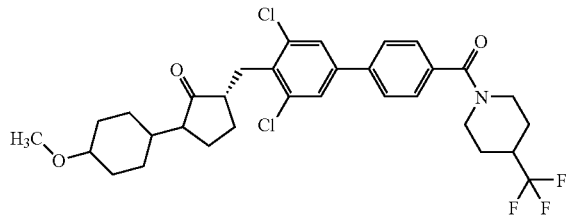

Mix 3',5'-dichloro-4'-[(R)-trans-1-(4-methoxy-cyclohexyl)-2-oxo-pyrrolidin-3-ylmethyl]-biphenyl-4-carboxylic acid (0.350 g, 0.74 mmol), 1-(3-dimethylaminopropyl)-3-ethylcarbodiimide hydrochloride (0.216 g, 1.11 mmol), N-methylmorpholine (0.33 mL, 2.95 mmol), hydroxybenzotriazole (0.247 g, 0.74 mmol) and 4-trifluoromethyl-piperidine hydrochloride (0.226 g, 1.47 mmol) in CH$_2$Cl$_2$ (10 mL). Stir for 12 hours at room temperature. Quench with 1N HCl and extract with ethyl acetate. Wash the extract with saturated aqueous sodium bicarbonate brine. Dry over magnesium sulfate, filter, and concentrate under vacuum. Purify by flash column chromatography to recover 0.350 g (78%) of the title compound: MS (m/z): 611 (M+).

EXAMPLE 126

(R)-3-[3,5-Dichloro-4'-(4,4-difluoro-piperidine-1-carbonyl)-biphenyl-4-ylmethyl]-trans-1-(4-methoxy-cyclohexyl)-pyrrolidin-2-one

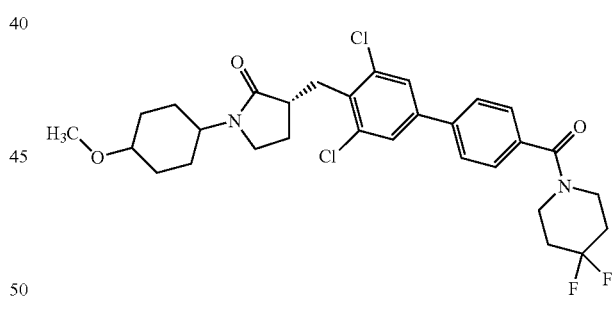

Prepare the title compound essentially as described in Preparation 48 starting from 3',5'-dichloro-4'-[(R)-trans-1-(4-methoxy-cyclohexyl)-2-oxo-pyrrolidin-3-ylmethyl]-biphenyl-4-carboxylic acid and 4,4-difluoropiperazine. MS (m/z): 580 (M+).

In the following section enzyme and functional assays are described which are useful for evaluating the compounds of the invention.

11β-HSD Type 1 Enzyme Assay

Human 11β-HSD type 1 activity is measured by assaying NADPH production by fluorescence assay. Solid compounds are dissolved in DMSO to a concentration of 10 mM. Twenty microliters of each are then transferred to a column of a 96-well polypropylene Nunc plate where they are further diluted 50-fold followed by subsequent two-fold titration, ten times across the plate with additional DMSO using a Tecan Genesis 200 automated system. Plates are then transferred to a Tecan Freedom 200 system with an attached Tecan Temo 96-well head and an Ultra 384 plate reader. Reagents are supplied in 96-well polypropylene Nunc plates and are dispensed individually into black 96-well Molecular Devices High Efficiency assay plates (40 µL/well capacity) in the following fashion: 9 µL/well of substrate (2.22 mM NADP, 55.5 µM Cortisol, 10 mM Tris, 0.25% Prionex, 0.1% Triton X100), 3 µL/well of water to compound wells or 3 µL to control and standard wells, 6 µL/well recombinant human 11β-HSD type 1 enzyme, 2 µL/well of compound dilutions. For ultimate calculation of percent inhibition, a series of wells are added that represent assay minimum and maximum: one set containing substrate with 667 µM carbenoxolone (background), and another set containing substrate and enzyme without compound (maximum signal). Final DMSO concentration is 0.5% for all compounds, controls and standards. Plates are then placed on a shaker by the robotic arm of the Tecan for 15 seconds before being covered and stacked for a three hour incubation period at room temperature. Upon completion of this incubation, the Tecan robotic arm removes each plate individually from the stacker and places them in position for addition of 5 µL/well of a 250 µM carbenoxolone solution to stop the enzymatic reaction. Plates are then shaken once more for 15 seconds then placed into an Ultra 384 microplate reader (355EX/460EM) for detection of NADPH fluorescence.

Data for example compounds in the 11-βHSD1 assay are shown below:

of $9 \times 10^4$ cells/mL in 0.5% FBS assay medium containing 12 ng/mL hTNFα to induce expression of 11β-HSD1. Cells are seeded into 96-well tissue culture assay plates at 100 µL/well ($9 \times 10^3$ cells/well) and incubated for 48 hours at 37° C., 5% $CO_2$. Following induction, cells are incubated for 4 hours at 37° C., 5% $CO_2$ in assay medium containing test compounds then treated with 10 µL/well of 10 µM cortisone solubilized in assay medium, and incubated for 16 hours at 37° C., 5% $CO_2$. Medium from each well is transferred to a plate for subsequent analysis of cortisol using a competitive fluorescence resonance time resolved immunoassay. In solution, an allophycocyanin (APC)-cortisol conjugate and free cortisol analyte compete for binding to a mouse anti-cortisol antibody/Europium (Eu)-anti mouse IgG complex. Higher levels of free cortisol result in diminishing energy transfer from the Europium-IgG to the APC-cortisol complex resulting in less APC fluorescence. Fluorescent intensities for Europium and APC are measured using a LJL Analyst AD. Europium and APC excitation is measured using 360 nm excitation and 615 nm and 650 nm emission filters respectively. Time resolved parameters for Europuium were 1000 µs integration time with a 200 µs delay. APC parameters are set at 150 µs integration time with a 50 µs delay. Fluorescent intensities measured for APC are modified by dividing by the Eu fluorescence (APC/Eu). This ratio is then used to determine the unknown cortisol concentration by interpolation using a cortisol standard curve fitted with a 4-parameter logistic equation. These concentrations are then used to determine compound activity by plotting concentration versus % inhibition, fitting with a 4-parameter curve and reporting the $IC_{50}$.

| Example | Structure | Human 11-βHSD1 $IC_{50}$ (nM) |
|---|---|---|
| 62 | 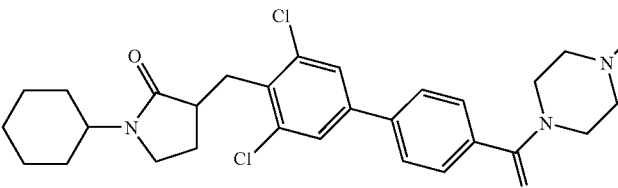 | 115 |
| 92 | 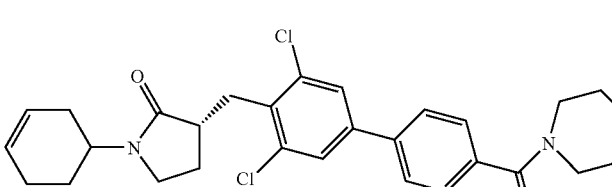 | 633 |

Human Aortic Smooth Muscle Cell Assay

Primary human aortic smooth muscle cells (AoSMC) are cultured in 5% FBS growth medium to a passage number of 6, then pelleted by centrifugation and resuspended at a density Examples disclosed herein possess activity in the human aortic smooth muscle cell assay with an $IC_{50}$ of less than 300 nM. Data for example compounds in the human aortic smooth muscle cell assay are shown below:

| Example | Structure | IC$_{50}$ (nM) |
|---|---|---|
| 4 | 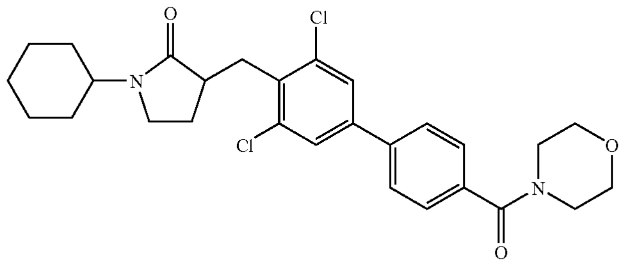 | 4.3 |
| 5 | 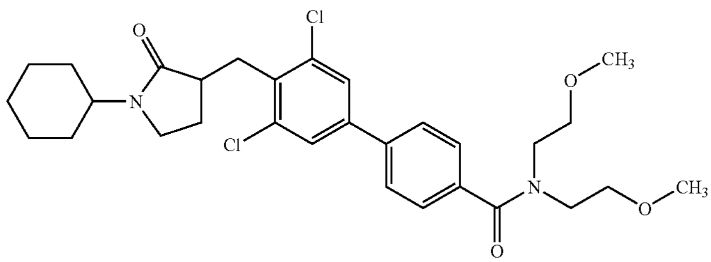 | 6.4 |
| 49 | 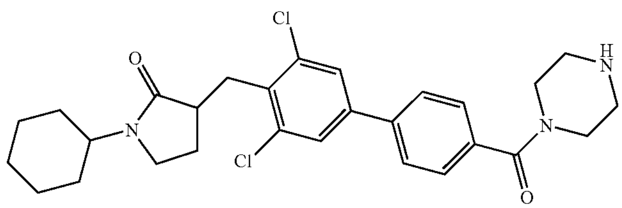 | 11.4 |
| 74 | 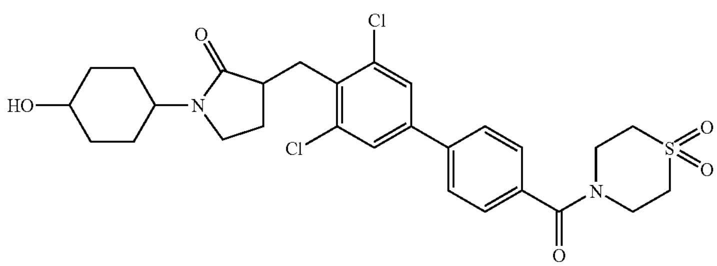 | 6.0 |
| 92 | 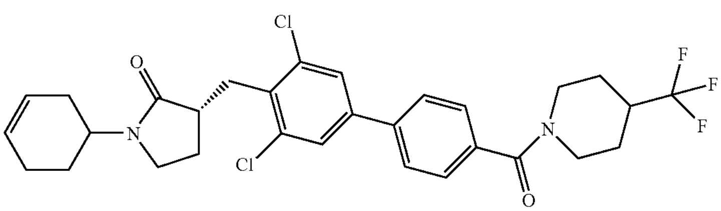 | 36.8 |
| 99 | 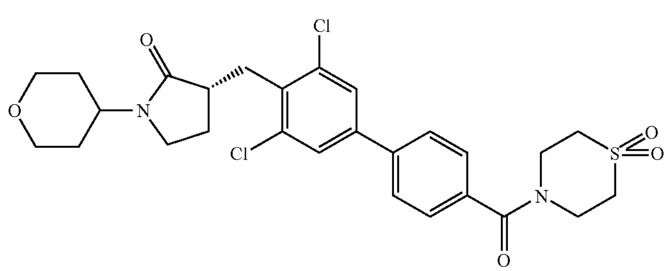 | 72.8 |

Acute In Vivo Cortisone Conversion Assay

In general, compounds are dosed orally into mice, the mice are challenged with a subcutaneous injection of cortisone at a set timepoint after compound injection, and the blood of each animal is collected some time later. Separated serum is then isolated and analyzed for levels of cortisone and cortisol by LC-MS/MS, followed by calculation of mean cortisol and percent inhibition of each dosing group. Specifically, male C57BL/6 mice are obtained from Harlan Sprague Dawley at average weight of 25 grams. Exact weights are taken upon arrival and the mice randomized into groups of similar weights. Compounds are prepared in 1% w-w HEC, 0.25% w-w polysorbate 80, 0.05% w-w Dow Corning antifoam #1510-US at various doses based on assumed average weight of 25 grams. Compounds are dosed orally, 200 μl per animal, followed by a subcutaneous dose, 200 μl per animal, of 30 mg/kg cortisone at 1 to 24 hours post compound dose. At 10 minutes post cortisone challenge, each animal is euthanized for 1 minute in a $CO_2$ chamber, followed by blood collection via cardiac puncture into serum separator tubes. Once fully clotted, tubes are spun at 2500×g, 4° C. for 15 minutes, the serum transferred to wells of 96-well plates (Corning Inc, Costar #4410, cluster tubes, 1.2 ml, polypropylene), and the plates are frozen at −20° C. until analysis by LC-MS/MS. For analysis, serum samples are thawed and the proteins are precipitated by the addition of acetonitrile containing d4-cortisol internal standard. Samples are vortex mixed and centrifuged. The supernatant is removed and dried under a stream of warm nitrogen. Extracts are reconstituted in methanol/water (1:1) and injected onto the LC-MS/MS system. The levels of cortisone and cortisol are assayed by selective reaction monitoring mode following positive ACPI ionization on a triple quadrupole mass spectrophotometer.

Data for example compounds in the acute in vivo cortisone conversion assay are shown below:

Pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977. The compounds of the present invention are preferably formulated as pharmaceutical compositions administered by a variety of routes. Most preferably, such compositions are for oral administration. Such pharmaceutical compositions and processes for preparing same are well known in the art. See, e.g. REMINGTON: THE SCIENCE AND PRACTICE OF PHARMACY (A. Gennaro, et al., eds., 19$^{th}$ ed., Mack Publishing Co., 1995).

The particular dosage of a compound of formula (I) or a pharmaceutically acceptable salt thereof required to constitute an effective amount according to this invention will depend upon the particular circumstances of the conditions to be treated. Considerations such as dosage, route of administration, and frequency of dosing are best decided by the attending physician. Generally, accepted and effective dose ranges for oral or parenteral administration will be from about 0.1 mg/kg/day to about 10 mg/kg/day which translates into about 6 mg to 600 mg, and more typically between 30 mg and 200 mg for human patients. Such dosages will be administered to a patient in need of treatment from one to three times each day or as often as needed to effectively treat a disease selected from those described herein.

One skilled in the art of preparing formulations can readily select the proper form and mode of administration depending upon the particular characteristics of the compound selected, the disorder or condition to be treated, the stage of the disorder or condition, and other relevant circumstances. (Remington's Pharmaceutical Sciences, 18th Edition, Mack Publishing Co. (1990)). The compounds claimed herein can be administered by a variety of routes. In effecting treatment of a patient afflicted with or at risk of developing the disorders described herein, a compound of formula (I) or a pharmaceutically acceptable salt thereof can be administered in any form or mode that makes the compound bioavailable in an effective amount, including oral and parenteral routes. For example, the active compounds can be administered rectally, orally, by inhalation, or by the subcutaneous, intramuscular, intrave-

| Example | Structure | % Inhibition after 16 hours (dose of 10 (mg/kg)) |
|---|---|---|
| 95 | 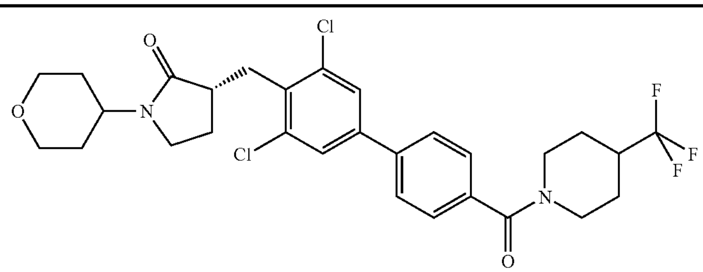 | 80 |
| 62 | | 85 | nous, transdermal, intranasal, rectal, occular, topical, sublingual, buccal, or other routes. Oral administration may be preferred for treatment of the disorders described herein. In those instances where oral administration is impossible or not preferred, the composition may be made available in a form suitable for parenteral administration, e.g., intravenous, intraperitoneal or intramuscular.

We claim:
1. A compound structurally represented by the formula:

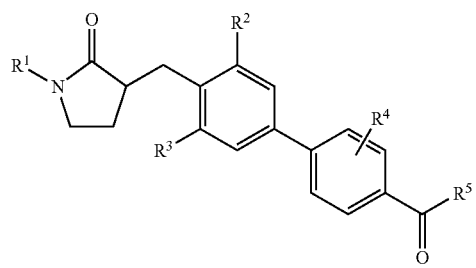

wherein:
$R^1$ is

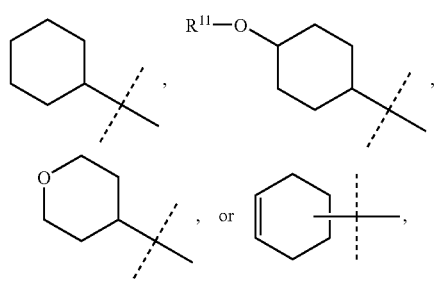

wherein the dashed line represents the point of attachment to the $R^1$ position;
$R^2$ is
—H, -halogen, —$CH_3$ (optionally substituted with 1 to 3 halogens), or —O—$CH_3$ (optionally substituted with 1 to 3 halogens);
$R^3$ is
-halogen, —$CH_3$ (optionally substituted with 1 to 3 halogens), or —O—$CH_3$ (optionally substituted with 1 to 3 halogens);
$R^4$ is —H or -halogen;
$R^5$ is

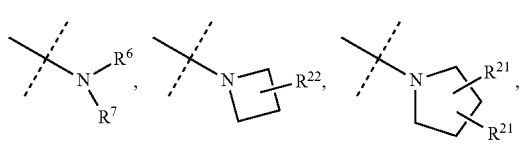

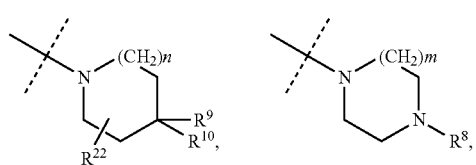

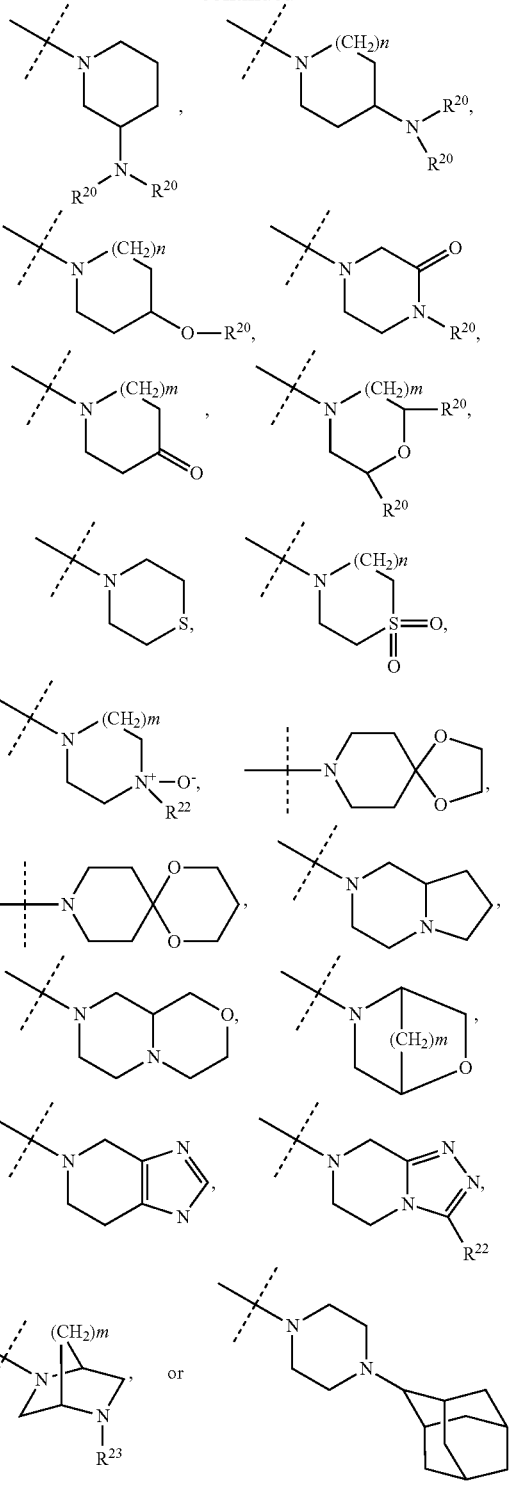

wherein the dashed line represents the point of attachment to the $R^5$ position;
wherein n is 0, 1, or 2, and wherein when n is 0, then "$(CH_2)n$" is a bond;
wherein m is 1 or 2;
$R^6$ is
—H, —$(C_1-C_3)$alkyl (optionally substituted with 1 to 3 halogens), —$(C_1-C_3)$alkyl-O—$R^{20}$, —$(C_1-C_3)$alkyl-pyrrolidinyl, phenyl, -$HET^1$, -$HET^2$, —$CH_2$-phenyl, —CH$_2$-HET$^1$, —CH$_2$-HET$^2$, —(C$_1$-C$_3$)alkyl-N(R$^{20}$)(R$^{20}$), —(C$_1$-C$_3$)alkyl-N$^+$(O$^-$)(CH$_3$)$_2$, —(C$_1$-C$_3$)alkyl-C(O)N(R$^{41}$)(R$^{41}$), —CH(C(O)OH)(CH$_2$OR$^{20}$), —CH(C(O)OH)(CH$_2$N(R$^{20}$)(R$^{20}$)), —(C$_1$-C$_3$)alkyl-C(O)O—R$^{20}$,

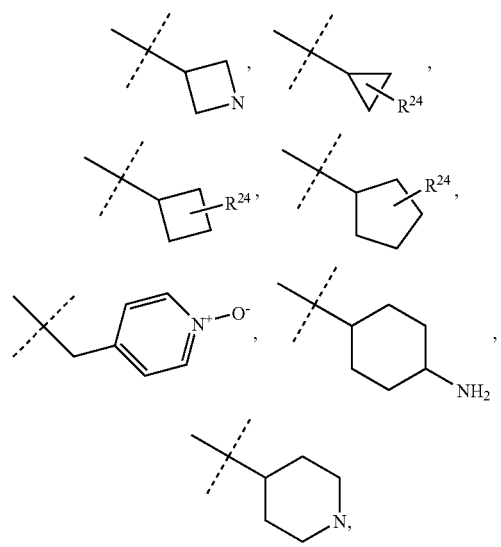

wherein the dashed line indicates the point of attachment to the position indicated by R$^6$;

HET$^1$ is

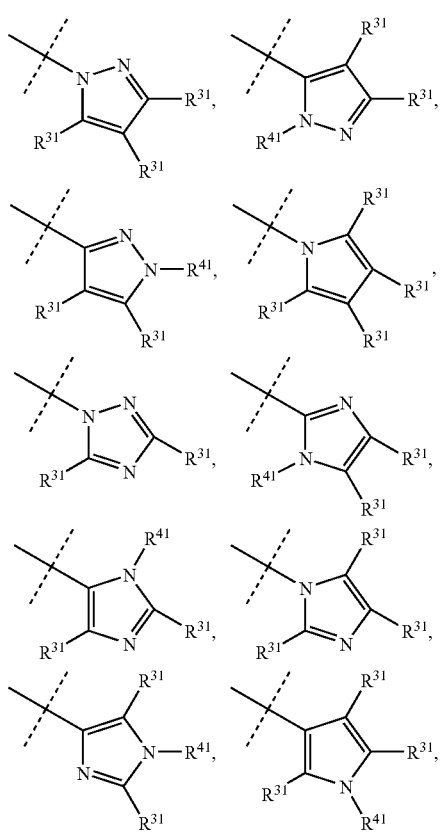

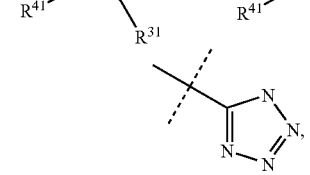

wherein the dashed line indicates the point of attachment to the position indicated by HET$^1$;

HET$^2$ is

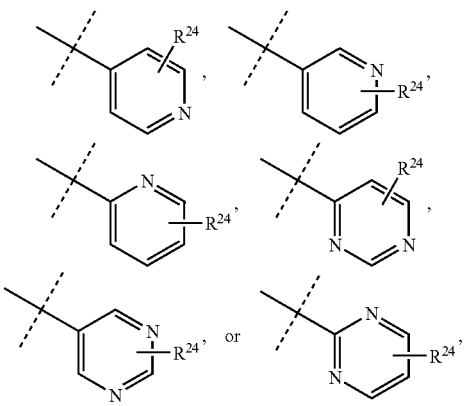

wherein the dashed line indicates the point of attachment to the position indicated by HET$^2$;

R$^7$ is
—H, —(C$_1$-C$_3$)alkyl (optionally substituted with 1 to 3 halogens), or —(C$_1$-C$_3$)alkyl-O—R$^{20}$;

R$^8$ is
—H, —OH, —(C$_1$-C$_6$)alkyl (optionally substituted with 1 to 3 halogens), —(C$_1$-C$_3$)alkyl-O—R$^{20}$, —C(O)—(C$_1$-C$_4$)alkyl (optionally substituted with 1 to 3 halogens), —C(O)O—(C$_1$-C$_4$)alkyl (optionally substituted with 1 to 3 halogens), or —C(O)—N(R$^{20}$)(R$^{20}$);

R$^9$ is
—H, -halogen, —CH$_3$ (optionally substituted with 1 to 3 halogens), or —O—CH$_3$ (optionally substituted with 1 to 3 halogens);

R$^{10}$ is independently at each occurrence —H, or -halogen;
R$^{11}$ is independently at each occurrence —H, —CH$_3$ or —CH$_2$—CH$_3$;
R$^{20}$ is independently at each occurrence —H, or —(C$_1$-C$_4$)alkyl (optionally substituted with 1 to 3 halogens);
R$^{21}$ is independently at each occurrence —H, -halogen, or —(C$_1$-C$_4$)alkyl (optionally substituted with 1 to 3 halogens);
R$^{22}$ is independently at each occurrence —H, or —(C$_1$-C$_6$)alkyl (optionally substituted with 1 to 3 halogens);
R$^{23}$ is independently at each occurrence —H, —(C$_1$-C$_4$)alkyl, or —C(O)O—(C$_1$-C$_4$)alkyl;
R$^{24}$ is independently at each occurrence —H, -halogen, or —(C$_1$-C$_6$)alkyl (optionally substituted with 1 to 3 halogens);

R³¹ is independently at each occurrence —H, -halogen, or —(C₁-C₆)alkyl (optionally substituted with 1 to 3 halogens); and R⁴¹ is independently at each occurrence —H, or —(C₁-C₆)alkyl (optionally substituted with 1 to 3 halogens);

provided the compound is not {[3'-Chloro-4'-(1-cyclohexyl-2-oxo-pyrrolidin-3-ylmethyl)-biphenyl-4-carbonyl]-amino}-acetic acid, 4-{[3'-Chloro-4'-(1-cyclohexyl-2-oxo-pyrrolidin-3-ylmethyl)-biphenyl-4-carbonyl]-amino}-butyric acid, 3'-Chloro-4'-(1-cyclohexyl-2-oxo-pyrrolidin-3-ylmethyl)-biphenyl-4-carboxylic acid piperidin-4-ylamide, or 3-[3-Chloro-4'-(4-methyl-piperazine-1-carbonyl)-biphenyl-4-ylmethyl]-1-cyclohexyl-pyrrolidin-2-one;

or a pharmaceutically acceptable salt thereof.

2. A compound of claim 1 wherein R¹ is

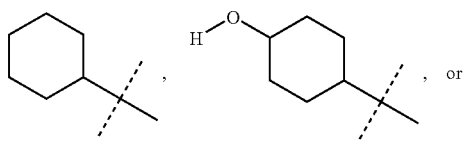

or a pharmaceutically acceptable salt thereof.

3. A compound of claim 2 wherein R² and R³ are chlorine, or a pharmaceutically acceptable salt thereof.

4. A compound as claimed by claim 3 wherein R⁴ is hydrogen, or a pharmaceutically acceptable salt thereof.

5. A compound as claimed by claim 4 wherein R¹ is

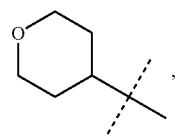

or a pharmaceutically acceptable salt thereof.

6. A compound as claimed by claim 4 wherein R¹ is

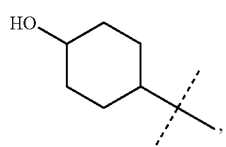

or a pharmaceutically acceptable salt thereof.

7. A compound as claimed by claim 4 wherein R¹ is

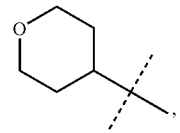

or a pharmaceutically acceptable salt thereof.

8. A compound as claimed by claim 4 wherein R⁵ is

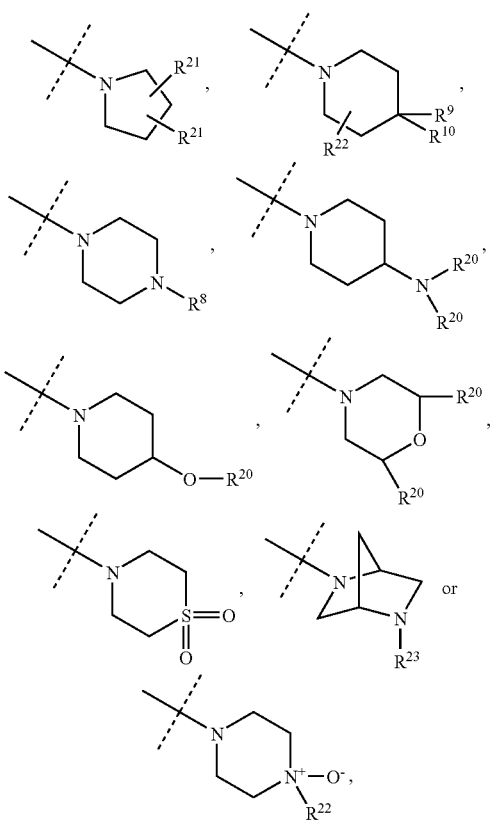

wherein

R⁸ is —H, —(C₁-C₄)alkyl (optionally substituted with 1 to 3 halogens), —(C₂-C₃)alkyl-O—R²⁰, —C(O)—(C₁-C₄)alkyl, —C(O)O—(C₁-C₄)alkyl, or —C(O)—N(R²⁰)(R²⁰);

R⁹ is —H, -halogen, —CH₃ (optionally substituted with 1 to 3 halogens), or —O—CH₃ (optionally substituted with 1 to 3 halogens);

R¹⁰ is independently at each occurrence —H or -halogen;

R²⁰ is independently at each occurrence —H, or —(C₁-C₃)alkyl (optionally substituted with 1 to 3 halogens);

R²¹ is independently at each occurrence —H, -halogen, or —(C₁-C₃)alkyl;

R²² is independently at each occurrence —H or —(C₁-C₃)alkyl (optionally substituted with 1 to 3 halogens); and R²³ is independently at each occurrence —H, —(C₁-C₃)alkyl, or —C(O)O—(C₁-C₄)alkyl;

or a pharmaceutically acceptable salt thereof.

9. A compound as claimed by claim 4 wherein $R^5$ is

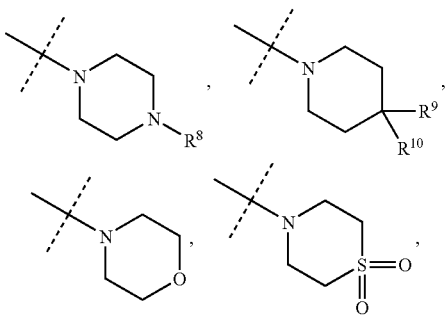

wherein $R^8$ is —($C_1$-$C_4$)alkyl (optionally substituted with 1 to 3 halogens);

$R^9$ is —H, -halogen, —$CH_3$ (optionally substituted with 1 to 3 halogens; and $R^{10}$ is independently at each occurrence —H or -halogen; or a pharmaceutically acceptable salt thereof.

10. A compound as claimed by claim 4 wherein $R^5$ is

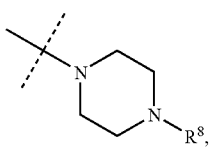

wherein $R^8$ is —($C_1$-$C_3$)alkyl (optionally substituted with 1 to 3 halogens), or a pharmaceutically acceptable salt thereof.

11. A compound as claimed by claim 4 wherein $R^5$ is

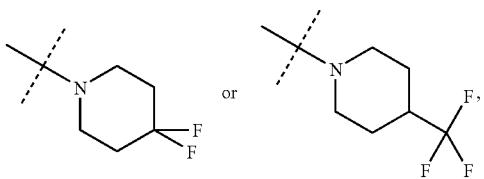

or a pharmaceutically acceptable salt thereof.

12. A compound as claimed by claim 4 wherein $R^5$ is

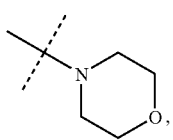

or a pharmaceutically acceptable salt thereof.

13. A compound as claimed by claim 4 wherein $R^5$ is

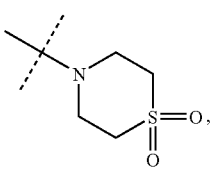

or a pharmaceutically acceptable salt thereof.

14. A compound that is 1-cyclohexyl-3-{3,5-dichloro-4'-[4-(2-fluoro-ethyl)-piperazine-1-carbonyl]-biphenyl-4-ylmethyl}-pyrrolidin-2-one or a pharmaceutically acceptable salt thereof.

15. A compound that is (R)-3-[3,5-dichloro-4'-(4-trifluoromethyl-piperidine-1-carbonyl)-biphenyl-4-ylmethyl]-1-(tetrahydro-pyran-4-yl)-pyrrolidin-2-one or a pharmaceutically acceptable salt thereof.

16. A pharmaceutical composition which comprises a compound of claim 1, or a pharmaceutically acceptable salt thereof, and a pharmaceutically acceptable carrier.

17. A method for treating metabolic syndrome in a patient in need thereof which comprises administering to said patient an effective amount of a compound claim 1, or a pharmaceutically acceptable salt thereof.

18. A method for treating type 2 diabetes in a patient in need thereof which comprises administering to said patient an effective amount of a compound of claim 1, or a pharmaceutically acceptable salt thereof.

19. A method for treating atherosclerosis in a patient in need thereof which comprises administering to said patient an effective amount of a compound of claim 1, or a pharmaceutically acceptable salt thereof.

20. A compound of claim 1 selected from the group consisting of:

3',5'-dichloro-4'-(1-cyclohexyl-2-oxo-pyrrolidin-3-ylmethyl)-3-fluoro-biphenyl-4-carboxylic acid amide;

1-Cyclohexyl-3-{3,5-dichloro-4'-[4-(2-hydroxy-ethyl)-piperazine-1-carbonyl]-biphenyl-4-ylmethyl}-pyrrolidin-2-one;

1-cyclohexyl-3-[3,5-dichloro-4'-(piperidine-1-carbonyl)-biphenyl-4-ylmethyl]-pyrrolidin-2-one;

1-Cyclohexyl-3-[3,5-dichloro-4'-(morpholine-4-carbonyl)-biphenyl-4-ylmethyl]-pyrrolidin-2-one;

3',5'-Dichloro-4'-(1-cyclohexyl-2-oxo-pyrrolidin-3-ylmethyl)-biphenyl-4-carboxylic acid bis-(2-hydroxyethyl)-amide;

1-Cyclohexyl-3-[3,5-dichloro-4'-(4-isopropyl-piperazine-1-carbonyl)-biphenyl-4-ylmethyl]-pyrrolidin-2-one;

3',5'-Dichloro-4'-(1-cyclohexyl-2-oxo-pyrrolidin-3-ylmethyl)-biphenyl-4-carboxylic acid(2-dimethylaminoethyl)-amide;

3',5'-Dichloro-4'-(1-cyclohexyl-2-oxo-pyrrolidin-3-ylmethyl)-biphenyl-4-carboxylic acid(2-dimethylaminoethyl)-methyl-amide;

1-Cyclohexyl-3-[3,5-dichloro-4'-(4-trifluoromethyl-piperidine-1-carbonyl)-biphenyl-4-ylmethyl]-pyrrolidin-2-one;

1-Cyclohexyl-3-[3,5-dichloro-4'-(4-hydroxy-piperidine-1-carbonyl)-biphenyl-4-ylmethyl]-pyrrolidin-2-one;

3',5'-Dichloro-4'-(1-cyclohexyl-2-oxo-pyrrolidin-3-ylmethyl)-biphenyl-4-carboxylic acid(2-hydroxy-ethyl)-methyl-amide;

1-Cyclohexyl-3-[3,5-dichloro-4'-(thiomorpholine-4-carbonyl)-biphenyl-4-ylmethyl]-pyrrolidin-2-one;
3',5'-Dichloro-4'-(1-cyclohexyl-2-oxo-pyrrolidin-3-ylmethyl)-biphenyl-4-carboxylic acid (2,2,2-trifluoro-ethyl)-amide;
1-Cyclohexyl-3-{3,5-dichloro-4'-[4-(2-fluoro-ethyl)-piperazine-1-carbonyl]-biphenyl-4-ylmethyl}-pyrrolidin-2-one;
3',5'-Dichloro-4'-(1-cyclohexyl-2-oxo-pyrrolidin-3-ylmethyl)-biphenyl-4-carboxylic acid methylamide;
3',5'-Dichloro-4'-(1-cyclohexyl-2-oxo-pyrrolidin-3-ylmethyl)-biphenyl-4-carboxylic acid dimethylamide;
3',5'-Dichloro-4'-(1-cyclohexyl-2-oxo-pyrrolidin-3-ylmethyl)-biphenyl-4-carboxylic acid isopropylamide;
3',5'-Dichloro-4'-(1-cyclohexyl-2-oxo-pyrrolidin-3-ylmethyl)-biphenyl-4-carboxylic acid ethylamide;
3',5'-Dichloro-4'-(1-cyclohexyl-2-oxo-pyrrolidin-3-ylmethyl)-biphenyl-4-carboxylic acid (pyridin-4-ylmethyl)-amide;
3',5'-Dichloro-4'-(1-cyclohexyl-2-oxo-pyrrolidin-3-ylmethyl)-biphenyl-4-carboxylic acid cyclopropylamide;
3',5'-Dichloro-4'-(1-cyclohexyl-2-oxo-pyrrolidin-3-ylmethyl)-biphenyl-4-carboxylic acid cyclobutylamide;
3-[4'-(Azetidine-1-carbonyl)-3,5-dichloro-biphenyl-4-ylmethyl]-1-cyclohexyl-pyrrolidin-2-one;
3',5'-Dichloro-4'-(1-cyclohexyl-2-oxo-pyrrolidin-3-ylmethyl)-biphenyl-4-carboxylic acid bis-(2-hydroxyethyl)-amide;
1-[3',5'-Dichloro-4'-(1-cyclohexyl-2-oxo-pyrrolidin-3-ylmethyl)-biphenyl-4-carbonyl]-piperidin-4-one;
3',5'-Dichloro-4'-(1-cyclohexyl-2-oxo-pyrrolidin-3-ylmethyl)-biphenyl-4-carboxylic acid (4-amino-cyclohexyl)-amide;
4-[3',5'-Dichloro-4'-(1-cyclohexyl-2-oxo-pyrrolidin-3-ylmethyl)-biphenyl-4-carbonyl]-piperazine-1-carboxylic acid dimethylamide;
1-Cyclohexyl-3-[3,5-dichloro-4'-(hexahydro-pyrrolo[1,2a]pyrazine-2-carbonyl)-biphenyl-4-ylmethyl]-pyrrolidin-2-one;
1-Cyclohexyl-3-[3,5-dichloro-4'-(hexahydro-pyrazino[2,1-c][1,4]oxazine-8-carbonyl)-biphenyl-4-ylmethyl]-pyrrolidin-2-one;
1-Cyclohexyl-3-[3,5-dichloro-4'-(1,4,6,7-tetrahydro-imidazo[4,5-c]pyridine-5-carbonyl)-biphenyl-4-ylmethyl]-pyrrolidin-2-one;
1-Cyclohexyl-3-[3,5-dichloro-4'-(hexahydro-pyrrolo[1,2-a]pyrazine-2-carbonyl)-biphenyl-4-ylmethyl]-pyrrolidin-2-one;
5-[3',5'-Dichloro-4'-(1-cyclohexyl-2-oxo-pyrrolidin-3-ylmethyl)-biphenyl-4-carbonyl]-2,5-diaza-bicyclo[2.2.1]heptane-2-carboxylic acid tert-butyl ester;
1-Cyclohexyl-3-[3,5-dichloro-4'-(pyrrolidine-1-carbonyl)-biphenyl-4-ylmethyl]-pyrrolidin-2-one;
{[3',5'-dichloro-4'-(1-cyclohexyl-2-oxo-pyrrolidin-3-ylmethyl)-biphenyl-4-carbonyl]-amino}-acetic acid;
(S)-2-{[3',5'-Dichloro-4'-(1-cyclohexyl-2-oxo-pyrrolidin-3-ylmethyl)-biphenyl-4-carbonyl]-amino}-3-hydroxypropionic acid;
(R)-2-{[3',5'-Dichloro-4'-(1-cyclohexyl-2-oxo-pyrrolidin-3-ylmethyl)-biphenyl-4-carbonyl]-amino}-3-hydroxypropionic acid;
2-{[3',5'-Dichloro-4'-(1-cyclohexyl-2-oxo-pyrrolidin-3-ylmethyl)-biphenyl-4-carbonyl]-amino}-3-dimethylamino-propionic acid;
3',5'-Dichloro-4'-(1-cyclohexyl-2-oxo-pyrrolidin-3-ylmethyl)-biphenyl-4-carboxylic acid methyl-(1H-tetrazol-5-yl)-amide;
3-[4'-(4-tert-Butyl-piperazine-1-carbonyl)-3,5-dichloro-biphenyl-4-ylmethyl]-1-cyclohexyl-pyrrolidin-2-one;
1-Cyclohexyl-3-[3,5-dichloro-4'-(3-trifluoromethyl-5,6-dihydro-8H-[1,2,4]triazolo[4,3-a]pyrazine-7-carbonyl)-biphenyl-4-ylmethyl]-pyrrolidin-2-one;
1-cyclohexyl-3-[3,5-dichloro-4'-(4-methyl-piperazine-1-carbonyl)-biphenyl-4-ylmethyl]-pyrrolidin-2-one;
3',5'-dichloro-4'-(1-cyclohexyl-2-oxo-pyrrolidin-3-ylmethyl)-biphenyl-4-carboxylic acid azetidin-3-ylamide;
3',5'-dichloro-4'-(1-cyclohexyl-2-oxo-pyrrolidin-3-ylmethyl)-biphenyl-4-carboxylic acid (3-amino-cyclohexyl)-amide;
1-cyclohexyl-3-[3,5-dichloro-4'-(piperazine-1-carbonyl)-biphenyl-4-ylmethyl]-pyrrolidin-2-one;
3',5'-dichloro-4'-(1-cyclohexyl-2-oxo-pyrrolidin-3-ylmethyl)-biphenyl-4-carboxylic acid (4-amino-cyclohexyl)-amide;
3',5'-dichloro-4'-(1-cyclohexyl-2-oxo-pyrrolidin-3-ylmethyl)-biphenyl-4-carboxylic acid (2-dimethylaminoethyl)-amide N-oxide;
3',5'-dichloro-4'-(1-cyclohexyl-2-oxo-pyrrolidin-3-ylmethyl)-biphenyl-4-carboxylic acid (1-oxy-pyridin-4-ylmethyl)-amide;
3-[4'-(4-acetyl-piperazine-1-carbonyl)-3,5-dichloro-biphenyl-4-ylmethyl]-1-cyclohexyl-pyrrolidin-2-one;
4-[3',5'-dichloro-4'-(1-cyclohexyl-2-oxo-pyrrolidin-3-ylmethyl)-biphenyl-4-carbonyl]-piperazine-1-carboxylic acid amide;
1-cyclohexyl-3-[3,5-dichloro-4'-(1,1-dioxo-1 lambda*6*-thiomorpholine-4-carbonyl)-biphenyl-4-ylmethyl]-pyrrolidin-2-one;
3',5'-dichloro-4'-(1-cyclohexyl-2-oxo-pyrrolidin-3-ylmethyl)-biphenyl-4-carboxylic acid (2-amino-ethyl)-amide;
3',5'-dichloro-4'-(1-cyclohexyl-2-oxo-pyrrolidin-3-ylmethyl)-biphenyl-4-carboxylic acid piperidin-4-ylamide;
4-[3',5'-dichloro-4'-(1-cyclohexyl-2-oxo-pyrrolidin-3-ylmethyl)-biphenyl-4-carbonyl]-1-methyl-piperazin-2-one;
1-cyclohexyl-3-[3,5-dichloro-4'-((1S,4S)-5-isopropyl-2,5-diaza-bicyclo[2.2.1]heptane-2-carbonyl)-biphenyl-4-ylmethyl]-pyrrolidin-2-one;
1-cyclohexyl-3-{3,5-dichloro-4'-[4-(2-fluoro-ethyl)-piperazine-1-carbonyl]-biphenyl-4-ylmethyl}-pyrrolidin-2-one;
1-cyclohexyl-3-[3,5-dichloro-4'-(morpholine-4-carbonyl)-biphenyl-4-ylmethyl]-pyrrolidin-2-one;
1-cyclohexyl-3-[3,5-dichloro-4'-(4-methyl-piperazine-1-carbonyl)-biphenyl-4-ylmethyl]-pyrrolidin-2-one;
1-cyclohexyl-3-[3,5-dichloro-4'-(4-isopropyl-piperazine-1-carbonyl)-biphenyl-4-ylmethyl]-pyrrolidin-2-one;
1-cyclohexyl-3-[3,5-dichloro-4'-(4-methyl-4-oxy-piperazine-1-carbonyl)-biphenyl-4-ylmethyl]-pyrrolidin-2-one;
1-cyclohexyl-3-[3,5-dichloro-4'-(4-methyl-4-oxy-piperazine-1-carbonyl)-biphenyl-4-ylmethyl]-pyrrolidin-2-one;
1-cyclohexyl-3-[3,5-dichloro-4'-(4-isopropyl-4-oxy-piperazine-1-carbonyl)-biphenyl-4-ylmethyl]-pyrrolidin-2-one;
1-cyclohexyl-3-{3,5-dichloro-4'-[4-(2,2,2-trifluoro-ethyl)-piperazine-1-carbonyl]-biphenyl-4-ylmethyl}-pyrrolidin-2-one;
3-{3,5-Dichloro-4'-[4-(2-fluoro-ethyl)-piperazine-1-carbonyl]-biphenyl-4-ylmethyl}-cis-1-(4-hydroxy-cyclohexyl)-pyrrolidin-2-one;

3-[3,5-Dichloro-4'-(1,1-dioxo-1-lambda*6*-thiomorpholine-4-carbonyl)-biphenyl-4-ylmethyl]-cis-1-(4-hydroxy-cyclohexyl)-pyrrolidin-2-one;
(R)-3-[3,5-Dichloro-4'-(morpholine-4-carbonyl)-biphenyl-4-ylmethyl]-cis-1-(4-hydroxy-cyclohexyl)-pyrrolidin-2-one;
(R)-3-{3,5-Dichloro-4'-[4-(2-fluoro-ethyl)-piperazine-1-carbonyl]-biphenyl-4-ylmethyl}-cis-1-(4-hydroxy-cyclohexyl)-pyrrolidin-2-one;
(R)-3-[3,5-Dichloro-4'-(4-trifluoromethyl-piperidine-1-carbonyl)-biphenyl-4-ylmethyl]-cis-1-(4-hydroxy-cyclohexyl)-pyrrolidin-2-one;
(R)-3-[4'-(4-tert-Butyl-piperazine-1-carbonyl)-3,5-dichloro-biphenyl-4-ylmethyl]-cis-1-(4-hydroxy-cyclohexyl)-pyrrolidin-2-one;
(R)-3-[3,5-Dichloro-4'-([1,4]oxazepane-4-carbonyl)-biphenyl-4-ylmethyl]-cis-1-(4-hydroxy-cyclohexyl)-pyrrolidin-2-one;
(R)-3-[3,5-Dichloro-4'-(4,4-difluoro-piperidine-1-carbonyl)-biphenyl-4-ylmethyl]-cis-1-(4-hydroxy-cyclohexyl)-pyrrolidin-2-one;
(R)-3-[3,5-Dichloro-4'-(3,3-difluoro-pyrrolidine-1-carbonyl)-biphenyl-4-ylmethyl]-cis-1-(4-hydroxy-cyclohexyl)-pyrrolidin-2-one;
(R)-3-[3,5-Dichloro-4'-(4-methoxy-piperidine-1-carbonyl)-biphenyl-4-ylmethyl]-cis-1-(4-hydroxy-cyclohexyl)-pyrrolidin-2-one;
(R)-3-[3,5-Dichloro-4'-(2,6-cis-dimethyl-morpholine-4-carbonyl)-biphenyl-4-ylmethyl]-cis-1-(4-hydroxy-cyclohexyl)-pyrrolidin-2-one;
(R)-3-[3,5-Dichloro-4'-(piperazine-1-carbonyl)-biphenyl-4-ylmethyl]-cis-1-(4-hydroxy-cyclohexyl)-pyrrolidin-2-one;
(R)-3-{3,5-Dichloro-4'-[4-(2,2,2-trifluoro-ethyl)-piperazine-1-carbonyl]-biphenyl-4-ylmethyl}-cis-1-(4-hydroxy-cyclohexyl)-pyrrolidin-2-one;
(R)-3-[3,5-Dichloro-4'-(2-oxa-5-aza-bicyclo[2.2.1]heptane-5-carbonyl)-biphenyl-4-ylmethyl]-cis-1-(4-hydroxy-cyclohexyl)-pyrrolidin-2-one;
(R)-3-[3,5-Dichloro-4'-(4-trifluoromethyl-piperidine-1-carbonyl)-biphenyl-4-ylmethyl]-trans-1-(4-hydroxy-cyclohexyl)-pyrrolidin-2-one;
(R)-3-{3,5-Dichloro-4'-[4-(2,2,2-trifluoro-ethyl)-piperazine-1-carbonyl]-biphenyl-4-ylmethyl}-trans-1-(4-hydroxy-cyclohexyl)-pyrrolidin-2-one;
(R)-3-[3,5-Dichloro-4'-(morpholine-4-carbonyl)-biphenyl-4-ylmethyl]-trans-1-(4-hydroxy-cyclohexyl)-pyrrolidin-2-one;
(R)-3-{3,5-Dichloro-4'-[4-(2-fluoro-ethyl)-piperazine-1-carbonyl]-biphenyl-4-ylmethyl}-trans-1-(4-hydroxy-cyclohexyl)-pyrrolidin-2-one;
(R)-3-[4'-(4-tert-Butyl-piperazine-1-carbonyl)-3,5-dichloro-biphenyl-4-ylmethyl]-trans-1-(4-hydroxy-cyclohexyl)-pyrrolidin-2-one;
(R)-1-cyclohex-3-enyl-3-[3,5-dichloro-4'-(4-trifluoromethyl-piperidine-1-carbonyl)-biphenyl-4-ylmethyl]-pyrrolidin-2-one;
(R)-3-{3,5-dichloro-4'-[4-(2-fluoro-ethyl)-4-oxy-piperazine-1-carbonyl]-biphenyl-4-ylmethyl}-cis-1-(4-hydroxy-cyclohexyl)-pyrrolidin-2-one;
(R)-3-[3,5-dichloro-4'-(1,1-dioxo-1-lambda*6*-thiomorpholine-4-carbonyl)-biphenyl-4-ylmethyl]-trans-1-(4-hydroxy-cyclohexyl)-pyrrolidin-2-one;
(R)-3-[3,5-dichloro-4'-(4-trifluoromethyl-piperidine-1-carbonyl)-biphenyl-4-ylmethyl]-1-(tetrahydro-pyran-4-yl)-pyrrolidin-2-one;
(R)-3-[3,5-Dichloro-4'-(4-methyl-piperazine-1-carbonyl)-biphenyl-4-ylmethyl]-1-(tetrahydro-pyran-4-yl)-pyrrolidin-2-one;
(R)-3-[3,5-Dichloro-4'-(4-isopropyl-piperazine-1-carbonyl)-biphenyl-4-ylmethyl]-1-(tetrahydro-pyran-4-yl)-pyrrolidin-2-one;
(R)-3-[3,5-Dichloro-4'-(morpholine-4-carbonyl)-biphenyl-4-ylmethyl]-1-(tetrahydro-pyran-4-yl)-pyrrolidin-2-one;
(R)-3-[3,5-Dichloro-4'-(1,1-dioxo-1 16-thiomorpholine-4-carbonyl)-biphenyl-4-ylmethyl]-1-(tetrahydro-pyran-4-yl)-pyrrolidin-2-one;
(R)-3-{3,5-Dichloro-4'-[4-(2-fluoro-ethyl)-piperazine-1-carbonyl]-biphenyl-4-ylmethyl}-1-(tetrahydro-pyran-4-yl)-pyrrolidin-2-one;
(R)-3-{3,5-Dichloro-4'-[4-(2,2,2-trifluoro-ethyl)-piperazine-1-carbonyl]-biphenyl-4-ylmethyl}-1-(tetrahydro-pyran-4-yl)-pyrrolidin-2-one;
(R)-3-[4'-(4-Adamantan-2-yl-piperazine-1-carbonyl)-3,5-dichloro-biphenyl-4-ylmethyl]-1-(tetrahydro-pyran-4-yl)-pyrrolidin-2-one;
(R)-3-[3,5-Dichloro-4'-(4,4-difluoro-piperidine-1-carbonyl)-biphenyl-4-ylmethyl]-1-(tetrahydro-pyran-4-yl)-pyrrolidin-2-one;
(R)-3-[3,5-dichloro-4'-(4,4-difluoro-piperidine-1-carbonyl)-biphenyl-4-ylmethyl]-trans-1-(4-hydroxy-cyclohexyl)-pyrrolidin-2-one;
1-Cyclohexyl-3-[4'-(4-methyl-piperazine-1-carbonyl)-3-trifluoromethoxy-biphenyl-4-ylmethyl]-pyrrolidin-2-one;
1-Cyclohexyl-3-[4'-(4-isopropyl-piperazine-1-carbonyl)-3-trifluoromethoxy-biphenyl-4-ylmethyl]-pyrrolidin-2-one;
1-Cyclohexyl-3-[4'-(morpholine-4-carbonyl)-3-trifluoromethoxy-biphenyl-4-ylmethyl]-pyrrolidin-2-one;
1-Cyclohexyl-3-[3-trifluoromethoxy-4'-(4-trifluoromethyl-piperidine-1-carbonyl)-biphenyl-4-ylmethyl]-pyrrolidin-2-one;
1-Cyclohexyl-3-[4'-(1,1-dioxo-1 16-thiomorpholine-4-carbonyl)-3-trifluoromethoxy-biphenyl-4-ylmethyl]-pyrrolidin-2-one;
3-[4'-(4-tert-Butyl-piperazine-1-carbonyl)-3-trifluoromethoxy-biphenyl-4-ylmethyl]-1-cyclohexyl-pyrrolidin-2-one;
1-Cyclohexyl-3-[4'-(4,4-difluoro-piperidine-1-carbonyl)-3-trifluoromethoxy-biphenyl-4-ylmethyl]-pyrrolidin-2-one;
1-Cyclohexyl-3-{4'-[4-(2-fluoro-ethyl)-piperazine-1-carbonyl]-3-trifluoromethoxy-biphenyl-4-ylmethyl}-pyrrolidin-2-one;
1-Cyclohexyl-3-{4'-[4-(2,2,2-trifluoro-ethyl)-piperazine-1-carbonyl]-3-trifluoromethoxy-biphenyl-4-ylmethyl}-pyrrolidin-2-one;
3-[4'-(4-Adamantan-2-yl-piperazine-1-carbonyl)-3-trifluoromethoxy-biphenyl-4-ylmethyl]-1-cyclohexyl-pyrrolidin-2-one;
1-Cyclohexyl-3-[4'-(1,1-dioxo-1 lambda*6*-thiomorpholine-4-carbonyl)-3-trifluoromethyl-biphenyl-4-ylmethyl]-pyrrolidin-2-one;
3-[4'-(4-tert-Butyl-piperazine-1-carbonyl)-3-trifluoromethyl-biphenyl-4-ylmethyl]-1-cyclohexyl-pyrrolidin-2-one;
1-Cyclohexyl-3-[4'-(piperazine-1-carbonyl)-3-trifluoromethyl-biphenyl-4-ylmethyl]-pyrrolidin-2-one;
1-Cyclohexyl-3-{4'-[4-(2-fluoro-ethyl)-piperazine-1-carbonyl]-3-trifluoromethyl-biphenyl-4-ylmethyl}-pyrrolidin-2-one;

1-Cyclohexyl-3-[3-trifluoromethyl-4'-(4-trifluoromethyl-piperidine-1-carbonyl)-biphenyl-4-ylmethyl]-pyrrolidin-2-one;

1-Cyclohexyl-3-[4'-(4-methyl-piperazine-1-carbonyl)-3-trifluoromethyl-biphenyl-4-ylmethyl]-pyrrolidin-2-one;

3',5'-Dichloro-4'-[(R)-trans-1-(4-hydroxy-cyclohexyl)-2-oxo-pyrrolidin-3-ylmethyl]-biphenyl-4-carboxylic acid methylcarbamoylmethyl-amide;

(R)-3-[3,5-Dichloro-4'-(4-methyl-piperidine-1-carbonyl)-biphenyl-4-ylmethyl]-trans-1-(4-hydroxy-cyclohexyl)-pyrrolidin-2-one;

3',5'-Dichloro-4'-[(R)-trans-1-(4-hydroxy-cyclohexyl)-2-oxo-pyrrolidin-3-ylmethyl]-biphenyl-4-carboxylic acid dimethylcarbamoylmethyl-amide;

3',5'-Dichloro-4'-[(R)-trans-1-(4-hydroxy-cyclohexyl)-2-oxo-pyrrolidin-3-ylmethyl]-biphenyl-4-carboxylic acid carbamoylmethyl-amide;

(R)-3-[3,5-Dichloro-4'-(4-trifluoromethyl-piperidine-1-carbonyl)-biphenyl-4-ylmethyl]-trans-1-(4-methoxy-cyclohexyl)-pyrrolidin-2-one; and (R)-3-[3,5-Dichloro-4'-(4,4-difluoro-piperidine-1-carbonyl)-biphenyl-4-ylmethyl]-trans-1-(4-methoxy-cyclohexyl)-pyrrolidin-2-one;

or a pharmaceutically acceptable salt thereof.

* * * * *